(12) United States Patent
Dietz et al.

(10) Patent No.: US 8,153,819 B2
(45) Date of Patent: Apr. 10, 2012

(54) FUNGICIDAL MIXTURES COMPRISING SUBSTITUTED 1-METHYLPYRAZOL-4-YLCARBOXANILIDES

(75) Inventors: Jochen Dietz, Mannheim (DE); Markus Gewehr, Kastellaun (DE); Siegfried Strathmann, Limburgerhof (DE); Reinhard Stierl, Freinsheim (DE); Frank Werner, Neustadt (DE); Maria Scherer, Landau (DE)

(73) Assignee: BASF SE, Ludwigshafen (DE)

( * ) Notice: Subject to any disclaimer, the term of this patent is extended or adjusted under 35 U.S.C. 154(b) by 895 days.

(21) Appl. No.: 11/997,860

(22) PCT Filed: Aug. 1, 2006

(86) PCT No.: PCT/EP2006/064907
§ 371 (c)(1),
(2), (4) Date: Feb. 4, 2008

(87) PCT Pub. No.: WO2006/064907
PCT Pub. Date: Feb. 15, 2007

(65) Prior Publication Data
US 2008/0293798 A1     Nov. 27, 2008

(30) Foreign Application Priority Data

Aug. 5, 2005 (DE) .................... 10 2005 037 677
Feb. 2, 2006 (EP) ..................... 06101198

(51) Int. Cl.
*C07D 487/00* (2006.01)
*C07D 231/00* (2006.01)
(52) U.S. Cl. .................. 548/359.1; 548/356.1
(58) Field of Classification Search .......... 548/359.1, 548/356.1
See application file for complete search history.

(56) References Cited

U.S. PATENT DOCUMENTS

| | | | |
|---|---|---|---|
| 5,330,995 A | 7/1994 | Eicken et al. | |
| 5,438,070 A | 8/1995 | Eicken et al. | |
| 5,480,897 A | 1/1996 | Eicken et al. | |
| 5,556,988 A | 9/1996 | Eicken et al. | |
| 5,589,493 A | 12/1996 | Eicken et al. | |
| 6,147,104 A | 11/2000 | Eicken et al. | |
| 6,369,093 B1 | 4/2002 | Elbe et al. | |
| 7,173,055 B1 * | 2/2007 | Walter | 514/406 |
| 7,329,633 B2 * | 2/2008 | Dunkel et al. | 504/280 |
| 2007/0060579 A1 | 3/2007 | Wachendorff-Neumann et al. | |
| 2007/0197556 A1 | 8/2007 | Tormo I Blasco et al. | |

FOREIGN PATENT DOCUMENTS

| | | |
|---|---|---|
| CA | 2 563 814 | 11/2005 |
| CA | 2 590 367 | 7/2006 |
| CA | 2 590 368 | 7/2006 |
| EP | 545 099 | 6/1993 |
| EP | 589 301 | 3/1994 |
| WO | WO 99/09013 | 2/1999 |
| WO | WO 00/14071 | 3/2000 |
| WO | WO 01/42223 | 6/2001 |
| WO | WO03/070705 | * 8/2003 |
| WO | WO 2005/034628 | 4/2005 |
| WO | WO 2005/110089 | 11/2005 |
| WO | WO 2006/069715 | 7/2006 |
| WO | WO 2006/069716 | 7/2006 |
| WO | WO 2006/087343 | 8/2006 |
| WO | WO 2007/000462 | 1/2007 |
| WO | WO 2007/003540 | 1/2007 |
| WO | WO 2007/003564 | 1/2007 |
| WO | WO 2007/003603 | 1/2007 |
| WO | WO 2007/003643 | 1/2007 |
| WO | WO 2007/003644 | 1/2007 |
| WO | WO 2007/006806 | 1/2007 |
| WO | WO 2007/012598 | 2/2007 |

OTHER PUBLICATIONS

George Patani & Edmond LaVoie, Bioisosterism: A Rational Approach in Drug Design, 96 Chem. Rev. 3147 (1996).*
International Preliminary Report on Patentability for International Application No. PCT/EP2006/064907; International filing date: Aug. 1, 2006, Eng. Translation.
Petrova, D., "Thioamides. XIII. The Preparation of Some Substituted Bisthioamides", Croatica Chemica ACTA, 1976, p. 49-52, vol. 48, No. 1.

* cited by examiner

*Primary Examiner* — Karlheinz R Skowronek
*Assistant Examiner* — Sean Basquill
(74) *Attorney, Agent, or Firm* — Brinks Hofer Gilson & Lione

(57) ABSTRACT

Fungicidal mixtures, comprising as active components
1) at least one 1-methylpyrazol-4-ylcarboxanilides of the formula I

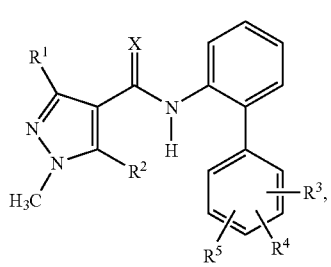

where X=O or S, $R^1$=$C_1$-$C_4$-alkyl or $C_1$-$C_4$-haloalkyl, $R^2$=hydrogen or halogen, $R^3$, $R^4$ and $R^5$=independently of one another cyano, nitro, halogen, $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio;
and
2) at least one active compound II, selected from the active compound groups A) to F):
A) azoles;
B) strobilurins;
C) carboxamides;
D) heterocyclic compounds;
E) carbamates;
F) other fungicides; in a synergistically effective amount, methods for controlling harmful fungi using mixtures of at least one compound I and at least one active compound II and the use of the compound(s) I with active compounds II for preparing such mixtures, and also compositions and seed comprising such mixtures.

16 Claims, No Drawings

FUNGICIDAL MIXTURES COMPRISING SUBSTITUTED 1-METHYLPYRAZOL-4-YLCARBOXANILIDES

This application is a National Stage application of International Application No. PCT/EP2006/064907, filed Aug. 1, 2006, the entire contents of which is hereby incorporated herein by reference. This application also claims the benefit under 35 U.S.C. §119 of German Patent Application No. 102005037677.0, filed Aug. 5, 2005 and European Patent Application No. 06101198.7, filed Feb. 2, 2006.

The present invention relates to fungicidal mixtures comprising, as active components, 1) at least one 1-methylpyrazol-4-ylcarboxanilides of the formula I

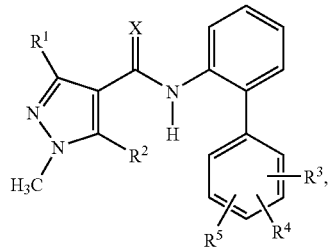

in which the substituents are as defined below:
X is oxygen or sulfur;
$R^1$ is $C_1$-$C_4$-alkyl or $C_1$-$C_4$-haloalkyl;
$R^2$ is hydrogen or halogen;
$R^3$, $R^4$ and $R^5$ independently of one another are cyano, nitro, halogen, $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio;

and 2) at least one active compound II selected from the active compound groups A) to F):

A) azoles selected from the group consisting of bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thiabendazole, fuberidazole, ethaboxam, etridiazole and hymexazole;

B) strobilurins selected from the group consisting of azoxystrobin, dimoxystrobin, enestroburin, fluoxastrobin, kresoxim-methyl, methominostrobin, orysastrobin, picoxystrobin, pyraclostrobin, trifloxystrobin, enestroburin, methyl (2-chloro-5-[1-(3-methyl-benzyloxyimino)ethyl]benzyl)carbamate, methyl (2-chloro-5-[1-(6-methylpyridin-2-ylmethoxyimino)ethyl]benzyl) carbamate and methyl 2-(ortho-(2,5-dimethylphenyloxymethylene)phenyl)-3-methoxyacrylate;

C) carboxamides selected from the group consisting of carboxin, benalaxyl; boscalid, fenhexamid, flutolanil, furametpyr, mepronil, metalaxyl, mefenoxam, ofurace, oxadixyl, oxycarboxin, penthiopyrad, thifluzamide, tiadinil, 3,4-dichloro-N-(2-cyanophenyl)isothiazole-5-carboxamide, dimethomorph, flumorph, flumetover, fluopicolide (picobenzamid), zoxamide, carpropamid, diclocymet, mandipropamid, N-(2-(4-[3-(4-chlorophenyl)prop-2-ynyloxy]-3-methoxyphenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide, methyl 3-(4-chlorophenyl)-3-(2-isopropoxycarbonylamino-3-methylbutyrylamino) propionate, compounds of the formula III

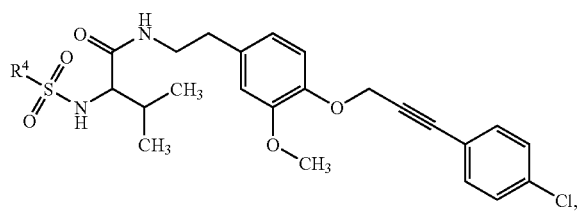

in which $R^4$ is methyl or ethyl,
N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(3',4'-dichloro-5-fluorobiphenyl-2-yl)-3-difluoromethyl-1-methylpyrazole-4-ylcarboxamide and N-(2-cyanophenyl)-3,4-dichloroisothiazole-5-carboxamide;

D) heterocyclic compounds selected from the group consisting of fluazinam, pyrifenox, bupirimate, cyprodinil, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, probenazole, 5-chloro-7-(4-methylpiperidin-1-yl)-6-(2,4,6-trifluorophenyl)-[1,2,4]triazolo[1,5-a]pyrimidine, anilazine, diclomezine, pyroquilon, proquinazid, tricyclazole, the compound of the formula IV (2-butoxy-6-iodo-3-propylchromen-4-one)

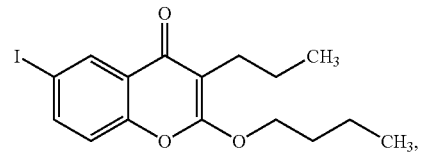

acibenzolar-S-methyl, captafol, captan, dazomet, folpet, fenoxanil, quinoxyfen and
N,N-dimethyl-3-(3-bromo-6-fluoro-2-methylindole-1-sulfonyl)-[1,2,4]triazole-1-sulfonamide of the formula V

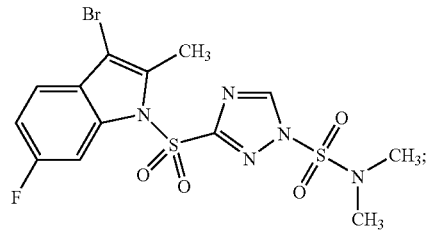

E) carbamates selected from the group consisting of mancozeb, maneb, metam, metiram, ferbam, propineb, thiram, zineb, ziram, diethofencarb, iprovalicarb, flubenthiavalicarb, propamocarb, 4-fluorophenyl N-(1-(1-(4-cyanophenyl)ethanesulfonyl)but-2-yl)carbamate, methyl 3-(4-chlorophenyl)-3-(2-isopropoxycarbonylamino-3-methylbutyrylamino)propanoate of the formula VI

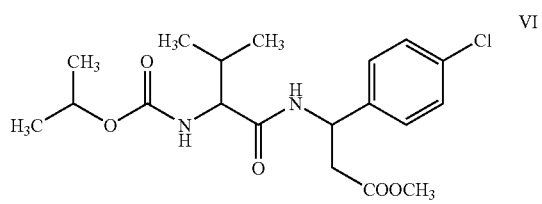

and carbamate oxime ethers of the formula VII

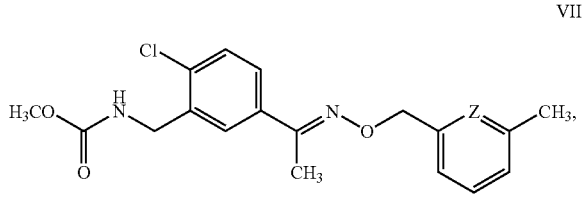

in which Z is N or CH;

F) other fungicides selected from the group consisting of guanidine, dodine, iminoctadine, guazatine, antibiotics: kasugamycin, streptomycin, polyoxin, validamycin A, nitrophenyl derivatives: binapacryl, dinocap, dinobuton, sulfur-containing heterocyclyl compounds: dithianon, isoprothiolane, organometallic compounds: fentin salts such as fentin acetate, organophosphorus compounds: edifenphos, iprobenfos, fosetyl, fosetyl-aluminum, phosphorous acid and its salts, pyrazophos, tolclofos-methyl, organochlorine compounds: chlorothalonil, dichlofluanid, flusulfamide, hexachlorobenzene, phthalide, pencycuron, quintozene, thiophanate-methyl, tolylfluanid, inorganic active compounds: Bordeaux mixture, copper acetate, copper hydroxide, copper oxychloride, basic copper sulfate, sulfur, others: cyflufenamid, cymoxanil, dimethirimol, ethirimol, furalaxyl, metrafenone and spiroxamine;

in a synergistically effective amount.

Moreover, the invention relates to a method for controlling harmful fungi using a mixture of at least one compound I and at least one of the active compounds II, to the use of the compound(s) I with active compound(s) II for preparing such mixtures, and also to compositions and seed comprising such mixtures.

The 1-methylpyrazol-4-ylcarboxanilides of the formula I, referred to above as component 1), their preparation and their action against harmful fungi are known from the literature (cf., for example, EP-A 545 099, EP-A 589 301 and WO 99/09013), or they can be prepared in the manner described therein.

The compounds I in which X is sulfur can be prepared, for example, by sulfurizing the corresponding compounds I in which X is oxygen (cf. e.g. D. Petrova & K. Jakobcic, Croat. Chem. Acta 48, 49 (1976) and WO 01/42223).

However, the known 1-methylpyrazol-4-ylcarboxanilides of the formula I are, in particular at low application rates, not entirely satisfactory.

The active compounds II mentioned above as component 2, their preparation and their action against harmful fungi are generally known (cf., for example, http://www.hclrss.demon.co.uk/index.html); they are commercially available.

Benalaxyl, methyl N-(phenylacetyl)-N-(2,6-xylyl)-DL-alaninate (DE 29 03 612);

metalaxyl, methyl N-(methoxyacetyl)-N-(2,6-xylyl)-DL-alaninate (GB 15 00 581);

ofurace, (RS)-α-(2-chloro-N-2,6-xylylacetamido)-γ-butyrolactone [CAS RN 58810-48-3];

oxadixyl; N-(2,6-dimethylphenyl)-2-methoxy-N-(2-oxo-3-oxazolidinyl)acetamide (GB 20 58 059);

aldimorph, "4-alkyl-2,5(or 2,6)-dimethylmorpholine", comprising 65-75% of 2,6-dimethylmorpholine and 25-35% of 2,5-dimethylmorpholine, comprising more than 85% of 4-dodecyl-2,5(or 2,6)-dimethylmorpholine, where "alkyl" also includes octyl, decyl, tetradecyl and hexadecyl, with a cis/trans ratio of 1:1 [CAS RN 91315-15-0];

dodine, 1-dodecylguanidinium acetate (Plant Dis. Rep., Vol. 41, p. 1029 (1957));

dodemorph, 4-cyclododecyl-2,6-dimethylmorpholine (DE-A 1198125);

fenpropimorph, (RS)-cis-4-[3-(4-tert-butylphenyl)-2-methylpropyl]-2,6-dimethyl-morpholine (DE-A 27 52 096);

fenpropidin, (RS)-1-[3-(4-tert-butylphenyl)-2-methylpropyl]piperidine (DE-A 27 52 096);

guazatine, mixture of the reaction products from the amidation of technical grade iminodi(octamethylene)diamine, comprising various guanidines and polyamines [CAS RN 108173-90-6];

iminoctadine, 1,1'-iminodi(octamethylene)diguanidine (Congr. Plant Pathol., 1., p. 27 (1968);

spiroxamine, (8-tert-butyl-1,4-dioxaspiro[4.5]dec-2-yl)diethylamine (EP-A 281 842);

tridemorph, 2,6-dimethyl-4-tridecylmorpholine (DE-A 11 64 152);

pyrimethanil, 4,6-dimethylpyrimidin-2-ylphenylamine (DD-A 151 404);

mepanipyrim, (4-methyl-6-prop-1-ynylpyrimidin-2-yl)phenylamine (EP-A 224 339);

cyprodinil, (4-cyclopropyl-6-methylpyrimidin-2-yl)phenylamine (EP-A 310 550);

cycloheximide, 4-{(2R)-2-[(1S,3S,5S)-3,5-dimethyl-2-oxocyclohexyl]-2-hydroxyethyl}piperidine-2,6-dione [CAS RN 66-81-9];

griseofulvin, 7-chloro-2',4,6-trimethoxy-6'-methylspiro[benzofuran-2(3H), 1'-cyclohex-2'-ene]-3,4'-dione [CAS RN 126-07-8];

kasugamycin, 3-O-[2-amino-4-[(carboxyiminomethyl)amino]-2,3,4,6-tetradeoxy-α-D-arabino-hexopyranosyl]-D-chiro-inositol [CAS RN 6980-18-3];

natamycin, (8E,14E,16E,18E,20E)-(1R,3S,5R,7R,12R,22R,24S,25R,26S)-22-(3-amino-3,6-dideoxy-β-D-mannopyranosyloxy)-1,3,26-trihydroxy-12-methyl-10-oxo-6,11,28-trioxatricyclo[22.3.1.0$^{5,7}$]octacosa-8,14,16,18,20-pentaene-25-carboxylic acid [CAS RN 7681-93-8];

polyoxin, 5-(2-amino-5-O-carbamoyl-2-deoxy-L-xylonamido)-1-(5-carboxy-1,2,3,4-tetrahydro-2,4-dioxopyrimidin-1-yl)-1,5-dideoxy-β-D-allofuranuronic acid [CAS RN 22976-86-9];

streptomycin, 1,1'-{1-L-(1,3,5/2,4,6)-4-[5-deoxy-2-O-(2-deoxy-2-methylamino-α-L-glucopyranosyl)-3-C-formyl- α-L-lyxofuranosyloxy]-2,5,6-trihydroxycyclohex-1,3-ylene}diguanidine (J. Am. Chem. Soc. Vol. 69, p. 1234 (1947));

bitertanol, β-([1,1'-biphenyl]-4-yloxy)-α-(1,1-dimethylethyl)-1H-1,2,4-triazole-1-ethanol (DE-A 23 24 020);

bromuconazole, 1-[[4-bromo-2-(2,4-dichlorophenyl)tetrahydro-2-furanyl]methyl]-1H-1,2,4-triazole (Proc. 1990 Br. Crop. Prot. Conf.—Pests Dis. Vol. 1, p. 459);

cyproconazole, 2-(4-chlorophenyl)-3-cyclopropyl-1-[1,2,4]triazol-1-ylbutan-2-ol (U.S. Pat. No. 4,664,696);

difenoconazole, 1-{2-[2-chloro-4-(4-chlorophenoxy)phenyl]-4-methyl-[1,3]dioxolan-2-ylmethyl}-1H-[1,2,4]triazole (GB-A 2 098 607);

diniconazole, (βE)-β-[(2,4-dichlorophenyl)methylene]-α-(1,1-dimethylethyl)-1H-1,2,4-triazole-1-ethanol (Noyaku Kagaku, 1983, Vol. 8, p. 575);

enilconazole (imazalil), 1-[2-(2,4-dichlorophenyl)-2-(2-propenyloxy)ethyl]-1H-imidazole (Fruits, 1973, Vol. 28, p. 545);

epoxiconazole, (2RS,3SR)-1-[3-(2-chlorophenyl)-2,3-epoxy-2-(4-fluorophenyl)propyl]-1H-1,2,4-triazole (EP-A 196 038);

fenbuconazole, α-[2-(4-chlorophenyl)ethyl]-α-phenyl-1H-1,2,4-triazole-1-propanenitrile (Proc. 1988 Br. Crop Prot. Conf.—Pests Dis., Vol. 1, p. 33);

fluquinconazole, 3-(2,4-dichlorophenyl)-6-fluoro-2-[1,2,4]-triazol-1-yl-3H-quinazolin-4-one (Proc. Br. Crop Prot. Conf.—Pests Dis., 5-3, 411 (1992));

flusilazole, 1-{[bis(4-fluorophenyl)methylsilanyl]methyl}-1H-[1,2,4]triazole (Proc. Br. Crop Prot. Conf.—Pests Dis., Vol. 1, p. 413 (1984));

flutriafol, α-(2-fluorophenyl)-α-(4-fluorophenyl)-1H-1,2,4-triazole-1-ethanol (EP-A 15 756);

hexaconazole, 2-(2,4-dichlorophenyl)-1-[1,2,4]triazol-1-ylhexan-2-ol (CAS RN 79983-71-4);

ipconazole, 2-[(4-chlorophenyl)methyl]-5-(1-methylethyl)-1-(1H-1,2,4-triazol-1-yl-methyl)cyclopentanol (EP-A 267 778), metconazole, 5-(4-chlorobenzyl)-2,2-dimethyl-1-[1,2,4]triazol-1-ylmethylcyclopentanol (GB 857 383);

myclobutanil, 2-(4-chlorophenyl)-2-[1,2,4]triazol-1-ylmethylpentanenitrile (CAS RN 88671-89-0);

penconazole, 1-[2-(2,4-dichlorophenyl)pentyl]-1H-[1,2,4] triazole (Pesticide Manual, 12th Ed. 2000, p. 712);

propiconazole, 1-[[2-(2,4-dichlorophenyl)-4-propyl-1,3-dioxolan-2-yl]methyl]-1H-1,2,4-triazole (BE 835 579);

prochloraz, N-(propyl-[2-(2,4,6-trichlorophenoxy)ethyl]) imidazole-1-carboxamide (U.S. Pat. No. 3,991,071);

prothioconazole, 2-[2-(1-chlorocyclopropyl)-3-(2-chlorophenyl)-2-hydroxypropyl]-2,4-dihydro[1,2,4]triazole-3-thione (WO 96/16048);

simeconazole, α-(4-fluorophenyl)-α-[(trimethylsilyl)methyl]-1H-1,2,4-triazole-1-ethanol [CAS RN 149508-90-7], tebuconazole, 1-(4-chlorophenyl)-4,4-dimethyl-3-[1,2,4] triazol-1-ylmethylpentan-3-ol (EP-A 40 345);

tetraconazole, 1-[2-(2,4-dichlorophenyl)-3-(1,1,2,2-tetrafluoroethoxy)propyl]-1H-1,2,4-triazole (EP-A 234 242);

triadimefon, 1-(4-chlorophenoxy)-3,3-dimethyl-1-(1H-1,2,4-triazol-1-yl)-2-butanone (BE 793 867);

triadimenol, β-(4-chlorophenoxy)-α-(1,1-dimethylethyl)-1H-1,2,4-triazole-1-ethanol (DE-A 23 24 010);

triflumizol, (4-chloro-2-trifluoromethylphenyl)-(2-propoxy-1-[1,2,4]triazol-1-ylethylidene)-amine (JP-A 79/1.19 462);

triticonazole, (5E)-5-[(4-chlorophenyl)methylene]-2,2-dimethyl-1-(1H-1,2,4-triazol-1-ylmethyl)cyclopentanol (FR 26 41 277);

iprodione, N-isopropyl-3-(3,5-dichlorophenyl)-2,4-dioxoimidazolidine-1-carboxamide (GB 13 12 536);

myclozolin, (RS)-3-(3,5-dichlorophenyl)-5-methoxymethyl-5-methyl-1,3-oxazolidine-2,4-dione [CAS RN 54864-61-8];

procymidone, N-(3,5-dichlorophenyl)-1,2-dimethylcyclopropane-1,2-dicarboximide (U.S. Pat. No. 3,903,090);

vinclozolin, 3-(3,5-dichlorophenyl)-5-methyl-5-vinyloxazolidine-2,4-dione (DE-A 22 07 576);

ferbam, iron(3+) dimethyldithiocarbamate (U.S. Pat. No. 1,972,961);

nabam, disodium ethylenebis(dithiocarbamate) (U.S. Pat. No. 2,317,765);

maneb, manganese ethylenebis(dithiocarbamate) (U.S. Pat. No. 2,504,404);

mancozeb, manganese ethylenebis(dithiocarbamate) polymer complex zinc salt (GB 996 264);

metam, methyldithiocarbaminic acid (U.S. Pat. No. 2,791,605);

metiram, zinc ammoniate ethylenebis(dithiocarbamate) (U.S. Pat. No. 3,248,400);

propineb, zinc propylenebis(dithiocarbamate) polymer (BE 611 960);

polycarbamate, bis(dimethylcarbamodithioato-κS,κS')[μ-[[1,2-ethanediylbis[carbamodithioato-κS,κS']](2−)]]di[zinc] [CAS RN 64440-88-6];

thiram, bis(dimethylthiocarbamoyl)disulfide (DE-A 642 532);

ziram, dimethyldithiocarbamate [CAS RN 137-30-4];

zineb, zinc ethylenebis(dithiocarbamate) (U.S. Pat. No. 2,457,674);

anilazine, 4,6-dichloro-N-(2-chlorophenyl)-1,3,5-triazine-2-amine (U.S. Pat. No. 2,720,480);

benomyl, N-butyl-2-acetylaminobenzimidazole-1-carboxamide (U.S. Pat. No. 3,631,176);

boscalid, 2-chloro-N-(4'-chlorobiphenyl-2-yl)nicotinamide (EP-A 545 099);

carbendazim, methyl (1H-benzimidazol-2-yl)carbamate (U.S. Pat. No. 3,657,443);

carboxin, 5,6-dihydro-2-methyl-N-phenyl-1,4-oxathiine-3-carboxamide (U.S. Pat. No. 3,249,499);

oxycarboxin, 5,6-dihydro-2-methyl-1,4-oxathiine-3-carboxanilide 4,4-dioxide (U.S. Pat. No. 3,399,214);

cyazofamid, 4-chloro-2-cyano-N,N-dimethyl-5-(4-methylphenyl)-1H-imidazole-1-sulfon-amide (CAS RN 120116-88-3];

dazomet, 3,5-dimethyl-1,3,5-thiadiazinane-2-thione (Bull. Soc. Chim. Fr. Vol. 15, p. 891 (1897));

diflufenzopyr, 2-{1-[4-(3,5-difluorophenyl)semicarbazono] ethyl}nicotinic acid [CAS RN 109293-97-2];

dithianon, 5,10-dioxo-5,10-dihydronaphtho[2,3-b][1,4] dithiin-2,3-dicarbonitrile (GB 857 383);

famoxadone, (RS)-3-anilino-S-methyl-5-(4-phenoxyphenyl)-1,3-oxazolidine-2,4-dione [CAS RN 131807-57-3];

fenamidone, (S)-1-anilino-4-methyl-2-methylthio-4-phenylimidazolin-5-one [CAS RN 161326-34-7];

fenarimol, α-(2-chlorophenyl)-α-(4-chlorophenyl)-5-pyrimidinemethanol (GB 12 18 623);

fuberidazole, 2-(2-furanyl)-1H-benzimidazole (DE-A 12 09 799);

flutolanil, α,α,α-trifluoro-3'-isopropoxy-o-toluanilide (JP 1104514);

furametpyr, 5-chloro-N-(1,3-dihydro-1,1,3-trimethyl-4-isobenzofuranyl)-1,3-dimethyl-1H-pyrazole-4-carboxamide [CAS RN 123572-88-3];

isoprothiolane, diisopropyl 1,3-dithiolan-2-ylidenemalonate (Proc. Insectic. Fungic. Conf. 8. Vol. 2, p. 715 (1975));

mepronil, 3'-isopropoxy-o-toluanilide (U.S. Pat. No. 3,937,840);

nuarimol, α-(2-chlorophenyl)-α-(4-fluorophenyl)-5-pyrimidinemethanol (GB 12 18 623);

fluopicolide (picobenzamid), 2,6-dichloro-N-(3-chloro-5-trifluoromethylpyridin-2-ylmethyl)benzamide (WO 99/42447);

probenazole, 3-allyloxy-1,2-benzothiazole 1,1-dioxide (Agric. Biol. Chem. Vol. 37, p. 737 (1973));

proquinazid, 6-iodo-2-propoxy-3-propylquinazolin-4(3H)-one (WO 97/48684);

pyrifenox, 2',4'-dichloro-2-(3-pyridyl)acetophenone (EZ)-O-methyloxime (EP 49 854);

pyroquilon, 1,2,5,6-tetrahydropyrrolo[3,2,1-ij]quinolin-4-one (GB 139 43 373) quinoxyfen, 5,7-dichloro-4-(4-fluorophenoxy)quinoline (U.S. Pat. No. 5,240,940);

silthiofam, N-allyl-4,5-dimethyl-2-(trimethylsilyl)thiophene-3-carboxamide [CAS RN 175217-20-6];

thiabendazole, 2-(1,3-thiazol-4-yl)benzimidazole (U.S. Pat. No. 3,017,415);

thifluzamide, 2',6'-dibromo-2-methyl-4'-trifluoromethoxy-4-trifluoromethyl-1,3-thiazole-5-carboxanilide [CAS RN 130000-40-7];

thiophanate-methyl, 1,2-phenylenebis(iminocarbonothioyl) bis(dimethylcarbamate) (DE-A 19 30-540);

tiadinil, 3'-chloro-4,4'-dimethyl-1,2,3-thiadiazole-5-carboxanilide [CAS RN 223580-51-6];

tricyclazole, 5-methyl-1,2,4-triazolo[3,4-b][1,3]benzothiazole [CAS RN 41814-78-2];

triforine, N,N'-{piperazine-1,4-diylbis[(trichloromethyl)methylene]}diformamide (DE-A 19 01 421);

5-chloro-7-(4-methylpiperidin-1-yl)-6-(2,4,6-trifluorophenyl)-[1,2,4]triazolo[1,5-a]pyrimidine (WO 98/46607);

Bordeaux mixture, mixture of $CuSO_4 \times_3 Cu(OH)_2 \times 3CaSO_4$ [CAS RN 8011-63-0] copper acetate, $Cu(OCOCH_3)_2$ [CAS RN 8011-63-0];

copper oxychloride, $CU_2Cl(OH)_3$ [CAS RN 1332-40-7];

basic copper sulfate, $CuSO_4$ [CAS RN 1344-73-6];

binapacryl, (RS)-2-sec-butyl-4,6-dinitrophenyl 3-methylcrotonate [CAS RN 485-31-4];

dinocap, mixture of 2,6-dinitro-4-octylphenylcrotonate and 2,4-dinitro-6-octyl-phenylcrotonate, where "octyl" is a mixture of 1-methylheptyl, 1-ethylhexyl and 1-propylpentyl (U.S. Pat. No. 2,526,660);

dinobuton, (RS)-2-sec-butyl-4,6-dinitrophenyl isopropyl carbonate [CAS RN 973-21-7];

nitrothal-isopropyl, diisopropyl 5-nitroisophthalate (Proc. Br. Insectic. Fungic. Conf. 7., Vol. 2, p. 673 (1973));

fenpiclonil, 4-(2,3-dichlorophenyl)-1H-pyrrole-3-carbonitrile (Proc. 1988 Br. Crop Prot. Conf.—Pests Dis., Vol. 1, p. 65);

fludioxonil, 4-(2,2-difluorobenzo[1,3]dioxol-4-yl)-1H-pyrrole-3-carbonitrile (The Pesticide Manual, publ. The British Crop Protection Council, 10th ed. 1995, p. 482);

acibenzolar-S-methyl, methyl 1,2,3-benzothiadiazole-7-carbothioate [CAS RN 135158-54-2];

flubenthiavalicarb (benthiavalicarb), isopropyl {(S)-1-[(1R)-1-(6-fluorobenzothiazol-2-yl)-ethylcarbamoyl]-2-methylpropyl}carbamate (JP-A 09/323,984);

carpropamid, 2,2-dichloro-N-[1-(4-chlorophenyl)ethyl]-1-ethyl-3-methylcyclopropane-carboxamide [CAS RN 104030-54-8];

chlorothalonil, 2,4,5,6-tetrachloroisophthalonitrile (U.S. Pat. No. 3,290,353);

cyflufenamid, (Z)—N-[α-(cyclopropylmethoxyimino)-2,3-difluoro-6-(trifluoromethyl)benzyl]-2-phenylacetamide (WO 96/19442);

cymoxanil, 1-(2-cyano-2-methoxyiminoacetyl)-3-ethylurea (U.S. Pat. No. 3,957,847);

diclomezine, 6-(3,5-dichlorophenyl-p-tolyl)pyridazin-3(2H)-one (U.S. Pat. No. 4,052,395) diclocymet, (RS)-2-cyano-N—[(R)-1-(2,4-dichlorophenyl)ethyl]-3,3-dimethylbutyramide [CAS RN 139920-32-4];

diethofencarb, isopropyl 3,4-diethoxycarbanilate (EP-A 78 663);

edifenphos, O-ethyl S,S-diphenyl phosphorodithioate (DE-A 14 93 736) ethaboxam, N-(cyano-2-thienylmethyl)-4-ethyl-2-(ethylamino)-5-thiazolecarboxamide (EP-A 639 574);

fenhexamid, N-(2,3-dichloro-4-hydroxyphenyl)-1-methylcyclohexanecarboxamide (Proc. Br. Crop Prot. Conf.—Pests Dis., 1998, Vol. 2, p. 327);

fentin-acetate, triphenyltin (U.S. Pat. No. 3,499,086);

fenoxanil, N-(1-cyano-1,2-dimethylpropyl)-2-(2,4-dichlorophenoxy)propanamide (EP-A 262 393);

ferimzone, (Z)-2'-methylacetophenone-4,6-dimethylpyrimidin-2-ylhydrazone [CAS RN 89269-64-7];

fluazinam, 3-chloro-N-[3-chloro-2,6-dinitro-4-(trifluoromethyl)phenyl]-5-(trifluoromethyl)-2-pyridinamine (The Pesticide Manual, publ. The British Crop Protection Council, 10th ed. (1995), p. 474);

fosetyl, fosetyl-aluminum, ethylphosphonate (FR 22 54 276);

iprovalicarb, isopropyl [(1S)-2-methyl-1-(1-p-tolylethylcarbamoyl)propyl]carbamate (EP-A 472 996);

hexachlorobenzene (C. R. Seances Acad. Agric. Fr., Vol. 31, p. 24 (1945));

mandipropamid, (RS)-2-(4-chlorophenyl)-N-[3-methoxy-4-(prop-2-ynyloxy)phenethyl]-2-(prop-2-ynyloxy)acetamide (WO 03/042166);

metrafenone, 3'-bromo-2,3,4,6'-tetramethoxy-2',6-dimethylbenzophenone (U.S. Pat. No. 5,945,567);

pencycuron, 1-(4-chlorobenzyl)-1-cyclopentyl-3-phenylurea (DE-A 27 32 257);

penthiopyrad, (RS)—N-[2-(1,3-dimethylbutyl)-3-thienyl]-1-methyl-3-(trifluoromethyl)-1H-pyrazole-4-carboxamide (JP 10/130,268);

propamocarb, isopropyl 3-(dimethylamino)propylcarbamate (DE-A 15 67 169);

phthalide (DE-A 16 43 347);

toloclofos-methyl, O-2,6-dichloro-p-tolyl O,O-dimethyl phosphorothioate (GB 14 67 561);

quintozene, pentachloronitrobenzene (DE-A 682 048);

zoxamide, (RS)-3,5-dichloro-N-(3-chloro-1-ethyl-1-methyl-2-oxopropyl)-p-toluamide [CAS RN 156052-68-5];

captafol, N-(1,1,2,2-tetrachloroethylthio)cyclohex-4-ene-1,2-dicarboximide (Phytopathology, Vol. 52, p. 754 (1962));

captan, N-(trichloromethylthio)cyclohex-4-ene-1,2-dicarboximide (U.S. Pat. No. 2,553,770);

dichlofluanid, N-dichlorofluoromethylthio-N',N'-dimethyl-N-phenylsulfamide (DE-A 11 93 498);

folpet, N-(trichloromethylthio)phthalimide (U.S. Pat. No. 2,553,770);

tolylfluanid, N-dichlorofluoromethylthio-N',N'-dimethyl-N-p-tolylsulfamide (DE-A 11 93 498);

dimethomorph, 3-(4-chlorophenyl)-3-(3,4-dimethoxyphenyl)-1-morpholin-4-yl-propenone (EP-A 120 321);

flumetover, 2-(3,4-dimethoxyphenyl)-N-ethyl-α,α,α-trifluoro-N-methyl-p-toluamide [AGROW no. 243, 22 (1995)];

flumorph, 3-(4-fluorophenyl)-3-(3,4-dimethoxyphenyl)-1-morpholin-4-ylpropenone (EP-A 860 438);
N-(4'-bromobiphenyl-2-yl)-4-difluoromethyl-2-methylthiazole-5-carboxamide,
N-(4'-trifluoromethylbiphenyl-2-yl)-4-difluoromethyl-2-methylthiazole-5-carboxamide, N-(4'-chloro-3'-7-fluorobiphenyl-2-yl)-4-difluoromethyl-2-methylthiazole-5-carboxamide (WO 03/66610);
N-(3',4'-dichloro-4-fluorobiphenyl-2-yl)-3-difluoromethyl-1-methylpyrazole-4-carboxamide and N-(3',4'-dichloro-5-fluorobiphenyl-2-yl)-3-difluoromethyl-1-methylpyrazole-4-carboxamide (WO 03/70705);
N-(2-cyanophenyl)-3,4-dichloroisothiazole-5-carboxamide (WO 99/24413);
N-(2-(4-[3-(4-chlorophenyl)prop-2-ynyloxy]-3-methoxyphenyl)ethyl)-2-methane-sulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide (WO 04/49804);
3-[5-(4-chlorophenyl)-2,3-dimethylisoxazolidin-3-yl]pyridine (EP-A 10 35 122);
2-butoxy-6-iodo-3-propylchromen-4-one (WO 03/14103);
N,N-dimethyl-3-(3-bromo-6-fluoro-2-methylindole-1-sulfonyl)-[1,2,4]triazole-1-sulfon-amide (EP-A 10 31 571);
methyl (2-chloro-5-[1-(3-methylbenzyloxyimino)ethyl]benzyl)carbamate,
methyl (2-chloro-5-[1-(6-methylpyridin-2-ylmethoxyimino)ethyl]benzyl)carbamate (EP-A 12 01 648);
methyl 3-(4-chlorophenyl)-3-(2-isopropoxycarbonylamino-3-methylbutyrylamino)-propionate (EP-A 10 28 125);
azoxystrobin, methyl 2-{2-[6-(2-cyano-1-vinylpenta-1,3-dienyloxy)pyrimidin-4-yloxy]phenyl}-3-methoxyacrylate (EP-A 382 375),
dimoxystrobin, (E)-2-(methoxyimino)-N-methyl-2-[α-(2,5-xylyloxy)-o-tolyl]acetamide (EP-A 477 631);
fluoxastrobin, (E)-{2-[6-(2-chlorophenoxy)-5-fluoropyrimidin-4-yloxy]phenyl}(5,6-dihydro-1,4,2-dioxazin-3-yl)methanone O-methyloxime (WO 97/27189);
kresoxim-methyl, methyl (E)-methoxyimino[α-(o-tolyloxy)-o-tolyl]acetate (EP-A 253 213);
metominostrobin, (E)-2-(methoxyimino)-N-methyl-2-(2-phenoxyphenyl)acetamide (EP-A 398 692);
orysastrobin, (2E)-2-(methoxyimino)-2-{2-[(3E,5E,6E)-5-(methoxyimino)-4,6-dimethyl-2,8-dioxa-3,7-diazanona-3,6-dien-1-yl]phenyl}-N-methylacetamide (WO 97/15552);
picoxystrobin, methyl 3-methoxy-2-[2-(6-trifluoromethylpyridin-2-yloxymethyl)phenyl]-acrylate (EP-A 278 595);
pyraclostrobin, methyl N-{2-[1-(4-chlorophenyl)-1H-pyrazol-3-yloxymethyl]phenyl}(N-methoxy)carbamate (WO 96/01256);
trifloxystrobin, methyl (E)-methoxyimino-{(E)-α-[1-(α,α,α-trifluoro-m-tolyl)ethylidene-aminooxy]-o-tolyl}acetate (EP-A 460 575);
methyl 2-[ortho-(2,5-dimethylphenyloxymethylene)phenyl]-3-methoxyacrylate (EP-A 226 917);
5-chloro-7-(4-methylpiperidin-1-yl)-6-(2,4,6-trifluorophenyl)-[1,2,4]triazolo[1,5-a]pyrimidine (WO 98/46608);
3,4-dichloro-N-(2-cyanophenyl)isothiazole-5-carboxamide (WO 99/24413), compounds of the formula III (WO 04/049804);
N-(2-(4-[3-(4-chlorophenyl)prop-2-ynyloxy]-3-methoxyphenyl)ethyl)-2-methane-sulfonylamino-3-methylbutyramide and N-(2-(4-[3-(4-chlorophenyl)prop-2-ynyloxy]-3-methoxyphenyl)ethyl)-2-ethanesulfonylamino-3-methylbutyramide (WO 03/66609);
2-butoxy-6-iodo-3-propylchromen-4-one (WO 03/14103);
N,N-dimethyl-3-(3-bromo-6-fluoro-2-methylindole-1-sulfonyl)-[1,2,4]triazole-1-sulfonamide (WO 03/053145);
methyl 3-(4-chlorophenyl)-3-(2-isopropoxycarbonylamino-3-methylbutyrylamino)-propanoate (EP-A 1028125).

It is an object of the present invention, with a view to reducing the application rates and broadening the activity spectrum of the active compounds I and II, to provide mixtures which, at a reduced total amount of active compounds applied, have improved activity against harmful fungi, in particular for certain indications.

We have accordingly found that this object is achieved by the mixtures, defined at the outset, of the active compounds I and II. Moreover, we have found that simultaneous, that is joint or separate, application of at least one compound I and at least one of the active compounds II or successive application of the compound(s) I and at least one of the active compounds II allows better control of harmful fungi than is possible with the individual compounds alone (synergistic mixtures).

The compounds I can be used as synergists for a large number of different fungicidal active compounds. By simultaneous, that is joint or separate, application of compound(s) I with at least one active compound II, the fungicidal activity is increased in a superadditive manner.

The compounds I can be present in different crystal modifications, which may differ in biological activity.

In the formula I, halogen is fluorine, chlorine, bromine or iodine, preferably fluorine or chlorine;
$C_1$-$C_4$-alkyl is methyl, ethyl, n-propyl, 1-methylethyl, n-butyl, 1-methylpropyl, 2-methylpropyl or 1,1-dimethylethyl, preferably methyl or ethyl;
$C_1$-$C_4$-haloalkyl is a partially or fully halogenated $C_1$-$C_4$-alkyl radical, where the halogen atom(s) is/are in particular fluorine, chlorine and/or bromine, i.e., for example, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, heptafluoropropyl or nonafluorobutyl, in particular halomethyl, with particular preference $CH_2$—Cl, $CH(Cl)_2$, $CH_2$—F, $CHF_2$, $CF_3$, $CHFCl$, $CF_2Cl$ or $CF(Cl)_2$, in particular $CHF_2$ or $CF_3$;
$C_1$-$C_4$-alkoxy is $OCH_3$, $OC_2H_5$, $OCH_2$—$C_2H_5$, $OCH(CH_3)_2$, n-butoxy, $OCH(CH_3)$—$C_2H_5$, $OCH_2$—$CH(CH_3)_2$ or $OC(CH_3)_3$, preferably $OCH_3$ or $OC_2H_5$;
$C_1$-$C_4$-haloalkoxy is a partially or fully halogenated $C_1$-$C_4$-alkoxy radical, where the halogen atom(s) is/are in particular fluorine, chlorine and/or bromine, i.e., for example, chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, heptafluoropropoxy or nonafluorobutoxy, in particular halomethoxy, particularly preferably $OCH_2$—Cl, $OCH(Cl)_2$, $OCH_2$—F, $OCH(F)_2$, $OCF_3$, $OCHFCl$, $OCF_2Cl$ or $OCF(Cl)_2$;
$C_1$-$C_4$-alkylthio is $SCH_3$, $SC_2H_5$, $SCH_2$—$C_2H_5$, $SCH(CH_3)_2$, n-butylthio, $SCH(CH_3)$—$C_2H_5$, $SCH_2$—$CH(CH_3)_2$ or $SC(CH_3)_3$, preferably $SCH_3$ or $SC_2H_5$.

Preferred 1-methylpyrazol-4-ylcarboxanilides I are, on the one hand, those in which X is oxygen.

On the other hand, preferred compounds I are those in which X is sulfur.

For the mixtures according to the invention, preference is given to compounds of the formula I in which $R^1$ is methyl or halomethyl, in particular $CH_3$, $CHF_2$, $CH_2F$, $CF_3$, $CHFCl$ or $CF_2Cl$.

Preference is furthermore given to compounds I in which $R^2$ is hydrogen, fluorine or chlorine, in particular hydrogen.

Preference is furthermore given to those compounds I in which $R^3$ is halogen, $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio, preferably halogen, methyl, halomethyl, methoxy, halomethoxy or methylthio, in particular F, Cl, $CH_3$, $CF_3$, $OCH_3$, $OCHF_2$, $OCF_3$ or $SCH_3$, particularly preferably fluorine.

Moreover, preference is given to those compounds I in which $R^4$ is halogen, in particular fluorine.

Preference is furthermore given to those compounds I in which $R^5$ is halogen, in particular fluorine.

Particular preference is given to the compounds I listed in Table 1 below in which X is oxygen.

TABLE 1

| Compound | $R^1$ | $R^2$ | $R^3$ | $R^4$ | $R^5$ | M.p. [° C.] |
|---|---|---|---|---|---|---|
| No. 1 | $CH_3$ | H | 2-F | 3-F | 4-F | |
| No. 2 | $CH_3$ | H | 2-F | 3-F | 5-F | |
| No. 3 | $CH_3$ | H | 2-F | 4-F | 5-F | |
| No. 4 | $CH_3$ | H | 2-F | 4-F | 6-F | |
| No. 5 | $CH_3$ | H | 3-F | 4-F | 5-F | |
| No. 6 | $CH_3$ | H | 3-F | 5-F | 6-F | |
| No. 7 | $CH_2F$ | H | 2-F | 3-F | 4-F | |
| No. 8 | $CH_2F$ | H | 2-F | 3-F | 5-F | |
| No. 9 | $CH_2F$ | H | 2-F | 4-F | 5-F | |
| No. 10 | $CH_2F$ | H | 2-F | 4-F | 6-F | |
| No. 11 | $CH_2F$ | H | 3-F | 4-F | 5-F | |
| No. 12 | $CH_2F$ | H | 3-F | 5-F | 6-F | |
| No. 13 | $CHF_2$ | H | 2-F | 3-F | 4-F | |
| No. 14 | $CHF_2$ | H | 2-F | 3-F | 5-F | |
| No. 15 | $CHF_2$ | H | 2-F | 4-F | 5-F | |
| No. 16 | $CHF_2$ | H | 2-F | 4-F | 6-F | |
| No. 17 | $CHF_2$ | H | 3-F | 4-F | 5-F | |
| No. 18 | $CHF_2$ | H | 3-F | 5-F | 6-F | |
| No. 19 | $CF_3$ | H | 2-F | 3-F | 4-F | |
| No. 20 | $CF_3$ | H | 2-F | 3-F | 5-F | |
| No. 21 | $CF_3$ | H | 2-F | 4-F | 5-F | |
| No. 22 | $CF_3$ | H | 2-F | 4-F | 6-F | |
| No. 23 | $CF_3$ | H | 3-F | 4-F | 5-F | |
| No. 24 | $CF_3$ | H | 3-F | 5-F | 6-F | |
| No. 25 | CHFCl | H | 2-F | 3-F | 4-F | |
| No. 26 | CHFCl | H | 2-F | 3-F | 5-F | |
| No. 27 | CHFCl | H | 2-F | 4-F | 5-F | |
| No. 28 | CHFCl | H | 2-F | 4-F | 6-F | |
| No. 29 | CHFCl | H | 3-F | 4-F | 5-F | |
| No. 30 | CHFCl | H | 3-F | 5-F | 6-F | |
| No. 31 | $CF_2Cl$ | H | 2-F | 3-F | 4-F | |
| No. 32 | $CF_2Cl$ | H | 2-F | 3-F | 5-F | |
| No. 33 | $CF_2Cl$ | H | 2-F | 4-F | 5-F | |
| No. 34 | $CF_2Cl$ | H | 2-F | 4-F | 6-F | |
| No. 35 | $CF_2Cl$ | H | 3-F | 4-F | 5-F | |
| No. 36 | $CF_2Cl$ | H | 3-F | 5-F | 6-F | |
| No. 37 | $CH_3$ | F | 2-F | 3-F | 4-F | |
| No. 38 | $CH_3$ | F | 2-F | 3-F | 5-F | |
| No. 39 | $CH_3$ | F | 2-F | 4-F | 5-F | |
| No. 40 | $CH_3$ | F | 2-F | 4-F | 6-F | |
| No. 41 | $CH_3$ | F | 3-F | 4-F | 5-F | |
| No. 42 | $CH_3$ | F | 3-F | 5-F | 6-F | |
| No. 43 | $CH_2F$ | F | 2-F | 3-F | 4-F | |
| No. 44 | $CH_2F$ | F | 2-F | 3-F | 5-F | |
| No. 45 | $CH_2F$ | F | 2-F | 4-F | 5-F | |
| No. 46 | $CH_2F$ | F | 2-F | 4-F | 6-F | |
| No. 47 | $CH_2F$ | F | 3-F | 4-F | 5-F | |
| No. 48 | $CH_2F$ | F | 3-F | 5-F | 6-F | |
| No. 49 | $CHF_2$ | F | 2-F | 3-F | 4-F | |
| No. 50 | $CHF_2$ | F | 2-F | 3-F | 5-F | |
| No. 51 | $CHF_2$ | F | 2-F | 4-F | 5-F | |
| No. 52 | $CHF_2$ | F | 2-F | 4-F | 6-F | |
| No. 53 | $CHF_2$ | F | 3-F | 4-F | 5-F | |
| No. 54 | $CHF_2$ | F | 3-F | 5-F | 6-F | |
| No. 55 | $CF_3$ | F | 2-F | 3-F | 4-F | |
| No. 56 | $CF_3$ | F | 2-F | 3-F | 5-F | |
| No. 57 | $CF_3$ | F | 2-F | 4-F | 5-F | |
| No. 58 | $CF_3$ | F | 2-F | 4-F | 6-F | |
| No. 59 | $CF_3$ | F | 3-F | 4-F | 5-F | |
| No. 60 | $CF_3$ | F | 3-F | 5-F | 6-F | |
| No. 61 | CHFCl | F | 2-F | 3-F | 4-F | |
| No. 62 | CHFCl | F | 2-F | 3-F | 5-F | |
| No. 63 | CHFCl | F | 2-F | 4-F | 5-F | |
| No. 64 | CHFCl | F | 2-F | 4-F | 6-F | |
| No. 65 | CHFCl | F | 3-F | 4-F | 5-F | |
| No. 66 | CHFCl | F | 3-F | 5-F | 6-F | |
| No. 67 | $CF_2Cl$ | F | 2-F | 3-F | 4-F | |
| No. 68 | $CF_2Cl$ | F | 2-F | 3-F | 5-F | |
| No. 69 | $CF_2Cl$ | F | 2-F | 4-F | 5-F | |
| No. 70 | $CF_2Cl$ | F | 2-F | 4-F | 6-F | |
| No. 71 | $CF_2Cl$ | F | 3-F | 4-F | 5-F | |
| No. 72 | $CF_2Cl$ | F | 3-F | 5-F | 6-F | |
| No. 73 | $CH_3$ | Cl | 2-F | 3-F | 4-F | |
| No. 74 | $CH_3$ | Cl | 2-F | 3-F | 5-F | |
| No. 75 | $CH_3$ | Cl | 2-F | 4-F | 5-F | |
| No. 76 | $CH_3$ | Cl | 2-F | 4-F | 6-F | |
| No. 77 | $CH_3$ | Cl | 3-F | 4-F | 5-F | |
| No. 78 | $CH_3$ | Cl | 3-F | 5-F | 6-F | |
| No. 79 | $CH_2F$ | Cl | 2-F | 3-F | 4-F | |
| No. 80 | $CH_2F$ | Cl | 2-F | 3-F | 5-F | |
| No. 81 | $CH_2F$ | Cl | 2-F | 4-F | 5-F | |
| No. 82 | $CH_2F$ | Cl | 2-F | 4-F | 6-F | |
| No. 83 | $CH_2F$ | Cl | 3-F | 4-F | 5-F | |
| No. 84 | $CH_2F$ | Cl | 3-F | 5-F | 6-F | |
| No. 85 | $CHF_2$ | Cl | 2-F | 3-F | 4-F | |
| No. 86 | $CHF_2$ | Cl | 2-F | 3-F | 5-F | |
| No. 87 | $CHF_2$ | Cl | 2-F | 4-F | 5-F | |
| No. 88 | $CHF_2$ | Cl | 2-F | 4-F | 6-F | |
| No. 89 | $CHF_2$ | Cl | 3-F | 4-F | 5-F | |
| No. 90 | $CHF_2$ | Cl | 3-F | 5-F | 6-F | |
| No. 91 | $CF_3$ | Cl | 2-F | 3-F | 4-F | |
| No. 92 | $CF_3$ | Cl | 2-F | 3-F | 5-F | |
| No. 93 | $CF_3$ | Cl | 2-F | 4-F | 5-F | |
| No. 94 | $CF_3$ | Cl | 2-F | 4-F | 6-F | |
| No. 95 | $CF_3$ | Cl | 3-F | 4-F | 5-F | |
| No. 96 | $CF_3$ | Cl | 3-F | 5-F | 6-F | |
| No. 97 | CHFCl | Cl | 2-F | 3-F | 4-F | |
| No. 98 | CHFCl | Cl | 2-F | 3-F | 5-F | |
| No. 99 | CHFCl | Cl | 2-F | 4-F | 5-F | |
| No. 100 | CHFCl | Cl | 2-F | 4-F | 6-F | |
| No. 101 | CHFCl | Cl | 3-F | 4-F | 5-F | |
| No. 102 | CHFCl | Cl | 3-F | 5-F | 6-F | |
| No. 103 | $CF_2Cl$ | Cl | 2-F | 3-F | 4-F | |
| No. 104 | $CF_2Cl$ | Cl | 2-F | 3-F | 5-F | |
| No. 105 | $CF_2Cl$ | Cl | 2-F | 4-F | 5-F | |
| No. 106 | $CF_2Cl$ | Cl | 2-F | 4-F | 6-F | |
| No. 107 | $CF_2Cl$ | Cl | 3-F | 4-F | 5-F | |
| No. 108 | $CF_2Cl$ | Cl | 3-F | 5-F | 6-F | |

Particular preference is furthermore given to 1-methylpyrazol-4-ylcarboxanilides of the formula Ia (I where X=O, $R^1$=$CF_3$ and $R^2$=H)

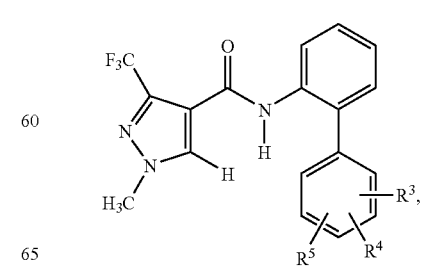

Ia in particular to the compounds Ia.1 to Ia.1009 listed in Table 2 below:

TABLE 2

| Compound No. | $R^1$ | $R^2$ | $R^3$ | $R^4$ | $R^5$ | M.p. [°C.] |
|---|---|---|---|---|---|---|
| Ia.1 | $CF_3$ | H | 2-fluoro | 3-fluoro | 4-fluoro | 123-125 |
| Ia.2 | $CF_3$ | H | 2-fluoro | 3-chloro | 4-fluoro | |
| Ia.3 | $CF_3$ | H | 2-fluoro | 3-CN | 4-fluoro | |
| Ia.4 | $CF_3$ | H | 2-fluoro | 3-methyl | 4-fluoro | |
| Ia.5 | $CF_3$ | H | 2-fluoro | 3-$CF_3$ | 4-fluoro | |
| Ia.6 | $CF_3$ | H | 2-fluoro | 3-$OCH_3$ | 4-fluoro | |
| Ia.7 | $CF_3$ | H | 2-fluoro | 3-$OCF_3$ | 4-fluoro | |
| Ia.8 | $CF_3$ | H | 2-chloro | 3-fluoro | 4-fluoro | |
| Ia.9 | $CF_3$ | H | 2-chloro | 3-chloro | 4-fluoro | |
| Ia.10 | $CF_3$ | H | 2-chloro | 3-CN | 4-fluoro | |
| Ia.11 | $CF_3$ | H | 2-chloro | 3-methyl | 4-fluoro | |
| Ia.12 | $CF_3$ | H | 2-chloro | 3-$CF_3$ | 4-fluoro | |
| Ia.13 | $CF_3$ | H | 2-chloro | 3-$OCH_3$ | 4-fluoro | |
| Ia.14 | $CF_3$ | H | 2-chloro | 3-$OCF_3$ | 4-fluoro | |
| Ia.15 | $CF_3$ | H | 2-CN | 3-fluoro | 4-fluoro | |
| Ia.16 | $CF_3$ | H | 2-CN | 3-chloro | 4-fluoro | |
| Ia.17 | $CF_3$ | H | 2-CN | 3-CN | 4-fluoro | |
| Ia.18 | $CF_3$ | H | 2-CN | 3-methyl | 4-fluoro | |
| Ia.19 | $CF_3$ | H | 2-CN | 3-$CF_3$ | 4-fluoro | |
| Ia.20 | $CF_3$ | H | 2-CN | 3-$OCH_3$ | 4-fluoro | |
| Ia.21 | $CF_3$ | H | 2-CN | 3-$OCF_3$ | 4-fluoro | |
| Ia.22 | $CF_3$ | H | 2-methyl | 3-fluoro | 4-fluoro | |
| Ia.23 | $CF_3$ | H | 2-methyl | 3-chloro | 4-fluoro | |
| Ia.24 | $CF_3$ | H | 2-methyl | 3-CN | 4-fluoro | |
| Ia.25 | $CF_3$ | H | 2-methyl | 3-methyl | 4-fluoro | |
| Ia.26 | $CF_3$ | H | 2-methyl | 3-$CF_3$ | 4-fluoro | |
| Ia.27 | $CF_3$ | H | 2-methyl | 3-$OCH_3$ | 4-fluoro | |
| Ia.28 | $CF_3$ | H | 2-methyl | 3-$OCF_3$ | 4-fluoro | |
| Ia.29 | $CF_3$ | H | 2-$CF_3$ | 3-fluoro | 4-fluoro | |
| Ia.30 | $CF_3$ | H | 2-$CF_3$ | 3-chloro | 4-fluoro | |
| Ia.31 | $CF_3$ | H | 2-$CF_3$ | 3-CN | 4-fluoro | |
| Ia.32 | $CF_3$ | H | 2-$CF_3$ | 3-methyl | 4-fluoro | |
| Ia.33 | $CF_3$ | H | 2-$CF_3$ | 3-$CF_3$ | 4-fluoro | |
| Ia.34 | $CF_3$ | H | 2-$CF_3$ | 3-$OCH_3$ | 4-fluoro | |
| Ia.35 | $CF_3$ | H | 2-$CF_3$ | 3-$OCF_3$ | 4-fluoro | |
| Ia.36 | $CF_3$ | H | 2-$OCH_3$ | 3-fluoro | 4-fluoro | |
| Ia.37 | $CF_3$ | H | 2-$OCH_3$ | 3-chloro | 4-fluoro | |
| Ia.38 | $CF_3$ | H | 2-$OCH_3$ | 3-CN | 4-fluoro | |
| Ia.39 | $CF_3$ | H | 2-$OCH_3$ | 3-methyl | 4-fluoro | |
| Ia.40 | $CF_3$ | H | 2-$OCH_3$ | 3-$CF_3$ | 4-fluoro | |
| Ia.41 | $CF_3$ | H | 2-$OCH_3$ | 3-$OCH_3$ | 4-fluoro | |
| Ia.42 | $CF_3$ | H | 2-$OCH_3$ | 3-$OCF_3$ | 4-fluoro | |
| Ia.43 | $CF_3$ | H | 2-$OCF_3$ | 3-fluoro | 4-fluoro | |
| Ia.44 | $CF_3$ | H | 2-$OCF_3$ | 3-chloro | 4-fluoro | |
| Ia.45 | $CF_3$ | H | 2-$OCF_3$ | 3-CN | 4-fluoro | |
| Ia.46 | $CF_3$ | H | 2-$OCF_3$ | 3-methyl | 4-fluoro | |
| Ia.47 | $CF_3$ | H | 2-$OCF_3$ | 3-$CF_3$ | 4-fluoro | |
| Ia.48 | $CF_3$ | H | 2-$OCF_3$ | 3-$OCH_3$ | 4-fluoro | |
| Ia.49 | $CF_3$ | H | 2-$OCF_3$ | 3-$OCF_3$ | 4-fluoro | |
| Ia.50 | $CF_3$ | H | 2-fluoro | 3-fluoro | 4-chloro | |
| Ia.51 | $CF_3$ | H | 2-fluoro | 3-chloro | 4-chloro | |
| Ia.52 | $CF_3$ | H | 2-fluoro | 3-CN | 4-chloro | |
| Ia.53 | $CF_3$ | H | 2-fluoro | 3-methyl | 4-chloro | |
| Ia.54 | $CF_3$ | H | 2-fluoro | 3-$CF_3$ | 4-chloro | |
| Ia.55 | $CF_3$ | H | 2-fluoro | 3-$OCH_3$ | 4-chloro | |
| Ia.56 | $CF_3$ | H | 2-fluoro | 3-$OCF_3$ | 4-chloro | |
| Ia.57 | $CF_3$ | H | 2-chloro | 3-fluoro | 4-chloro | |
| Ia.58 | $CF_3$ | H | 2-chloro | 3-chloro | 4-chloro | |
| Ia.59 | $CF_3$ | H | 2-chloro | 3-CN | 4-chloro | |
| Ia.60 | $CF_3$ | H | 2-chloro | 3-methyl | 4-chloro | |
| Ia.61 | $CF_3$ | H | 2-chloro | 3-$CF_3$ | 4-chloro | |
| Ia.62 | $CF_3$ | H | 2-chloro | 3-$OCH_3$ | 4-chloro | |
| Ia.63 | $CF_3$ | H | 2-chloro | 3-$OCF_3$ | 4-chloro | |
| Ia.64 | $CF_3$ | H | 2-CN | 3-fluoro | 4-chloro | |
| Ia.65 | $CF_3$ | H | 2-CN | 3-chloro | 4-chloro | |
| Ia.66 | $CF_3$ | H | 2-CN | 3-CN | 4-chloro | |
| Ia.67 | $CF_3$ | H | 2-CN | 3-methyl | 4-chloro | |
| Ia.68 | $CF_3$ | H | 2-CN | 3-$CF_3$ | 4-chloro | |
| Ia.69 | $CF_3$ | H | 2-CN | 3-$OCH_3$ | 4-chloro | |
| Ia.70 | $CF_3$ | H | 2-CN | 3-$OCF_3$ | 4-chloro | |
| Ia.71 | $CF_3$ | H | 2-methyl | 3-fluoro | 4-chloro | |
| Ia.72 | $CF_3$ | H | 2-methyl | 3-chloro | 4-chloro | |
| Ia.73 | $CF_3$ | H | 2-methyl | 3-CN | 4-chloro | |
| Ia.74 | $CF_3$ | H | 2-methyl | 3-methyl | 4-chloro | |
| Ia.75 | $CF_3$ | H | 2-methyl | 3-$CF_3$ | 4-chloro | |
| Ia.76 | $CF_3$ | H | 2-methyl | 3-$OCH_3$ | 4-chloro | |
| Ia.77 | $CF_3$ | H | 2-methyl | 3-$OCF_3$ | 4-chloro | |
| Ia.78 | $CF_3$ | H | 2-$CF_3$ | 3-fluoro | 4-chloro | |
| Ia.79 | $CF_3$ | H | 2-$CF_3$ | 3-chloro | 4-chloro | |
| Ia.80 | $CF_3$ | H | 2-$CF_3$ | 3-CN | 4-chloro | |
| Ia.81 | $CF_3$ | H | 2-$CF_3$ | 3-methyl | 4-chloro | |
| Ia.82 | $CF_3$ | H | 2-$CF_3$ | 3-$CF_3$ | 4-chloro | |
| Ia.83 | $CF_3$ | H | 2-$CF_3$ | 3-$OCH_3$ | 4-chloro | |
| Ia.84 | $CF_3$ | H | 2-$CF_3$ | 3-$OCF_3$ | 4-chloro | |
| Ia.85 | $CF_3$ | H | 2-$OCH_3$ | 3-fluoro | 4-chloro | |
| Ia.86 | $CF_3$ | H | 2-$OCH_3$ | 3-chloro | 4-chloro | |
| Ia.87 | $CF_3$ | H | 2-$OCH_3$ | 3-CN | 4-chloro | |
| Ia.88 | $CF_3$ | H | 2-$OCH_3$ | 3-methyl | 4-chloro | |
| Ia.89 | $CF_3$ | H | 2-$OCH_3$ | 3-$CF_3$ | 4-chloro | |
| Ia.90 | $CF_3$ | H | 2-$OCH_3$ | 3-$OCH_3$ | 4-chloro | |
| Ia.91 | $CF_3$ | H | 2-$OCH_3$ | 3-$OCF_3$ | 4-chloro | |
| Ia.92 | $CF_3$ | H | 2-$OCF_3$ | 3-fluoro | 4-chloro | |
| Ia.93 | $CF_3$ | H | 2-$OCF_3$ | 3-chloro | 4-chloro | |
| Ia.94 | $CF_3$ | H | 2-$OCF_3$ | 3-CN | 4-chloro | |
| Ia.95 | $CF_3$ | H | 2-$OCF_3$ | 3-methyl | 4-chloro | |
| Ia.96 | $CF_3$ | H | 2-$OCF_3$ | 3-$CF_3$ | 4-chloro | |
| Ia.97 | $CF_3$ | H | 2-$OCF_3$ | 3-$OCH_3$ | 4-chloro | |
| Ia.98 | $CF_3$ | H | 2-$OCF_3$ | 3-$OCF_3$ | 4-chloro | |
| Ia.99 | $CF_3$ | H | 2-fluoro | 3-fluoro | 4-CN | |
| Ia.100 | $CF_3$ | H | 2-fluoro | 3-chloro | 4-CN | |
| Ia.101 | $CF_3$ | H | 2-fluoro | 3-CN | 4-CN | |
| Ia.102 | $CF_3$ | H | 2-fluoro | 3-methyl | 4-CN | |
| Ia.103 | $CF_3$ | H | 2-fluoro | 3-$CF_3$ | 4-CN | |
| Ia.104 | $CF_3$ | H | 2-fluoro | 3-$OCH_3$ | 4-CN | |
| Ia.105 | $CF_3$ | H | 2-fluoro | 3-$OCF_3$ | 4-CN | |
| Ia.106 | $CF_3$ | H | 2-chloro | 3-fluoro | 4-CN | |
| Ia.107 | $CF_3$ | H | 2-chloro | 3-chloro | 4-CN | |
| Ia.108 | $CF_3$ | H | 2-chloro | 3-CN | 4-CN | |
| Ia.109 | $CF_3$ | H | 2-chloro | 3-methyl | 4-CN | |
| Ia.110 | $CF_3$ | H | 2-chloro | 3-$CF_3$ | 4-CN | |
| Ia.111 | $CF_3$ | H | 2-chloro | 3-$OCH_3$ | 4-CN | |
| Ia.112 | $CF_3$ | H | 2-chloro | 3-$OCF_3$ | 4-CN | |
| Ia.113 | $CF_3$ | H | 2-CN | 3-fluoro | 4-CN | |
| Ia.114 | $CF_3$ | H | 2-CN | 3-chloro | 4-CN | |
| Ia.115 | $CF_3$ | H | 2-CN | 3-CN | 4-CN | |
| Ia.116 | $CF_3$ | H | 2-CN | 3-methyl | 4-CN | |
| Ia.117 | $CF_3$ | H | 2-CN | 3-$CF_3$ | 4-CN | |
| Ia.118 | $CF_3$ | H | 2-CN | 3-$OCH_3$ | 4-CN | |
| Ia.119 | $CF_3$ | H | 2-CN | 3-$OCF_3$ | 4-CN | |
| Ia.120 | $CF_3$ | H | 2-methyl | 3-fluoro | 4-CN | |
| Ia.121 | $CF_3$ | H | 2-methyl | 3-chloro | 4-CN | |
| Ia.122 | $CF_3$ | H | 2-methyl | 3-CN | 4-CN | |
| Ia.123 | $CF_3$ | H | 2-methyl | 3-methyl | 4-CN | |
| Ia.124 | $CF_3$ | H | 2-methyl | 3-$CF_3$ | 4-CN | |
| Ia.125 | $CF_3$ | H | 2-methyl | 3-$OCH_3$ | 4-CN | |
| Ia.126 | $CF_3$ | H | 2-methyl | 3-$OCF_3$ | 4-CN | |
| Ia.127 | $CF_3$ | H | 2-$CF_3$ | 3-fluoro | 4-CN | |
| Ia.128 | $CF_3$ | H | 2-$CF_3$ | 3-chloro | 4-CN | |
| Ia.129 | $CF_3$ | H | 2-$CF_3$ | 3-CN | 4-CN | |
| Ia.130 | $CF_3$ | H | 2-$CF_3$ | 3-methyl | 4-CN | |
| Ia.131 | $CF_3$ | H | 2-$CF_3$ | 3-$CF_3$ | 4-CN | |
| Ia.132 | $CF_3$ | H | 2-$CF_3$ | 3-$OCH_3$ | 4-CN | |
| Ia.133 | $CF_3$ | H | 2-$CF_3$ | 3-$OCF_3$ | 4-CN | |
| Ia.134 | $CF_3$ | H | 2-$OCH_3$ | 3-fluoro | 4-CN | |
| Ia.135 | $CF_3$ | H | 2-$OCH_3$ | 3-chloro | 4-CN | |
| Ia.136 | $CF_3$ | H | 2-$OCH_3$ | 3-CN | 4-CN | |
| Ia.137 | $CF_3$ | H | 2-$OCH_3$ | 3-methyl | 4-CN | |
| Ia.138 | $CF_3$ | H | 2-$OCH_3$ | 3-$CF_3$ | 4-CN | |
| Ia.139 | $CF_3$ | H | 2-$OCH_3$ | 3-$OCH_3$ | 4-CN | |
| Ia.140 | $CF_3$ | H | 2-$OCH_3$ | 3-$OCF_3$ | 4-CN | |
| Ia.141 | $CF_3$ | H | 2-$OCF_3$ | 3-fluoro | 4-CN | |
| Ia.142 | $CF_3$ | H | 2-$OCF_3$ | 3-chloro | 4-CN | |
| Ia.143 | $CF_3$ | H | 2-$OCF_3$ | 3-CN | 4-CN | |
| Ia.144 | $CF_3$ | H | 2-$OCF_3$ | 3-methyl | 4-CN | |
| Ia.145 | $CF_3$ | H | 2-$OCF_3$ | 3-$CF_3$ | 4-CN | |
| Ia.146 | $CF_3$ | H | 2-$OCF_3$ | 3-$OCH_3$ | 4-CN | |
| Ia.147 | $CF_3$ | H | 2-$OCF_3$ | 3-$OCF_3$ | 4-CN | |
| Ia.148 | $CF_3$ | H | 2-fluoro | 3-fluoro | 4-methyl | |
| Ia.149 | $CF_3$ | H | 2-fluoro | 3-chloro | 4-methyl | |
| Ia.150 | $CF_3$ | H | 2-fluoro | 3-CN | 4-methyl | |

TABLE 2-continued

| Compound No. | R¹ | R² | R³ | R⁴ | R⁵ | M.p. [° C.] |
|---|---|---|---|---|---|---|
| Ia.151 | CF₃ | H | 2-fluoro | 3-methyl | 4-methyl | |
| Ia.152 | CF₃ | H | 2-fluoro | 3-CF₃ | 4-methyl | |
| Ia.153 | CF₃ | H | 2-fluoro | 3-OCH₃ | 4-methyl | |
| Ia.154 | CF₃ | H | 2-fluoro | 3-OCF₃ | 4-methyl | |
| Ia.155 | CF₃ | H | 2-chloro | 3-fluoro | 4-methyl | |
| Ia.156 | CF₃ | H | 2-chloro | 3-chloro | 4-methyl | |
| Ia.157 | CF₃ | H | 2-chloro | 3-CN | 4-methyl | |
| Ia.158 | CF₃ | H | 2-chloro | 3-methyl | 4-methyl | |
| Ia.159 | CF₃ | H | 2-chloro | 3-CF₃ | 4-methyl | |
| Ia.160 | CF₃ | H | 2-chloro | 3-OCH₃ | 4-methyl | |
| Ia.161 | CF₃ | H | 2-chloro | 3-OCF₃ | 4-methyl | |
| Ia.162 | CF₃ | H | 2-CN | 3-fluoro | 4-methyl | |
| Ia.163 | CF₃ | H | 2-CN | 3-chloro | 4-methyl | |
| Ia.164 | CF₃ | H | 2-CN | 3-CN | 4-methyl | |
| Ia.165 | CF₃ | H | 2-CN | 3-methyl | 4-methyl | |
| Ia.166 | CF₃ | H | 2-CN | 3-CF₃ | 4-methyl | |
| Ia.167 | CF₃ | H | 2-CN | 3-OCH₃ | 4-methyl | |
| Ia.168 | CF₃ | H | 2-CN | 3-OCF₃ | 4-methyl | |
| Ia.169 | CF₃ | H | 2-methyl | 3-fluoro | 4-methyl | |
| Ia.170 | CF₃ | H | 2-methyl | 3-chloro | 4-methyl | |
| Ia.171 | CF₃ | H | 2-methyl | 3-CN | 4-methyl | |
| Ia.172 | CF₃ | H | 2-methyl | 3-methyl | 4-methyl | |
| Ia.173 | CF₃ | H | 2-methyl | 3-CF₃ | 4-methyl | |
| Ia.174 | CF₃ | H | 2-methyl | 3-OCH₃ | 4-methyl | |
| Ia.175 | CF₃ | H | 2-methyl | 3-OCF₃ | 4-methyl | |
| Ia.176 | CF₃ | H | 2-CF₃ | 3-fluoro | 4-methyl | |
| Ia.177 | CF₃ | H | 2-CF₃ | 3-chloro | 4-methyl | |
| Ia.178 | CF₃ | H | 2-CF₃ | 3-CN | 4-methyl | |
| Ia.179 | CF₃ | H | 2-CF₃ | 3-methyl | 4-methyl | |
| Ia.180 | CF₃ | H | 2-CF₃ | 3-CF₃ | 4-methyl | |
| Ia.181 | CF₃ | H | 2-CF₃ | 3-OCH₃ | 4-methyl | |
| Ia.182 | CF₃ | H | 2-CF₃ | 3-OCF₃ | 4-methyl | |
| Ia.183 | CF₃ | H | 2-OCH₃ | 3-fluoro | 4-methyl | |
| Ia.184 | CF₃ | H | 2-OCH₃ | 3-chloro | 4-methyl | |
| Ia.185 | CF₃ | H | 2-OCH₃ | 3-CN | 4-methyl | |
| Ia.186 | CF₃ | H | 2-OCH₃ | 3-methyl | 4-methyl | |
| Ia.187 | CF₃ | H | 2-OCH₃ | 3-CF₃ | 4-methyl | |
| Ia.188 | CF₃ | H | 2-OCH₃ | 3-OCH₃ | 4-methyl | |
| Ia.189 | CF₃ | H | 2-OCH₃ | 3-OCF₃ | 4-methyl | |
| Ia.190 | CF₃ | H | 2-OCF₃ | 3-fluoro | 4-methyl | |
| Ia.191 | CF₃ | H | 2-OCF₃ | 3-chloro | 4-methyl | |
| Ia.192 | CF₃ | H | 2-OCF₃ | 3-CN | 4-methyl | |
| Ia.193 | CF₃ | H | 2-OCF₃ | 3-methyl | 4-methyl | |
| Ia.194 | CF₃ | H | 2-OCF₃ | 3-CF₃ | 4-methyl | |
| Ia.195 | CF₃ | H | 2-OCF₃ | 3-OCH₃ | 4-methyl | |
| Ia.196 | CF₃ | H | 2-OCF₃ | 3-OCF₃ | 4-methyl | |
| Ia.197 | CF₃ | H | 2-fluoro | 3-fluoro | 4-CF3 | |
| Ia.198 | CF₃ | H | 2-fluoro | 3-chloro | 4-CF3 | |
| Ia.199 | CF₃ | H | 2-fluoro | 3-CN | 4-CF3 | |
| Ia.200 | CF₃ | H | 2-fluoro | 3-methyl | 4-CF3 | |
| Ia.201 | CF₃ | H | 2-fluoro | 3-CF₃ | 4-CF3 | |
| Ia.202 | CF₃ | H | 2-fluoro | 3-OCH₃ | 4-CF3 | |
| Ia.203 | CF₃ | H | 2-fluoro | 3-OCF₃ | 4-CF3 | |
| Ia.204 | CF₃ | H | 2-chloro | 3-fluoro | 4-CF₃ | |
| Ia.205 | CF₃ | H | 2-chloro | 3-chloro | 4-CF₃ | |
| Ia.206 | CF₃ | H | 2-chloro | 3-CN | 4-CF₃ | |
| Ia.207 | CF₃ | H | 2-chloro | 3-methyl | 4-CF₃ | |
| Ia.208 | CF₃ | H | 2-chloro | 3-CF₃ | 4-CF₃ | |
| Ia.209 | CF₃ | H | 2-chloro | 3-OCH₃ | 4-CF₃ | |
| Ia.210 | CF₃ | H | 2-chloro | 3-OCF₃ | 4-CF₃ | |
| Ia.211 | CF₃ | H | 2-CN | 3-fluoro | 4-CF₃ | |
| Ia.212 | CF₃ | H | 2-CN | 3-chloro | 4-CF₃ | |
| Ia.213 | CF₃ | H | 2-CN | 3-CN | 4-CF₃ | |
| Ia.214 | CF₃ | H | 2-CN | 3-methyl | 4-CF₃ | |
| Ia.215 | CF₃ | H | 2-CN | 3-CF₃ | 4-CF₃ | |
| Ia.216 | CF₃ | H | 2-CN | 3-OCH₃ | 4-CF₃ | |
| Ia.217 | CF₃ | H | 2-CN | 3-OCF₃ | 4-CF₃ | |
| Ia.218 | CF₃ | H | 2-methyl | 3-fluoro | 4-CF3 | |
| Ia.219 | CF₃ | H | 2-methyl | 3-chloro | 4-CF3 | |
| Ia.220 | CF₃ | H | 2-methyl | 3-CN | 4-CF3 | |
| Ia.221 | CF₃ | H | 2-methyl | 3-methyl | 4-CF3 | |
| Ia.222 | CF₃ | H | 2-methyl | 3-CF₃ | 4-CF3 | |
| Ia.223 | CF₃ | H | 2-methyl | 3-OCH₃ | 4-CF3 | |
| Ia.224 | CF₃ | H | 2-methyl | 3-OCF₃ | 4-CF3 | |
| Ia.225 | CF₃ | H | 2-CF₃ | 3-fluoro | 4-CF3 | |
| Ia.226 | CF₃ | H | 2-CF₃ | 3-chloro | 4-CF3 | |
| Ia.227 | CF₃ | H | 2-CF₃ | 3-CN | 4-CF3 | |
| Ia.228 | CF₃ | H | 2-CF₃ | 3-methyl | 4-CF3 | |
| Ia.229 | CF₃ | H | 2-CF₃ | 3-CF₃ | 4-CF3 | |
| Ia.230 | CF₃ | H | 2-CF₃ | 3-OCH₃ | 4-CF3 | |
| Ia.231 | CF₃ | H | 2-CF₃ | 3-OCF₃ | 4-CF3 | |
| Ia.232 | CF₃ | H | 2-OCH₃ | 3-fluoro | 4-CF3 | |
| Ia.233 | CF₃ | H | 2-OCH₃ | 3-chloro | 4-CF3 | |
| Ia.234 | CF₃ | H | 2-OCH₃ | 3-CN | 4-CF3 | |
| Ia.235 | CF₃ | H | 2-OCH₃ | 3-methyl | 4-CF3 | |
| Ia.236 | CF₃ | H | 2-OCH₃ | 3-CF₃ | 4-CF3 | |
| Ia.237 | CF₃ | H | 2-OCH₃ | 3-OCH₃ | 4-CF₃ | |
| Ia.238 | CF₃ | H | 2-OCH₃ | 3-OCF₃ | 4-CF₃ | |
| Ia.239 | CF₃ | H | 2-OCF₃ | 3-fluoro | 4-CF₃ | |
| Ia.240 | CF₃ | H | 2-OCF₃ | 3-chloro | 4-CF₃ | |
| Ia.241 | CF₃ | H | 2-OCF₃ | 3-CN | 4-CF₃ | |
| Ia.242 | CF₃ | H | 2-OCF₃ | 3-methyl | 4-CF₃ | |
| Ia.243 | CF₃ | H | 2-OCF₃ | 3-CF₃ | 4-CF₃ | |
| Ia.244 | CF₃ | H | 2-OCF₃ | 3-OCH₃ | 4-CF₃ | |
| Ia.245 | CF₃ | H | 2-OCF₃ | 3-OCF₃ | 4-CF₃ | |
| Ia.246 | CF₃ | H | 2-fluoro | 3-fluoro | 4-OCH₃ | |
| Ia.247 | CF₃ | H | 2-fluoro | 3-chloro | 4-OCH₃ | |
| Ia.248 | CF₃ | H | 2-fluoro | 3-CN | 4-OCH₃ | |
| Ia.249 | CF₃ | H | 2-fluoro | 3-methyl | 4-OCH₃ | |
| Ia.250 | CF₃ | H | 2-fluoro | 3-CF₃ | 4-OCH₃ | |
| Ia.251 | CF₃ | H | 2-fluoro | 3-OCH₃ | 4-OCH₃ | |
| Ia.252 | CF₃ | H | 2-fluoro | 3-OCF₃ | 4-OCH₃ | |
| Ia.253 | CF₃ | H | 2-chloro | 3-fluoro | 4-OCH₃ | |
| Ia.254 | CF₃ | H | 2-chloro | 3-chloro | 4-OCH₃ | |
| Ia.255 | CF₃ | H | 2-chloro | 3-CN | 4-OCH₃ | |
| Ia.256 | CF₃ | H | 2-chloro | 3-methyl | 4-OCH₃ | |
| Ia.257 | CF₃ | H | 2-chloro | 3-CF₃ | 4-OCH₃ | |
| Ia.258 | CF₃ | H | 2-chloro | 3-OCH₃ | 4-OCH₃ | |
| Ia.259 | CF₃ | H | 2-chloro | 3-OCF₃ | 4-OCH₃ | |
| Ia.260 | CF₃ | H | 2-CN | 3-fluoro | 4-OCH₃ | |
| Ia.261 | CF₃ | H | 2-CN | 3-chloro | 4-OCH₃ | |
| Ia.262 | CF₃ | H | 2-CN | 3-CN | 4-OCH₃ | |
| Ia.263 | CF₃ | H | 2-CN | 3-methyl | 4-OCH₃ | |
| Ia.264 | CF₃ | H | 2-CN | 3-CF₃ | 4-OCH₃ | |
| Ia.265 | CF₃ | H | 2-CN | 3-OCH₃ | 4-OCH₃ | |
| Ia.266 | CF₃ | H | 2-CN | 3-OCF₃ | 4-OCH₃ | |
| Ia.267 | CF₃ | H | 2-methyl | 3-fluoro | 4-OCH₃ | |
| Ia.268 | CF₃ | H | 2-methyl | 3-chloro | 4-OCH₃ | |
| Ia.269 | CF₃ | H | 2-methyl | 3-CN | 4-OCH₃ | |
| Ia.270 | CF₃ | H | 2-methyl | 3-methyl | 4-OCH₃ | |
| Ia.271 | CF₃ | H | 2-methyl | 3-CF₃ | 4-OCH₃ | |
| Ia.272 | CF₃ | H | 2-methyl | 3-OCH₃ | 4-OCH₃ | |
| Ia.273 | CF₃ | H | 2-methyl | 3-OCF₃ | 4-OCH₃ | |
| Ia.274 | CF₃ | H | 2-CF₃ | 3-fluoro | 4-OCH₃ | |
| Ia.275 | CF₃ | H | 2-CF₃ | 3-chloro | 4-OCH₃ | |
| Ia.276 | CF₃ | H | 2-CF₃ | 3-CN | 4-OCH₃ | |
| Ia.277 | CF₃ | H | 2-CF₃ | 3-methyl | 4-OCH₃ | |
| Ia.278 | CF₃ | H | 2-CF₃ | 3-CF₃ | 4-OCH₃ | |
| Ia.279 | CF₃ | H | 2-CF₃ | 3-OCH₃ | 4-OCH₃ | |
| Ia.280 | CF₃ | H | 2-CF₃ | 3-OCF₃ | 4-OCH₃ | |
| Ia.281 | CF₃ | H | 2-OCH₃ | 3-fluoro | 4-OCH₃ | |
| Ia.282 | CF₃ | H | 2-OCH₃ | 3-chloro | 4-OCH₃ | |
| Ia.283 | CF₃ | H | 2-OCH₃ | 3-CN | 4-OCH₃ | |
| Ia.284 | CF₃ | H | 2-OCH₃ | 3-methyl | 4-OCH₃ | |
| Ia.285 | CF₃ | H | 2-OCH₃ | 3-CF₃ | 4-OCH₃ | |
| Ia.286 | CF₃ | H | 2-OCH₃ | 3-OCH₃ | 4-OCH₃ | |
| Ia.287 | CF₃ | H | 2-OCH₃ | 3-OCF₃ | 4-OCH₃ | |
| Ia.288 | CF₃ | H | 2-OCF₃ | 3-fluoro | 4-OCH₃ | |
| Ia.289 | CF₃ | H | 2-OCF₃ | 3-chloro | 4-OCH₃ | |
| Ia.290 | CF₃ | H | 2-OCF₃ | 3-CN | 4-OCH₃ | |
| Ia.291 | CF₃ | H | 2-OCF₃ | 3-methyl | 4-OCH₃ | |
| Ia.292 | CF₃ | H | 2-OCF₃ | 3-CF₃ | 4-OCH₃ | |
| Ia.293 | CF₃ | H | 2-OCF₃ | 3-OCH₃ | 4-OCH₃ | |
| Ia.294 | CF₃ | H | 2-OCF₃ | 3-OCF₃ | 4-OCH₃ | |
| Ia.295 | CF₃ | H | 2-fluoro | 3-fluoro | 4-OCF₃ | |
| Ia.296 | CF₃ | H | 2-fluoro | 3-chloro | 4-OCF₃ | |
| Ia.297 | CF₃ | H | 2-fluoro | 3-CN | 4-OCF₃ | |
| Ia.298 | CF₃ | H | 2-fluoro | 3-methyl | 4-OCF₃ | |
| Ia.299 | CF₃ | H | 2-fluoro | 3-CF₃ | 4-OCF₃ | |
| Ia.300 | CF₃ | H | 2-fluoro | 3-OCH₃ | 4-OCF₃ | |
| Ia.301 | CF₃ | H | 2-fluoro | 3-OCF₃ | 4-OCF₃ | |
| Ia.302 | CF₃ | H | 2-chloro | 3-fluoro | 4-OCF₃ | |
| Ia.303 | CF₃ | H | 2-chloro | 3-chloro | 4-OCF₃ | |
| Ia.304 | CF₃ | H | 2-chloro | 3-CN | 4-OCF₃ | |

TABLE 2-continued

| Compound No. | $R^1$ | $R^2$ | $R^3$ | $R^4$ | $R^5$ | M.p. [° C.] |
|---|---|---|---|---|---|---|
| Ia.305 | $CF_3$ | H | 2-chloro | 3-methyl | 4-$OCF_3$ | |
| Ia.306 | $CF_3$ | H | 2-chloro | 3-$CF_3$ | 4-$OCF_3$ | |
| Ia.307 | $CF_3$ | H | 2-chloro | 3-$OCH_3$ | 4-$OCF_3$ | |
| Ia.308 | $CF_3$ | H | 2-chloro | 3-$OCF_3$ | 4-$OCF_3$ | |
| Ia.309 | $CF_3$ | H | 2-CN | 3-fluoro | 4-$OCF_3$ | |
| Ia.310 | $CF_3$ | H | 2-CN | 3-chloro | 4-$OCF_3$ | |
| Ia.311 | $CF_3$ | H | 2-CN | 3-CN | 4-$OCF_3$ | |
| Ia.312 | $CF_3$ | H | 2-CN | 3-methyl | 4-$OCF_3$ | |
| Ia.313 | $CF_3$ | H | 2-CN | 3-$CF_3$ | 4-$OCF_3$ | |
| Ia.314 | $CF_3$ | H | 2-CN | 3-$OCH_3$ | 4-$OCF_3$ | |
| Ia.315 | $CF_3$ | H | 2-CN | 3-$OCF_3$ | 4-$OCF_3$ | |
| Ia.316 | $CF_3$ | H | 2-methyl | 3-fluoro | 4-$OCF_3$ | |
| Ia.317 | $CF_3$ | H | 2-methyl | 3-chloro | 4-$OCF_3$ | |
| Ia.318 | $CF_3$ | H | 2-methyl | 3-CN | 4-$OCF_3$ | |
| Ia.319 | $CF_3$ | H | 2-methyl | 3-methyl | 4-$OCF_3$ | |
| Ia.320 | $CF_3$ | H | 2-methyl | 3-$CF_3$ | 4-$OCF_3$ | |
| Ia.321 | $CF_3$ | H | 2-methyl | 3-$OCH_3$ | 4-$OCF_3$ | |
| Ia.322 | $CF_3$ | H | 2-methyl | 3-$OCF_3$ | 4-$OCF_3$ | |
| Ia.323 | $CF_3$ | H | 2-$CF_3$ | 3-fluoro | 4-$OCF_3$ | |
| Ia.324 | $CF_3$ | H | 2-$CF_3$ | 3-chloro | 4-$OCF_3$ | |
| Ia.325 | $CF_3$ | H | 2-$CF_3$ | 3-CN | 4-$OCF_3$ | |
| Ia.326 | $CF_3$ | H | 2-$CF_3$ | 3-methyl | 4-$OCF_3$ | |
| Ia.327 | $CF_3$ | H | 2-$CF_3$ | 3-$CF_3$ | 4-$OCF_3$ | |
| Ia.328 | $CF_3$ | H | 2-$CF_3$ | 3-$OCH_3$ | 4-$OCF_3$ | |
| Ia.329 | $CF_3$ | H | 2-$CF_3$ | 3-$OCF_3$ | 4-$OCF_3$ | |
| Ia.330 | $CF_3$ | H | 2-$OCH_3$ | 3-fluoro | 4-$OCF_3$ | |
| Ia.331 | $CF_3$ | H | 2-$OCH_3$ | 3-chloro | 4-$OCF_3$ | |
| Ia.332 | $CF_3$ | H | 2-$OCH_3$ | 3-CN | 4-$OCF_3$ | |
| Ia.333 | $CF_3$ | H | 2-$OCH_3$ | 3-methyl | 4-$OCF_3$ | |
| Ia.334 | $CF_3$ | H | 2-$OCH_3$ | 3-$CF_3$ | 4-$OCF_3$ | |
| Ia.335 | $CF_3$ | H | 2-$OCH_3$ | 3-$OCH_3$ | 4-$OCF_3$ | |
| Ia.336 | $CF_3$ | H | 2-$OCH_3$ | 3-$OCF_3$ | 4-$OCF_3$ | |
| Ia.337 | $CF_3$ | H | 2-$OCF_3$ | 3-fluoro | 4-$OCF_3$ | |
| Ia.338 | $CF_3$ | H | 2-$OCF_3$ | 3-chloro | 4-$OCF_3$ | |
| Ia.339 | $CF_3$ | H | 2-$OCF_3$ | 3-CN | 4-$OCF_3$ | |
| Ia.340 | $CF_3$ | H | 2-$OCF_3$ | 3-methyl | 4-$OCF_3$ | |
| Ia.341 | $CF_3$ | H | 2-$OCF_3$ | 3-$CF_3$ | 4-$OCF_3$ | |
| Ia.342 | $CF_3$ | H | 2-$OCF_3$ | 3-$OCH_3$ | 4-$OCF_3$ | |
| Ia.343 | $CF_3$ | H | 2-$OCF_3$ | 3-$OCF_3$ | 4-$OCF_3$ | |
| Ia.344 | $CF_3$ | H | 3-fluoro | 4-fluoro | 5-fluoro | 120-124 |
| Ia.345 | $CF_3$ | H | 3-chloro | 4-fluoro | 5-fluoro | |
| Ia.346 | $CF_3$ | H | 3-CN | 4-fluoro | 5-fluoro | |
| Ia.347 | $CF_3$ | H | 3-$CH_3$ | 4-fluoro | 5-fluoro | |
| Ia.348 | $CF_3$ | H | 3-$CF_3$ | 4-fluoro | 5-fluoro | |
| Ia.349 | $CF_3$ | H | 3-$OCH_3$ | 4-fluoro | 5-fluoro | |
| Ia.350 | $CF_3$ | H | 3-$OCF_3$ | 4-fluoro | 5-fluoro | |
| Ia.351 | $CF_3$ | H | 3-fluoro | 4-fluoro | 5-chloro | |
| Ia.352 | $CF_3$ | H | 3-chloro | 4-fluoro | 5-chloro | |
| Ia.353 | $CF_3$ | H | 3-CN | 4-fluoro | 5-chloro | |
| Ia.354 | $CF_3$ | H | 3-$CH_3$ | 4-fluoro | 5-chloro | |
| Ia.355 | $CF_3$ | H | 3-$CF_3$ | 4-fluoro | 5-chloro | |
| Ia.356 | $CF_3$ | H | 3-$OCH_3$ | 4-fluoro | 5-chloro | |
| Ia.357 | $CF_3$ | H | 3-$OCF_3$ | 4-fluoro | 5-chloro | |
| Ia.358 | $CF_3$ | H | 3-fluoro | 4-fluoro | 5-CN | |
| Ia.359 | $CF_3$ | H | 3-chloro | 4-fluoro | 5-CN | |
| Ia.360 | $CF_3$ | H | 3-CN | 4-fluoro | 5-CN | |
| Ia.361 | $CF_3$ | H | 3-$CH_3$ | 4-fluoro | 5-CN | |
| Ia.362 | $CF_3$ | H | 3-$CF_3$ | 4-fluoro | 5-CN | |
| Ia.363 | $CF_3$ | H | 3-$OCH_3$ | 4-fluoro | 5-CN | |
| Ia.364 | $CF_3$ | H | 3-$OCF_3$ | 4-fluoro | 5-CN | |
| Ia.365 | $CF_3$ | H | 3-fluoro | 4-fluoro | 5-$CH_3$ | |
| Ia.366 | $CF_3$ | H | 3-chloro | 4-fluoro | 5-$CH_3$ | |
| Ia.367 | $CF_3$ | H | 3-CN | 4-fluoro | 5-$CH_3$ | |
| Ia.368 | $CF_3$ | H | 3-$CH_3$ | 4-fluoro | 5-$CH_3$ | |
| Ia.369 | $CF_3$ | H | 3-$CF_3$ | 4-fluoro | 5-$CH_3$ | |
| Ia.370 | $CF_3$ | H | 3-$OCH_3$ | 4-fluoro | 5-$CH_3$ | |
| Ia.371 | $CF_3$ | H | 3-$OCF_3$ | 4-fluoro | 5-$CH_3$ | |
| Ia.372 | $CF_3$ | H | 3-fluoro | 4-fluoro | 5-$CF_3$ | |
| Ia.373 | $CF_3$ | H | 3-chloro | 4-fluoro | 5-$CF_3$ | |
| Ia.374 | $CF_3$ | H | 3-CN | 4-fluoro | 5-$CF_3$ | |
| Ia.375 | $CF_3$ | H | 3-$CH_3$ | 4-fluoro | 5-$CF_3$ | |
| Ia.376 | $CF_3$ | H | 3-$CF_3$ | 4-fluoro | 5-$CF_3$ | |
| Ia.377 | $CF_3$ | H | 3-$OCH_3$ | 4-fluoro | 5-$CF_3$ | |
| Ia.378 | $CF_3$ | H | 3-$OCF_3$ | 4-fluoro | 5-$CF_3$ | |
| Ia.379 | $CF_3$ | H | 3-fluoro | 4-fluoro | 5-$OCH_3$ | |
| Ia.380 | $CF_3$ | H | 3-chloro | 4-fluoro | 5-$OCH_3$ | |
| Ia.381 | $CF_3$ | H | 3-CN | 4-fluoro | 5-$OCH_3$ | |
| Ia.382 | $CF_3$ | H | 3-$CH_3$ | 4-fluoro | 5-$OCH_3$ | |
| Ia.383 | $CF_3$ | H | 3-$CF_3$ | 4-fluoro | 5-$OCH_3$ | |
| Ia.384 | $CF_3$ | H | 3-$OCH_3$ | 4-fluoro | 5-$OCH_3$ | |
| Ia.385 | $CF_3$ | H | 3-$OCF_3$ | 4-fluoro | 5-$OCH_3$ | |
| Ia.386 | $CF_3$ | H | 3-fluoro | 4-fluoro | 5-$OCF_3$ | |
| Ia.387 | $CF_3$ | H | 3-chloro | 4-fluoro | 5-$OCF_3$ | |
| Ia.388 | $CF_3$ | H | 3-CN | 4-fluoro | 5-$OCF_3$ | |
| Ia.389 | $CF_3$ | H | 3-$CH_3$ | 4-fluoro | 5-$OCF_3$ | |
| Ia.390 | $CF_3$ | H | 3-$CF_3$ | 4-fluoro | 5-$OCF_3$ | |
| Ia.391 | $CF_3$ | H | 3-$OCH_3$ | 4-fluoro | 5-$OCF_3$ | |
| Ia.392 | $CF_3$ | H | 3-$OCF_3$ | 4-fluoro | 5-$OCF_3$ | |
| Ia.393 | $CF_3$ | H | 3-fluoro | 4-chloro | 5-fluoro | |
| Ia.394 | $CF_3$ | H | 3-chloro | 4-chloro | 5-fluoro | |
| Ia.395 | $CF_3$ | H | 3-CN | 4-chloro | 5-fluoro | |
| Ia.396 | $CF_3$ | H | 3-$CH_3$ | 4-chloro | 5-fluoro | |
| Ia.397 | $CF_3$ | H | 3-$CF_3$ | 4-chloro | 5-fluoro | |
| Ia.398 | $CF_3$ | H | 3-$OCH_3$ | 4-chloro | 5-fluoro | |
| Ia.399 | $CF_3$ | H | 3-$OCF_3$ | 4-chloro | 5-fluoro | |
| Ia.400 | $CF_3$ | H | 3-fluoro | 4-chloro | 5-chloro | |
| Ia.401 | $CF_3$ | H | 3-chloro | 4-chloro | 5-chloro | |
| Ia.402 | $CF_3$ | H | 3-CN | 4-chloro | 5-chloro | |
| Ia.403 | $CF_3$ | H | 3-$CH_3$ | 4-chloro | 5-chloro | |
| Ia.404 | $CF_3$ | H | 3-$CF_3$ | 4-chloro | 5-chloro | |
| Ia.405 | $CF_3$ | H | 3-$OCH_3$ | 4-chloro | 5-chloro | |
| Ia.406 | $CF_3$ | H | 3-$OCF_3$ | 4-chloro | 5-chloro | |
| Ia.407 | $CF_3$ | H | 3-fluoro | 4-chloro | 5-CN | |
| Ia.408 | $CF_3$ | H | 3-chloro | 4-chloro | 5-CN | |
| Ia.409 | $CF_3$ | H | 3-CN | 4-chloro | 5-CN | |
| Ia.410 | $CF_3$ | H | 3-$CH_3$ | 4-chloro | 5-CN | |
| Ia.411 | $CF_3$ | H | 3-$CF_3$ | 4-chloro | 5-CN | |
| Ia.412 | $CF_3$ | H | 3-$OCH_3$ | 4-chloro | 5-CN | |
| Ia.413 | $CF_3$ | H | 3-$OCF_3$ | 4-chloro | 5-CN | |
| Ia.414 | $CF_3$ | H | 3-fluoro | 4-chloro | 5-$CH_3$ | |
| Ia.415 | $CF_3$ | H | 3-chloro | 4-chloro | 5-$CH_3$ | |
| Ia.416 | $CF_3$ | H | 3-CN | 4-chloro | 5-$CH_3$ | |
| Ia.417 | $CF_3$ | H | 3-$CH_3$ | 4-chloro | 5-$CH_3$ | |
| Ia.418 | $CF_3$ | H | 3-$CF_3$ | 4-chloro | 5-$CH_3$ | |
| Ia.419 | $CF_3$ | H | 3-$OCH_3$ | 4-chloro | 5-$CH_3$ | |
| Ia.420 | $CF_3$ | H | 3-$OCF_3$ | 4-chloro | 5-$CH_3$ | |
| Ia.421 | $CF_3$ | H | 3-fluoro | 4-chloro | 5-$CF_3$ | |
| Ia.422 | $CF_3$ | H | 3-chloro | 4-chloro | 5-$CF_3$ | |
| Ia.423 | $CF_3$ | H | 3-CN | 4-chloro | 5-$CF_3$ | |
| Ia.424 | $CF_3$ | H | 3-$CH_3$ | 4-chloro | 5-$CF_3$ | |
| Ia.425 | $CF_3$ | H | 3-$CF_3$ | 4-chloro | 5-$CF_3$ | |
| Ia.426 | $CF_3$ | H | 3-$OCH_3$ | 4-chloro | 5-$CF_3$ | |
| Ia.427 | $CF_3$ | H | 3-$OCF_3$ | 4-chloro | 5-$CF_3$ | |
| Ia.428 | $CF_3$ | H | 3-fluoro | 4-chloro | 5-$OCH_3$ | |
| Ia.429 | $CF_3$ | H | 3-chloro | 4-chloro | 5-$OCH_3$ | |
| Ia.430 | $CF_3$ | H | 3-CN | 4-chloro | 5-$OCH_3$ | |
| Ia.431 | $CF_3$ | H | 3-$CH_3$ | 4-chloro | 5-$OCH_3$ | |
| Ia.432 | $CF_3$ | H | 3-$CF_3$ | 4-chloro | 5-$OCH_3$ | |
| Ia.433 | $CF_3$ | H | 3-$OCH_3$ | 4-chloro | 5-$OCH_3$ | |
| Ia.434 | $CF_3$ | H | 3-$OCF_3$ | 4-chloro | 5-$OCH_3$ | |
| Ia.435 | $CF_3$ | H | 3-fluoro | 4-chloro | 5-$OCF_3$ | |
| Ia.436 | $CF_3$ | H | 3-chloro | 4-chloro | 5-$OCF_3$ | |
| Ia.437 | $CF_3$ | H | 3-CN | 4-chloro | 5-$OCF_3$ | |
| Ia.438 | $CF_3$ | H | 3-$CH_3$ | 4-chloro | 5-$OCF_3$ | |
| Ia.439 | $CF_3$ | H | 3-$CF_3$ | 4-chloro | 5-$OCF_3$ | |
| Ia.440 | $CF_3$ | H | 3-$OCH_3$ | 4-chloro | 5-$OCF_3$ | |
| Ia.441 | $CF_3$ | H | 3-$OCF_3$ | 4-chloro | 5-$OCF_3$ | |
| Ia.442 | $CF_3$ | H | 3-fluoro | 4-CN | 5-fluoro | |
| Ia.443 | $CF_3$ | H | 3-chloro | 4-CN | 5-fluoro | |
| Ia.444 | $CF_3$ | H | 3-CN | 4-CN | 5-fluoro | |
| Ia.445 | $CF_3$ | H | 3-$CH_3$ | 4-CN | 5-fluoro | |
| Ia.446 | $CF_3$ | H | 3-$CF_3$ | 4-CN | 5-fluoro | |
| Ia.447 | $CF_3$ | H | 3-$OCH_3$ | 4-CN | 5-fluoro | |
| Ia.448 | $CF_3$ | H | 3-$OCF_3$ | 4-CN | 5-fluoro | |
| Ia.449 | $CF_3$ | H | 3-fluoro | 4-CN | 5-chloro | |
| Ia.450 | $CF_3$ | H | 3-chloro | 4-CN | 5-chloro | |
| Ia.451 | $CF_3$ | H | 3-CN | 4-CN | 5-chloro | |
| Ia.452 | $CF_3$ | H | 3-$CH_3$ | 4-CN | 5-chloro | |
| Ia.453 | $CF_3$ | H | 3-$CF_3$ | 4-CN | 5-chloro | |
| Ia.454 | $CF_3$ | H | 3-$OCH_3$ | 4-CN | 5-chloro | |
| Ia.455 | $CF_3$ | H | 3-$OCF_3$ | 4-CN | 5-chloro | |
| Ia.456 | $CF_3$ | H | 3-fluoro | 4-CN | 5-CN | |
| Ia.457 | $CF_3$ | H | 3-chloro | 4-CN | 5-CN | |
| Ia.458 | $CF_3$ | H | 3-CN | 4-CN | 5-CN | |

TABLE 2-continued

| Compound No. | R¹ | R² | R³ | R⁴ | R⁵ | M.p. [° C.] |
|---|---|---|---|---|---|---|
| Ia.459 | CF₃ | H | 3-CH₃ | 4-CN | 5-CN | |
| Ia.460 | CF₃ | H | 3-CF₃ | 4-CN | 5-CN | |
| Ia.461 | CF₃ | H | 3-OCH₃ | 4-CN | 5-CN | |
| Ia.462 | CF₃ | H | 3-OCF₃ | 4-CN | 5-CN | |
| Ia.463 | CF₃ | H | 3-fluoro | 4-CN | 5-CH₃ | |
| Ia.464 | CF₃ | H | 3-chloro | 4-CN | 5-CH₃ | |
| Ia.465 | CF₃ | H | 3-CN | 4-CN | 5-CH₃ | |
| Ia.466 | CF₃ | H | 3-CH₃ | 4-CN | 5-CH₃ | |
| Ia.467 | CF₃ | H | 3-CF₃ | 4-CN | 5-CH₃ | |
| Ia.468 | CF₃ | H | 3-OCH₃ | 4-CN | 5-CH₃ | |
| Ia.469 | CF₃ | H | 3-OCF₃ | 4-CN | 5-CH₃ | |
| Ia.470 | CF₃ | H | 3-fluoro | 4-CN | 5-CF₃ | |
| Ia.471 | CF₃ | H | 3-chloro | 4-CN | 5-CF₃ | |
| Ia.472 | CF₃ | H | 3-CN | 4-CN | 5-CF₃ | |
| Ia.473 | CF₃ | H | 3-CH₃ | 4-CN | 5-CF₃ | |
| Ia.474 | CF₃ | H | 3-CF₃ | 4-CN | 5-CF₃ | |
| Ia.475 | CF₃ | H | 3-OCH₃ | 4-CN | 5-CF₃ | |
| Ia.476 | CF₃ | H | 3-OCF₃ | 4-CN | 5-CF₃ | |
| Ia.477 | CF₃ | H | 3-fluoro | 4-CN | 5-OCH₃ | |
| Ia.478 | CF₃ | H | 3-chloro | 4-CN | 5-OCH₃ | |
| Ia.479 | CF₃ | H | 3-CN | 4-CN | 5-OCH₃ | |
| Ia.480 | CF₃ | H | 3-CH₃ | 4-CN | 5-OCH₃ | |
| Ia.481 | CF₃ | H | 3-CF₃ | 4-CN | 5-OCH₃ | |
| Ia.482 | CF₃ | H | 3-OCH₃ | 4-CN | 5-OCH₃ | |
| Ia.483 | CF₃ | H | 3-OCF₃ | 4-CN | 5-OCH₃ | |
| Ia.484 | CF₃ | H | 3-fluoro | 4-CN | 5-OCF₃ | |
| Ia.485 | CF₃ | H | 3-chloro | 4-CN | 5-OCF₃ | |
| Ia.486 | CF₃ | H | 3-CN | 4-CN | 5-OCF₃ | |
| Ia.487 | CF₃ | H | 3-CH₃ | 4-CN | 5-OCF₃ | |
| Ia.488 | CF₃ | H | 3-CF₃ | 4-CN | 5-OCF₃ | |
| Ia.489 | CF₃ | H | 3-OCH₃ | 4-CN | 5-OCF₃ | |
| Ia.490 | CF₃ | H | 3-OCF₃ | 4-CN | 5-OCF₃ | |
| Ia.491 | CF₃ | H | 3-fluoro | 4-CH₃ | 5-fluoro | |
| Ia.492 | CF₃ | H | 3-chloro | 4-CH₃ | 5-fluoro | |
| Ia.493 | CF₃ | H | 3-CN | 4-CH₃ | 5-fluoro | |
| Ia.494 | CF₃ | H | 3-CH₃ | 4-CH₃ | 5-fluoro | |
| Ia.495 | CF₃ | H | 3-CF₃ | 4-CH₃ | 5-fluoro | |
| Ia.496 | CF₃ | H | 3-OCH₃ | 4-CH₃ | 5-fluoro | |
| Ia.497 | CF₃ | H | 3-OCF₃ | 4-CH₃ | 5-fluoro | |
| Ia.498 | CF₃ | H | 3-fluoro | 4-CH₃ | 5-chloro | |
| Ia.499 | CF₃ | H | 3-chloro | 4-CH₃ | 5-chloro | |
| Ia.500 | CF₃ | H | 3-CN | 4-CH₃ | 5-chloro | |
| Ia.501 | CF₃ | H | 3-CH₃ | 4-CH₃ | 5-chloro | |
| Ia.502 | CF₃ | H | 3-CF₃ | 4-CH₃ | 5-chloro | |
| Ia.503 | CF₃ | H | 3-OCH₃ | 4-CH₃ | 5-chloro | |
| Ia.504 | CF₃ | H | 3-OCF₃ | 4-CH₃ | 5-chloro | |
| Ia.505 | CF₃ | H | 3-fluoro | 4-CH₃ | 5-CN | |
| Ia.506 | CF₃ | H | 3-chloro | 4-CH₃ | 5-CN | |
| Ia.507 | CF₃ | H | 3-CN | 4-CH₃ | 5-CN | |
| Ia.508 | CF₃ | H | 3-CH₃ | 4-CH₃ | 5-CN | |
| Ia.509 | CF₃ | H | 3-CF₃ | 4-CH₃ | 5-CN | |
| Ia.510 | CF₃ | H | 3-OCH₃ | 4-CH₃ | 5-CN | |
| Ia.511 | CF₃ | H | 3-OCF₃ | 4-CH₃ | 5-CN | |
| Ia.512 | CF₃ | H | 3-fluoro | 4-CH₃ | 5-CH₃ | |
| Ia.513 | CF₃ | H | 3-chloro | 4-CH₃ | 5-CH₃ | |
| Ia.514 | CF₃ | H | 3-CN | 4-CH₃ | 5-CH₃ | |
| Ia.515 | CF₃ | H | 3-CH₃ | 4-CH₃ | 5-CH₃ | |
| Ia.516 | CF₃ | H | 3-CF₃ | 4-CH₃ | 5-CH₃ | |
| Ia.517 | CF₃ | H | 3-OCH₃ | 4-CH₃ | 5-CH₃ | |
| Ia.518 | CF₃ | H | 3-OCF₃ | 4-CH₃ | 5-CH₃ | |
| Ia.519 | CF₃ | H | 3-fluoro | 4-CH₃ | 5-CF₃ | |
| Ia.520 | CF₃ | H | 3-chloro | 4-CH₃ | 5-CF₃ | |
| Ia.521 | CF₃ | H | 3-CN | 4-CH₃ | 5-CF₃ | |
| Ia.522 | CF₃ | H | 3-CH₃ | 4-CH₃ | 5-CF₃ | |
| Ia.523 | CF₃ | H | 3-CF₃ | 4-CH₃ | 5-CF₃ | |
| Ia.524 | CF₃ | H | 3-OCH₃ | 4-CH₃ | 5-CF₃ | |
| Ia.525 | CF₃ | H | 3-OCF₃ | 4-CH₃ | 5-CF₃ | |
| Ia.526 | CF₃ | H | 3-fluoro | 4-CH₃ | 5-OCH₃ | |
| Ia.527 | CF₃ | H | 3-chloro | 4-CH₃ | 5-OCH₃ | |
| Ia.528 | CF₃ | H | 3-CN | 4-CH₃ | 5-OCH₃ | |
| Ia.529 | CF₃ | H | 3-CH₃ | 4-CH₃ | 5-OCH₃ | |
| Ia.530 | CF₃ | H | 3-CF₃ | 4-CH₃ | 5-OCH₃ | |
| Ia.531 | CF₃ | H | 3-OCH₃ | 4-CH₃ | 5-OCH₃ | |
| Ia.532 | CF₃ | H | 3-OCF₃ | 4-CH₃ | 5-OCH₃ | |
| Ia.533 | CF₃ | H | 3-fluoro | 4-CH₃ | 5-OCF₃ | |
| Ia.534 | CF₃ | H | 3-chloro | 4-CH₃ | 5-OCF₃ | |
| Ia.535 | CF₃ | H | 3-CN | 4-CH₃ | 5-OCF₃ | |
| Ia.536 | CF₃ | H | 3-CH₃ | 4-CH₃ | 5-OCF₃ | |
| Ia.537 | CF₃ | H | 3-CF₃ | 4-CH₃ | 5-OCF₃ | |
| Ia.538 | CF₃ | H | 3-OCH₃ | 4-CH₃ | 5-OCF₃ | |
| Ia.539 | CF₃ | H | 3-OCF₃ | 4-CH₃ | 5-OCF₃ | |
| Ia.540 | CF₃ | H | 3-fluoro | 4-CF₃ | 5-fluoro | |
| Ia.541 | CF₃ | H | 3-chloro | 4-CF₃ | 5-fluoro | |
| Ia.542 | CF₃ | H | 3-CN | 4-CF₃ | 5-fluoro | |
| Ia.543 | CF₃ | H | 3-CH₃ | 4-CF₃ | 5-fluoro | |
| Ia.544 | CF₃ | H | 3-CF₃ | 4-CF₃ | 5-fluoro | |
| Ia.545 | CF₃ | H | 3-OCH₃ | 4-CF₃ | 5-fluoro | |
| Ia.546 | CF₃ | H | 3-OCF₃ | 4-CF₃ | 5-fluoro | |
| Ia.547 | CF₃ | H | 3-fluoro | 4-CF₃ | 5-chloro | |
| Ia.548 | CF₃ | H | 3-chloro | 4-CF₃ | 5-chloro | |
| Ia.549 | CF₃ | H | 3-CN | 4-CF₃ | 5-chloro | |
| Ia.550 | CF₃ | H | 3-CH₃ | 4-CF₃ | 5-chloro | |
| Ia.551 | CF₃ | H | 3-CF₃ | 4-CF₃ | 5-chloro | |
| Ia.552 | CF₃ | H | 3-OCH₃ | 4-CF₃ | 5-chloro | |
| Ia.553 | CF₃ | H | 3-OCF₃ | 4-CF₃ | 5-chloro | |
| Ia.554 | CF₃ | H | 3-fluoro | 4-CF₃ | 5-CN | |
| Ia.555 | CF₃ | H | 3-chloro | 4-CF₃ | 5-CN | |
| Ia.556 | CF₃ | H | 3-CN | 4-CF₃ | 5-CN | |
| Ia.557 | CF₃ | H | 3-CH₃ | 4-CF₃ | 5-CN | |
| Ia.558 | CF₃ | H | 3-CF₃ | 4-CF₃ | 5-CN | |
| Ia.559 | CF₃ | H | 3-OCH₃ | 4-CF₃ | 5-CN | |
| Ia.560 | CF₃ | H | 3-OCF₃ | 4-CF₃ | 5-CN | |
| Ia.561 | CF₃ | H | 3-fluoro | 4-CF₃ | 5-CH₃ | |
| Ia.562 | CF₃ | H | 3-chloro | 4-CF₃ | 5-CH₃ | |
| Ia.563 | CF₃ | H | 3-CN | 4-CF₃ | 5-CH₃ | |
| Ia.564 | CF₃ | H | 3-CH₃ | 4-CF₃ | 5-CH₃ | |
| Ia.565 | CF₃ | H | 3-CF₃ | 4-CF₃ | 5-CH₃ | |
| Ia.566 | CF₃ | H | 3-OCH₃ | 4-CF₃ | 5-CH₃ | |
| Ia.567 | CF₃ | H | 3-OCF₃ | 4-CF₃ | 5-CH₃ | |
| Ia.568 | CF₃ | H | 3-fluoro | 4-CF₃ | 5-OCF₃ | |
| Ia.569 | CF₃ | H | 3-chloro | 4-CF₃ | 5-CF₃ | |
| Ia.570 | CF₃ | H | 3-CN | 4-CF₃ | 5-CF₃ | |
| Ia.571 | CF₃ | H | 3-CH₃ | 4-CF₃ | 5-CF₃ | |
| Ia.572 | CF₃ | H | 3-CF₃ | 4-CF₃ | 5-CF₃ | |
| Ia.573 | CF₃ | H | 3-OCH₃ | 4-CF₃ | 5-CF₃ | |
| Ia.574 | CF₃ | H | 3-OCF₃ | 4-CF₃ | 5-CF₃ | |
| Ia.575 | CF₃ | H | 3-fluoro | 4-CF₃ | 5-OCH₃ | |
| Ia.576 | CF₃ | H | 3-chloro | 4-CF₃ | 5-OCH₃ | |
| Ia.577 | CF₃ | H | 3-CN | 4-CF₃ | 5-OCH₃ | |
| Ia.578 | CF₃ | H | 3-CH₃ | 4-CF₃ | 5-OCH₃ | |
| Ia.579 | CF₃ | H | 3-CF₃ | 4-CF₃ | 5-OCH₃ | |
| Ia.560 | CF₃ | H | 3-OCH₃ | 4-CF₃ | 5-OCH₃ | |
| Ia.561 | CF₃ | H | 3-OCF₃ | 4-CF₃ | 5-OCH₃ | |
| Ia.562 | CF₃ | H | 3-fluoro | 4-CF₃ | 5-OCF₃ | |
| Ia.563 | CF₃ | H | 3-chloro | 4-CF₃ | 5-OCF₃ | |
| Ia.564 | CF₃ | H | 3-CN | 4-CF₃ | 5-OCF₃ | |
| Ia.565 | CF₃ | H | 3-CH₃ | 4-CF₃ | 5-OCF₃ | |
| Ia.566 | CF₃ | H | 3-CF₃ | 4-CF₃ | 5-OCF₃ | |
| Ia.567 | CF₃ | H | 3-OCH₃ | 4-CF₃ | 5-OCF₃ | |
| Ia.568 | CF₃ | H | 3-OCF₃ | 4-CF₃ | 5-OCF₃ | |
| Ia.569 | CF₃ | H | 3-fluoro | 4-OCH₃ | 5-fluoro | |
| Ia.570 | CF₃ | H | 3-chloro | 4-OCH₃ | 5-fluoro | |
| Ia.571 | CF₃ | H | 3-CN | 4-OCH₃ | 5-fluoro | |
| Ia.572 | CF₃ | H | 3-CH₃ | 4-OCH₃ | 5-fluoro | |
| Ia.573 | CF₃ | H | 3-CF₃ | 4-OCH₃ | 5-fluoro | |
| Ia.574 | CF₃ | H | 3-OCH₃ | 4-OCH₃ | 5-fluoro | |
| Ia.575 | CF₃ | H | 3-OCF₃ | 4-OCH₃ | 5-fluoro | |
| Ia.576 | CF₃ | H | 3-fluoro | 4-OCH₃ | 5-chloro | |
| Ia.577 | CF₃ | H | 3-chloro | 4-OCH₃ | 5-chloro | |
| Ia.578 | CF₃ | H | 3-CN | 4-OCH₃ | 5-chloro | |
| Ia.579 | CF₃ | H | 3-CH₃ | 4-OCH₃ | 5-chloro | |
| Ia.580 | CF₃ | H | 3-CF₃ | 4-OCH₃ | 5-chloro | |
| Ia.581 | CF₃ | H | 3-OCH₃ | 4-OCH₃ | 5-chloro | |
| Ia.582 | CF₃ | H | 3-OCF₃ | 4-OCH₃ | 5-chloro | |
| Ia.583 | CF₃ | H | 3-fluoro | 4-OCH₃ | 5-CN | |
| Ia.584 | CF₃ | H | 3-chloro | 4-OCH₃ | 5-CN | |
| Ia.585 | CF₃ | H | 3-CN | 4-OCH₃ | 5-CN | |
| Ia.586 | CF₃ | H | 3-CH₃ | 4-OCH₃ | 5-CN | |
| Ia.587 | CF₃ | H | 3-CF₃ | 4-OCH₃ | 5-CN | |
| Ia.588 | CF₃ | H | 3-OCH₃ | 4-OCH₃ | 5-CN | |
| Ia.589 | CF₃ | H | 3-OCF₃ | 4-OCH₃ | 5-CN | |
| Ia.590 | CF₃ | H | 3-fluoro | 4-OCH₃ | 5-CH₃ | |
| Ia.591 | CF₃ | H | 3-chloro | 4-OCH₃ | 5-CH₃ | |
| Ia.592 | CF₃ | H | 3-CN | 4-OCH₃ | 5-CH₃ | |

TABLE 2-continued

| Compound No. | R¹ | R² | R³ | R⁴ | R⁵ | M.p. [° C.] |
|---|---|---|---|---|---|---|
| Ia.593 | CF₃ | H | 3-CH₃ | 4-OCH₃ | 5-CH₃ | |
| Ia.594 | CF₃ | H | 3-CF₃ | 4-OCH₃ | 5-CH₃ | |
| Ia.595 | CF₃ | H | 3-OCH₃ | 4-OCH₃ | 5-CH₃ | |
| Ia.596 | CF₃ | H | 3-OCF₃ | 4-OCH₃ | 5-CH₃ | |
| Ia.597 | CF₃ | H | 3-fluoro | 4-OCH₃ | 5-CF₃ | |
| Ia.598 | CF₃ | H | 3-chloro | 4-OCH₃ | 5-CF₃ | |
| Ia.599 | CF₃ | H | 3-CN | 4-OCH₃ | 5-CF₃ | |
| Ia.600 | CF₃ | H | 3-CH₃ | 4-OCH₃ | 5-CF₃ | |
| Ia.601 | CF₃ | H | 3-CF₃ | 4-OCH₃ | 5-CF₃ | |
| Ia.602 | CF₃ | H | 3-OCH₃ | 4-OCH₃ | 5-CF₃ | |
| Ia.603 | CF₃ | H | 3-OCF₃ | 4-OCH₃ | 5-CF₃ | |
| Ia.604 | CF₃ | H | 3-fluoro | 4-OCH₃ | 5-OCH₃ | |
| Ia.605 | CF₃ | H | 3-chloro | 4-OCH₃ | 5-OCH₃ | |
| Ia.606 | CF₃ | H | 3-CN | 4-OCH₃ | 5-OCH₃ | |
| Ia.607 | CF₃ | H | 3-CH₃ | 4-OCH₃ | 5-OCH₃ | |
| Ia.608 | CF₃ | H | 3-CF₃ | 4-OCH₃ | 5-OCH₃ | |
| Ia.609 | CF₃ | H | 3-OCH₃ | 4-OCH₃ | 5-OCH₃ | |
| Ia.610 | CF₃ | H | 3-OCF₃ | 4-OCH₃ | 5-OCH₃ | |
| Ia.611 | CF₃ | H | 3-fluoro | 4-OCH₃ | 5-OCF₃ | |
| Ia.612 | CF₃ | H | 3-chloro | 4-OCH₃ | 5-OCF₃ | |
| Ia.613 | CF₃ | H | 3-CN | 4-OCH₃ | 5-OCF₃ | |
| Ia.614 | CF₃ | H | 3-CH₃ | 4-OCH₃ | 5-OCF₃ | |
| Ia.615 | CF₃ | H | 3-CF₃ | 4-OCH₃ | 5-OCF₃ | |
| Ia.616 | CF₃ | H | 3-OCH₃ | 4-OCH₃ | 5-OCF₃ | |
| Ia.617 | CF₃ | H | 3-OCF₃ | 4-OCH₃ | 5-OCF₃ | |
| Ia.618 | CF₃ | H | 3-fluoro | 4-OCF₃ | 5-fluoro | |
| Ia.619 | CF₃ | H | 3-chloro | 4-OCF₃ | 5-fluoro | |
| Ia.620 | CF₃ | H | 3-CN | 4-OCF₃ | 5-fluoro | |
| Ia.621 | CF₃ | H | 3-CH₃ | 4-OCF₃ | 5-fluoro | |
| Ia.622 | CF₃ | H | 3-CF₃ | 4-OCF₃ | 5-fluoro | |
| Ia.623 | CF₃ | H | 3-OCH₃ | 4-OCF₃ | 5-fluoro | |
| Ia.624 | CF₃ | H | 3-OCF₃ | 4-OCF₃ | 5-fluoro | |
| Ia.625 | CF₃ | H | 3-fluoro | 4-OCF₃ | 5-chloro | |
| Ia.626 | CF₃ | H | 3-chloro | 4-OCF₃ | 5-chloro | |
| Ia.627 | CF₃ | H | 3-CN | 4-OCF₃ | 5-chloro | |
| Ia.628 | CF₃ | H | 3-CH₃ | 4-OCF₃ | 5-chloro | |
| Ia.629 | CF₃ | H | 3-CF₃ | 4-OCF₃ | 5-chloro | |
| Ia.630 | CF₃ | H | 3-OCH₃ | 4-OCF₃ | 5-chloro | |
| Ia.631 | CF₃ | H | 3-OCF₃ | 4-OCF₃ | 5-chloro | |
| Ia.632 | CF₃ | H | 3-fluoro | 4-OCF₃ | 5-CN | |
| Ia.633 | CF₃ | H | 3-chloro | 4-OCF₃ | 5-CN | |
| Ia.634 | CF₃ | H | 3-CN | 4-OCF₃ | 5-CN | |
| Ia.635 | CF₃ | H | 3-CH₃ | 4-OCF₃ | 5-CN | |
| Ia.636 | CF₃ | H | 3-CF₃ | 4-OCF₃ | 5-CN | |
| Ia.637 | CF₃ | H | 3-OCH₃ | 4-OCF₃ | 5-CN | |
| Ia.638 | CF₃ | H | 3-OCF₃ | 4-OCF₃ | 5-CN | |
| Ia.639 | CF₃ | H | 3-fluoro | 4-OCF₃ | 5-CH₃ | |
| Ia.640 | CF₃ | H | 3-chloro | 4-OCF₃ | 5-CH₃ | |
| Ia.641 | CF₃ | H | 3-CN | 4-OCF₃ | 5-CH₃ | |
| Ia.642 | CF₃ | H | 3-CH₃ | 4-OCF₃ | 5-CH₃ | |
| Ia.643 | CF₃ | H | 3-CF3 | 4-OCF₃ | 5-CH₃ | |
| Ia.644 | CF₃ | H | 3-OCH₃ | 4-OCF₃ | 5-CH₃ | |
| Ia.645 | CF₃ | H | 3-OCF₃ | 4-OCF₃ | 5-CH₃ | |
| Ia.646 | CF₃ | H | 3-fluoro | 4-OCF₃ | 5-CF₃ | |
| Ia.647 | CF₃ | H | 3-chloro | 4-OCF₃ | 5-CF₃ | |
| Ia.648 | CF₃ | H | 3-CN | 4-OCF₃ | 5-CF₃ | |
| Ia.649 | CF₃ | H | 3-CH₃ | 4-OCF₃ | 5-CF₃ | |
| Ia.650 | CF₃ | H | 3-CF₃ | 4-OCF₃ | 5-CF₃ | |
| Ia.651 | CF₃ | H | 3-OCH₃ | 4-OCF₃ | 5-CF₃ | |
| Ia.652 | CF₃ | H | 3-OCF₃ | 4-OCF₃ | 5-CF₃ | |
| Ia.653 | CF₃ | H | 3-fluoro | 4-OCF₃ | 5-OCH₃ | |
| Ia.654 | CF₃ | H | 3-chloro | 4-OCF₃ | 5-OCH₃ | |
| Ia.655 | CF₃ | H | 3-CN | 4-OCF₃ | 5-OCH₃ | |
| Ia.656 | CF₃ | H | 3-CH₃ | 4-OCF₃ | 5-OCH₃ | |
| Ia.657 | CF₃ | H | 3-CF₃ | 4-OCF₃ | 5-OCH₃ | |
| Ia.658 | CF₃ | H | 3-OCH₃ | 4-OCF₃ | 5-OCH₃ | |
| Ia.659 | CF₃ | H | 3-OCF₃ | 4-OCF₃ | 5-OCH₃ | |
| Ia.660 | CF₃ | H | 3-fluoro | 4-OCF₃ | 5-OCF₃ | |
| Ia.661 | CF₃ | H | 3-chloro | 4-OCF₃ | 5-OCF₃ | |
| Ia.662 | CF₃ | H | 3-CN | 4-OCF₃ | 5-OCF₃ | |
| Ia.663 | CF₃ | H | 3-CH₃ | 4-OCF₃ | 5-OCF₃ | |
| Ia.664 | CF₃ | H | 3-CF₃ | 4-OCF₃ | 5-OCF₃ | |
| Ia.665 | CF₃ | H | 3-OCH₃ | 4-OCF₃ | 5-OCF₃ | |
| Ia.666 | CF₃ | H | 3-OCF₃ | 4-OCF₃ | 5-OCF₃ | |
| Ia.667 | CF₃ | H | 2-fluoro | 4-fluoro | 5-fluoro | 110-113 |
| Ia.668 | CF₃ | H | 2-fluoro | 4-fluoro | 5-chloro | |
| Ia.669 | CF₃ | H | 2-fluoro | 4-fluoro | 5-CN | |
| Ia.670 | CF₃ | H | 2-fluoro | 4-fluoro | 5-CH₃ | |
| Ia.671 | CF₃ | H | 2-fluoro | 4-fluoro | 5-CF₃ | |
| Ia.672 | CF₃ | H | 2-fluoro | 4-fluoro | 5-OCH₃ | |
| Ia.673 | CF₃ | H | 2-fluoro | 4-fluoro | 5-OCF₃ | |
| Ia.674 | CF₃ | H | 2-chloro | 4-fluoro | 5-fluoro | |
| Ia.675 | CF₃ | H | 2-chloro | 4-fluoro | 5-chloro | |
| Ia.676 | CF₃ | H | 2-chloro | 4-fluoro | 5-CN | |
| Ia.677 | CF₃ | H | 2-chloro | 4-fluoro | 5-CH₃ | |
| Ia.678 | CF₃ | H | 2-chloro | 4-fluoro | 5-CF₃ | |
| Ia.679 | CF₃ | H | 2-chloro | 4-fluoro | 5-OCH₃ | |
| Ia.680 | CF₃ | H | 2-chloro | 4-fluoro | 5-OCF₃ | |
| Ia.681 | CF₃ | H | 2-CN | 4-fluoro | 5-fluoro | |
| Ia.682 | CF₃ | H | 2-CN | 4-fluoro | 5-chloro | |
| Ia.683 | CF₃ | H | 2-CN | 4-fluoro | 5-CN | |
| Ia.684 | CF₃ | H | 2-CN | 4-fluoro | 5-CH₃ | |
| Ia.685 | CF₃ | H | 2-CN | 4-fluoro | 5-CF₃ | |
| Ia.686 | CF₃ | H | 2-CN | 4-fluoro | 5-OCH₃ | |
| Ia.687 | CF₃ | H | 2-CN | 4-fluoro | 5-OCF₃ | |
| Ia.688 | CF₃ | H | 2-methyl | 4-fluoro | 5-fluoro | |
| Ia.689 | CF₃ | H | 2-methyl | 4-fluoro | 5-chloro | |
| Ia.690 | CF₃ | H | 2-methyl | 4-fluoro | 5-CN | |
| Ia.691 | CF₃ | H | 2-methyl | 4-fluoro | 5-CH₃ | |
| Ia.692 | CF₃ | H | 2-methyl | 4-fluoro | 5-CF₃ | |
| Ia.693 | CF₃ | H | 2-methyl | 4-fluoro | 5-OCH₃ | |
| Ia.694 | CF₃ | H | 2-methyl | 4-fluoro | 5-OCF₃ | |
| Ia.695 | CF₃ | H | 2-CF₃ | 4-fluoro | 5-fluoro | |
| Ia.696 | CF₃ | H | 2-CF₃ | 4-fluoro | 5-chloro | |
| Ia.697 | CF₃ | H | 2-CF₃ | 4-fluoro | 5-CN | |
| Ia.698 | CF₃ | H | 2-CF₃ | 4-fluoro | 5-CH₃ | |
| Ia.699 | CF₃ | H | 2-CF₃ | 4-fluoro | 5-CF₃ | |
| Ia.700 | CF₃ | H | 2-CF₃ | 4-fluoro | 5-OCH₃ | |
| Ia.701 | CF₃ | H | 2-CF₃ | 4-fluoro | 5-OCF₃ | |
| Ia.702 | CF₃ | H | 2-OCH₃ | 4-fluoro | 5-fluoro | |
| Ia.703 | CF₃ | H | 2-OCH₃ | 4-fluoro | 5-chloro | |
| Ia.704 | CF₃ | H | 2-OCH₃ | 4-fluoro | 5-CN | |
| Ia.705 | CF₃ | H | 2-OCH₃ | 4-fluoro | 5-CH₃ | |
| Ia.706 | CF₃ | H | 2-OCH₃ | 4-fluoro | 5-CF₃ | |
| Ia.707 | CF₃ | H | 2-OCH₃ | 4-fluoro | 5-OCH₃ | |
| Ia.708 | CF₃ | H | 2-OCH₃ | 4-fluoro | 5-OCF₃ | |
| Ia.709 | CF₃ | H | 2-OCF₃ | 4-fluoro | 5-fluoro | |
| Ia.710 | CF₃ | H | 2-OCF₃ | 4-fluoro | 5-chloro | |
| Ia.711 | CF₃ | H | 2-OCF₃ | 4-fluoro | 5-CN | |
| Ia.712 | CF₃ | H | 2-OCF₃ | 4-fluoro | 5-CH₃ | |
| Ia.713 | CF₃ | H | 2-OCF₃ | 4-fluoro | 5-CF₃ | |
| Ia.714 | CF₃ | H | 2-OCF₃ | 4-fluoro | 5-OCH₃ | |
| Ia.715 | CF₃ | H | 2-OCF₃ | 4-fluoro | 5-OCF₃ | |
| Ia.716 | CF₃ | H | 2-fluoro | 4-chloro | 5-fluoro | |
| Ia.717 | CF₃ | H | 2-fluoro | 4-chloro | 5-chloro | |
| Ia.718 | CF₃ | H | 2-fluoro | 4-chloro | 5-CN | |
| Ia.719 | CF₃ | H | 2-fluoro | 4-chloro | 5-CH₃ | 106-108 |
| Ia.720 | CF₃ | H | 2-fluoro | 4-chloro | 5-CF₃ | |
| Ia.721 | CF₃ | H | 2-fluoro | 4-chloro | 5-OCH₃ | 119-121 |
| Ia.722 | CF₃ | H | 2-fluoro | 4-chloro | 5-OCF₃ | |
| Ia.723 | CF₃ | H | 2-chloro | 4-chloro | 5-fluoro | |
| Ia.724 | CF₃ | H | 2-chloro | 4-chloro | 5-chloro | |
| Ia.725 | CF₃ | H | 2-chloro | 4-chloro | 5-CN | |
| Ia.726 | CF₃ | H | 2-chloro | 4-chloro | 5-CH₃ | |
| Ia.727 | CF₃ | H | 2-chloro | 4-chloro | 5-CF₃ | |
| Ia.728 | CF₃ | H | 2-chloro | 4-chloro | 5-OCH₃ | |
| Ia.729 | CF₃ | H | 2-chloro | 4-chloro | 5-OCF₃ | |
| Ia.730 | CF₃ | H | 2-CN | 4-chloro | 5-fluoro | |
| Ia.731 | CF₃ | H | 2-CN | 4-chloro | 5-chloro | |
| Ia.732 | CF₃ | H | 2-CN | 4-chloro | 5-CN | |
| Ia.733 | CF₃ | H | 2-CN | 4-chloro | 5-CH₃ | |
| Ia.734 | CF₃ | H | 2-CN | 4-chloro | 5-CF₃ | |
| Ia.735 | CF₃ | H | 2-CN | 4-chloro | 5-OCH₃ | |
| Ia.736 | CF₃ | H | 2-CN | 4-chloro | 5-OCF₃ | |
| Ia.737 | CF₃ | H | 2-methyl | 4-chloro | 5-fluoro | |
| Ia.738 | CF₃ | H | 2-methyl | 4-chloro | 5-chloro | |
| Ia.739 | CF₃ | H | 2-methyl | 4-chloro | 5-CN | |
| Ia.740 | CF₃ | H | 2-methyl | 4-chloro | 5-CH₃ | |
| Ia.741 | CF₃ | H | 2-methyl | 4-chloro | 5-CF₃ | |
| Ia.742 | CF₃ | H | 2-methyl | 4-chloro | 5-OCH₃ | |
| Ia.743 | CF₃ | H | 2-methyl | 4-chloro | 5-OCF₃ | |
| Ia.744 | CF₃ | H | 2-CF₃ | 4-chloro | 5-fluoro | |
| Ia.745 | CF₃ | H | 2-CF₃ | 4-chloro | 5-chloro | |
| Ia.746 | CF₃ | H | 2-CF₃ | 4-chloro | 5-CN | |

TABLE 2-continued

| Compound No. | R¹ | R² | R³ | R⁴ | R⁵ | M.p. [° C.] |
|---|---|---|---|---|---|---|
| Ia.747 | CF₃ | H | 2-CF₃ | 4-chloro | 5-CH₃ | |
| Ia.748 | CF₃ | H | 2-CF₃ | 4-chloro | 5-CF₃ | |
| Ia.749 | CF₃ | H | 2-CF₃ | 4-chloro | 5-OCH₃ | |
| Ia.750 | CF₃ | H | 2-CF₃ | 4-chloro | 5-OCF₃ | |
| Ia.751 | CF₃ | H | 2-OCH₃ | 4-chloro | 5-fluoro | |
| Ia.752 | CF₃ | H | 2-OCH₃ | 4-chloro | 5-chloro | |
| Ia.753 | CF₃ | H | 2-OCH₃ | 4-chloro | 5-CN | |
| Ia.754 | CF₃ | H | 2-OCH₃ | 4-chloro | 5-CH₃ | |
| Ia.755 | CF₃ | H | 2-OCH₃ | 4-chloro | 5-CF₃ | |
| Ia.756 | CF₃ | H | 2-OCH₃ | 4-chloro | 5-OCH₃ | |
| Ia.757 | CF₃ | H | 2-OCH₃ | 4-chloro | 5-OCF₃ | |
| Ia.758 | CF₃ | H | 2-OCF₃ | 4-chloro | 5-fluoro | |
| Ia.759 | CF₃ | H | 2-OCF₃ | 4-chloro | 5-chloro | |
| Ia.760 | CF₃ | H | 2-OCF₃ | 4-chloro | 5-CN | |
| Ia.761 | CF₃ | H | 2-OCF₃ | 4-chloro | 5-CH₃ | |
| Ia.762 | CF₃ | H | 2-OCF₃ | 4-chloro | 5-CF₃ | |
| Ia.763 | CF₃ | H | 2-OCF₃ | 4-chloro | 5-OCH₃ | |
| Ia.764 | CF₃ | H | 2-OCF₃ | 4-chloro | 5-OCF₃ | |
| Ia.765 | CF₃ | H | 2-fluoro | 4-CN | 5-fluoro | |
| Ia.766 | CF₃ | H | 2-fluoro | 4-CN | 5-chloro | |
| Ia.767 | CF₃ | H | 2-fluoro | 4-CN | 5-CN | |
| Ia.768 | CF₃ | H | 2-fluoro | 4-CN | 5-CH₃ | |
| Ia.769 | CF₃ | H | 2-fluoro | 4-CN | 5-CF₃ | |
| Ia.770 | CF₃ | H | 2-fluoro | 4-CN | 5-OCH₃ | |
| Ia.771 | CF₃ | H | 2-fluoro | 4-CN | 5-OCF₃ | |
| Ia.772 | CF₃ | H | 2-fluoro | 4-CN | 5-fluoro | |
| Ia.773 | CF₃ | H | 2-chloro | 4-CN | 5-chloro | |
| Ia.774 | CF₃ | H | 2-chloro | 4-CN | 5-CN | |
| Ia.775 | CF₃ | H | 2-chloro | 4-CN | 5-CH₃ | |
| Ia.776 | CF₃ | H | 2-chloro | 4-CN | 5-CF₃ | |
| Ia.777 | CF₃ | H | 2-chloro | 4-CN | 5-OCH₃ | |
| Ia.778 | CF₃ | H | 2-chloro | 4-CN | 5-OCF₃ | |
| Ia.779 | CF₃ | H | 2-CN | 4-CN | 5-fluoro | |
| Ia.780 | CF₃ | H | 2-CN | 4-CN | 5-chloro | |
| Ia.781 | CF₃ | H | 2-CN | 4-CN | 5-CN | |
| Ia.782 | CF₃ | H | 2-CN | 4-CN | 5-CH₃ | |
| Ia.783 | CF₃ | H | 2-CN | 4-CN | 5-CF₃ | |
| Ia.784 | CF₃ | H | 2-CN | 4-CN | 5-OCH₃ | |
| Ia.785 | CF₃ | H | 2-CN | 4-CN | 5-OCF₃ | |
| Ia.786 | CF₃ | H | 2-methyl | 4-CN | 5-fluoro | |
| Ia.787 | CF₃ | H | 2-methyl | 4-CN | 5-chloro | |
| Ia.788 | CF₃ | H | 2-methyl | 4-CN | 5-CN | |
| Ia.789 | CF₃ | H | 2-methyl | 4-CN | 5-CH₃ | |
| Ia.790 | CF₃ | H | 2-methyl | 4-CN | 5-CF₃ | |
| Ia.791 | CF₃ | H | 2-methyl | 4-CN | 5-OCH₃ | |
| Ia.792 | CF₃ | H | 2-methyl | 4-CN | 5-OCF₃ | |
| Ia.793 | CF₃ | H | 2-CF₃ | 4-CN | 5-fluoro | |
| Ia.794 | CF₃ | H | 2-CF₃ | 4-CN | 5-chloro | |
| Ia.795 | CF₃ | H | 2-CF₃ | 4-CN | 5-CN | |
| Ia.796 | CF₃ | H | 2-CF₃ | 4-CN | 5-CH₃ | |
| Ia.797 | CF₃ | H | 2-CF₃ | 4-CN | 5-CF₃ | |
| Ia.798 | CF₃ | H | 2-CF₃ | 4-CN | 5-OCH₃ | |
| Ia.799 | CF₃ | H | 2-CF₃ | 4-CN | 5-OCF₃ | |
| Ia.800 | CF₃ | H | 2-OCH₃ | 4-CN | 5-fluoro | |
| Ia.801 | CF₃ | H | 2-OCH₃ | 4-CN | 5-chloro | |
| Ia.802 | CF₃ | H | 2-OCH₃ | 4-CN | 5-CN | |
| Ia.803 | CF₃ | H | 2-OCH₃ | 4-CN | 5-CH₃ | |
| Ia.804 | CF₃ | H | 2-OCH₃ | 4-CN | 5-CF₃ | |
| Ia.805 | CF₃ | H | 2-OCH₃ | 4-CN | 5-OCH₃ | |
| Ia.806 | CF₃ | H | 2-OCH₃ | 4-CN | 5-OCF₃ | |
| Ia.807 | CF₃ | H | 2-OCF₃ | 4-CN | 5-fluoro | |
| Ia.808 | CF₃ | H | 2-OCF₃ | 4-CN | 5-chloro | |
| Ia.809 | CF₃ | H | 2-OCF₃ | 4-CN | 5-CN | |
| Ia.810 | CF₃ | H | 2-OCF₃ | 4-CN | 5-CH₃ | |
| Ia.811 | CF₃ | H | 2-OCF₃ | 4-CN | 5-CF₃ | |
| Ia.812 | CF₃ | H | 2-OCF₃ | 4-CN | 5-OCH₃ | |
| Ia.813 | CF₃ | H | 2-OCF₃ | 4-CN | 5-OCF₃ | |
| Ia.814 | CF₃ | H | 2-fluoro | 4-CH₃ | 5-fluoro | |
| Ia.815 | CF₃ | H | 2-fluoro | 4-CH₃ | 5-chloro | |
| Ia.816 | CF₃ | H | 2-fluoro | 4-CH₃ | 5-CN | |
| Ia.817 | CF₃ | H | 2-fluoro | 4-CH₃ | 5-CH₃ | |
| Ia.818 | CF₃ | H | 2-fluoro | 4-CH₃ | 5-CF₃ | |
| Ia.819 | CF₃ | H | 2-fluoro | 4-CH₃ | 5-OCH₃ | |
| Ia.820 | CF₃ | H | 2-fluoro | 4-CH₃ | 5-OCF₃ | |
| Ia.821 | CF₃ | H | 2-chloro | 4-CH₃ | 5-fluoro | |
| Ia.822 | CF₃ | H | 2-chloro | 4-CH₃ | 5-chloro | |
| Ia.823 | CF₃ | H | 2-chloro | 4-CH₃ | 5-CN | |
| Ia.824 | CF₃ | H | 2-chloro | 4-CH₃ | 5-CH₃ | |
| Ia.825 | CF₃ | H | 2-chloro | 4-CH₃ | 5-CF₃ | |
| Ia.826 | CF₃ | H | 2-chloro | 4-CH₃ | 5-OCH₃ | |
| Ia.827 | CF₃ | H | 2-chloro | 4-CH₃ | 5-OCF₃ | |
| Ia.828 | CF₃ | H | 2-CN | 4-CH₃ | 5-fluoro | |
| Ia.829 | CF₃ | H | 2-CN | 4-CH₃ | 5-chloro | |
| Ia.830 | CF₃ | H | 2-CN | 4-CH₃ | 5-CN | |
| Ia.831 | CF₃ | H | 2-CN | 4-CH₃ | 5-CH₃ | |
| Ia.832 | CF₃ | H | 2-CN | 4-CH₃ | 5-CF₃ | |
| Ia.833 | CF₃ | H | 2-CN | 4-CH₃ | 5-OCH₃ | |
| Ia.834 | CF₃ | H | 2-CN | 4-CH₃ | 5-OCF₃ | |
| Ia.835 | CF₃ | H | 2-methyl | 4-CH₃ | 5-fluoro | |
| Ia.836 | CF₃ | H | 2-methyl | 4-CH₃ | 5-chloro | |
| Ia.837 | CF₃ | H | 2-methyl | 4-CH₃ | 5-CN | |
| Ia.838 | CF₃ | H | 2-methyl | 4-CH₃ | 5-CH₃ | |
| Ia.839 | CF₃ | H | 2-methyl | 4-CH₃ | 5-CF₃ | |
| Ia.840 | CF₃ | H | 2-methyl | 4-CH₃ | 5-OCH₃ | |
| Ia.841 | CF₃ | H | 2-methyl | 4-CH₃ | 5-OCF₃ | |
| Ia.842 | CF₃ | H | 2-CF₃ | 4-CH₃ | 5-fluoro | |
| Ia.843 | CF₃ | H | 2-CF₃ | 4-CH₃ | 5-chloro | |
| Ia.844 | CF₃ | H | 2-CF₃ | 4-CH₃ | 5-CN | |
| Ia.845 | CF₃ | H | 2-CF₃ | 4-CH₃ | 5-CH₃ | |
| Ia.846 | CF₃ | H | 2-CF₃ | 4-CH₃ | 5-CF₃ | |
| Ia.847 | CF₃ | H | 2-CF₃ | 4-CH₃ | 5-OCH₃ | |
| Ia.848 | CF₃ | H | 2-CF₃ | 4-CH₃ | 5-OCF₃ | |
| Ia.849 | CF₃ | H | 2-OCH₃ | 4-CH₃ | 5-fluoro | |
| Ia.850 | CF₃ | H | 2-OCH₃ | 4-CH₃ | 5-chloro | |
| Ia.851 | CF₃ | H | 2-OCH₃ | 4-CH₃ | 5-CN | |
| Ia.852 | CF₃ | H | 2-OCH₃ | 4-CH₃ | 5-CH₃ | |
| Ia.853 | CF₃ | H | 2-OCH₃ | 4-CH₃ | 5-CF₃ | |
| Ia.854 | CF₃ | H | 2-OCH₃ | 4-CH₃ | 5-OCH₃ | |
| Ia.855 | CF₃ | H | 2-OCH₃ | 4-CH₃ | 5-OCF₃ | |
| Ia.856 | CF₃ | H | 2-OCF₃ | 4-CH₃ | 5-fluoro | |
| Ia.857 | CF₃ | H | 2-OCF₃ | 4-CH₃ | 5-chloro | |
| Ia.858 | CF₃ | H | 2-OCF₃ | 4-CH₃ | 5-CN | |
| Ia.859 | CF₃ | H | 2-OCF₃ | 4-CH₃ | 5-CH₃ | |
| Ia.860 | CF₃ | H | 2-OCF₃ | 4-CH₃ | 5-CF₃ | |
| Ia.861 | CF₃ | H | 2-OCF₃ | 4-CH₃ | 5-OCH₃ | |
| Ia.862 | CF₃ | H | 2-OCF₃ | 4-CH₃ | 5-OCF₃ | |
| Ia.863 | CF₃ | H | 2-fluoro | 4-CF₃ | 5-fluoro | |
| Ia.864 | CF₃ | H | 2-fluoro | 4-CF₃ | 5-chloro | |
| Ia.865 | CF₃ | H | 2-fluoro | 4-CF₃ | 5-CN | |
| Ia.866 | CF₃ | H | 2-fluoro | 4-CF₃ | 5-CH₃ | |
| Ia.867 | CF₃ | H | 2-fluoro | 4-CF₃ | 5-CF₃ | |
| Ia.868 | CF₃ | H | 2-fluoro | 4-CF₃ | 5-OCH₃ | |
| Ia.869 | CF₃ | H | 2-fluoro | 4-CF₃ | 5-OCF₃ | |
| Ia.870 | CF₃ | H | 2-chloro | 4-CF₃ | 5-fluoro | |
| Ia.871 | CF₃ | H | 2-chloro | 4-CF₃ | 5-chloro | |
| Ia.872 | CF₃ | H | 2-chloro | 4-CF₃ | 5-CN | |
| Ia.873 | CF₃ | H | 2-chloro | 4-CF₃ | 5-CH₃ | |
| Ia.874 | CF₃ | H | 2-chloro | 4-CF₃ | 5-CF₃ | |
| Ia.875 | CF₃ | H | 2-chloro | 4-CF₃ | 5-OCH₃ | |
| Ia.876 | CF₃ | H | 2-chloro | 4-CF₃ | 5-OCF₃ | |
| Ia.877 | CF₃ | H | 2-CN | 4-CF₃ | 5-fluoro | |
| Ia.878 | CF₃ | H | 2-CN | 4-CF₃ | 5-chloro | |
| Ia.879 | CF₃ | H | 2-CN | 4-CF₃ | 5-CN | |
| Ia.880 | CF₃ | H | 2-CN | 4-CF₃ | 5-CH₃ | |
| Ia.881 | CF₃ | H | 2-CN | 4-CF₃ | 5-CF₃ | |
| Ia.882 | CF₃ | H | 2-CN | 4-CF₃ | 5-OCH₃ | |
| Ia.883 | CF₃ | H | 2-CN | 4-CF₃ | 5-OCF₃ | |
| Ia.884 | CF₃ | H | 2-methyl | 4-CF₃ | 5-fluoro | |
| Ia.885 | CF₃ | H | 2-methyl | 4-CF₃ | 5-chloro | |
| Ia.886 | CF₃ | H | 2-methyl | 4-CF₃ | 5-CN | |
| Ia.887 | CF₃ | H | 2-methyl | 4-CF₃ | 5-CH₃ | |
| Ia.888 | CF₃ | H | 2-methyl | 4-CF₃ | 5-CF₃ | |
| Ia.889 | CF₃ | H | 2-methyl | 4-CF₃ | 5-OCH₃ | |
| Ia.890 | CF₃ | H | 2-methyl | 4-CF₃ | 5-OCF₃ | |
| Ia.891 | CF₃ | H | 2-CF₃ | 4-CF₃ | 5-fluoro | |
| Ia.892 | CF₃ | H | 2-CF₃ | 4-CF₃ | 5-chloro | |
| Ia.893 | CF₃ | H | 2-CF₃ | 4-CF₃ | 5-CN | |
| Ia.894 | CF₃ | H | 2-CF₃ | 4-CF₃ | 5-CH₃ | |
| Ia.895 | CF₃ | H | 2-CF₃ | 4-CF₃ | 5-CF₃ | |
| Ia.896 | CF₃ | H | 2-CF₃ | 4-CF₃ | 5-OCH₃ | |
| Ia.897 | CF₃ | H | 2-CF₃ | 4-CF₃ | 5-OCF₃ | |
| Ia.898 | CF₃ | H | 2-OCH₃ | 4-CF₃ | 5-fluoro | |
| Ia.899 | CF₃ | H | 2-OCH₃ | 4-CF₃ | 5-chloro | |
| Ia.900 | CF₃ | H | 2-OCH₃ | 4-CF₃ | 5-CN | |

TABLE 2-continued

| Compound No. | R¹ | R² | R³ | R⁴ | R⁵ | M.p. [° C.] |
|---|---|---|---|---|---|---|
| Ia.901 | CF₃ | H | 2-OCH₃ | 4-CF₃ | 5-CH₃ | |
| Ia.902 | CF₃ | H | 2-OCH₃ | 4-CF₃ | 5-CF₃ | |
| Ia.903 | CF₃ | H | 2-OCH₃ | 4-CF₃ | 5-OCH₃ | |
| Ia.904 | CF₃ | H | 2-OCH₃ | 4-CF₃ | 5-OCF₃ | |
| Ia.905 | CF₃ | H | 2-OCF₃ | 4-CF₃ | 5-fluoro | |
| Ia.906 | CF₃ | H | 2-OCF₃ | 4-CF₃ | 5-chloro | |
| Ia.907 | CF₃ | H | 2-OCF₃ | 4-CF₃ | 5-CN | |
| Ia.908 | CF₃ | H | 2-OCF₃ | 4-CF₃ | 5-CH₃ | |
| Ia.909 | CF₃ | H | 2-OCF₃ | 4-CF₃ | 5-CF₃ | |
| Ia.910 | CF₃ | H | 2-OCF₃ | 4-CF₃ | 5-OCH₃ | |
| Ia.911 | CF₃ | H | 2-OCF₃ | 4-CF₃ | 5-OCF₃ | |
| Ia.912 | CF₃ | H | 2-fluoro | 4-OCH₃ | 5-fluoro | |
| Ia.913 | CF₃ | H | 2-fluoro | 4-OCH₃ | 5-chloro | |
| Ia.914 | CF₃ | H | 2-fluoro | 4-OCH₃ | 5-CN | |
| Ia.915 | CF₃ | H | 2-fluoro | 4-OCH₃ | 5-CH₃ | |
| Ia.916 | CF₃ | H | 2-fluoro | 4-OCH₃ | 5-CF₃ | |
| Ia.917 | CF₃ | H | 2-fluoro | 4-OCH₃ | 5-OCH₃ | |
| Ia.918 | CF₃ | H | 2-fluoro | 4-OCH₃ | 5-OCF₃ | |
| Ia.919 | CF₃ | H | 2-chloro | 4-OCH₃ | 5-fluoro | |
| Ia.920 | CF₃ | H | 2-chloro | 4-OCH₃ | 5-chloro | |
| Ia.921 | CF₃ | H | 2-chloro | 4-OCH₃ | 5-CN | |
| Ia.922 | CF₃ | H | 2-chloro | 4-OCH₃ | 5-CH₃ | |
| Ia.923 | CF₃ | H | 2-chloro | 4-OCH₃ | 5-CF₃ | |
| Ia.924 | CF₃ | H | 2-chloro | 4-OCH₃ | 5-OCH₃ | |
| Ia.925 | CF₃ | H | 2-chloro | 4-OCH₃ | 5-OCF₃ | |
| Ia.926 | CF₃ | H | 2-CN | 4-OCH₃ | 5-fluoro | |
| Ia.927 | CF₃ | H | 2-CN | 4-OCH₃ | 5-chloro | |
| Ia.928 | CF₃ | H | 2-CN | 4-OCH₃ | 5-CN | |
| Ia.929 | CF₃ | H | 2-CN | 4-OCH₃ | 5-CH₃ | |
| Ia.930 | CF₃ | H | 2-CN | 4-OCH₃ | 5-CF₃ | |
| Ia.931 | CF₃ | H | 2-CN | 4-OCH₃ | 5-OCH₃ | |
| Ia.932 | CF₃ | H | 2-CN | 4-OCH₃ | 5-OCF₃ | |
| Ia.933 | CF₃ | H | 2-methyl | 4-OCH₃ | 5-fluoro | |
| Ia.934 | CF₃ | H | 2-methyl | 4-OCH₃ | 5-chloro | |
| Ia.935 | CF₃ | H | 2-methyl | 4-OCH₃ | 5-CN | |
| Ia.936 | CF₃ | H | 2-methyl | 4-OCH₃ | 5-CH₃ | |
| Ia.937 | CF₃ | H | 2-methyl | 4-OCH₃ | 5-CF₃ | |
| Ia.938 | CF₃ | H | 2-methyl | 4-OCH₃ | 5-OCH₃ | |
| Ia.939 | CF₃ | H | 2-methyl | 4-OCH₃ | 5-OCF₃ | |
| Ia.940 | CF₃ | H | 2-CF₃ | 4-OCH₃ | 5-fluoro | |
| Ia.941 | CF₃ | H | 2-CF₃ | 4-OCH₃ | 5-chloro | |
| Ia.942 | CF₃ | H | 2-CF₃ | 4-OCH₃ | 5-CN | |
| Ia.943 | CF₃ | H | 2-CF₃ | 4-OCH₃ | 5-CH₃ | |
| Ia.944 | CF₃ | H | 2-CF₃ | 4-OCH₃ | 5-CF₃ | |
| Ia.945 | CF₃ | H | 2-CF₃ | 4-OCH₃ | 5-OCH₃ | |
| Ia.946 | CF₃ | H | 2-CF₃ | 4-OCH₃ | 5-OCF₃ | |
| Ia.947 | CF₃ | H | 2-OCH₃ | 4-OCH₃ | 5-fluoro | |
| Ia.948 | CF₃ | H | 2-OCH₃ | 4-OCH₃ | 5-chloro | |
| Ia.949 | CF₃ | H | 2-OCH₃ | 4-OCH₃ | 5-CN | |
| Ia.950 | CF₃ | H | 2-OCH₃ | 4-OCH₃ | 5-CH₃ | |
| Ia.951 | CF₃ | H | 2-OCH₃ | 4-OCH₃ | 5-CF₃ | |
| Ia.952 | CF₃ | H | 2-OCH₃ | 4-OCH₃ | 5-OCH₃ | |
| Ia.953 | CF₃ | H | 2-OCH₃ | 4-OCH₃ | 5-OCF₃ | |
| Ia.954 | CF₃ | H | 2-OCF₃ | 4-OCH₃ | 5-fluoro | |
| Ia.955 | CF₃ | H | 2-OCF₃ | 4-OCH₃ | 5-chloro | |
| Ia.956 | CF₃ | H | 2-OCF₃ | 4-OCH₃ | 5-CN | |
| Ia.957 | CF₃ | H | 2-OCF₃ | 4-OCH₃ | 5-CH₃ | |
| Ia.958 | CF₃ | H | 2-OCF₃ | 4-OCH₃ | 5-CF₃ | |
| Ia.959 | CF₃ | H | 2-OCF₃ | 4-OCH₃ | 5-OCH₃ | |
| Ia.960 | CF₃ | H | 2-OCF₃ | 4-OCH₃ | 5-OCF₃ | |
| Ia.961 | CF₃ | H | 2-fluoro | 4-OCF₃ | 5-fluoro | |
| Ia.962 | CF₃ | H | 2-fluoro | 4-OCF₃ | 5-chloro | |
| Ia.963 | CF₃ | H | 2-fluoro | 4-OCF₃ | 5-CN | |
| Ia.964 | CF₃ | H | 2-fluoro | 4-OCF₃ | 5-CH₃ | |
| Ia.965 | CF₃ | H | 2-fluoro | 4-OCF₃ | 5-CF₃ | |
| Ia.966 | CF₃ | H | 2-fluoro | 4-OCF₃ | 5-OCH₃ | |
| Ia.967 | CF₃ | H | 2-fluoro | 4-OCF₃ | 5-OCF₃ | |
| Ia.968 | CF₃ | H | 2-chloro | 4-OCF₃ | 5-fluoro | |
| Ia.969 | CF₃ | H | 2-chloro | 4-OCF₃ | 5-chloro | |
| Ia.970 | CF₃ | H | 2-chloro | 4-OCF₃ | 5-CN | |
| Ia.971 | CF₃ | H | 2-chloro | 4-OCF₃ | 5-CH₃ | |
| Ia.972 | CF₃ | H | 2-chloro | 4-OCF₃ | 5-CF₃ | |
| Ia.973 | CF₃ | H | 2-chloro | 4-OCF₃ | 5-OCH₃ | |
| Ia.974 | CF₃ | H | 2-chloro | 4-OCF₃ | 5-OCF₃ | |
| Ia.975 | CF₃ | H | 2-CN | 4-OCF₃ | 5-fluoro | |
| Ia.976 | CF₃ | H | 2-CN | 4-OCF₃ | 5-chloro | |
| Ia.977 | CF₃ | H | 2-CN | 4-OCF₃ | 5-CN | |
| Ia.978 | CF₃ | H | 2-CN | 4-OCF₃ | 5-CH₃ | |
| Ia.979 | CF₃ | H | 2-CN | 4-OCF₃ | 5-CF₃ | |
| Ia.980 | CF₃ | H | 2-CN | 4-OCF₃ | 5-OCH₃ | |
| Ia.981 | CF₃ | H | 2-CN | 4-OCF₃ | 5-OCF₃ | |
| Ia.982 | CF₃ | H | 2-methyl | 4-OCF₃ | 5-fluoro | |
| Ia.983 | CF₃ | H | 2-methyl | 4-OCF₃ | 5-chloro | |
| Ia.984 | CF₃ | H | 2-methyl | 4-OCF₃ | 5-CN | |
| Ia.985 | CF₃ | H | 2-methyl | 4-OCF₃ | 5-CH₃ | |
| Ia.986 | CF₃ | H | 2-methyl | 4-OCF₃ | 5-CF₃ | |
| Ia.987 | CF₃ | H | 2-methyl | 4-OCF₃ | 5-OCH₃ | |
| Ia.988 | CF₃ | H | 2-methyl | 4-OCF₃ | 5-OCF₃ | |
| Ia.989 | CF₃ | H | 2-CF₃ | 4-OCF₃ | 5-fluoro | |
| Ia.990 | CF₃ | H | 2-CF₃ | 4-OCF₃ | 5-chloro | |
| Ia.991 | CF₃ | H | 2-CF₃ | 4-OCF₃ | 5-CN | |
| Ia.992 | CF₃ | H | 2-CF₃ | 4-OCF₃ | 5-CH₃ | |
| Ia.993 | CF₃ | H | 2-CF₃ | 4-OCF₃ | 5-CF₃ | |
| Ia.994 | CF₃ | H | 2-CF₃ | 4-OCF₃ | 5-OCH₃ | |
| Ia.995 | CF₃ | H | 2-CF₃ | 4-OCF₃ | 5-OCF₃ | |
| Ia.996 | CF₃ | H | 2-OCH₃ | 4-OCF₃ | 5-fluoro | |
| Ia.997 | CF₃ | H | 2-OCH₃ | 4-OCF₃ | 5-chloro | |
| Ia.998 | CF₃ | H | 2-OCH₃ | 4-OCF₃ | 5-CN | |
| Ia.999 | CF₃ | H | 2-OCH₃ | 4-OCF₃ | 5-CH₃ | |
| Ia.1000 | CF₃ | H | 2-OCH₃ | 4-OCF₃ | 5-CF₃ | |
| Ia.1001 | CF₃ | H | 2-OCH₃ | 4-OCF₃ | 5-OCH₃ | |
| Ia.1002 | CF₃ | H | 2-OCH₃ | 4-OCF₃ | 5-OCF₃ | |
| Ia.1003 | CF₃ | H | 2-OCF₃ | 4-OCF₃ | 5-fluoro | |
| Ia.1004 | CF₃ | H | 2-OCF₃ | 4-OCF₃ | 5-chloro | |
| Ia.1005 | CF₃ | H | 2-OCF₃ | 4-OCF₃ | 5-CN | |
| Ia.1006 | CF₃ | H | 2-OCF₃ | 4-OCF₃ | 5-CH₃ | |
| Ia.1007 | CF₃ | H | 2-OCF₃ | 4-OCF₃ | 5-CF₃ | |
| Ia.1008 | CF₃ | H | 2-OCF₃ | 4-OCF₃ | 5-OCH₃ | |
| Ia.1009 | CF₃ | H | 2-OCF₃ | 4-OCF₃ | 5-OCF₃ | |

Particular preference is furthermore given to 1-methylpyrazol-4-ylcarboxanilides of the formulae Ib to If, in particular to the compounds Ib.1 to Ib.1009 which differ from the corresponding compounds Ia.1 to Ia.1009 only in that R² is fluorine:

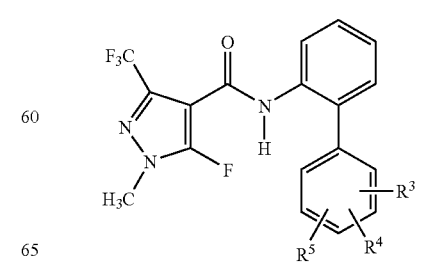

Ib the compounds Ic.1 to Ic.1009 which differ from the corresponding compounds Ia.1 to Ia.1009 only in that $R^2$ is chlorine:

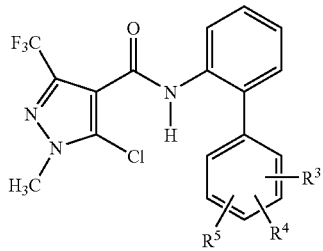

Ic the compounds Id.1 to Id.1009 which differ from the corresponding compounds Ia.1 to Ia.1009 only in that $R^1$ is difluoromethyl:

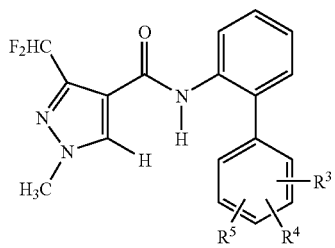

Id

| Compound | M.p. [° C.] |
|---|---|
| No. Id. 721 | 150-152 |
| No. Id. 719 | 120-122 |
| No. Id. 667 | 122-125 |
| No. Id. 344 | 156-158 | the compounds Ie.1 to Ie.1009 which differ from the corresponding compounds Ia.1 to Ia.1009 only in that $R^1$ is difluoromethyl and $R^2$ is fluorine:

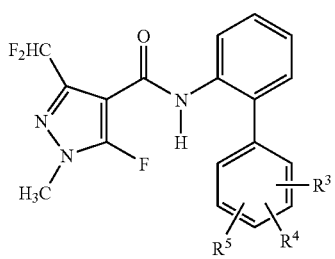

Ie the compounds If.1 to If.1009 which differ from the corresponding compounds Ia.1 to Ia.1009 only in that $R^1$ is difluoromethyl and $R^2$ is chlorine:

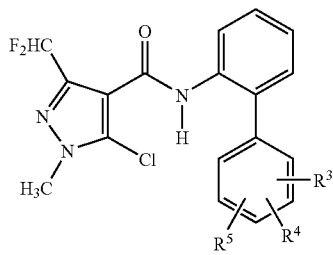

If the compounds Ig.1 to Ig.1009 which differ from the corresponding compounds Ia.1 to Ia.1009 only in that $R^1$ is fluoromethyl:

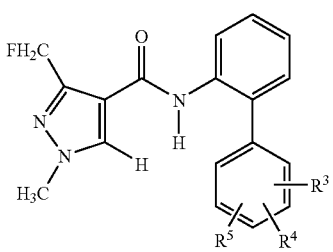

Ig

| Compound | M.p. [° C.] |
|---|---|
| No. Ig. 344 | 152-156 |
| No. Ig. 1 | 126-129 | the compounds Ih.1 to Ih.1009 which differ from the corresponding compounds Ia.1 to Ia.1009 only in that $R^1$ is $CF_2Cl$:

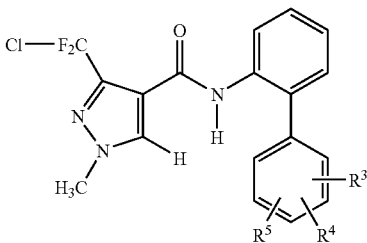

Ih

| Compound | M.p. [° C.] |
|---|---|
| No. Ih. 344 | 158-161 | the compounds Ij.1 to Ij.1009 which differ from the corresponding compounds Ia.1 to Ia.1009 only in that $R^1$ is chlorofluoromethyl:

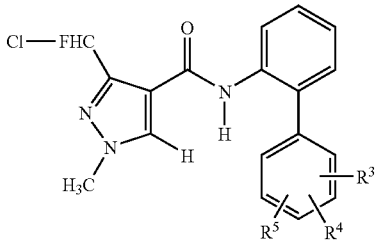

Ij

| Compound | M.p. [° C.] |
|---|---|
| No. Ij. 344 | 154-157 |

Very particular preference is given to N-(2'-fluoro-4'-chloro-5'-methoxybiphenyl-2-yl)-3-trifluoromethyl-1-methyl-1H-pyrazole-4-carboxamide, N-(2'-fluoro-4'-chloro-5'-methylbiphenyl-2-yl)-3-trifluoromethyl-1-methyl-1H-pyrazole-4-carboxamide, N-(3',4',5'-trifluorobiphenyl-2-yl)-3-trifluoro-methyl-1-methyl-1H-pyrazole-4-carboxamide, N-(2',4',5'-trifluorobiphenyl-2-yl)-3-tri-fluoromethyl-1-methyl-1H-pyrazole-4-carboxamide, N-(2'-fluoro-4'-chloro-5'-methoxy-biphenyl-2-yl)-3-difluoromethyl-1-methyl-1H-pyrazole-4-carboxamide, N-(2',3',4'-tri-fluorobiphenyl-2-yl)-3-trifluoromethyl-1-methyl-1H-pyrazole-4-carboxamide, N-(2'-fluoro-4'-chloro-5'-methylbiphenyl-2-yl)-3-difluoromethyl-1-methyl-1H-pyrazole-4-carboxamide, N-(3',4',5'-trifluorobiphenyl-2-yl)-3-difluoromethyl-1-methyl-1H-pyrazole-4-carboxamide, N-(2',4',5'-trifluorobiphenyl-2-yl)-3-difluoromethyl-1-methyl-1H-pyrazole-4-carboxamide, N-(3',4',5'-trifluorobiphenyl-2-yl)-3-fluoromethyl-1-methyl-1H-pyrazole-4-carboxamide, N-(3',4',5'-trifluorobiphenyl-2-yl)-3-chlorodifluoromethyl-1-methyl-1H-pyrazole-4-carboxamide, N-(3',4',5'-trifluorobiphenyl-2-yl)-3-chlorofluoromethyl-1-methyl-1H-pyrazole-4-carboxamide, N-(2',3',4'-trifluorobiphenyl-2-yl)-3-fluoro-methyl-1-methyl-1H-pyrazole-4-carboxamide and N-(2',4',5'-trifluorobiphenyl-2-yl)-3-fluoromethyl-1-methyl-1H-pyrazole-4-carboxamide.

Preference is given to mixtures of a compound of the formula I with at least one active compound selected from the group of the A) azoles.

Preference is also given to mixtures of a compound of the formula I with at least one active compound selected from the group of the B) strobilurins.

Preference is given to mixtures of a compound of the formula I with at least one active compound selected from the group of the C) carboxamides.

Preference is furthermore also given to mixtures of a compound of the formula I with at least one active compound selected from the group of the D) heterocyclic compounds.

Preference is furthermore also given to mixtures of a compound of the formula I with at least one active compound selected from the group of the E) carbamates.

Preference is furthermore also given to mixtures of a compound of the formula I with at least one active compound selected from the group of the F) other fungicides.

Preference is furthermore also given to mixtures of a compound of the formula I with at least one active compound selected from the group of the A) azoles selected from the group consisting of cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, cyazofamid, benomyl, carbendazim and ethaboxam.

Particular preference is also given to mixtures of a compound of the formula I with at least one active compound selected from the group of the A) azoles selected from the group consisting of cyproconazole, difenoconazole, epoxiconazole, fluquinconazole, flusilazole, flutriafol, metconazole, myclobutanil, propiconazole, prothioconazole, triadimefon, triadimenol, tebuconazole, tetraconazole, triticonazole, prochloraz, cyazofamid, benomyl and carbendazim.

Very particular preference is also given to mixtures of a compound of the formula I with at least one active compound selected from the group of the A) azoles selected from the group consisting of epoxiconazole, fluquinconazole, flutriafol, metconazole, tebuconazole, triticonazole, prochloraz and carbendazim.

Preference is also given to mixtures of a compound of the formula I with at least one active compound selected from the group of the B) strobilurins selected from the group consisting of azoxystrobin, dimoxystrobin, fluoxastrobin, kresoxim-methyl, orysastrobin, picoxystrobin, pyraclostrobin and trifloxystrobin.

Particular preference is also given to mixtures of a compound of the formula I with at least one active compound selected from the group of the B) strobilurins selected from the group consisting of kresoxim-methyl, orysastrobin and pyraclostrobin.

Very particular preference is also given to mixtures of a compound of the formula I with pyraclostrobin.

Preference is also given to mixtures of a compound of the formula I with at least one active compound selected from the group of the C) carboxamides selected from the group consisting of fenhexamid, metalaxyl, mefenoxam, ofurace, dimethomorph, flumorph, fluopicolide (picobenzamid), zoxamide, carpropamid and mandipropamid.

Particular preference is also given to mixtures of a compound of the formula I with at least one active compound selected from the group of the C) carboxamides selected from the group consisting of fenhexamid, metalaxyl, mefenoxam, ofurace, dimethomorph, zoxamide and carpropamid.

Preference is also given to mixtures of a compound of the formula I with at least one active compound selected from the group of the D) heterocyclic compounds selected from the group consisting of fluazinam, cyprodinil, fenarimol, mepanipyrim, pyrimethanil, triforine, fludioxonil, dodemorph, fenpropimorph, tridemorph, fenpropidin, iprodione, vinclozolin, famoxadone, fenamidone, probenazole, 5-chloro-7-(4-methyl-piperidin-1-yl)-6-(2,4,6-trifluorophenyl)-[1,2,4]triazolo[1,5-a]pyrimidine, proquinazid, acibenzolar-S-methyl, captafol, folpet, fenoxanil and quinoxyfen, in particular fluazinam, cyprodinil, fenarimol, mepanipyrim, pyrimethanil, triforine, fludioxonil, dodemorph, fenpropimorph, tridemorph, fenpropidin, iprodione, vinclozolin, famoxadone, fenamidone, probenazole, proquinazid, acibenzolar-S-methyl, captafol, folpet, fenoxanil and quinoxyfen.

Particular preference is also given to mixtures of a compound of the formula I with at least one active compound selected from the group of the D) heterocyclic compounds selected from the group consisting of pyrimethanil, dodemorph, fenpropimorph, tridemorph, iprodione, vinclozolin, 5-chloro-7-(4-methylpiperidin-1-yl)-6-(2,4,6-trifluoro-phenyl)-[1,2,4]triazolo[1,5-a]pyrimidine and quinoxyfen, in particular pyrimethanil, dodemorph, fenpropimorph, tridemorph, iprodione, vinclozolin and quinoxyfen.

Preference is also given to mixtures of a compound of the formula I with at least one active compound selected from the group of the E) carbamates selected from the group consisting of mancozeb, metiram, propineb, thiram, iprovalicarb, flubenthiavalicarb and propamocarb.

Particular preference is also given to mixtures of a compound of the formula I with at least one active compound selected from the group of the E) carbamates selected from the group consisting of mancozeb and metiram.

Preference is also given to mixtures of a compound of the formula I with at least one active compound selected from the group of the F) other fungicides selected from the group consisting of dithianon, fentin salts, such as fentin acetate, fosetyl, fosetyl-aluminum, phosphorous acid and its salts, chlorothalonil, dichlofluanid, thiophanate-methyl, copper acetate, copper hydroxide, copper oxychloride, basic copper sulfate, sulfur, cymoxanil, metrafenone and spiroxamine.

Particular preference is also given to mixtures of a compound of the formula I with at least one active compound selected from the group of the F) other fungicides selected from the group consisting of phosphorous acid and its salts, chlorothalonil and metrafenone.

Preference is also given to three-component mixtures of one compound of the formula I with two of the active compounds II mentioned above.

Preferred active compound combinations are listed in Tables 3 to 9 below:

TABLE 3

Active compound combinations of compounds
I with active compounds II of group A):

| Mixture | Compound of the formula I (X = oxygen) | Active compound II |
| --- | --- | --- |
| No. A.1 | $R^1 = CH_3; R^2 = H; R^3 = 3\text{-}F; R^4 = 4\text{-}F; R^5 = 5\text{-}F$ | epoxiconazole |
| No. A.2 | $R^1 = CH_3; R^2 = F; R^3 = 3\text{-}F; R^4 = 4\text{-}F; R^5 = 5\text{-}F$ | epoxiconazole |
| No. A.3 | $R^1 = CH_3; R^2 = Cl; R^3 = 3\text{-}F; R^4 = 4\text{-}F; R^5 = 5\text{-}F$ | epoxiconazole |
| No. A.4 | $R^1 = CH_2F; R^2 = H; R^3 = 3\text{-}F; R^4 = 4\text{-}F; R^5 = 5\text{-}F$ | epoxiconazole |
| No. A.5 | $R^1 = CHFCl; R^2 = H; R^3 = 3\text{-}F; R^4 = 4\text{-}F; R^5 = 5\text{-}F$ | epoxiconazole |
| No. A.6 | $R^1 = CHF_2; R^2 = H; R^3 = 3\text{-}F; R^4 = 4\text{-}F; R^5 = 5\text{-}F$ | epoxiconazole |
| No. A.7 | $R^1 = CHF_2; R^2 = F; R^3 = 3\text{-}F; R^4 = 4\text{-}F; R^5 = 5\text{-}F$ | epoxiconazole |
| No. A.8 | $R^1 = CHF_2; R^2 = Cl; R^6 = 3\text{-}F; R^4 = 4\text{-}F; R^5 = 5\text{-}F$ | epoxiconazole |
| No. A.9 | $R^1 = CF_2Cl; R^2 = H; R^3 = 3\text{-}F; R^4 = 4\text{-}F; R^5 = 5\text{-}F$ | epoxiconazole |
| No. A.10 | $R^1 = CF_3; R^2 = H; R^3 = 3\text{-}F; R^4 = 4\text{-}F; R^5 = 5\text{-}F$ | epoxiconazole |
| No. A.11 | $R^1 = CF_3; R^2 = F; R^3 = 3\text{-}F; R^4 = 4\text{-}F; R^5 = 5\text{-}F$ | epoxiconazole |
| No. A.12 | $R^1 = CF_3; R^2 = Cl; R^3 = 3\text{-}F; R^4 = 4\text{-}F; R^5 = 5\text{-}F$ | epoxiconazole |
| No. A.13 | $R^1 = CH_3; R^2 = H; R^3 = 2\text{-}F; R^4 = 4\text{-}F; R^5 = 5\text{-}F$ | epoxiconazole |
| No. A.14 | $R^1 = CH_3; R^2 = F; R^3 = 2\text{-}F; R^4 = 4\text{-}F; R^5 = 5\text{-}F$ | epoxiconazole |
| No. A.15 | $R^1 = CH_3; R^2 = Cl; R^3 = 2\text{-}F; R^4 = 4\text{-}F; R^5 = 5\text{-}F$ | epoxiconazole |
| No. A.16 | $R^1 = CH_2F; R^2 = H; R^3 = 2\text{-}F; R^4 = 4\text{-}F; R^5 = 5\text{-}F$ | epoxiconazole |
| No. A.17 | $R^1 = CHFCl; R^2 = H; R^3 = 2\text{-}F; R^4 = 4\text{-}F; R^5 = 5\text{-}F$ | epoxiconazole |
| No. A.18 | $R^1 = CHF_2; R^2 = H; R^3 = 2\text{-}F; R^4 = 4\text{-}F; R^5 = 5\text{-}F$ | epoxiconazole |
| No. A.19 | $R^1 = CHF_2; R^2 = F; R^3 = 2\text{-}F; R^4 = 4\text{-}F; R^5 = 5\text{-}F$ | epoxiconazole |
| No. A.20 | $R^1 = CHF_2; R^2 = Cl; R^3 = 2\text{-}F; R^4 = 4\text{-}F; R^5 = 5\text{-}F$ | epoxiconazole |
| No. A.21 | $R^1 = CF_2Cl; R^2 = H; R^3 = 2\text{-}F; R^4 = 4\text{-}F; R^5 = 5\text{-}F$ | epoxiconazole |
| No. A.22 | $R^1 = CF_3; R^2 = H; R^3 = 2\text{-}F; R^4 = 4\text{-}F; R^5 = 5\text{-}F$ | epoxiconazole |
| No. A.23 | $R^1 = CF_3; R^2 = F; R^3 = 2\text{-}F; R^4 = 4\text{-}F; R^5 = 5\text{-}F$ | epoxiconazole |
| No. A.24 | $R^1 = CF_3; R^2 = Cl; R^3 = 2\text{-}F; R^4 = 4\text{-}F; R^5 = 5\text{-}F$ | epoxiconazole |
| No. A.25 | $R^1 = CH_3; R^2 = H; R^3 = 3\text{-}F; R^4 = 4\text{-}F; R^5 = 5\text{-}F$ | metconazole |
| No. A.26 | $R^1 = CH_3; R^2 = F; R^3 = 3\text{-}F; R^4 = 4\text{-}F; R^5 = 5\text{-}F$ | metconazole |
| No. A.27 | $R^1 = CH_3; R^2 = Cl; R^3 = 3\text{-}F; R^4 = 4\text{-}F; R^5 = 5\text{-}F$ | metconazole |
| No. A.28 | $R^1 = CH_2F; R^2 = H; R^3 = 3\text{-}F; R^4 = 4\text{-}F; R^5 = 5\text{-}F$ | metconazole |
| No. A.29 | $R^1 = CHFCl; R^2 = H; R^3 = 3\text{-}F; R^4 = 4\text{-}F; R^5 = 5\text{-}F$ | metconazole |
| No. A.30 | $R^1 = CHF_2; R^2 = H; R^3 = 3\text{-}F; R^4 = 4\text{-}F; R^5 = 5\text{-}F$ | metconazole |
| No. A.31 | $R^1 = CHF_2; R^2 = F; R^3 = 3\text{-}F; R^4 = 4\text{-}F; R^5 = 5\text{-}F$ | metconazole |
| No. A.32 | $R^1 = CHF_2; R^2 = Cl; R^3 = 3\text{-}F; R^4 = 4\text{-}F; R^5 = 5\text{-}F$ | metconazole |
| No. A.33 | $R^1 = CF_2Cl; R^2 = H; R^3 = 3\text{-}F; R^4 = 4\text{-}F; R^5 = 5\text{-}F$ | metconazole |
| No. A.34 | $R^1 = CF_3; R^2 = H; R^3 = 3\text{-}F; R^4 = 4\text{-}F; R^5 = 5\text{-}F$ | metconazole |
| No. A.35 | $R^1 = CF_3; R^2 = F; R^3 = 3\text{-}F; R^4 = 4\text{-}F; R^5 = 5\text{-}F$ | metconazole |
| No. A.36 | $R^1 = CF_3; R^2 = Cl; R^3 = 3\text{-}F; R^4 = 4\text{-}F; R^5 = 5\text{-}F$ | metconazole |
| No. A.37 | $R^1 = CH_3; R^2 = H; R^3 = 2\text{-}F; R^4 = 4\text{-}F; R^5 = 5\text{-}F$ | metconazole |
| No. A.38 | $R^1 = CH_3; R^2 = F; R^3 = 2\text{-}F; R^4 = 4\text{-}F; R^5 = 5\text{-}F$ | metconazole |
| No. A.39 | $R^1 = CH_3; R^2 = Cl; R^3 = 2\text{-}F; R^4 = 4\text{-}F; R^5 = 5\text{-}F$ | metconazole |
| No. A.40 | $R^1 = CH_2F; R^2 = H; R^3 = 2\text{-}F; R^4 = 4\text{-}F; R^5 = 5\text{-}F$ | metconazole |
| No. A.41 | $R^1 = CHFCl; R^2 = H; R^3 = 2\text{-}F; R^4 = 4\text{-}F; R^5 = 5\text{-}F$ | metconazole |
| No. A.42 | $R^1 = CHF_2; R^2 = H; R^3 = 2\text{-}F; R^4 = 4\text{-}F; R^5 = 5\text{-}F$ | metconazole |
| No. A.43 | $R^1 = CHF_2; R^2 = F; R^3 = 2\text{-}F; R^4 = 4\text{-}F; R^5 = 5\text{-}F$ | metconazole |
| No. A.44 | $R^1 = CHF_2; R^2 = Cl; R^3 = 2\text{-}F; R^4 = 4\text{-}F; R^5 = 5\text{-}F$ | metconazole |
| No. A.45 | $R^1 = CF_2Cl; R^2 = H; R^3 = 2\text{-}F; R^4 = 4\text{-}F; R^5 = 5\text{-}F$ | metconazole |
| No. A.46 | $R^1 = CF_3; R^2 = H; R^3 = 2\text{-}F; R^4 = 4\text{-}F; R^5 = 5\text{-}F$ | metconazole |
| No. A.47 | $R^1 = CF_3; R^2 = F; R^3 = 2\text{-}F; R^4 = 4\text{-}F; R^5 = 5\text{-}F$ | metconazole |
| No. A.48 | $R^1 = CF_3; R^2 = Cl; R^3 = 2\text{-}F; R^4 = 4\text{-}F; R^5 = 5\text{-}F$ | metconazole |
| No. A.49 | $R^1 = CH_3; R^2 = H; R^3 = 3\text{-}F; R^4 = 4\text{-}F; R^5 = 5\text{-}F$ | tebuconazole |
| No. A.50 | $R^1 = CH_3; R^2 = F; R^3 = 3\text{-}F; R^4 = 4\text{-}F; R^5 = 5\text{-}F$ | tebuconazole |
| No. A.51 | $R^1 = CH_3; R^2 = Cl; R^3 = 3\text{-}F; R^4 = 4\text{-}F; R^5 = 5\text{-}F$ | tebuconazole |
| No. A.52 | $R^1 = CH_2F; R^2 = H; R^3 = 3\text{-}F; R^4 = 4\text{-}F; R^5 = 5\text{-}F$ | tebuconazole |
| No. A.53 | $R^1 = CHFCl; R^2 = H; R^3 = 3\text{-}F; R^4 = 4\text{-}F; R^5 = 5\text{-}F$ | tebuconazole |
| No. A.54 | $R^1 = CHF_2; R^2 = H; R^3 = 3\text{-}F; R^4 = 4\text{-}F; R^5 = 5\text{-}F$ | tebuconazole |

TABLE 3-continued

Active compound combinations of compounds
I with active compounds II of group A):

| Mixture | Compound of the formula I (X = oxygen) | Active compound II |
|---|---|---|
| No. A.55 | $R^1 = CHF_2; R^2 = F; R^3 = 3\text{-}F; R^4 = 4\text{-}F; R^5 = 5\text{-}F$ | tebuconazole |
| No. A.56 | $R^1 = CHF_2; R^2 = Cl; R^3 = 3\text{-}F; R^4 = 4\text{-}F; R^5 = 5\text{-}F$ | tebuconazole |
| No. A.57 | $R^1 = CF_2Cl; R^2 = H; R^3 = 3\text{-}F; R^4 = 4\text{-}F; R^5 = 5\text{-}F$ | tebuconazole |
| No. A.58 | $R^1 = CF_3; R^2 = H; R^3 = 3\text{-}F; R^4 = 4\text{-}F; R^5 = 5\text{-}F$ | tebuconazole |
| No. A.59 | $R^1 = CF_3; R^2 = F; R^3 = 3\text{-}F; R^4 = 4\text{-}F; R^5 = 5\text{-}F$ | tebuconazole |
| No. A.60 | $R^1 = CF_3; R^2 = Cl; R^3 = 3\text{-}F; R^4 = 4\text{-}F; R^5 = 5\text{-}F$ | tebuconazole |
| No. A.61 | $R^1 = CH_3; R^2 = H; R^3 = 2\text{-}F; R^4 = 4\text{-}F; R^5 = 5\text{-}F$ | tebuconazole |
| No. A.62 | $R^1 = CH_3; R^2 = F; R^3 = 2\text{-}F; R^4 = 4\text{-}F; R^5 = 5\text{-}F$ | tebuconazole |
| No. A.63 | $R^1 = CH_3; R^2 = Cl; R^3 = 2\text{-}F; R^4 = 4\text{-}F; R^5 = 5\text{-}F$ | tebuconazole |
| No. A.64 | $R^1 = CH_2F; R^2 - H; R^3 = 2\text{-}F; R^4 = 4\text{-}F; R^5 = 5\text{-}F$ | tebuconazole |
| No. A.65 | $R^1 = CHFCl; R^2 = H; R^3 = 2\text{-}F; R^4 = 4\text{-}F; R^5 = 5\text{-}F$ | tebuconazole |
| No. A.66 | $R^1 = CHF_2; R^2 = H; R^3 = 2\text{-}F; R^4 = 4\text{-}F; R^5 = 5\text{-}F$ | tebuconazole |
| No, A.67 | $R^1 = CHF_2; R^2 = F; R^3 = 2\text{-}F; R^4 = 4\text{-}F; R^{\&} = 5\text{-}F$ | tebuconazole |
| No. A.68 | $R^1 = CHF_2; R^2 = Cl; R^3 = 2\text{-}F; R^4 = 4\text{-}F; R^6 = 5\text{-}F$ | tebuconazole |
| No. A.69 | $R^1 = CF_2Cl; R^2 = H; R^3 = 2\text{-}F; R^4 = 4\text{-}F; R^5 = 5\text{-}F$ | tebuconazole |
| No. A.70 | $R^1 = CF_3; R^2 = H; R^3 = 2\text{-}F; R^4 = 4\text{-}F; R^5 = 5\text{-}F$ | tebuconazole |
| No. A.71 | $R^1 = CF_3; R^2 = F; R^3 = 2\text{-}F; R^4 = 4\text{-}F; R^5 = 5\text{-}F$ | tebuconazole |
| No. A.72 | $R^1 = CF_3; R^2 = Cl; R^3 = 2\text{-}F; R^4 = 4\text{-}F; R^5 = 5\text{-}F$ | tebuconazole |
| No. A.73 | $R^1 = CH_3; R^2 = H; R^3 = 3\text{-}F; R^4 = 4\text{-}F; R^5 = 5\text{-}F$ | fluquinconazole |
| No. A.74 | $R^1 = CH_3; R^2 = F; R^3 = 3\text{-}F; R^4 = 4\text{-}F; R^5 = 5\text{-}F$ | fluquinconazole |
| No. A.75 | $R^1 = CH_3; R^2 = Cl; R^3 = 3\text{-}F; R^4 = 4\text{-}F; R^5 = 5\text{-}F$ | fluquinconazole |
| No. A.76 | $R^1 = CH_2F; R^2 = H; R^3 = 3\text{-}F; R^4 = 4\text{-}F; R^5 = 5\text{-}F$ | fluquinconazole |
| No. A.77 | $R^1 = CHFCl; R^2 = H; R^3 = 3\text{-}F; R^4 = 4\text{-}F; R^5 = 5\text{-}F$ | fluquinconazole |
| No. A.78 | $R^1 = CHF_2; R^2 = H; R^3 = 3\text{-}F; R^4 = 4\text{-}F; R^5 = 5\text{-}F$ | fluquinconazole |
| No. A.79 | $R^1 = CHF_2; R^2 = F; R^3 = 3\text{-}F; R^4 = 4\text{-}F; R^5 = 5\text{-}F$ | fluquinconazole |
| No. A.80 | $R^1 = CHF_2; R^2 = Cl; R^3 = 3\text{-}F; R^4 = 4\text{-}F; R^6 = 5\text{-}F$ | fluquinconazole |
| No. A.81 | $R^1 = CF_2Cl; R^2 = H; R^3 = 3\text{-}F; R^4 = 4\text{-}F; R^5 = 5\text{-}F$ | fluquinconazole |
| No. A.82 | $R^1 = CF_3; R^2 = H; R^3 = 3\text{-}F; R^4 = 4\text{-}F; R^5 = 5\text{-}F$ | fluquinconazole |
| No. A.83 | $R^1 = CF_3; R^2 = F; R^3 = 3\text{-}F; R^4 = 4\text{-}F; R^5 = 5\text{-}F$ | fluquinconazole |
| No. A.84 | $R^1 = CF_3; R^2 = Cl; R^3 = 3\text{-}F; R^4 = 4\text{-}F; R^5 = 5\text{-}F$ | fluquinconazole |
| No. A.85 | $R^1 = CH_3; R^2 = H; R^3 = 2\text{-}F; R^4 = 4\text{-}F; R^5 = 5\text{-}F$ | fluquinconazole |
| No. A.86 | $R^1 = CH_3; R^2 = F; R^3 = 2\text{-}F; R^4 = 4\text{-}F; R^5 = 5\text{-}F$ | fluquinconazole |
| No. A.87 | $R^1 = CH_3; R^2 = Cl; R^3 = 2\text{-}F; R^4 = 4\text{-}F; R^5 = 5\text{-}F$ | fluquinconazole |
| No. A.88 | $R^1 = CH_2F; R^2 = H; R^3 = 2\text{-}F; R^4 = 4\text{-}F; R^5 = 5\text{-}F$ | fluquinconazole |
| No. A.89 | $R^1 = CHFCl; R^2 = H; R^3 = 2\text{-}F; R^4 = 4\text{-}F; R^5 = 5\text{-}F$ | fluquinconazole |
| No. A.90 | $R^1 = CHF_2; R^2 = H; R^3 = 2\text{-}F; R^4 = 4\text{-}F; R^5 = 5\text{-}F$ | fluquinconazole |
| No. A.91 | $R^1 = CHF_2; R^2 = F; R^3 = 2\text{-}F; R^4 = 4\text{-}F; R^5 = 5\text{-}F$ | fluquinconazole |
| No. A.92 | $R^1 = CHF_2; R^2 = Cl; R^3 = 2\text{-}F; R^4 = 4\text{-}F; R^5 = 5\text{-}F$ | fluquinconazole |
| No. A.93 | $R^1 = CF_2Cl; R^2 = H; R^3 = 2\text{-}F; R^4 = 4\text{-}F; R^5 = 5\text{-}F$ | fluquinconazole |
| No. A.94 | $Ri = CF_3; R^2 = H; R^3 = 2\text{-}F; R^4 = 4\text{-}F; R^5 = 5\text{-}F$ | fluquinconazole |
| No. A.95 | $R^1 = CF_3; R^2 = F; R^3 = 2\text{-}F; R^4 = 4\text{-}F; R^5 = 5\text{-}F$ | fluquinconazole |
| No. A.96 | $R^1 = CF_3; R^2 = Cl; R^3 = 2\text{-}F; R^4 = 4\text{-}F; R^5 = 5\text{-}F$ | fluquinconazole |
| No. A.97 | $R^1 = CH_3; R^2 = H; R^3 = 3\text{-}F; R^4 = 4\text{-}F; R^5 = 5\text{-}F$ | flutriafol |
| No. A.98 | $R^1 = CH_3; R^2 = F; R^3 = 3\text{-}F; R^4 = 4\text{-}F; R^5 = 5\text{-}F$ | flutriafol |
| No. A.99 | $R^1 = CH_3; R^2 = Cl; R^3 = 3\text{-}F; R^4 = 4\text{-}F; R^5 = 5\text{-}F$ | flutriafol |
| No. A.100 | $R^1 = CH_2F; R^2 = H; R^3 = 3\text{-}F; R^4 = 4\text{-}F; R^5 = 5\text{-}F$ | flutriafol |
| No. A.101 | $R^1 = CHFCl; R^2 = H; R^3 = 3\text{-}F; R^4 = 4\text{-}F; R^5 = 5\text{-}F$ | flutriafol |
| No. A.102 | $R^1 = CHF_2; R^2 = H; R^3 = 3\text{-}F; R^4 = 4\text{-}F; R^5 = 5\text{-}F$ | flutriafol |
| No. A.103 | $R^1 = CHF_2; R^2 = F; R^3 = 3\text{-}F; R^4 = 4\text{-}F; R^5 = 5\text{-}F$ | flutriafol |
| No. A.104 | $R^1 = CHF_2; R^2 = Cl; R^3 = 3\text{-}F; R^4 = 4\text{-}F; R^5 = 5\text{-}F$ | flutriafol |
| No. A.105 | $R^1 = CF_2Cl; R^2 = H; R^3 = 3\text{-}F; R^4 = 4\text{-}F; R^5 = 5\text{-}F$ | flutriafol |
| No. A.106 | $R^1 = CF_3; R^2 = H; R^3 = 3\text{-}F; R^4 = 4\text{-}F; R^5 = 5\text{-}F$ | flutriafol |
| No. A.107 | $R^1 = CF_3; R^2 = F; R^3 = 3\text{-}F; R^4 = 4\text{-}F; R^5 = 5\text{-}F$ | flutriafol |
| No. A.108 | $R^1 = CF_3; R^2 = Cl; R^3 = 3\text{-}F; R^4 = 4\text{-}F; R^5 = 5\text{-}F$ | flutriafol |
| No. A.109 | $R^1 = CH_3; R^2 = H; R^3 = 2\text{-}F; R^4 = 4\text{-}F; R^5 = 5\text{-}F$ | flutriafol |
| No. A.110 | $R^1 = CH_3; R^2 = F; R^3 = 2\text{-}F; R^4 = 4\text{-}F; R^5 = 5\text{-}F$ | flutriafol |
| No. A.111 | $R^1 = CH_3; R^2 = Cl; R^3 = 2\text{-}F; R^4 = 4\text{-}F; R^5 = 5\text{-}F$ | flutriafol |
| No. A.112 | $R^1 = CH_2F; R^2 = H; R^3 = 2\text{-}F; R^4 = 4\text{-}F; R^5 = 5\text{-}F$ | flutriafol |
| No. A.113 | $R^1 = CHFCl; R^2 = H; R^3 = 2\text{-}F; R^4 = 4\text{-}F; R^5 = 5\text{-}F$ | flutriafol |
| No. A.114 | $R^1 = CHF_2; R^2 = H; R^3 = 2\text{-}F; R^4 = 4\text{-}F; R^5 = 5\text{-}F$ | flutriafol |
| No. A.115 | $R^1 = CHF_2; R^2 = F; R^3 = 2\text{-}F; R^4 = 4\text{-}F; R^5 = 5\text{-}F$ | flutriafol |
| No. A.116 | $R^1 = CHF_2; R^2 = Cl; R^3 = 2\text{-}F; R^4 = 4\text{-}F; R^5 = 5\text{-}F$ | flutriafol |
| No. A.117 | $R^1 = CF_2Cl; R^2 = H; R^3 = 2\text{-}F; R^4 = 4\text{-}F; R^5 = 5\text{-}F$ | flutriafol |
| No. A.118 | $R^1 = CF_3; R^2 = H; R^3 = 2\text{-}F; R^4 = 4\text{-}F; R^5 = 5\text{-}F$ | flutriafol |
| No. A.119 | $R^1 = CF_3; R^2 = F; R^3 = 2\text{-}F; R^4 = 4\text{-}F; R^5 = 5\text{-}F$ | flutriafol |
| No. A.120 | $R^1 = CF_3; R^2 = Cl; R^3 = 2\text{-}F; R^4 = 4\text{-}F; R^5 = 5\text{-}F$ | flutriafol |
| No. A.121 | $R^1 = CH_3; R^2 = H; R^3 = 3\text{-}F; R^4 = 4\text{-}F; R^5 = 5\text{-}F$ | triticonazole |
| No. A.122 | $R^1 = CH_3; R^2 = F; R^3 = 3\text{-}F; R^4 = 4\text{-}F; R^5 = 5\text{-}F$ | triticonazole |
| No. A.123 | $R^1 = CH_3; R^2 = Cl; R^3 = 3\text{-}F; R^4 = 4\text{-}F; R^5 = 5\text{-}F$ | triticonazole |
| No. A.124 | $R^1 = CH_2F; R^2 = H; R^3 = 3\text{-}F; R^4 = 4\text{-}F; R^5 = 5\text{-}F$ | triticonazole |
| No. A.125 | $R^1 = CHFCl; R^2 = H; R^3 = 3\text{-}F; R^4 = 4\text{-}F; R^5 = 5\text{-}F$ | triticonazole |
| No. A.126 | $R^1 = CHF_2; R^2 = H; R^3 = 3\text{-}F; R^4 = 4\text{-}F; R^5 = 5\text{-}F$ | triticonazole |
| No. A.127 | $R^1 = CHF_2; R^2 = F; R^3 = 3\text{-}F; R^4 = 4\text{-}F; R^5 = 5\text{-}F$ | triticonazole |
| No. A.128 | $R^1 = CHF_2; R^2 = Cl; R^3 = 3\text{-}F; R^4 = 4\text{-}F; R^5 = 5\text{-}F$ | triticonazole |
| No. A.129 | $R^1 = CF_2Cl; R^2 = H; R^3 = 3\text{-}F; R^4 = 4\text{-}F; R^5 = 5\text{-}F$ | triticonazole |

TABLE 3-continued

Active compound combinations of compounds
I with active compounds II of group A):

| Mixture | Compound of the formula I (X = oxygen) | Active compound II |
|---|---|---|
| No. A.130 | $R^1 = CF_3$; $R^2 = H$; $R^3 = 3$-F; $R^4 = 4$-F; $R^5 = 5$-F | triticonazole |
| No. A.131 | $R^1 = CF_3$; $R^2 = F$; $R^3 = 3$-F; $R^4 = 4$-F; $R^5 = 5$-F | triticonazole |
| No. A.132 | $R^1 = CF_3$; $R^2 = Cl$; $R^3 = 3$-F; $R^4 = 4$-F; $R^5 = 5$-F | triticonazole |
| No. A.133 | $R^1 = CH_3$; $R^2 = H$; $R^3 = 2$-F; $R^4 = 4$-F; $R^5 = 5$-F | triticonazole |
| No. A.134 | $R^1 = CH_3$; $R^2 = F$; $R^3 = 2$-F; $R^4 = 4$-F; $R^5 = 5$-F | triticonazole |
| No. A.135 | $R^1 = CH_3$; $R^2 = Cl$; $R^3 = 2$-F; $R^4 = 4$-F; $R^5 = 5$-F | triticonazole |
| No. A.136 | $R^1 = CH_2F$; $R^2 = H$; $R^3 = 2$-F; $R^4 = 4$-F; $R^5 = 5$-F | triticonazole |
| No. A.137 | $R^1 = CHFCl$; $R^2 = H$; $R^3 = 2$-F; $R^4 = 4$-F; $R^5 = 5$-F | triticonazole |
| No. A.138 | $R^1 = CHF_2$; $R^2 = H$; $R^3 = 2$-F; $R^4 = 4$-F; $R^5 = 5$-F | triticonazole |
| No. A.139 | $R^1 = CHF_2$; $R^2 = F$; $R^3 = 2$-F; $R^4 = 4$-F; $R^5 = 5$-F | triticonazole |
| No. A.140 | $R^1 = CHF_2$; $R^2 = Cl$; $R^3 = 2$-F; $R^4 = 4$-F; $R^5 = 5$-F | triticonazole |
| No. A.141 | $R^1 = CF_2Cl$; $R^2 = H$; $R^3 = 2$-F; $R^4 = 4$-F; $R^5 = 5$-F | triticonazole |
| No. A.142 | $R^1 = CF_3$; $R^2 = H$; $R^3 = 2$-F; $R^4 = 4$-F; $R^5 = 5$-F | triticonazole |
| No. A.143 | $R^1 = CF_3$; $R^2 = F$; $R^J = 2$-F; $R^4 = 4$-F; $R^5 = 5$-F | triticonazole |
| No. A.144 | $R^1 = CF_3$; $R^2 = Cl$; $R^3 = 2$-F; $R^4 = 4$-F; $R^5 = 5$-F | triticonazole |
| No. A.145 | $R^1 = CH_3$; $R^2 = H$; $R^3 = 3$-F; $R^4 = 4$-F; $R^6 = 5$-F | prochloraz |
| No. A.146 | $R^1 = CH_3$; $R^2 = F$; $R^3 = 3$-F; $R^4 = 4$-F; $R^5 = 5$-F | prochloraz |
| No. A.147 | $R^1 = CH_3$; $R^2 = Cl$; $R^3 = 3$-F; $R^4 = 4$-F; $R^5 = 5$-F | prochloraz |
| No. A.148 | $R^1 = CH_2F$; $R^2 = H$; $R^3 = 3$-F; $R^4 = 4$-F; $R^5 = 5$-F | prochloraz |
| No. A.149 | $R^1 = CHFCl$; $R^2 = H$; $R^3 = 3$-F; $R^4 = 4$-F; $R^5 = 5$-F | prochloraz |
| No. A.150 | $R^1 = CHF_2$; $R^2 = H$; $R^3 = 3$-F; $R^4 = 4$-F; $R^5 = 5$-F | prochloraz |
| No. A.151 | $R^1 = CHF_2$; $R^2 = F$; $R^3 = 3$-F; $R^4 = 4$-F; $R^5 = 5$-F | prochloraz |
| No. A.152 | $R^1 = CHF_2$; $R^2 = Cl$; $R^3 = 3$-F; $R^4 = 4$-F; $R^5 = 5$-F | prochloraz |
| No. A.153 | $R^1 = CF_2Cl$; $R^2 = H$; $R^3 = 3$-F; $R^4 = 4$-F; $R^5 = 5$-F | prochloraz |
| No. A.154 | $R^1 = CF_3$; $R^2 = H$; $R^3 = 3$-F; $R^4 = 4$-F; $R^5 = 5$-F | prochloraz |
| No. A.155 | $R^1 = CF_3$; $R^2 = F$; $R^3 = 3$-F; $R^4 = 4$-F; $R^5 = 5$-F | prochloraz |
| No. A.156 | $R^1 = CF_3$; $R^2 = Cl$; $R^3 = 3$-F; $R^4 = 4$-F; $R^5 = 5$-F | prochloraz |
| No. A.157 | $R^1 = CH_3$; $R^2 = H$; $R^3 = 2$-F; $R^4 = 4$-F; $R^5 = 5$-F | prochloraz |
| No. A.158 | $R^1 = CH_3$; $R^2 = F$; $R^3 = 2$-F; $R^4 = 4$-F; $R^5 = 5$-F | prochloraz |
| No. A.159 | $R^1 = CH_3$; $R^2 = Cl$; $R^3 = 2$-F; $R^4 = 4$-F; $R^5 = 5$-F | prochloraz |
| No. A.160 | $R^1 = CH_2F$; $R^2 = H$; $R^3 = 2$-F; $R^4 = 4$-F; $R^5 = 5$-F | prochloraz |
| No. A.161 | $R^1 = CHFCl$; $R^2 = H$; $R^3 = 2$-F; $R^4 = 4$-F; $R^5 = 5$-F | prochloraz |
| No. A.162 | $R^1 = CHF_2$; $R^2 = H$; $R^3 = 2$-F; $R^4 = 4$-F; $R^5 = 5$-F | prochloraz |
| No. A.163 | $R^1 = CHF_2$; $R^2 = F$; $R^3 = 2$-F; $R^4 = 4$-F; $R^5 = 5$-F | prochloraz |
| No. A.164 | $R^1 = CHF_2$; $R^2 = Cl$; $R^3 = 2$-F; $R^4 = 4$-F; $R^5 = 5$-F | prochloraz |
| No. A.165 | $R^1 = CF_2Cl$; $R^2 = H$; $R^3 = 2$-F; $R^4 = 4$-F; $R^5 = 5$-F | prochloraz |
| No. A.166 | $R^1 = CF_3$; $R^2 = H$; $R^3 = 2$-F; $R^4 = 4$-F; $R^5 = 5$-F | prochloraz |
| No. A.167 | $R^1 = CF_3$; $R^2 = F$; $R^3 = 2$-F; $R^4 = 4$-F; $R^5 = 5$-F | prochloraz |
| No. A.168 | $R^1 = CF_3$; $R^2 = Cl$; $R^3 = 2$-F; $R^4 = 4$-F; $R^5 = 5$-F | prochloraz |
| No. A.169 | $R^1 = CH_3$; $R^2 = H$; $R^3 = 3$-F; $R^4 = 4$-F; $R^5 = 5$-F | carbendazim |
| No. A.170 | $R^1 = CH_3$; $R^2 = F$; $R^3 = 3$-F; $R^4 = 4$-F; $R^5 = 5$-F | carbendazim |
| No. A.171 | $R^1 = CH_3$; $R^2 = Cl$; $R^3 = 3$-F; $R^4 = 4$-F; $R^5 = 5$-F | carbendazim |
| No. A.172 | $R^1 = CH_2F$; $R^2 = H$; $R^3 = 3$-F; $R^4 = 4$-F; $R^5 = 5$-F | carbendazim |
| No. A.173 | $R^1 = CHFCl$; $R^2 = H$; $R^3 = 3$-F; $R^4 = 4$-F; $R^5 = 5$-F | carbendazim |
| No. A.174 | $R^1 = CHF_2$; $R^2 = H$; $R^3 = 3$-F; $R^4 = 4$-F; $R^5 = 5$-F | carbendazim |
| No. A.175 | $R^1 = CHF_2$; $R^2 = F$; $R^3 = 3$-F; $R^4 = 4$-F; $R^5 = 5$-F | carbendazim |
| No. A.176 | $R^1 = CHF_2$; $R^2 = Cl$; $R^3 = 3$-F; $R^4 = 4$-F; $R^5 = 5$-F | carbendazim |
| No. A.177 | $R^1 = CF_2Cl$; $R^2 = H$; $R^3 = 3$-F; $R^4 = 4$-F; $R^5 = 5$-F | carbendazim |
| No. A.178 | $R^1 = CF_3$; $R^2 = H$; $R^3 = 3$-F; $R^4 = 4$-F; $R^5 = 5$-F | carbendazim |
| No. A.179 | $R^1 = CF_3$; $R^2 = F$; $R^3 = 3$-F; $R^4 = 4$-F; $R^5 = 5$-F | carbendazim |
| No. A.180 | $R^1 = CF_3$; $R^2 = Cl$; $R^3 = 3$-F; $R^4 = 4$-F; $R^5 = 5$-F | carbendazim |
| No. A.181 | $R^1 = CH_3$; $R^2 = H$; $R^3 = 2$-F; $R^4 = 4$-F;. $R^5 = 5$-F | carbendazim |
| No. A.182 | $R^1 = CH_3$; $R^2 = F$; $R^3 = 2$-F; $R^4 = 4$-F; $R^5 = 5$-F | carbendazim |
| No. A.183 | $R^1 = CH_3$; $R^2 = Cl$; $R^3 = 2$-F; $R^4 = 4$-F; $R^5 = 5$-F | carbendazim |
| No. A.184 | $R^1 = CH_2F$; $R^2 = H$; $R^3 = 2$-F; $R^4 = 4$-F; $R^5 = 5$-F | carbendazim |
| No. A.185 | $R^1 = CHFCl$; $R^2 = H$; $R^3 = 2$-F; $R^4 = 4$-F; $R^5 = 5$-F | carbendazim |
| No. A.186 | $R^1 = CHF_2$; $R^2 = H$; $R^3 = 2$-F; $R^4 = 4$-F; $R^5 = 5$-F | carbendazim |
| No. A.187 | $R^1 = CHF_2$; $R^2 = F$; $R^3 = 2$-F; $R^4 = 4$-F; $R^5 = 5$-F | carbendazim |
| No. A.188 | $R^1 = CHF_2$; $R^2 = Cl$; $R^3 = 2$-F; $R^4 = 4$-F; $R^5 = 5$-F | carbendazim |
| No. A.189 | $R^1 = CF_2Cl$; $R^2 = H$; $R^3 = 2$-F; $R^4 = 4$-F; $R^5 = 5$-F | carbendazim |
| No. A.190 | $R^1 = CF_3$; $R^2 = H$; $R^3 = 2$-F; $R^4 = 4$-F; $R^5 = 5$-F | carbendazim |
| No. A.191 | $R^1 = CF_3$; $R^2 = F$; $R^3 = 2$-F; $R^4 = 4$-F; $R^5 = 5$-F | carbendazim |
| No. A.192 | $R^1 = CF_3$; $R^2 = Cl$; $R^3 = 2$-F; $R^4 = 4$-F; $R^5 = 5$-F | carbendazim |

TABLE 4

Active compound combinations of compounds I with active compounds II of group B):

| Mixture | Compounds of the formula I (X = oxygen) | Active compound II |
|---|---|---|
| No. B.1 | $R^1 = CH_3$; $R^2 = H$; $R^3 = 3\text{-}F$; $R^4 = 4\text{-}F$; $R^5 = 5\text{-}F$ | kresoxim-methyl |
| No. B.2 | $R^1 = CH_3$; $R^2 = F$; $R^3 = 3\text{-}F$; $R^4 = 4\text{-}F$; $R^5 = 5\text{-}F$ | kresoxim-methyl |
| No. B.3 | $R^1 = CH_3$; $R^2 = Cl$; $R^3 = 3\text{-}F$; $R^4 = 4\text{-}F$; $R^5 = 5\text{-}F$ | kresoxim-methyl |
| No. B.4 | $R^1 = CH_2F$; $R^2 = H$; $R^3 = 3\text{-}F$; $R^4 = 4\text{-}F$; $R^5 = 5\text{-}F$ | kresoxim-methyl |
| No. B.5 | $R^1 = CHFCl$; $R^2 = H$; $R^3 = 3\text{-}F$; $R^4 = 4\text{-}F$; $R^5 = 5\text{-}F$ | kresoxim-methyl |
| No. B.6 | $R^1 = CHF_2$; $R^2 = H$; $R^3 = 3\text{-}F$; $R^4 = 4\text{-}F$; $R^5 = 5\text{-}F$ | kresoxim-methyl |
| No. B.7 | $R^1 = CHF_2$; $R^2 = F$; $R^3 = 3\text{-}F$; $R^4 = 4\text{-}F$; $R^5 = 5\text{-}F$ | kresoxim-methyl |
| No. B.8 | $R^1 = CHF_2$; $R^2 = Cl$; $R^3 = 3\text{-}F$; $R^4 = 4\text{-}F$; $R^5 = 5\text{-}F$ | kresoxim-methyl |
| No. B.9 | $R^1 = CF_2Cl$; $R^2 = H$; $R^3 = 3\text{-}F$; $R^4 = 4\text{-}F$; $R^5 = 5\text{-}F$ | kresoxim-methyl |
| No. B.10 | $R^1 = CF_3$; $R^2 = H$; $R^3 = 3\text{-}F$; $R^4 = 4\text{-}F$; $R^5 = 5\text{-}F$ | kresoxim-methyl |
| No. B.11 | $R^1 = CF_3$; $R^2 = F$; $R^3 = 3\text{-}F$; $R^4 = 4\text{-}F$; $R^5 = 5\text{-}F$ | kresoxim-methyl |
| No. B.12 | $R^1 = CF_3$; $R^2 = Cl$; $R^3 = 3\text{-}F$; $R^4 = 4\text{-}F$; $R^5 = 5\text{-}F$ | kresoxim-methyl |
| No. B.13 | $R^1 = CH_3$; $R^2 = H$; $R^3 = 2\text{-}F$; $R^4 = 4\text{-}F$; $R^5 = 5\text{-}F$ | kresoxim-methyl |
| No. B.14 | $R^1 = CH_3$; $R^2 = F$; $R^3 = 2\text{-}F$; $R^4 = 4\text{-}F$; $R^5 = 5\text{-}F$ | kresoxim-methyl |
| No. B.15 | $R^1 = CH_3$; $R^2 = Cl$; $R^3 = 2\text{-}F$; $R^4 = 4\text{-}F$; $R^5 = 5\text{-}F$ | kresoxim-methyl |
| No. B.16 | $R^1 = CH_2F$; $R^2 = H$; $R^3 = 2\text{-}F$; $R^4 = 4\text{-}F$; $R^5 = 5\text{-}F$ | kresoxim-methyl |
| No. B.17 | $R^1 = CHFCl$; $R^2 = H$; $R^3 = 2\text{-}F$; $R^4 = 4\text{-}F$; $R^5 = 5\text{-}F$ | kresoxim-methyl |
| No. B.18 | $R^1 = CHF_2$; $R^2 = H$; $R^3 = 2\text{-}F$; $R^4 = 4\text{-}F$; $R^5 = 5\text{-}F$ | kresoxim-methyl |
| No. B.19 | $R^1 = CHF_2$; $R^2 = F$; $R^3 = 2\text{-}F$; $R^4 = 4\text{-}F$; $R^5 = 5\text{-}F$ | kresoxim-methyl |
| No. B.20 | $R^1 = CHF_2$; $R^2 = Cl$; $R^3 = 2\text{-}F$; $R^4 = 4\text{-}F$; $R^5 = 5\text{-}F$ | kresoxim-methyl |
| No. B.21 | $R^1 = CF_2Cl$; $R^2 = H$; $R^3 = 2\text{-}F$; $R^4 = 4\text{-}F$; $R^5 = 5\text{-}F$ | kresoxim-methyl |
| No. B.22 | $R^1 = CF_3$; $R^2 = H$; $R^3 = 2\text{-}F$; $R^4 = 4\text{-}F$; $R^5 = 5\text{-}F$ | kresoxim-methyl |
| No. B.23 | $R^1 = CF_3$; $R^2 = F$; $R^3 = 2\text{-}F$; $R^4 = 4\text{-}F$; $R^5 = 5\text{-}F$ | kresoxim-methyl |
| No. B.24 | $R^1 = CF_3$; $R^2 = Cl$; $R^3 = 2\text{-}F$; $R^4 = 4\text{-}F$; $R^5 = 5\text{-}F$ | kresoxim-methyl |
| No. B.25 | $R^1 = CH_3$; $R^2 = H$; $R^3 = 3\text{-}F$; $R^4 = 4\text{-}F$; $R^5 = 5\text{-}F$ | pyraclostrobin |
| No. B.26 | $R^1 = CH_3$; $R^2 = F$; $R^3 = 3\text{-}F$; $R^4 = 4\text{-}F$; $R^5 = 5\text{-}F$ | pyraclostrobin |
| No. B.27 | $R^1 = CH_3$; $R^2 = Cl$; $R^3 = 3\text{-}F$; $R^4 = 4\text{-}F$; $R^5 = 5\text{-}F$ | pyraclostrobin |
| No. B.28 | $R^1 = CH_2F$; $R^2 = H$; $R^3 = 3\text{-}F$; $R^4 = 4\text{-}F$; $R^5 = 5\text{-}F$ | pyraclostrobin |
| No. B.29 | $R^1 = CHFCl$; $R^2 = H$; $R^3 = 3\text{-}F$; $R^4 = 4\text{-}F$; $R^5 = 5\text{-}F$ | pyraclostrobin |
| No. B.30 | $R^1 = CHF_2$; $R^2 = H$; $R^3 = 3\text{-}F$; $R^4 = 4\text{-}F$; $R^5 = 5\text{-}F$ | pyraclostrobin |
| No. B.31 | $R^1 = CHF_2$; $R^2 = F$; $R^3 = 3\text{-}F$; $R^4 = 4\text{-}F$; $R^5 = 5\text{-}F$ | pyraclostrobin |
| No. B.32 | $R^1 = CHF_2$; $R^2 = Cl$; $R^3 = 3\text{-}F$; $R^4 = 4\text{-}F$; $R^5 = 5\text{-}F$ | pyraclostrobin |
| No. B.33 | $R^1 = CF_2Cl$; $R^2 = H$; $R^3 = 3\text{-}F$; $R^4 = 4\text{-}F$; $R^5 = 5\text{-}F$ | pyraclostrobin |
| No. B.34 | $R^1 = CF_3$; $R^2 = H$; $R^3 = 3\text{-}F$; $R^4 = 4\text{-}F$; $R^5 = 5\text{-}F$ | pyraclostrobin |
| No. B.35 | $R^1 = CF_3$; $R^2 = F$; $R^3 = 3\text{-}F$; $R^4 = 4\text{-}F$; $R^5 = 5\text{-}F$ | pyraclostrobin |
| No. B.36 | $R^1 = CF_3$; $R^2 = Cl$; $R^3 = 3\text{-}F$; $R^4 = 4\text{-}F$; $R^5 = 5\text{-}F$ | pyraclostrobin |
| No. B.37 | $R^1 = CH_3$; $R^2 = H$; $R^3 = 2\text{-}F$; $R^4 = 4\text{-}F$; $R^5 = 5\text{-}F$ | pyraclostrobin |
| No. B.38 | $R^1 = CH_3$; $R^2 = F$; $R^3 = 2\text{-}F$; $R^4 = 4\text{-}F$; $R^5 = 5\text{-}F$ | pyraclostrobin |
| No. B.39 | $R^1 = CH_3$; $R^2 = Cl$; $R^3 = 2\text{-}F$; $R^4 = 4\text{-}F$; $R^5 = 5\text{-}F$ | pyraclostrobin |
| No. B.40 | $R^1 = CH_2F$; $R^2 = H$; $R^3 = 2\text{-}F$; $R^4 = 4\text{-}F$; $R^5 = 5\text{-}F$ | pyraclostrobin |
| No. B.41 | $R^1 = CHFCl$; $R^2 = H$; $R^3 = 2\text{-}F$; $R^4 = 4\text{-}F$; $R^5 = 5\text{-}F$ | pyraclostrobin |
| No. B.42 | $R^1 = CHF_2$; $R^2 = H$; $R^3 = 2\text{-}F$; $R^4 = 4\text{-}F$; $R^5 = 5\text{-}F$ | pyraclostrobin |
| No. B.43 | $R^1 = CHF_2$; $R^2 = F$; $R^3 = 2\text{-}F$; $R^4 = 4\text{-}F$; $R^5 = 5\text{-}F$ | pyraclostrobin |
| No. B.44 | $R^1 = CHF_2$; $R^2 = Cl$; $R^3 = 2\text{-}F$; $R^4 = 4\text{-}F$; $R^5 = 5\text{-}F$ | pyraclostrobin |
| No. B.45 | $R^1 = CF_2Cl$; $R^2 = H$; $R^3 = 2\text{-}F$; $R^4 = 4\text{-}F$; $R^5 = 5\text{-}F$ | pyraclostrobin |
| No. B.46 | $R^1 = CF_3$; $R^2 = H$; $R^3 = 2\text{-}F$; $R^4 = 4\text{-}F$; $R^5 = 5\text{-}F$ | pyraclostrobin |
| No. B.47 | $R^1 = CF_3$; $R^2 = F$; $R^3 = 2\text{-}F$; $R^4 = 4\text{-}F$; $R^5 = 5\text{-}F$ | pyraclostrobin |
| No. B.48 | $R^1 = CF_3$; $R^2 = Cl$; $R^3 = 2\text{-}F$; $R^4 = 4\text{-}F$; $R^5 = 5\text{-}F$ | pyraclostrobin |
| No. B.49 | $R^1 = CH_3$; $R^2 = H$; $R^3 = 3\text{-}F$; $R^4 = 4\text{-}F$; $R^5 = 5\text{-}F$ | orysastrobin |
| No. B.50 | $R^1 = CH_3$; $R^2 = F$; $R^3 = 3\text{-}F$; $R^4 = 4\text{-}F$; $R^5 = 5\text{-}F$ | orysastrobin |
| No. B.51 | $R^1 = CH_3$; $R^2 = Cl$; $R^3 = 3\text{-}F$; $R^4 = 4\text{-}F$; $R^5 = 5\text{-}F$ | orysastrobin |
| No. B.52 | $R^1 = CH_2F$; $R^2 = H$; $R^3 = 3\text{-}F$; $R^4 = 4\text{-}F$; $R^5 = 5\text{-}F$ | orysastrobin |
| No. B.53 | $R^1 = CHFCl$; $R^2 = H$; $R^3 = 3\text{-}F$; $R^4 = 4\text{-}F$; $R^5 = 5\text{-}F$ | orysastrobin |
| No. B.54 | $R^1 = CHF_2$; $R^2 = H$; $R^3 = 3\text{-}F$; $R^4 = 4\text{-}F$; $R^5 = 5\text{-}F$ | orysastrobin |
| No. B.55 | $R^1 = CHF_2$; $R^2 = F$; $R^3 = 3\text{-}F$; $R^4 = 4\text{-}F$; $R^5 = 5\text{-}F$ | orysastrobin |
| No. B.56 | $R^1 = CHF_2$; $R^2 = Cl$; $R^3 = 3\text{-}F$; $R^4 = 4\text{-}F$; $R^5 = 5\text{-}F$ | orysastrobin |
| No. B.57 | $R^1 = CF_2Cl$; $R^2 = H$; $R^3 = 3\text{-}F$; $R^4 = 4\text{-}F$; $R^5 = 5\text{-}F$ | orysastrobin |
| No. B.58 | $R^1 = CF_3$; $R^2 = H$; $R^3 = 3\text{-}F$; $R^4 = 4\text{-}F$; $R^5 = 5\text{-}F$ | orysastrobin |
| No. B.59 | $R^1 = CF_3$; $R^2 = F$; $R^3 = 3\text{-}F$; $R^4 = 4\text{-}F$; $R^5 = 5\text{-}F$ | orysastrobin |
| No. B.60 | $R^1 = CF_3$; $R^2 = Cl$; $R^3 = 3\text{-}F$; $R^4 = 4\text{-}F$; $R^5 = 5\text{-}F$ | orysastrobin |
| No. B.61 | $R^1 = CH_3$; $R^2 = H$; $R^3 = 2\text{-}F$; $R^4 = 4\text{-}F$; $R^5 = 5\text{-}F$ | orysastrobin |
| No. B.62 | $R^1 = CH_3$; $R^2 = F$; $R^3 = 2\text{-}F$; $R^4 = 4\text{-}F$; $R^5 = 5\text{-}F$ | orysastrobin |
| No. B.63 | $R^1 = CH_3$; $R^2 = Cl$; $R^3 = 2\text{-}F$; $R^4 = 4\text{-}F$; $R^5 = 5\text{-}F$ | orysastrobin |
| No. B.64 | $R^1 = CH_2F$; $R^2 = H$; $R^3 = 2\text{-}F$; $R^4 = 4\text{-}F$; $R^5 = 5\text{-}F$ | orysastrobin |
| No. B.65 | $R^1 = CHFCl$; $R^2 = H$; $R^3 = 2\text{-}F$; $R^4 = 4\text{-}F$; $R^5 = 5\text{-}F$ | orysastrobin |
| No. B.66 | $R^1 = CHF_2$; $R^2 = H$; $R^3 = 2\text{-}F$; $R^4 = 4\text{-}F$; $R^5 = 5\text{-}F$ | orysastrobin |
| No. B.67 | $R^1 = CHF_2$; $R^2 = F$; $R^3 = 2\text{-}F$; $R^4 = 4\text{-}F$; $R^5 = 5\text{-}F$ | orysastrobin |
| No. B.68 | $R^1 = CHF_2$; $R^2 = Cl$; $R^3 = 2\text{-}F$; $R^4 = 4\text{-}F$; $R^5 = 5\text{-}F$ | orysastrobin |
| No. B.69 | $R^1 = CF_2Cl$; $R^2 = H$; $R^3 = 2\text{-}F$; $R^4 = 4\text{-}F$; $R^5 = 5\text{-}F$ | orysastrobin |
| No. B.70 | $R^1 = CF_3$; $R^2 = H$; $R^3 = 2\text{-}F$; $R^4 = 4\text{-}F$; $R^5 = 5\text{-}F$ | orysastrobin |
| No. B.71 | $R^1 = CF_3$; $R^2 = F$; $R^3 = 2\text{-}F$; $R^4 = 4\text{-}F$; $R^5 = 5\text{-}F$ | orysastrobin |
| No. B.72 | $R^1 = CF_3$; $R^2 = Cl$; $R^3 = 2\text{-}F$; $R^4 = 4\text{-}F$; $R^5 = 5\text{-}F$ | orysastrobin |

TABLE 5

Active compound combinations of compounds I with active compounds II of group C):

| Mixture | Compounds of the formula I (X = oxygen) | Active compound II |
|---|---|---|
| No. C.1 | $R^1 = CH_3$; $R^2 = H$; $R^3 = 3$-F; $R^4 = 4$-F; $R^5 = 5$-F | dimethomorph |
| No. C.2 | $R^1 = CH_3$; $R^2 = F$; $R^3 = 3$-F; $R^4 = 4$-F; $R^5 = 5$-F | dimethomorph |
| No. C.3 | $R^1 = CH_3$; $R^2 = Cl$; $R^3 = 3$-F; $R^4 = 4$-F; $R^5 = 5$-F | dimethomorph |
| No. C.4 | $R^1 = CH_2F$; $R^2 = H$; $R^3 = 3$-F; $R^4 = 4$-F; $R^5 = 5$-F | dimethomorph |
| No. C.5 | $R^1 = CHFCl$; $R^2 = H$; $R^3 = 3$-F; $R^4 = 4$-F; $R^5 = 5$-F | dimethomorph |
| No. C.6 | $R^1 = CHF_2$; $R^2 = H$; $R^3 = 3$-F; $R^4 = 4$-F; $R^5 = 5$-F | dimethomorph |
| No. C.7 | $R^1 = CHF_2$; $R^2 = F$; $R^3 = 3$-F; $R^4 = 4$-F; $R^5 = 5$-F | dimethomorph |
| No. C.8 | $R^1 = CHF_2$; $R^2 = Cl$; $R^3 = 3$-F; $R^4 = 4$-F; $R^5 = 5$-F | dimethomorph |
| No. C.9 | $R^1 = CF_2Cl$; $R^2 = H$; $R^3 = 3$-F; $R^4 = 4$-F; $R^5 = 5$-F | dimethomorph |
| No. C.10 | $R^1 = CF_3$; $R^2 = H$; $R^3 = 3$-F; $R^4 = 4$-F; $R^5 = 5$-F | dimethomorph |
| No. C.11 | $R^1 = CF_3$; $R^2 = F$; $R^3 = 3$-F; $R^4 = 4$-F; $R^5 = 5$-F | dimethomorph |
| No. C.12 | $R^1 = CF_3$; $R^2 = Cl$; $R^3 = 3$-F; $R^4 = 4$-F; $R^5 = 5$-F | dimethomorph |
| No. C.13 | $R^1 = CH_3$; $R^2 = H$; $R^3 = 2$-F; $R^4 = 4$-F; $R^5 = 5$-F | dimethomorph |
| No. C.14 | $R^1 = CH_3$; $R^2 = F$; $R^3 = 2$-F; $R^4 = 4$-F; $R^5 = 5$-F | dimethomorph |
| No. C.15 | $R^1 = CH_3$; $R^2 = Cl$; $R^3 = 2$-F; $R^4 = 4$-F; $R^5 = 5$-F | dimethomorph |
| No. C.16 | $R^1 = CH_2F$; $R^2 = H$; $R^3 = 2$-F; $R^4 = 4$-F; $R^5 = 5$-F | dimethomorph |
| No. C.17 | $R^1 = CHFCl$; $R^2 = H$; $R^3 = 2$-F; $R^4 = 4$-F; $R^5 = 5$-F | dimethomorph |
| No. C.18 | $R^1 = CHF_2$; $R^2 = H$; $R^3 = 2$-F; $R^4 = 4$-F; $R^5 = 5$-F | dimethomorph |
| No. C.19 | $R^1 = CHF_2$; $R^2 = F$; $R^3 = 2$-F; $R^4 = 4$-F; $R^5 = 5$-F | dimethomorph |
| No. C.20 | $R^1 = CHF_2$; $R^2 = Cl$; $R^3 = 2$-F; $R^4 = 4$-F; $R^5 = 5$-F | dimethomorph |
| No. C.21 | $R^1 = CF_2Cl$; $R^2 = H$; $R^3 = 2$-F; $R^4 = 4$-F; $R^5 = 5$-F | dimethomorph |
| No. C.22 | $R^1 = CF_3$; $R^2 = H$; $R^3 = 2$-F; $R^4 = 4$-F; $R^5 = 5$-F | dimethomorph |
| No. C.23 | $R^1 = CF_3$; $R^2 = F$; $R^3 = 2$-F; $R^4 = 4$-F; $R^5 = 5$-F | dimethomorph |
| No. C.24 | $R^1 = CF_3$; $R^2 = Cl$; $R^3 = 2$-F; $R^4 = 4$-F; $R^5 = 5$-F | dimethomorph |

TABLE 6

Active compound combinations of compounds I with active compounds II of group D):

| Mixture | Compounds of the formula I (X = oxygen) | Active compound II |
|---|---|---|
| No. D.1 | $R^1 = CH_3$; $R^2 = H$; $R^3 = 3$-F; $R^4 = 4$-F; $R^5 = 5$-F | pyrimethanil |
| No. D.2 | $R^1 = CH_3$; $R^2 = F$; $R^3 = 3$-F; $R^4 = 4$-F; $R^5 = 5$-F | pyrimethanil |
| No. D.3 | $R^1 = CH_3$; $R^2 = Cl$; $R^3 = 3$-F; $R^4 = 4$-F; $R^5 = 5$-F | pyrimethanil |
| No. D.4 | $R^1 = CH_2F$; $R^2 = H$; $R^3 = 3$-F; $R^4 = 4$-F; $R^5 = 5$-F | pyrimethanil |
| No. D.5 | $R^1 = CHFCl$; $R^2 = H$; $R^3 = 3$-F; $R^4 = 4$-F; $R^5 = 5$-F | pyrimethanil |
| No. D.6 | $R^1 = CHF_2$; $R^2 = H$; $R^3 = 3$-F; $R^4 = 4$-F; $R^5 = 5$-F | pyrimethanil |
| No. D.7 | $R^1 = CHF_2$; $R^2 = F$; $R^3 = 3$-F; $R^4 = 4$-F; $R^5 = 5$-F | pyrimethanil |
| No. D.8 | $R^1 = CHF_2$; $R^2 = Cl$; $R^3 = 3$-F; $R^4 = 4$-F; $R^5 = 5$-F | pyrimethanil |
| No. D.9 | $R^1 = CF_2Cl$; $R^2 = H$; $R^3 = 3$-F; $R^4 = 4$-F; $R^5 = 5$-F | pyrimethanil |
| No. D.10 | $R^1 = CF_3$; $R^2 = H$; $R^3 = 3$-F; $R^4 = 4$-F; $R^5 = 5$-F | pyrimethanil |
| No. D.11 | $R^1 = CF_3$; $R^2 = F$; $R^3 = 3$-F; $R^4 = 4$-F; $R^5 = 5$-F | pyrimethanil |
| No. D.12 | $R^1 = CF_3$; $R^2 = Cl$; $R^3 = 3$-F; $R^4 = 4$-F; $R^5 = 5$-F | pyrimethanil |
| No. D.13 | $R^1 = CH_3$; $R^2 = H$; $R^3 = 2$-F; $R^4 = 4$-F; $R^5 = 5$-F | pyrimethanil |
| No. D.14 | $R^1 = CH_3$; $R^2 = F$; $R^3 = 2$-F; $R^4 = 4$-F; $R^5 = 5$-F | pyrimethanil |
| No. D.15 | $R^1 = CH_3$; $R^2 = Cl$; $R^3 = 2$-F; $R^4 = 4$-F; $R^5 = 5$-F | pyrimethanil |
| No. D.16 | $R^1 = CH_2F$; $R^2 = H$; $R^3 = 2$-F; $R^4 = 4$-F; $R^5 = 5$-F | pyrimethanil |
| No. D.17 | $R^1 = CHFCl$; $R^2 = H$; $R^3 = 2$-F; $R^4 = 4$-F; $R^5 = 5$-F | pyrimethanil |
| No. D.18 | $R^1 = CHF_2$; $R^2 = H$; $R^3 = 2$-F; $R^4 = 4$-F; $R^5 = 5$-F | pyrimethanil |
| No. D.19 | $R^1 = CHF_2$; $R^2 = F$; $R^3 = 2$-F; $R^4 = 4$-F; $R^5 = 5$-F | pyrimethanil |
| No. D.20 | $R^1 = CHF_2$; $R^2 = Cl$; $R^3 = 2$-F; $R^4 = 4$-F; $R^5 = 5$-F | pyrimethanil |
| No. D.21 | $R^1 = CF_2Cl$; $R^2 = H$; $R^3 = 2$-F; $R^4 = 4$-F; $R^5 = 5$-F | pyrimethanil |
| No. D.22 | $R^1 = CF_3$; $R^2 = H$; $R^3 = 2$-F; $R^4 = 4$-F; $R^5 = 5$-F | pyrimethanil |
| No. D.23 | $R^1 = CF_3$; $R^2 = F$; $R^3 = 2$-F; $R^4 = 4$-F; $R^5 = 5$-F | pyrimethanil |
| No. D.24 | $R^1 = CF_3$; $R^2 = Cl$; $R^3 = 2$-F; $R^4 = 4$-F; $R^5 = 5$-F | pyrimethanil |
| No. D.25 | $R^1 = CH_3$; $R^2 = H$; $R^3 = 3$-F; $R^4 = 4$-F; $R^5 = 5$-F | 5-chloro-7-(4-methyl-piperidin-1-yl)-6-(2,4,6-trifluorophenyl)-[1,2,4]triazolo[1,5-a]pyrimidine |
| No. D.26 | $R^1 = CH_3$; $R^2 = F$; $R^3 = 3$-F; $R^4 = 4$-F; $R^5 = 5$-F | 5-chloro-7-(4-methyl-piperidin-1-yl)-6-(2,4,6-trifluorophenyl)-[1,2,4]triazolo[1,5-a]pyrimidine |
| No. D.27 | $R^1 = CH_3$; $R^2 = Cl$; $R^3 = 3$-F; $R^4 = 4$-F; $R^5 = 5$-F | 5-chloro-7-(4-methyl-piperidin-1-yl)-6-(2,4,6-trifluorophenyl)-[1,2,4]triazolo[1,5-a]pyrimidine |
| No. D.28 | $R^1 = CH_2F$; $R^2 = H$; $R^3 = 3$-F; $R^4 = 4$-F; $R^5 = 5$-F | 5-chloro-7-(4-methyl-piperidin-1-yl)-6-(2,4,6-trifluorophenyl)-[1,2,4]triazolo[1,5-a]pyrimidine |

TABLE 6-continued

Active compound combinations of compounds I with active compounds II of group D):

| Mixture | Compounds of the formula I (X = oxygen) | Active compound II |
|---|---|---|
| No. D.29 | $R^1$ = CHFCl; $R^2$ = H; $R^3$ = 3-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.30 | $R^1$ = $CHF_2$; $R^2$ = H; $R^3$ = 3-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.31 | $R^1$ = $CHF_2$; $R^2$ = F; $R^3$ = 3-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.32 | $R^1$ = $CHF_2$; $R^2$ = Cl; $R^3$ = 3-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.33 | $R^1$ = $CF_2Cl$; $R^2$ = H; $R^3$ = 3-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.34 | $R^1$ = $CF_3$; $R^2$ = H; $R^3$ = 3-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.35 | $R^1$ = $CF_3$; $R^2$ = F; $R^3$ = 3-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.36 | $R^1$ = $CF_3$; $R^2$ = Cl; $R^3$ = 3-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.37 | $R^1$ = $CH_3$; $R^2$ = H; $R^3$ = 2-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.38 | $R^1$ = $CH_3$; $R^2$ = F; $R^3$ = 2-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.39 | $R^1$ = $CH_3$; $R^2$ = Cl; $R^3$ = 2-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.40 | $R^1$ = $CH_2F$; $R^2$ = H; $R^3$ = 2-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.41 | $R^1$ = CHFCl; $R^2$ = H; $R^3$ = 2-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.42 | $R^1$ = $CHF_2$; $R^2$ = H; $R^3$ = 2-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.43 | $R^1$ = $CHF_2$; $R^2$ = F; $R^3$ = 2-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.44 | $R^1$ = $CHF_2$; $R^2$ = Cl; $R^3$ = 2-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.45 | $R^1$ = $CF_2Cl$; $R^2$ = H; $R^3$ = 2-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.46 | $R^1$ = $CF_3$; $R^2$ = H; $R^3$ = 2-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |
| No. D.47 | $R^1$ = $CF_3$; $R^2$ = F; $R^3$ = 2-F; $R^4$ = 4-F; $R^5$ = 5-F | 5-chloro-7-(4-methyl-piperidin-1-yl)-6-(2,4,6-trifluorophenyl)-[1,2,4]triazolo[1,5-a]pyrimidine |

TABLE 6-continued

Active compound combinations of compounds I with active compounds II of group D):

| Mixture | Compounds of the formula I (X = oxygen) | Active compound II |
|---|---|---|
| No. D.48 | $R^1 = CF_3$; $R^2 = Cl$; $R^3 = 2$-F; $R^4 = 4$-F; $R^5 = 5$-F | 5-chloro-7-(4-methyl-piperidin-1-yl)-6-(2,4,6-trifluorophenyl)-[1,2,4]triazolo[1,5-a]pyrimidine |
| No. D.49 | $R^1 = CH_3$; $R^2 = H$; $R^3 = 3$-F; $R^4 = 4$-F; $R^5 = 5$-F | dodemorph |
| No. D.50 | $R^1 = CH_3$; $R^2 = F$; $R^3 = 3$-F; $R^4 = 4$-F; $R^5 = 5$-F | dodemorph |
| No. D.51 | $R^1 = CH_3$; $R^2 = Cl$; $R^3 = 3$-F; $R^4 = 4$-F; $R^5 = 5$-F | dodemorph |
| No. D.52 | $R^1 = CH_2F$; $R^2 = H$; $R^3 = 3$-F; $R^4 = 4$-F; $R^5 = 5$-F | dodemorph |
| No. D.53 | $R^1 = CHFCl$; $R^2 = H$; $R^3 = 3$-F; $R^4 = 4$-F; $R^5 = 5$-F | dodemorph |
| No. D.54 | $R^1 = CHF_2$; $R^2 = H$; $R^3 = 3$-F; $R^4 = 4$-F; $R^5 = 5$-F | dodemorph |
| No. D.55 | $R^1 = CHF_2$; $R^2 = F$; $R^3 = 3$-F; $R^4 = 4$-F; $R^5 = 5$-F | dodemorph |
| No. D.56 | $R^1 = CHF_2$; $R^2 = Cl$; $R^3 = 3$-F; $R^4 = 4$-F; $R^5 = 5$-F | dodemorph |
| No. D.57 | $R^1 = CF_2Cl$; $R^2 = H$; $R^3 = 3$-F; $R^4 = 4$-F; $R^5 = 5$-F | dodemorph |
| No. D.58 | $R^1 = CF_3$; $R^2 = H$; $R^3 = 3$-F; $R^4 = 4$-F; $R^5 = 5$-F | dodemorph |
| No. D.59 | $R^1 = CF_3$; $R^2 = F$; $R^3 = 3$-F; $R^4 = 4$-F; $R^5 = 5$-F | dodemorph |
| No. D.60 | $R^1 = CF_3$; $R^2 = Cl$; $R^3 = 3$-F; $R^4 = 4$-F; $R^5 = 5$-F | dodemorph |
| No. D.61 | $R^1 = CH_3$; $R^2 = H$; $R^3 = 2$-F; $R^4 = 4$-F; $R^5 = 5$-F | dodemorph |
| No. D.62 | $R^1 = CH_3$; $R^2 = F$; $R^3 = 2$-F; $R^4 = 4$-F; $R^5 = 5$-F | dodemorph |
| No. D.63 | $R^1 = CH_3$; $R^2 = Cl$; $R^3 = 2$-F; $R^4 = 4$-F; $R^5 = 5$-F | dodemorph |
| No. D.64 | $R^1 = CH_2F$; $R^2 = H$; $R^3 = 2$-F; $R^4 = 4$-F; $R^5 = 5$-F | dodemorph |
| No. D.65 | $R^1 = CHFCl$; $R^2 = H$; $R^3 = 2$-F; $R^4 = 4$-F; $R^5 = 5$-F | dodemorph |
| No. D.66 | $R^1 = CHF_2$; $R^2 = H$; $R^3 = 2$-F; $R^4 = 4$-F; $R^5 = 5$-F | dodemorph |
| No. D.67 | $R^1 = CHF_2$; $R^2 = F$; $R^3 = 2$-F; $R^4 = 4$-F; $R^5 = 5$-F | dodemorph |
| No. D.68 | $R^1 = CHF_2$; $R^2 = Cl$; $R^3 = 2$-F; $R^4 = 4$-F; $R^5 = 5$-F | dodemorph |
| No. D.69 | $R^1 = CF_2Cl$; $R^2 = H$; $R^3 = 2$-F; $R^4 = 4$-F; $R^5 = 5$-F | dodemorph |
| No. D.70 | $R^1 = CF_3$; $R^2 = H$; $R^3 = 2$-F; $R^4 = 4$-F; $R^5 = 5$-F | dodemorph |
| No. D.71 | $R^1 = CF_3$; $R^2 = F$; $R^3 = 2$-F; $R^4 = 4$-F; $R^5 = 5$-F | dodemorph |
| No. D.72 | $R^1 = CF_3$; $R^2 = Cl$; $R^3 = 2$-F; $R^4 = 4$-F; $R^5 = 5$-F | dodemorph |
| No. D.73 | $R^1 = CH_3$; $R^2 = H$; $R^3 = 3$-F; $R^4 = 4$-F; $R^5 = 5$-F | fenpropimorph |
| No. D.74 | $R^1 = CH_3$; $R^2 = F$; $R^3 = 3$-F; $R^4 = 4$-F; $R^5 = 5$-F | fenpropimorph |
| No. D.75 | $R^1 = CH_3$; $R^2 = Cl$; $R^3 = 3$-F; $R^4 = 4$-F; $R^5 = 5$-F | fenpropimorph |
| No. D.76 | $R^1 = CH_2F$; $R^2 = H$; $R^3 = 3$-F; $R^4 = 4$-F; $R^5 = 5$-F | fenpropimorph |
| No. D.77 | $R^1 = CHFCl$; $R^2 = H$; $R^3 = 3$-F; $R^4 = 4$-F; $R^5 = 5$-F | fenpropimorph |
| No. D.78 | $R^1 = CHF_2$; $R^2 = H$; $R^3 = 3$-F; $R^4 = 4$-F; $R^5 = 5$-F | fenpropimorph |
| No. D.79 | $R^1 = CHF_2$; $R^2 = F$; $R^3 = 3$-F; $R^4 = 4$-F; $R^5 = 5$-F | fenpropimorph |
| No. D.80 | $R^1 = CHF_2$; $R^2 = Cl$; $R^3 = 3$-F; $R^4 = 4$-F; $R^5 = 5$-F | fenpropimorph |
| No. D.81 | $R^1 = CF_2Cl$; $R^2 = H$; $R^3 = 3$-F; $R^4 = 4$-F; $R^5 = 5$-F | fenpropimorph |
| No. D.82 | $R^1 = CF_3$; $R^2 = H$; $R^3 = 3$-F; $R^4 = 4$-F; $R^5 = 5$-F | fenpropimorph |
| No. D.83 | $R^1 = CF_3$; $R^2 = F$; $R^3 = 3$-F; $R^4 = 4$-F; $R^5 = 5$-F | fenpropimorph |
| No. D.84 | $R^1 = CF_3$; $R^2 = Cl$; $R^3 = 3$-F; $R^4 = 4$-F; $R^5 = 5$-F | fenpropimorph |
| No. D.85 | $R^1 = CH_3$; $R^2 = H$; $R^3 = 2$-F; $R^4 = 4$-F; $R^5 = 5$-F | fenpropimorph |
| No. D.86 | $R^1 = CH_3$; $R^2 = F$; $R^3 = 2$-F; $R^4 = 4$-F; $R^5 = 5$-F | fenpropimorph |
| No. D.87 | $R^1 = CH_3$; $R^2 = Cl$; $R^3 = 2$-F; $R^4 = 4$-F; $R^5 = 5$-F | fenpropimorph |
| No. D.88 | $R^1 = CH_2F$; $R^2 = H$; $R^3 = 2$-F; $R^4 = 4$-F; $R^5 = 5$-F | fenpropimorph |
| No. D.89 | $R^1 = CHFCl$; $R^2 = H$; $R^3 = 2$-F; $R^4 = 4$-F; $R^5 = 5$-F | fenpropimorph |
| No. D.90 | $R^1 = CHF_2$; $R^2 = H$; $R^3 = 2$-F; $R^4 = 4$-F; $R^5 = 5$-F | fenpropimorph |
| No. D.91 | $R^1 = CHF_2$; $R^2 = F$; $R^3 = 2$-F; $R^4 = 4$-F; $R^5 = 5$-F | fenpropimorph |
| No. D.92 | $R^1 = CHF_2$; $R^2 = Cl$; $R^3 = 2$-F; $R^4 = 4$-F; $R^5 = 5$-F | fenpropimorph |
| No. D.93 | $R^1 = CF_2Cl$; $R^2 = H$; $R^3 = 2$-F; $R^4 = 4$-F; $R^5 = 5$-F | fenpropimorph |
| No. D.94 | $R^1 = CF_3$; $R^2 = H$; $R^3 = 2$-F; $R^4 = 4$-F; $R^5 = 5$-F | fenpropimorph |
| No. D.95 | $R^1 = CF_3$; $R^2 = F$; $R^3 = 2$-F; $R^4 = 4$-F; $R^5 = 5$-F | fenpropimorph |
| No. D.96 | $R^1 = CF_3$; $R^2 = Cl$; $R^3 = 2$-F; $R^4 = 4$-F; $R^5 = 5$-F | fenpropimorph |
| No. D.97 | $R^1 = CH_3$; $R^2 = H$; $R^3 = 3$-F; $R^4 = 4$-F; $R^5 = 5$-F | tridemorph |
| No. D.98 | $R^1 = CH_3$; $R^2 = F$; $R^3 = 3$-F; $R^4 = 4$-F; $R^5 = 5$-F | tridemorph |
| No. D.99 | $R^1 = CH_3$; $R^2 = Cl$; $R^3 = 3$-F; $R^4 = 4$-F; $R^5 = 5$-F | tridemorph |
| No. D.100 | $R^1 = CH_2F$; $R^2 = H$; $R^3 = 3$-F; $R^4 = 4$-F; $R^5 = 5$-F | tridemorph |
| No. D.101 | $R^1 = CHFCl$; $R^2 = H$; $R^3 = 3$-F; $R^4 = 4$-F; $R^5 = 5$-F | tridemorph |
| No. D.102 | $R^1 = CHF_2$; $R^2 = H$; $R^3 = 3$-F; $R^4 = 4$-F; $R^5 = 5$-F | tridemorph |
| No. D.103 | $R^1 = CHF_2$; $R^2 = F$; $R^3 = 3$-F; $R^4 = 4$-F; $R^5 = 5$-F | tridemorph |
| No. D.104 | $R^1 = CHF_2$; $R^2 = Cl$; $R^3 = 3$-F; $R^4 = 4$-F; $R^5 = 5$-F | tridemorph |
| No. D.105 | $R^1 = CF_2Cl$; $R^2 = H$; $R^3 = 3$-F; $R^4 = 4$-F; $R^5 = 5$-F | tridemorph |
| No. D.106 | $R^1 = CF_3$; $R^2 = H$; $R^3 = 3$-F; $R^4 = 4$-F; $R^5 = 5$-F | tridemorph |
| No. D.107 | $R^1 = CF_3$; $R^2 = F$; $R^3 = 3$-F; $R^4 = 4$-F; $R^5 = 5$-F | tridemorph |
| No. D.108 | $R^1 = CF_3$; $R^2 = Cl$; $R^3 = 3$-F; $R^4 = 4$-F; $R^5 = 5$-F | tridemorph |
| No. D.109 | $R^1 = CH_3$; $R^2 = H$; $R^3 = 2$-F; $R^4 = 4$-F; $R^5 = 5$-F | tridemorph |

TABLE 6-continued

Active compound combinations of compounds I with active compounds II of group D):

| Mixture | Compounds of the formula I (X = oxygen) | Active compound II |
|---|---|---|
| No. D.110 | $R^1 = CH_3$; $R^2 = F$; $R^3 = 2$-F; $R^4 = 4$-F; $R^5 = 5$-F | tridemorph |
| No. D.111 | $R^1 = CH_3$; $R^2 = Cl$; $R^3 = 2$-F; $R^4 = 4$-F; $R^5 = 5$-F | tridemorph |
| No. D.112 | $R^1 = CH_2F$; $R^2 = H$; $R^3 = 2$-F; $R^4 = 4$-F; $R^5 = 5$-F | tridemorph |
| No. D.113 | $R^1 = CHFCl$; $R^2 = H$; $R^3 = 2$-F; $R^4 = 4$-F; $R^5 = 5$-F | tridemorph |
| No. D.114 | $R^1 = CHF_2$; $R^2 = H$; $R^3 = 2$-F; $R^4 = 4$-F; $R^5 = 5$-F | tridemorph |
| No. D.115 | $R^1 = CHF_2$; $R^2 = F$; $R^3 = 2$-F; $R^4 = 4$-F; $R^5 = 5$-F | tridemorph |
| No. D.116 | $R^1 = CHF_2$; $R^2 = Cl$; $R^3 = 2$-F; $R^4 = 4$-F; $R^5 = 5$-F | tridemorph |
| No. D.117 | $R^1 = CF_2Cl$; $R^2 = H$; $R^3 = 2$-F; $R^4 = 4$-F; $R^5 = 5$-F | tridemorph |
| No. D.118 | $R^1 = CF_3$; $R^2 = H$; $R^3 = 2$-F; $R^4 = 4$-F; $R^5 = 5$-F | tridemorph |
| No. D.119 | $R^1 = CF_3$; $R^2 = F$; $R^3 = 2$-F; $R^4 = 4$-F; $R^5 = 5$-F | tridemorph |
| No. D.120 | $R^1 = CF_3$; $R^2 = Cl$; $R^3 = 2$-F; $R^4 = 4$-F; $R^5 = 5$-F | tridemorph |
| No. D.121 | $R^1 = CH_3$; $R^2 = H$; $R^3 = 3$-F; $R^4 = 4$-F; $R^5 = 5$-F | iprodione |
| No. D.122 | $R^1 = CH_3$; $R^2 = F$; $R^3 = 3$-F; $R^4 = 4$-F; $R^5 = 5$-F | iprodione |
| No. D.123 | $R^1 = CH_3$; $R^2 = Cl$; $R^3 = 3$-F; $R^4 = 4$-F; $R^5 = 5$-F | iprodione |
| No. D.124 | $R^1 = CH_2F$; $R^2 = H$; $R^3 = 3$-F; $R^4 = 4$-F; $R^5 = 5$-F | iprodione |
| No. D.125 | $R^1 = CHFCl$; $R^2 = H$; $R^3 = 3$-F; $R^4 = 4$-F; $R^5 = 5$-F | iprodione |
| No. D.126 | $R^1 = CHF_2$; $R^2 = H$; $R^3 = 3$-F; $R^4 = 4$-F; $R^5 = 5$-F | iprodione |
| No. D.127 | $R^1 = CHF_2$; $R^2 = F$; $R^3 = 3$-F; $R^4 = 4$-F; $R^5 = 5$-F | iprodione |
| No. D.128 | $R^1 = CHF_2$; $R^2 = Cl$; $R^3 = 3$-F; $R^4 = 4$-F; $R^5 = 5$-F | iprodione |
| No. D.129 | $R^1 = CF_2Cl$; $R^2 = H$; $R^3 = 3$-F; $R^4 = 4$-F; $R^5 = 5$-F | iprodione |
| No. D.130 | $R^1 = CF_3$; $R^2 = H$; $R^3 = 3$-F; $R^4 = 4$-F; $R^5 = 5$-F | iprodione |
| No. D.131 | $R^1 = CF_3$; $R^2 = F$; $R^3 = 3$-F; $R^4 = 4$-F; $R^5 = 5$-F | iprodione |
| No. D.132 | $R^1 = CF_3$; $R^2 = Cl$; $R^3 = 3$-F; $R^4 = 4$-F; $R^5 = 5$-F | iprodione |
| No. D.133 | $R^1 = CH_3$; $R^2 = H$; $R^3 = 2$-F; $R^4 = 4$-F; $R^5 = 5$-F | iprodione |
| No. D.134 | $R^1 = CH_3$; $R^2 = F$; $R^3 = 2$-F; $R^4 = 4$-F; $R^5 = 5$-F | iprodione |
| No. D.135 | $R^1 = CH_3$; $R^2 = Cl$; $R^3 = 2$-F; $R^4 = 4$-F; $R^5 = 5$-F | iprodione |
| No. D.136 | $R^1 = CH_2F$; $R^2 = H$; $R^3 = 2$-F; $R^4 = 4$-F; $R^5 = 5$-F | iprodione |
| No. D.137 | $R^1 = CHFCl$; $R^2 = H$; $R^3 = 2$-F; $R^4 = 4$-F; $R^5 = 5$-F | iprodione |
| No. D.138 | $R^1 = CHF_2$; $R^2 = H$; $R^3 = 2$-F; $R^4 = 4$-F; $R^5 = 5$-F | iprodione |
| No. D.139 | $R^1 = CHF_2$; $R^2 = F$; $R^3 = 2$-F; $R^4 = 4$-F; $R^5 = 5$-F | iprodione |
| No. D.140 | $R^1 = CHF_2$; $R^2 = Cl$; $R^3 = 2$-F; $R^4 = 4$-F; $R^5 = 5$-F | iprodione |
| No. D.141 | $R^1 = CF_2Cl$; $R^2 = H$; $R^3 = 2$-F; $R^4 = 4$-F; $R^5 = 5$-F | iprodione |
| No. D.142 | $R^1 = CF_3$; $R^2 = H$; $R^3 = 2$-F; $R^4 = 4$-F; $R^5 = 5$-F | iprodione |
| No. D.143 | $R^1 = CF_3$; $R^2 = F$; $R^3 = 2$-F; $R^4 = 4$-F; $R^5 = 5$-F | iprodione |
| No. D.144 | $R^1 = CF_3$; $R^2 = Cl$; $R^3 = 2$-F; $R^4 = 4$-F; $R^5 = 5$-F | iprodione |
| No. D.145 | $R^1 = CH_3$; $R^2 = H$; $R^3 = 3$-F; $R^4 = 4$-F; $R^5 = 5$-F | vinclozolin |
| No. D.146 | $R^1 = CH_3$; $R^2 = F$; $R^3 = 3$-F; $R^4 = 4$-F; $R^5 = 5$-F | vinclozolin |
| No. D.147 | $R^1 = CH_3$; $R^2 = Cl$; $R^3 = 3$-F; $R^4 = 4$-F; $R^5 = 5$-F | vinclozolin |

TABLE 6-continued

Active compound combinations of compounds I with active compounds II of group D):

| Mixture | Compounds of the formula I (X = oxygen) | Active compound II |
|---|---|---|
| No. D.148 | $R^1 = CH_2F$; $R^2 = H$; $R^3 = 3$-F; $R^4 = 4$-F; $R^5 = 5$-F | vinclozolin |
| No. D.149 | $R^1 = CHFCl$; $R^2 = H$; $R^3 = 3$-F; $R^4 = 4$-F; $R^5 = 5$-F | vinclozolin |
| No. D.150 | $R^1 = CHF_2$; $R^2 = H$; $R^3 = 3$-F; $R^4 = 4$-F; $R^5 = 5$-F | vinclozolin |
| No. D.151 | $R^1 = CHF_2$; $R^2 = F$; $R^3 = 3$-F; $R^4 = 4$-F; $R^5 = 5$-F | vinclozolin |
| No. D.152 | $R^1 = CHF_2$; $R^2 = Cl$; $R^3 = 3$-F; $R^4 = 4$-F; $R^5 = 5$-F | vinclozolin |
| No. D.153 | $R^1 = CF_2Cl$; $R^2 = H$; $R^3 = 3$-F; $R^4 = 4$-F; $R^5 = 5$-F | vinclozolin |
| No. D.154 | $R^1 = CF_3$; $R^2 = H$; $R^3 = 3$-F; $R^4 = 4$-F; $R^5 = 5$-F | vinclozolin |
| No. D.155 | $R^1 = CF_3$; $R^2 = F$; $R^3 = 3$-F; $R^4 = 4$-F; $R^5 = 5$-F | vinclozolin |
| No. D.156 | $R^1 = CF_3$; $R^2 = Cl$; $R^3 = 3$-F; $R^4 = 4$-F; $R^5 = 5$-F | vinclozolin |
| No. D.157 | $R^1 = CH_3$; $R^2 = H$; $R^3 = 2$-F; $R^4 = 4$-F; $R^5 = 5$-F | vinclozolin |
| No. D.158 | $R^1 = CH_3$; $R^2 = F$; $R^3 = 2$-F; $R^4 = 4$-F; $R^5 = 5$-F | vinclozolin |
| No. D.159 | $R^1 = CH_3$; $R^2 = Cl$; $R^3 = 2$-F; $R^4 = 4$-F; $R^5 = 5$-F | vinclozolin |
| No. D.160 | $R^1 = CH_2F$; $R^2 = H$; $R^3 = 2$-F; $R^4 = 4$-F; $R^5 = 5$-F | vinclozolin |
| No. D.161 | $R^1 = CHFCl$; $R^2 = H$; $R^3 = 2$-F; $R^4 = 4$-F; $R^5 = 5$-F | vinclozolin |
| No. D.162 | $R^1 = CHF_2$; $R^2 = H$; $R^3 = 2$-F; $R^4 = 4$-F; $R^5 = 5$-F | vinclozolin |
| No. D.163 | $R^1 = CHF_2$; $R^2 = F$; $R^3 = 2$-F; $R^4 = 4$-F; $R^5 = 5$-F | vinclozolin |
| No. D.164 | $R^1 = CHF_2$; $R^2 = Cl$; $R^3 = 2$-F; $R^4 = 4$-F; $R^5 = 5$-F | vinclozolin |
| No. D.165 | $R^1 = CF_2Cl$; $R^2 = H$; $R^3 = 2$-F; $R^4 = 4$-F; $R^5 = 5$-F | vinclozolin |
| No. D.166 | $R^1 = CF_3$; $R^2 = H$; $R^3 = 2$-F; $R^4 = 4$-F; $R^5 = 5$-F | vinclozolin |
| No. D.167 | $R^1 = CF_3$; $R^2 = F$; $R^3 = 2$-F; $R^4 = 4$-F; $R^5 = 5$-F | vinclozolin |
| No. D.168 | $R^1 = CF_3$; $R^2 = Cl$; $R^3 = 2$-F; $R^4 = 4$-F; $R^5 = 5$-F | vinclozolin |

TABLE 7

Active compound combinations of compounds I with active compounds II of group E):

| Mixture | Compounds of the formula I (X = oxygen) | Active compound II |
|---|---|---|
| No. E.1 | $R^1 = CH_3$; $R^2 = H$; $R^3 = 3$-F; $R^4 = 4$-F; $R^5 = 5$-F | mancozeb |
| No. E.2 | $R^1 = CH_3$; $R^2 = F$; $R^3 = 3$-F; $R^4 = 4$-F; $R^5 = 5$-F | mancozeb |
| No. E.3 | $R^1 = CH_3$; $R^2 = Cl$; $R^3 = 3$-F; $R^4 = 4$-F; $R^5 = 5$-F | mancozeb |
| No. E.4 | $R^1 = CH_2F$; $R^2 = H$; $R^3 = 3$-F; $R^4 = 4$-F; $R^5 = 5$-F | mancozeb |
| No. E.5 | $R^1 = CHFCl$; $R^2 = H$; $R^3 = 3$-F; $R^4 = 4$-F; $R^5 = 5$-F | mancozeb |
| No. E.6 | $R^1 = CHF_2$; $R^2 = H$; $R^3 = 3$-F; $R^4 = 4$-F; $R^5 = 5$-F | mancozeb |
| No. E.7 | $R^1 = CHF_2$; $R^2 = F$; $R^3 = 3$-F; $R^4 = 4$-F; $R^5 = 5$-F | mancozeb |
| No. E.8 | $R^1 = CHF_2$; $R^2 = Cl$; $R^3 = 3$-F; $R^4 = 4$-F; $R^5 = 5$-F | mancozeb |
| No. E.9 | $R^1 = CF_2Cl$; $R^2 = H$; $R^3 = 3$-F; $R^4 = 4$-F; $R^5 = 5$-F | mancozeb |
| No. E.10 | $R^1 = CF_3$; $R^2 = H$; $R^3 = 3$-F; $R^4 = 4$-F; $R^5 = 5$-F | mancozeb |
| No. E.11 | $R^1 = CF_3$; $R^2 = F$; $R^3 = 3$-F; $R^4 = 4$-F; $R^5 = 5$-F | mancozeb |
| No. E.12 | $R^1 = CF_3$; $R^2 = Cl$; $R^3 = 3$-F; $R^4 = 4$-F; $R^5 = 5$-F | mancozeb |
| No. E.13 | $R^1 = CH_3$; $R^2 = H$; $R^3 = 2$-F; $R^4 = 4$-F; $R^5 = 5$-F | mancozeb |
| No. E.14 | $R^1 = CH_3$; $R^2 = F$; $R^3 = 2$-F; $R^4 = 4$-F; $R^5 = 5$-F | mancozeb |
| No. E.15 | $R^1 = CH_3$; $R^2 = Cl$; $R^3 = 2$-F; $R^4 = 4$-F; $R^5 = 5$-F | mancozeb |
| No. E.16 | $R^1 = CH_2F$; $R^2 = H$; $R^3 = 2$-F; $R^4 = 4$-F; $R^5 = 5$-F | mancozeb |
| No. E.17 | $R^1 = CHFCl$; $R^2 = H$; $R^3 = 2$-F; $R^4 = 4$-F; $R^5 = 5$-F | mancozeb |
| No. E.18 | $R^1 = CHF_2$; $R^2 = H$; $R^3 = 2$-F; $R^4 = 4$-F; $R^5 = 5$-F | mancozeb |
| No. E.19 | $R^1 = CHF_2$; $R^2 = F$; $R^3 = 2$-F; $R^4 = 4$-F; $R^5 = 5$-F | mancozeb |
| No. E.20 | $R^1 = CHF_2$; $R^2 = Cl$; $R^3 = 2$-F; $R^4 = 4$-F; $R^5 = 5$-F | mancozeb |
| No. E.21 | $R^1 = CF_2Cl$; $R^2 = H$; $R^3 = 2$-F; $R^4 = 4$-F; $R^5 = 5$-F | mancozeb |
| No. E.22 | $R^1 = CF_3$; $R^2 = H$; $R^3 = 2$-F; $R^4 = 4$-F; $R^5 = 5$-F | mancozeb |
| No. E.23 | $R^1 = CF_3$; $R^2 = F$; $R^3 = 2$-F; $R^4 = 4$-F; $R^5 = 5$-F | mancozeb |

TABLE 7-continued

Active compound combinations of compounds I with active compounds II of group E):

| Mixture | Compounds of the formula I (X = oxygen) | Active compound II |
|---|---|---|
| No. E.24 | $R^1 = CF_3$; $R^2 = Cl$; $R^3 = $ 2-F; $R^4 = $ 4-F; $R^5 = $ 5-F | mancozeb |
| No. E.25 | $R^1 = CH_3$; $R^2 = H$; $R^3 = $ 3-F; $R^4 = $ 4-F; $R^5 = $ 5-F | metiram |
| No. E.26 | $R^1 = CH_3$; $R^2 = F$; $R^3 = $ 3-F; $R^4 = $ 4-F; $R^5 = $ 5-F | metiram |
| No. E.27 | $R^1 = CH_3$; $R^2 = Cl$; $R^3 = $ 3-F; $R^4 = $ 4-F; $R^5 = $ 5-F | metiram |
| No. E.28 | $R^1 = CH_2F$; $R^2 = H$; $R^3 = $ 3-F; $R^4 = $ 4-F; $R^5 = $ 5-F | metiram |
| No. E.29 | $R^1 = CHFCl$; $R^2 = H$; $R^3 = $ 3-F; $R^4 = $ 4-F; $R^5 = $ 5-F | metiram |
| No. E.30 | $R^1 = CHF_2$; $R^2 = H$; $R^3 = $ 3-F; $R^4 = $ 4-F; $R^5 = $ 5-F | metiram |
| No. E.31 | $R^1 = CHF_2$; $R^2 = F$; $R^3 = $ 3-F; $R^4 = $ 4-F; $R^5 = $ 5-F | metiram |
| No. E.32 | $R^1 = CHF_2$; $R^2 = Cl$; $R^3 = $ 3-F; $R^4 = $ 4-F; $R^5 = $ 5-F | metiram |
| No. E.33 | $R^1 = CF_2Cl$; $R^2 = H$; $R^3 = $ 3-F; $R^4 = $ 4-F; $R^5 = $ 5-F | metiram |
| No. E.34 | $R^1 = CF_3$; $R^2 = H$; $R^3 = $ 3-F; $R^4 = $ 4-F; $R^5 = $ 5-F | metiram |
| No. E.35 | $R^1 = CF_3$; $R^2 = F$; $R^3 = $ 3-F; $R^4 = $ 4-F; $R^5 = $ 5-F | metiram |
| No. E.36 | $R^1 = CF_3$; $R^2 = Cl$; $R^3 = $ 3-F; $R^4 = $ 4-F; $R^5 = $ 5-F | metiram |
| No. E.37 | $R^1 = CH_3$; $R^2 = H$; $R^3 = $ 2-F; $R^4 = $ 4-F; $R^5 = $ 5-F | metiram |
| No. E.38 | $R^1 = CH_3$; $R^2 = F$; $R^3 = $ 2-F; $R^4 = $ 4-F; $R^5 = $ 5-F | metiram |
| No. E.39 | $R^1 = CH_3$; $R^2 = Cl$; $R^3 = $ 2-F; $R^4 = $ 4-F; $R^5 = $ 5-F | metiram |
| No. E.40 | $R^1 = CH_2F$; $R^2 = H$; $R^3 = $ 2-F; $R^4 = $ 4-F; $R^5 = $ 5-F | metiram |
| No. E.41 | $R^1 = CHFCl$; $R^2 = H$; $R^3 = $ 2-F; $R^4 = $ 4-F; $R^5 = $ 5-F | metiram |
| No. E.42 | $R^1 = CHF_2$; $R^2 = H$; $R^3 = $ 2-F; $R^4 = $ 4-F; $R^5 = $ 5-F | metiram |
| No. E.43 | $R^1 = CHF_2$; $R^2 = F$; $R^3 = $ 2-F; $R^4 = $ 4-F; $R^5 = $ 5-F | metiram |
| No. E.44 | $R^1 = CHF_2$; $R^2 = Cl$; $R^3 = $ 2-F; $R^4 = $ 4-F; $R^5 = $ 5-F | metiram |
| No. E.45 | $R^1 = CF_2Cl$; $R^2 = H$; $R^3 = $ 2-F; $R^4 = $ 4-F; $R^5 = $ 5-F | metiram |
| No. E.46 | $R^1 = CF_3$; $R^2 = H$; $R^3 = $ 2-F; $R^4 = $ 4-F; $R^5 = $ 5-F | metiram |
| No. E.47 | $R^1 = CF_3$; $R^2 = F$; $R^3 = $ 2-F; $R^4 = $ 4-F; $R^5 = $ 5-F | metiram |
| No. E.48 | $R^1 = CF_3$; $R^2 = Cl$; $R^3 = $ 2-F; $R^4 = $ 4-F; $R^5 = $ 5-F | metiram |

TABLE 8

Active compound combinations of compounds I with active compounds II of group F):

| Mixture | Compounds of the formula I (X = oxygen) | Active compound II |
|---|---|---|
| No. F.1 | $R^1 = CH_3$; $R^2 = H$; $R^3 = $ 3-F; $R^4 = $ 4-F; $R^5 = $ 5-F | chlorothalonil |
| No. F.2 | $R^1 = CH_3$; $R^2 = F$; $R^3 = $ 3-F; $R^4 = $ 4-F; $R^5 = $ 5-F | chlorothalonil |
| No. F.3 | $R^1 = CH_3$; $R^2 = Cl$; $R^3 = $ 3-F; $R^4 = $ 4-F; $R^5 = $ 5-F | chlorothalonil |
| No. F.4 | $R^1 = CH_2F$; $R^2 = H$; $R^3 = $ 3-F; $R^4 = $ 4-F; $R^5 = $ 5-F | chlorothalonil |
| No. F.5 | $R^1 = CHFCl$; $R^2 = H$; $R^3 = $ 3-F; $R^4 = $ 4-F; $R^5 = $ 5-F | chlorothalonil |
| No. F.6 | $R^1 = CHF_2$; $R^2 = H$; $R^3 = $ 3-F; $R^4 = $ 4-F; $R^5 = $ 5-F | chlorothalonil |
| No. F.7 | $R^1 = CHF_2$; $R^2 = F$; $R^3 = $ 3-F; $R^4 = $ 4-F; $R^5 = $ 5-F | chlorothalonil |
| No. F.8 | $R^1 = CHF_2$; $R^2 = Cl$; $R^3 = $ 3-F; $R^4 = $ 4-F; $R^5 = $ 5-F | chlorothalonil |
| No. F.9 | $R^1 = CF_2Cl$; $R^2 = H$; $R^3 = $ 3-F; $R^4 = $ 4-F; $R^5 = $ 5-F | chlorothalonil |
| No. F.10 | $R^1 = CF_3$; $R^2 = H$; $R^3 = $ 3-F; $R^4 = $ 4-F; $R^5 = $ 5-F | chlorothalonil |
| No. F.11 | $R^1 = CF_3$; $R^2 = F$; $R^3 = $ 3-F; $R^4 = $ 4-F; $R^5 = $ 5-F | chlorothalonil |
| No. F.12 | $R^1 = CF_3$; $R^2 = Cl$; $R^3 = $ 3-F; $R^4 = $ 4-F; $R^5 = $ 5-F | chlorothalonil |
| No. F.13 | $R^1 = CH_3$; $R^2 = H$; $R^3 = $ 2-F; $R^4 = $ 4-F; $R^5 = $ 5-F | chlorothalonil |
| No. F.14 | $R^1 = CH_3$; $R^2 = F$; $R^3 = $ 2-F; $R^4 = $ 4-F; $R^5 = $ 5-F | chlorothalonil |
| No. F.15 | $R^1 = CH_3$; $R^2 = Cl$; $R^3 = $ 2-F; $R^4 = $ 4-F; $R^5 = $ 5-F | chlorothalonil |
| No. F.16 | $R^1 = CH_2F$; $R^2 = H$; $R^3 = $ 2-F; $R^4 = $ 4-F; $R^5 = $ 5-F | chlorothalonil |
| No. F.17 | $R^1 = CHFCl$; $R^2 = H$; $R^3 = $ 2-F; $R^4 = $ 4-F; $R^5 = $ 5-F | chlorothalonil |
| No. F.18 | $R^1 = CHF_2$; $R^2 = H$; $R^3 = $ 2-F; $R^4 = $ 4-F; $R^5 = $ 5-F | chlorothalonil |
| No. F.19 | $R^1 = CHF_2$; $R^2 = F$; $R^3 = $ 2-F; $R^4 = $ 4-F; $R^5 = $ 5-F | chlorothalonil |
| No. F.20 | $R^1 = CHF_2$; $R^2 = Cl$; $R^3 = $ 2-F; $R^4 = $ 4-F; $R^5 = $ 5-F | chlorothalonil |
| No. F.21 | $R^1 = CF_2Cl$; $R^2 = H$; $R^3 = $ 2-F; $R^4 = $ 4-F; $R^5 = $ 5-F | chlorothalonil |
| No. F.22 | $R^1 = CF_3$; $R^2 = H$; $R^3 = $ 2-F; $R^4 = $ 4-F; $R^5 = $ 5-F | chlorothalonil |
| No. F.23 | $R^1 = CF_3$; $R^2 = F$; $R^3 = $ 2-F; $R^4 = $ 4-F; $R^5 = $ 5-F | chlorothalonil |
| No. F.24 | $R^1 = CF_3$; $R^2 = Cl$; $R^3 = $ 2-F; $R^4 = $ 4-F; $R^5 = $ 5-F | chlorothalonil |
| No. F.25 | $R^1 = CH_3$; $R^2 = H$; $R^3 = $ 3-F; $R^4 = $ 4-F; $R^5 = $ 5-F | metrafenone |
| No. F.26 | $R^1 = CH_3$; $R^2 = F$; $R^3 = $ 3-F; $R^4 = $ 4-F; $R^5 = $ 5-F | metrafenone |
| No. F.27 | $R^1 = CH_3$; $R^2 = Cl$; $R^3 = $ 3-F; $R^4 = $ 4-F; $R^5 = $ 5-F | metrafenone |
| No. F.28 | $R^1 = CH_2F$; $R^2 = H$; $R^3 = $ 3-F; $R^4 = $ 4-F; $R^5 = $ 5-F | metrafenone |
| No. F.29 | $R^1 = CHFCl$; $R^2 = H$; $R^3 = $ 3-F; $R^4 = $ 4-F; $R^5 = $ 5-F | metrafenone |
| No. F.30 | $R^1 = CHF_2$; $R^2 = H$; $R^3 = $ 3-F; $R^4 = $ 4-F; $R^5 = $ 5-F | metrafenone |
| No. F.31 | $R^1 = CHF_2$; $R^2 = F$; $R^3 = $ 3-F; $R^4 = $ 4-F; $R^5 = $ 5-F | metrafenone |
| No. F.32 | $R^1 = CHF_2$; $R^2 = Cl$; $R^3 = $ 3-F; $R^4 = $ 4-F; $R^5 = $ 5-F | metrafenone |
| No. F.33 | $R^1 = CF_2Cl$; $R^2 = H$; $R^3 = $ 3-F; $R^4 = $ 4-F; $R^5 = $ 5-F | metrafenone |
| No. F.34 | $R^1 = CF_3$; $R^2 = H$; $R^3 = $ 3-F; $R^4 = $ 4-F; $R^5 = $ 5-F | metrafenone |
| No. F.35 | $R^1 = CF_3$; $R^2 = F$; $R^3 = $ 3-F; $R^4 = $ 4-F; $R^5 = $ 5-F | metrafenone |
| No. F.36 | $R^1 = CF_3$; $R^2 = Cl$; $R^3 = $ 3-F; $R^4 = $ 4-F; $R^5 = $ 5-F | metrafenone |
| No. F.37 | $R^1 = CH_3$; $R^2 = H$; $R^3 = $ 2-F; $R^4 = $ 4-F; $R^5 = $ 5-F | metrafenone |
| No. F.38 | $R^1 = CH_3$; $R^2 = F$; $R^3 = $ 2-F; $R^4 = $ 4-F; $R^5 = $ 5-F | metrafenone |
| No. F.39 | $R^1 = CH_3$; $R^2 = Cl$; $R^3 = $ 2-F; $R^4 = $ 4-F; $R^5 = $ 5-F | metrafenone |

TABLE 8-continued

Active compound combinations of compounds I with active compounds II of group F):

| Mixture | Compounds of the formula I (X = oxygen) | Active compound II |
|---|---|---|
| No. F.40 | $R^1 = CH_2F; R^2 = H; R^3 = 2\text{-}F; R^4 = 4\text{-}F; R^5 = 5\text{-}F$ | metrafenone |
| No. F.41 | $R^1 = CHFCl; R^2 = H; R^3 = 2\text{-}F; R^4 = 4\text{-}F; R^5 = 5\text{-}F$ | metrafenone |
| No. F.42 | $R^1 = CHF_2; R^2 = H; R^3 = 2\text{-}F; R^4 = 4\text{-}F; R^5 = 5\text{-}F$ | metrafenone |
| No. F.43 | $R^1 = CHF_2; R^2 = F; R^3 = 2\text{-}F; R^4 = 4\text{-}F; R^5 = 5\text{-}F$ | metrafenone |
| No. F.44 | $R^1 = CHF_2; R^2 = Cl; R^3 = 2\text{-}F; R^4 = 4\text{-}F; R^5 = 5\text{-}F$ | metrafenone |
| No. F.45 | $R^1 = CF_2Cl; R^2 = H; R^3 = 2\text{-}F; R^4 = 4\text{-}F; R^5 = 5\text{-}F$ | metrafenone |
| No. F.46 | $R^1 = CF_3; R^2 = H; R^3 = 2\text{-}F; R^4 = 4\text{-}F; R^5 = 5\text{-}F$ | metrafenone |
| No. F.47 | $R^1 = CF_3; R^2 = F; R^3 = 2\text{-}F; R^4 = 4\text{-}F; R^5 = 5\text{-}F$ | metrafenone |
| No. F.48 | $R^1 = CF_3; R^2 = Cl; R^3 = 2\text{-}F; R^4 = 4\text{-}F; R^5 = 5\text{-}F$ | metrafenone |
| No. F.49 | $R^1 = CH_3; R^2 = H; R^3 = 3\text{-}F; R^4 = 4\text{-}F; R^5 = 5\text{-}F$ | phosphorous acid |
| No. F.50 | $R^1 = CH_3; R^2 = F; R^3 = 3\text{-}F; R^4 = 4\text{-}F; R^5 = 5\text{-}F$ | phosphorous acid |
| No. F.51 | $R^1 = CH_3; R^2 = Cl; R^3 = 3\text{-}F; R^4 = 4\text{-}F; R^5 = 5\text{-}F$ | phosphorous acid |
| No. F.52 | $R^1 = CH_2F; R^2 = H; R^3 = 3\text{-}F; R^4 = 4\text{-}F; R^5 = 5\text{-}F$ | phosphorous acid |
| No. F.53 | $R^1 = CHFCl; R^2 = H; R^3 = 3\text{-}F; R^4 = 4\text{-}F; R^5 = 5\text{-}F$ | phosphorous acid |
| No. F.54 | $R^1 = CHF_2; R^2 = H; R^3 = 3\text{-}F; R^4 = 4\text{-}F; R^5 = 5\text{-}F$ | phosphorous acid |
| No. F.55 | $R^1 = CHF_2; R^2 = F; R^3 = 3\text{-}F; R^4 = 4\text{-}F; R^5 = 5\text{-}F$ | phosphorous acid |
| No. F.56 | $R^1 = CHF_2; R^2 = Cl; R^3 = 3\text{-}F; R^4 = 4\text{-}F; R^5 = 5\text{-}F$ | phosphorous acid |
| No. F.57 | $R^1 = CF_2Cl; R^2 = H; R^3 = 3\text{-}F; R^4 = 4\text{-}F; R^5 = 5\text{-}F$ | phosphorous acid |
| No. F.58 | $R^1 = CF_3; R^2 = H; R^3 = 3\text{-}F; R^4 = 4\text{-}F; R^5 = 5\text{-}F$ | phosphorous acid |
| No. F.59 | $R^1 = CF_3; R^2 = F; R^3 = 3\text{-}F; R^4 = 4\text{-}F; R^5 = 5\text{-}F$ | phosphorous acid |
| No. F.60 | $R^1 = CF_3; R^2 = Cl; R^3 = 3\text{-}F; R^4 = 4\text{-}F; R^5 = 5\text{-}F$ | phosphorous acid |
| No. F.61 | $R^1 = CH_3; R^2 = H; R^3 = 2\text{-}F; R^4 = 4\text{-}F; R^5 = 5\text{-}F$ | phosphorous acid |
| No. F.62 | $R^1 = CH_3; R^2 = F; R^3 = 2\text{-}F; R^4 = 4\text{-}F; R^5 = 5\text{-}F$ | phosphorous acid |
| No. F.63 | $R^1 = CH_3; R^2 = Cl; R^3 = 2\text{-}F; R^4 = 4\text{-}F; R^5 = 5\text{-}F$ | phosphorous acid |
| No. F.64 | $R^1 = CH_2F; R^2 = H; R^3 = 2\text{-}F; R^4 = 4\text{-}F; R^5 = 5\text{-}F$ | phosphorous acid |
| No. F.65 | $R^1 = CHFCl; R^2 = H; R^3 = 2\text{-}F; R^4 = 4\text{-}F; R^5 = 5\text{-}F$ | phosphorous acid |
| No. F.66 | $R^1 = CHF_2; R^2 = H; R^3 = 2\text{-}F; R^4 = 4\text{-}F; R^5 = 5\text{-}F$ | phosphorous acid |
| No. F.67 | $R^1 = CHF_2; R^2 = F; R^3 = 2\text{-}F; R^4 = 4\text{-}F; R^5 = 5\text{-}F$ | phosphorous acid |
| No. F.68 | $R^1 = CHF_2; R^2 = Cl; R^3 = 2\text{-}F; R^4 = 4\text{-}F; R^5 = 5\text{-}F$ | phosphorous acid |
| No. F.69 | $R^1 = CF_2Cl; R^2 = H; R^3 = 2\text{-}F; R^4 = 4\text{-}F; R^5 = 5\text{-}F$ | phosphorous acid |
| No. F.70 | $R^1 = CF_3; R^2 = H; R^3 = 2\text{-}F; R^4 = 4\text{-}F; R^5 = 5\text{-}F$ | phosphorous acid |
| No. F.71 | $R^1 = CF_3; R^2 = F; R^3 = 2\text{-}F; R^4 = 4\text{-}F; R^5 = 5\text{-}F$ | phosphorous acid |
| No. F.72 | $R^1 = CF_3; R^2 = Cl; R^3 = 2\text{-}F; R^4 = 4\text{-}F; R^5 = 5\text{-}F$ | phosphorous acid |

TABLE 9

Active compound combinations of compounds I with two active compounds II:

| Mixture | Compound of the formula I | Active compound II | Active compound II |
|---|---|---|---|
| I-II-II.1 | N-(2'-fluoro-4'-chloro-5'-methyl-biphenyl-2-yl)-1-methyl-3-trifluoromethyl-1H-pyrazole-4-carboxamide | pyraclostrobin | epoxiconazole |
| I-II-II.2 | N-(3',4',5'-trifluorobiphenyl-2-yl)-1-methyl-3-trifluoromethyl-1H-pyrazole-4-carboxamide | pyraclostrobin | epoxiconazole |
| I-II-II.3 | N-(3',4',5'-trifluorobiphenyl-2-yl)-1-methyl-3-difluoromethyl-1H-pyrazole-4-carboxamide | pyraclostrobin | epoxiconazole |
| I-II-II.4 | N-(2',4'-5'-trifluorobiphenyl-2-yl)-1-methyl-3-difluoromethyl-1H-pyrazole-4-carboxamide | pyraclostrobin | epoxiconazole |
| I-II-II.5 | N-(3',4',5'-trifluorobiphenyl-2-yl)-3-chlorofluoromethyl-1-methyl-1H-pyrazole-4-carboxamide | pyraclostrobin | epoxiconazole |
| I-II-II.6 | N-(2'-fluoro-4'-chloro-5'-methyl-biphenyl-2-yl)-1-methyl-3-trifluoromethyl-1H-pyrazole-4-carboxamide | pyraclostrobin | metconazole |
| I-II-II.7 | N-(3',4',5'-trifluorobiphenyl-2-yl)-1-methyl-3-trifluoromethyl-1H-pyrazole-4-carboxamide | pyraclostrobin | metconazole |
| I-II-II.8 | N-(3',4',5'-trifluorobiphenyl-2-yl)-1-methyl-3-difluoromethyl-1H-pyrazole-4-carboxamide | pyraclostrobin | metconazole |
| I-II-II.9 | N-(2',4',5'-trifluorobiphenyl-2-yl)-1-methyl-3-difluoromethyl-1H-pyrazole-4-carboxamide | pyraclostrobin | metconazole |

TABLE 9-continued

Active compound combinations of compounds I with two active compounds II:

| Mixture | Compound of the formula I | Active compound II | Active compound II |
|---|---|---|---|
| I-II-II.10 | N-(3',4',5'-trifluorobiphenyl-2-yl)-3-chlorofluoromethyl-1-methyl-1H-pyrazole-4-carboxamide | pyraclostrobin | metconazole |
| I-II-II.11 | N-(2'-fluoro-4'-chloro-5'-methyl-biphenyl-2-yl)-1-methyl-3-trifluoromethyl-1H-pyrazole-4-carboxamide | pyraclostrobin | triticonazole |
| I-II-II.12 | N-(3',4',5'-trifluorobiphenyl-2-yl)-1-methyl-3-trifluoromethyl-1H-pyrazole-4-carboxamide | pyraclostrobin | triticonazole |
| I-II-II.13 | N-(3',4',5'-trifluorobiphenyl-2-yl)-1-methyl-3-difluoromethyl-1H-pyrazole-4-carboxamide | pyraclostrobin | triticonazole |
| I-II-II.14 | N-(2',4',5'-trifluorobiphenyl-2-yl)-1-methyl-3-difluoromethyl-1H-pyrazole-4-carboxamide | pyraclostrobin | triticonazole |
| I-II-II.15 | N-(3',4',5'-trifluorobiphenyl-2-yl)-3-chlorofluoromethyl-1-methyl-1H-pyrazole-4-carboxamide | pyraclostrobin | triticonazole |
| I-II-II.16 | N-(2'-fluoro-4'-chloro-5'-methyl-biphenyl-2-yl)-1-methyl-3-trifluoromethyl-1H-pyrazole-4-carboxamide | pyraclostrobin | fluquinconazole |
| I-II-II.17 | N-(3',4',5'-trifluorobiphenyl-2-yl)-1-methyl-3-trifluoromethyl-1H-pyrazole-4-carboxamide | pyraclostrobin | fluquinconazole |
| I-II-II.18 | N-(3',4',5'-trifluorobiphenyl-2-yl)-1-methyl-3-difluoromethyl-1H-pyrazole-4-carboxamide | pyraclostrobin | fluquinconazole |
| I-II-II.19 | N-(2',4',5'-trifluorobiphenyl-2-yl)-1-methyl-3-difluoromethyl-1H-pyrazole-4-carboxamide | pyraclostrobin | fluquinconazole |
| I-II-II.20 | N-(3',4',5'-trifluorobiphenyl-2-yl)-3-chlorofluoromethyl-1-methyl-1H-pyrazole-4-carboxamide | pyraclostrobin | fluquinconazole |
| I-II-II.21 | N-(2'-fluoro-4'-chloro-5'-methyl-biphenyl-2-yl)-1-methyl-3-trifluoromethyl-1H-pyrazole-4-carboxamide | pyraclostrobin | prothioconazole |
| I-II-II.22 | N-(3',4',5'-trifluorobiphenyl-2-yl)-1-methyl-3-trifluoromethyl-1H-pyrazole-4-carboxamide | pyraclostrobin | prothioconazole |
| I-II-II.23 | N-(3',4',5'-trifluorobiphenyl-2-yl)-1-methyl-3-difluoromethyl-1H-pyrazole-4-carboxamide | pyraclostrobin | prothioconazole |
| I-II-II.24 | N-(2',4',5'-trifluorobiphenyl-2-yl)-1-methyl-3-difluoromethyl-1H-pyrazole-4-carboxamide | pyraclostrobin | prothioconazole |
| I-II-II.25 | N-(3',4',5'-trifluorobiphenyl-2-yl)-3-chlorofluoromethyl-1-methyl-1H-pyrazole-4-carboxamide | pyraclostrobin | prothioconazole |
| I-II-II.26 | N-(2'-fluoro-4'-chloro-5'-methyl-biphenyl-2-yl)-1-methyl-3-trifluoromethyl-1H-pyrazole-4-carboxamide | pyraclostrobin | tebuconazole |
| I-II-II.27 | N-(3',4',5'-trifluorobiphenyl-2-yl)-1-methyl-3-trifluoromethyl-1H-pyrazole-4-carboxamide | pyraclostrobin | tebuconazole |
| I-II-II.28 | N-(3',4',5'-trifluorobiphenyl-2-yl)-1-methyl-3-difluoromethyl-1H-pyrazole-4-carboxamide | pyraclostrobin | tebuconazole |
| I-II-II.29 | N-(2',4',5'-trifluorobiphenyl-2-yl)-1-methyl-3-difluoromethyl-1H-pyrazole-4-carboxamide | pyraclostrobin | tebuconazole |
| I-II-II.30 | N-(3',4',5'-trifluorobiphenyl-2-yl)-3-chlorofluoromethyl-1-methyl-1H-pyrazole-4-carboxamide | pyraclostrobin | tebuconazole |
| I-II-II.31 | N-(2'-fluoro-4'-chloro-5'-methyl-biphenyl-2-yl)-1-methyl-3-trifluoromethyl-1H-pyrazole-4-carboxamide | pyraclostrobin | carbendazim |
| I-II-II.32 | N-(3',4',5'-trifluorobiphenyl-2-yl)-1-methyl-3-trifluoromethyl-1H-pyrazole-4-carboxamide | pyraclostrobin | carbendazim |

TABLE 9-continued

Active compound combinations of compounds I with two active compounds II:

| Mixture | Compound of the formula I | Active compound II | Active compound II |
|---|---|---|---|
| I-II-II.33 | N-(3',4',5'-trifluorobiphenyl-2-yl)-1-methyl-3-difluoromethyl-1H-pyrazole-4-carboxamide | pyraclostrobin | carbendazim |
| I-II-II.34 | N-(2',4',5'-trifluorobiphenyl-2-yl)-1-methyl-3-difluoromethyl-1H-pyrazole-4-carboxamide | pyraclostrobin | carbendazim |
| I-II-II.35 | N-(3',4',5'-trifluorobiphenyl-2-yl)-3-chlorofluoromethyl-1-methyl-1H-pyrazole-4-carboxamide | pyraclostrobin | carbendazim |
| I-II-II.36 | N-(2'-fluoro-4'-chloro-5'-methyl-biphenyl-2-yl)-1-methyl-3-trifluoromethyl-1H-pyrazole-4-carboxamide | pyraclostrobin | thiophanate-methyl |
| I-II-II.37 | N-(3',4',5'-trifluorobiphenyl-2-yl)-1-methyl-3-trifluoromethyl-1H-pyrazole-4-carboxamide | pyraclostrobin | thiophanate-methyl |
| I-II-II.38 | N-(3',4',5'-trifluorobiphenyl-2-yl)-1-methyl-3-difluoromethyl-1H-pyrazole-4-carboxamide | pyraclostrobin | thiophanate-methyl |
| I-II-II.39 | N-(2',4',5'-trifluorobiphenyl-2-yl)-1-methyl-3-difluoromethyl-1H-pyrazole-4-carboxamide | pyraclostrobin | thiophanate-methyl |
| I-II-II.40 | N-(3',4',5'-trifluorobiphenyl-2-yl)-3-chlorofluoromethyl-1-methyl-1H-pyrazole-4-carboxamide | pyraclostrobin | thiophanate-methyl |
| I-II-II.41 | N-(2'-fluoro-4'-chloro-5'-methyl-biphenyl-2-yl)-1-methyl-3-trifluoromethyl-1H-pyrazole-4-carboxamide | pyraclostrobin | benomyl |
| I-II-II.42 | N-(3',4',5'-trifluorobiphenyl-2-yl)-1-methyl-3-trifluoromethyl-1H-pyrazole-4-carboxamide | pyraclostrobin | benomyl |
| I-II-II.43 | N-(3',4',5'-trifluorobiphenyl-2-yl)-1-methyl-3-difluoromethyl-1H-pyrazole-4-carboxamide | pyraclostrobin | benomyl |
| I-II-II.44 | N-(2',4',5'-trifluorobiphenyl-2-yl)-1-methyl-3-difluoromethyl-1H-pyrazole-4-carboxamide | pyraclostrobin | benomyl |
| I-II-II.45 | N-(3',4',5'-trifluorobiphenyl-2-yl)-3-chlorofluoromethyl-1-methyl-1H-pyrazole-4-carboxamide | pyraclostrobin | benomyl |
| I-II-II.46 | N-(2'-fluoro-4'-chloro-5'-methyl-biphenyl-2-yl)-1-methyl-3-trifluoromethyl-1H-pyrazole-4-carboxamide | pyraclostrobin | fenpropimorph |
| I-II-II.47 | N-(3',4',5'-trifluorobiphenyl-2-yl)-1-methyl-3-trifluoromethyl-1H-pyrazole-4-carboxamide | pyraclostrobin | fenpropimorph |
| I-II-II.48 | N-(3',4',5'-trifluorobiphenyl-2-yl)-1-methyl-3-difluoromethyl-1H-pyrazole-4-carboxamide | pyraclostrobin | fenpropimorph |
| I-II-II.49 | N-(2',4',5'-trifluorobiphenyl-2-yl)-1-methyl-3-difluoromethyl-1H-pyrazole-4-carboxamide | pyraclostrobin | fenpropimorph |
| I-II-II.50 | N-(3',4',5'-trifluorobiphenyl-2-yl)-3-chlorofluoromethyl-1-methyl-1H-pyrazole-4-carboxamide | pyraclostrobin | fenpropimorph |
| I-II-II.51 | N-(2'-fluoro-4'-chloro-5'-methyl-biphenyl-2-yl)-1-methyl-3-trifluoromethyl-1H-pyrazole-4-carboxamide | pyraclostrobin | metrafenone |
| I-II-II.52 | N-(3',4',5'-trifluorobiphenyl-2-yl)-1-methyl-3-trifluoromethyl-1H-pyrazole-4-carboxamide | pyraclostrobin | metrafenone |
| I-II-II.53 | N-(3',4',5'-trifluorobiphenyl-2-yl)-1-methyl-3-difluoromethyl-1H-pyrazole-4-carboxamide | pyraclostrobin | metrafenone |
| I-II-II.54 | N-(2',4',5'-trifluorobiphenyl-2-yl)-1-methyl-3-difluoromethyl-1H-pyrazole-4-carboxamide | pyraclostrobin | metrafenone |
| I-II-II.55 | N-(3',4',5'-trifluorobiphenyl-2-yl)-3-chlorofluoromethyl-1-methyl-1H-pyrazole-4-carboxamide | pyraclostrobin | metrafenone |

TABLE 9-continued

Active compound combinations of compounds I with two active compounds II:

| Mixture | Compound of the formula I | Active compound II | Active compound II |
| --- | --- | --- | --- |
| I-II-II.56 | N-(2'-fluoro-4'-chloro-5'-methyl-biphenyl-2-yl)-1-methyl-3-trifluoromethyl-1H-pyrazole-4-carboxamide | kresoxim-methyl | epoxiconazole |
| I-II-II.57 | N-(3',4',5'-trifluorobiphenyl-2-yl)-1-methyl-3-trifluoromethyl-1H-pyrazole-4-carboxamide | kresoxim-methyl | epoxiconazole |
| I-II-II.58 | N-(3',4',5'-trifluorobiphenyl-2-yl)-1-methyl-3-difluoromethyl-1H-pyrazole-4-carboxamide | kresoxim-methyl | epoxiconazole |
| I-II-II.59 | N-(2',4',5'-trifluorobiphenyl-2-yl)-1-methyl-3-difluoromethyl-1H-pyrazole-4-carboxamide | kresoxim-methyl | epoxiconazole |
| I-II-II.60 | N-(3',4',5'-trifluorobiphenyl-2-yl)-3-chlorofluoromethyl-1-methyl-1H-pyrazole-4-carboxamide | kresoxim-methyl | epoxiconazole |
| I-II-II.61 | N-(2'-fluoro-4'-chloro-5'-methyl-biphenyl-2-yl)-1-methyl-3-trifluoromethyl-1H-pyrazole-4-carboxamide | kresoxim-methyl | metconazole |
| I-II-II.62 | N-(3',4',5'-trifluorobiphenyl-2-yl)-1-methyl-3-trifluoromethyl-1H-pyrazole-4-carboxamide | kresoxim-methyl | metconazole |
| I-II-II.63 | N-(3',4',5'-trifluorobiphenyl-2-yl)-1-methyl-3-difluoromethyl-1H-pyrazole-4-carboxamide | kresoxim-methyl | metconazole |
| I-II-II.64 | N-(2',4',5'-trifluorobiphenyl-2-yl)-1-methyl-3-difluoromethyl-1H-pyrazole-4-carboxamide | kresoxim-methyl | metconazole |
| I-II-II.65 | N-(3',4',5'-trifluorobiphenyl-2-yl)-3-chlorofluoromethyl-1-methyl-1H-pyrazole-4-carboxamide | kresoxim-methyl | metconazole |
| I-II-II.66 | N-(2'-fluoro-4'-chloro-5'-methyl-biphenyl-2-yl)-1-methyl-3-trifluoromethyl-1H-pyrazole-4-carboxamide | kresoxim-methyl | triticonazole |
| I-II-II.67 | N-(3',4',5'-trifluorobiphenyl-2-yl)-1-methyl-3-trifluoromethyl-1H-pyrazole-4-carboxamide | kresoxim-methyl | triticonazole |
| I-II-II.68 | N-(3',4',5'-trifluorobiphenyl-2-yl)-1-methyl-3-difluoromethyl-1H-pyrazole-4-carboxamide | kresoxim-methyl | triticonazole |
| I-II-II.69 | N-(2',4',5'-trifluorobiphenyl-2-yl)-1-methyl-3-difluoromethyl-1H-pyrazole-4-carboxamide | kresoxim-methyl | triticonazole |
| I-II-II.70 | N-(3',4',5'-trifluorobiphenyl-2-yl)-3-chlorofluoromethyl-1-methyl-1H-pyrazole-4-carboxamide | kresoxim-methyl | triticonazole |
| I-II-II.71 | N-(2'-fluoro-4'-chloro-5'-methyl-biphenyl-2-yl)-1-methyl-3-trifluoromethyl-1H-pyrazole-4-carboxamide | kresoxim-methyl | fluquinconazole |
| I-II-II.72 | N-(3',4',5'-trifluorobiphenyl-2-yl)-1-methyl-3-trifluoromethyl-1H-pyrazole-4-carboxamide | kresoxim-methyl | fluquinconazole |
| I-II-II.73 | N-(3',4',5'-trifluorobiphenyl-2-yl)-1-methyl-3-difluoromethyl-1H-pyrazole-4-carboxamide | kresoxim-methyl | fluquinconazole |
| I-II-II.74 | N-(2',4',5'-trifluorobiphenyl-2-yl)-1-methyl-3-difluoromethyl-1H-pyrazole-4-carboxamide | kresoxim-methyl | fluquinconazole |
| I-II-II.75 | N-(3',4',5'-trifluorobiphenyl-2-yl)-3-chlorofluoromethyl-1-methyl-1H-pyrazole-4-carboxamide | kresoxim-methyl | fluquinconazole |
| I-II-II.76 | N-(2'-fluoro-4'-chloro-5'-methyl-biphenyl-2-yl)-1-methyl-3-trifluoromethyl-1H-pyrazole-4-carboxamide | kresoxim-methyl | prothioconazole |
| I-II-II.77 | N-(3',4',5'-trifluorobiphenyl-2-yl)-1-methyl-3-trifluoromethyl-1H-pyrazole-4-carboxamide | kresoxim-methyl | prothioconazole |
| I-II-II.78 | N-(3',4',5'-trifluorobiphenyl-2-yl)-1-methyl-3-difluoromethyl-1H-pyrazole-4-carboxamide | kresoxim-methyl | prothioconazole |

TABLE 9-continued

Active compound combinations of compounds I with two active compounds II:

| Mixture | Compound of the formula I | Active compound II | Active compound II |
|---|---|---|---|
| I-II-II.79 | N-(2',4',5'-trifluorobiphenyl-2-yl)-1-methyl-3-difluoromethyl-1H-pyrazole-4-carboxamide | kresoxim-methyl | prothioconazole |
| I-II-II.80 | N-(3',4',5'-trifluorobiphenyl-2-yl)-3-chlorofluoromethyl-1-methyl-1H-pyrazole-4-carboxamide | kresoxim-methyl | prothioconazole |
| I-II-II.81 | N-(2'-fluoro-4'-chloro-5'-methyl-biphenyl-2-yl)-1-methyl-3-trifluoromethyl-1H-pyrazole-4-carboxamide | kresoxim-methyl | tebuconazole |
| I-II-II.82 | N-(3',4',5'-trifluorobiphenyl-2-yl)-1-methyl-3-trifluoromethyl-1H-pyrazole-4-carboxamide | kresoxim-methyl | tebuconazole |
| I-II-II.83 | N-(3',4',5'-trifluorobiphenyl-2-yl)-1-methyl-3-difluoromethyl-1H-pyrazole-4-carboxamide | kresoxim-methyl | tebuconazole |
| I-II-II.84 | N-(2',4',5'-trifluorobiphenyl-2-yl)-1-methyl-3-difluoromethyl-1H-pyrazole-4-carboxamide | kresoxim-methyl | tebuconazole |
| I-II-II.85 | N-(3',4',5'-trifluorobiphenyl-2-yl)-3-chlorofluoromethyl-1-methyl-1H-pyrazole-4-carboxamide | kresoxim-methyl | tebuconazole |
| I-II-II.86 | N-(2'-fluoro-4'-chloro-5'-methyl-biphenyl-2-yl)-1-methyl-3-trifluoromethyl-1H-pyrazole-4-carboxamide | kresoxim-methyl | carbendazim |
| I-II-II.87 | N-(3',4',5'-trifluorobiphenyl-2-yl)-1-methyl-3-trifluoromethyl-1H-pyrazole-4-carboxamide | kresoxim-methyl | carbendazim |
| I-II-II.88 | N-(3',4',5'-trifluorobiphenyl-2-yl)-1-methyl-3-difluoromethyl-1H-pyrazole-4-carboxamide | kresoxim-methyl | carbendazim |
| I-II-II.89 | N-(2',4',5'-trifluorobiphenyl-2-yl)-1-methyl-3-difluoromethyl-1H-pyrazole-4-carboxamide | kresoxim-methyl | carbendazim |
| I-II-II.90 | N-(3',4',5'-trifluorobiphenyl-2-yl)-3-chlorofluoromethyl-1-methyl-1H-pyrazole-4-carboxamide | kresoxim-methyl | carbendazim |
| I-II-II.91 | N-(2'-fluoro-4'-chloro-5'-methyl-biphenyl-2-yl)-1-methyl-3-trifluoromethyl-1H-pyrazole-4-carboxamide | kresoxim-methyl | thiophanate-methyl |
| I-II-II.92 | N-(3',4',5'-trifluorobiphenyl-2-yl)-1-methyl-3-trifluoromethyl-1H-pyrazole-4-carboxamide | kresoxim-methyl | thiophanate-methyl |
| I-II-II.93 | N-(3',4',5'-trifluorobiphenyl-2-yl)-1-methyl-3-difluoromethyl-1H-pyrazole-4-carboxamide | kresoxim-methyl | thiophanate-methyl |
| I-II-II.94 | N-(2',4',5'-trifluorobiphenyl-2-yl)-1-methyl-3-difluoromethyl-1H-pyrazole-4-carboxamide | kresoxim-methyl | thiophanate-methyl |
| I-II-II.95 | N-(3',4',5'-trifluorobiphenyl-2-yl)-3-chlorofluoromethyl-1-methyl-1H-pyrazole-4-carboxamide | kresoxim-methyl | thiophanate-methyl |
| I-II-II.96 | N-(2'-fluoro-4'-chloro-5'-methyl-biphenyl-2-yl)-1-methyl-3-trifluoromethyl-1H-pyrazole-4-carboxamide | kresoxim-methyl | benomyl |
| I-II-II.97 | N-(3',4',5'-trifluorobiphenyl-2-yl)-1-methyl-3-trifluoromethyl-1H-pyrazole-4-carboxamide | kresoxim-methyl | benomyl |
| I-II-II.98 | N-(3',4',5'-trifluorobiphenyl-2-yl)-1-methyl-3-difluoromethyl-1H-pyrazole-4-carboxamide | kresoxim-methyl | benomyl |
| I-II-II.99 | N-(2',4',5'-trifluorobiphenyl-2-yl)-1-methyl-3-difluoromethyl-1H-pyrazole-4-carboxamide | kresoxim-methyl | benomyl |
| I-II-II.100 | N-(3',4',5'-trifluorobiphenyl-2-yl)-3-chlorofluoromethyl-1-methyl-1H-pyrazole-4-carboxamide | kresoxim-methyl | benomyl |
| I-II-II.101 | N-(2'-fluoro-4'-chloro-5'-methyl-biphenyl-2-yl)-1-methyl-3-trifluoromethyl-1H-pyrazole-4-carboxamide | kresoxim-methyl | fenpropimorph |

TABLE 9-continued

Active compound combinations of compounds I with two active compounds II:

| Mixture | Compound of the formula I | Active compound II | Active compound II |
|---|---|---|---|
| I-II-II.102 | N-(3',4',5'-trifluorobiphenyl-2-yl)-1-methyl-3-trifluoromethyl-1H-pyrazole-4-carboxamide | kresoxim-methyl | fenpropimorph |
| I-II-II.103 | N-(3',4',5'-trifluorobiphenyl-2-yl)-1-methyl-3-difluoromethyl-1H-pyrazole-4-carboxamide | kresoxim-methyl | fenpropimorph |
| I-II-II.104 | N-(2',4',5'-trifluorobiphenyl-2-yl)-1-methyl-3-difluoromethyl-1H-pyrazole-4-carboxamide | kresoxim-methyl | fenpropimorph |
| I-II-II.105 | N-(3',4',5'-trifluorobiphenyl-2-yl)-3-chlorofluoromethyl-1-methyl-1H-pyrazole-4-carboxamide | kresoxim-methyl | fenpropimorph |
| I-II-II.106 | N-(2'-fluoro-4'-chloro-5'-methyl-biphenyl-2-yl)-1-methyl-3-trifluoromethyl-1H-pyrazole-4-carboxamide | kresoxim-methyl | metrafenone |
| I-II-II.107 | N-(3',4',5'-trifluorobiphenyl-2-yl)-1-methyl-3-trifluoromethyl-1H-pyrazole-4-carboxamide | kresoxim-methyl | metrafenone |
| I-II-II.108 | N-(3',4',5'-trifluorobiphenyl-2-yl)-1-methyl-3-difluoromethyl-1H-pyrazole-4-carboxamide | kresoxim-methyl | metrafenone |
| I-II-II.109 | N-(2',4',5'-trifluorobiphenyl-2-yl)-1-methyl-3-difluoromethyl-1H-pyrazole-4-carboxamide | kresoxim-methyl | metrafenone |
| I-II-II.110 | N-(3',4',5'-trifluorobiphenyl-2-yl)-3-chlorofluoromethyl-1-methyl-1H-pyrazole-4-carboxamide | kresoxim-methyl | metrafenone |
| I-II-II.111 | N-(2'-fluoro-4'-chloro-5'-methyl-biphenyl-2-yl)-1-methyl-3-trifluoromethyl-1H-pyrazole-4-carboxamide | epoxiconazole | 5-chloro-7-(4-methylpiperidin-1-yl)-6-(2,4,6-trifluorophenyl)-[1,2,4]triazolo[1,5-a]pyrimidine |
| I-II-II.112 | N-(3',4',5'-trifluorobiphenyl-2-yl)-1-methyl-3-trifluoromethyl-1H-pyrazole-4-carboxamide | epoxiconazole | 5-chloro-7-(4-methylpiperidin-1-yl)-6-(2,4,6-trifluorophenyl)-[1,2,4]triazolo[1,5-a]pyrimidine |
| I-II-II.113 | N-(3',4',5'-trifluorobiphenyl-2-yl)-1-methyl-3-difluoromethyl-1H-pyrazole-4-carboxamide | epoxiconazole | 5-chloro-7-(4-methylpiperidin-1-yl)-6-(2,4,6-trifluorophenyl)-[1,2,4]triazolo[1,5-a]pyrimidine |
| I-II-II.114 | N-(2',4',5'-trifluorobiphenyl-2-yl)-1-methyl-3-difluoromethyl-1H-pyrazole-4-carboxamide | epoxiconazole | 5-chloro-7-(4-methylpiperidin-1-yl)-6-(2,4,6-trifluorophenyl)-[1,2,4]triazolo[1,5-a]pyrimidine |
| I-II-II.115 | N-(3',4',5'-trifluorobiphenyl-2-yl)-3-chlorofluoromethyl-1-methyl-1H-pyrazole-4-carboxamide | epoxiconazole | 5-chloro-7-(4-methylpiperidin-1-yl)-6-(2,4,6-trifluorophenyl)-[1,2,4]triazolo[1,5-a]pyrimidine |
| I-II-II.116 | N-(2'-fluoro-4'-chloro-5'-methyl-biphenyl-2-yl)-1-methyl-3-trifluoromethyl-1H-pyrazole-4-carboxamide | epoxiconazole | carbendazim |
| I-II-II.117 | N-(3',4',5'-trifluorobiphenyl-2-yl)-1-methyl-3-trifluoromethyl-1H-pyrazole-4-carboxamide | epoxiconazole | carbendazim |
| I-II-II.118 | N-(3',4',5'-trifluorobiphenyl-2-yl)-1-methyl-3-difluoromethyl-1H-pyrazole-4-carboxamide | epoxiconazole | carbendazim |
| I-II-II.119 | N-(2',4',5'-trifluorobiphenyl-2-yl)-1-methyl-3-difluoromethyl-1H-pyrazole-4-carboxamide | epoxiconazole | carbendazim |
| I-II-II.120 | N-(3',4',5'-trifluorobiphenyl-2-yl)-3-chlorofluoromethyl-1-methyl-1H-pyrazole-4-carboxamide | epoxiconazole | carbendazim |

TABLE 9-continued

Active compound combinations of compounds I with two active compounds II:

| Mixture | Compound of the formula I | Active compound II | Active compound II |
|---|---|---|---|
| I-II-II.121 | N-(2'-fluoro-4'-chloro-5'-methyl-biphenyl-2-yl)-1-methyl-3-trifluoromethyl-1H-pyrazole-4-carboxamide | epoxiconazole | thiophanate-methyl |
| I-II-II.122 | N-(3',4',5'-trifluorobiphenyl-2-yl)-1-methyl-3-trifluoromethyl-1H-pyrazole-4-carboxamide | epoxiconazole | thiophanate-methyl |
| I-II-II.123 | N-(3',4',5'-trifluorobiphenyl-2-yl)-1-methyl-3-difluoromethyl-1H-pyrazole-4-carboxamide | epoxiconazole | thiophanate-methyl |
| I-II-II.124 | N-(2',4',5'-trifluorobiphenyl-2-yl)-1-methyl-3-difluoromethyl-1H-pyrazole-4-carboxamide | epoxiconazole | thiophanate-methyl |
| I-II-II.125 | N-(3',4',5'-trifluorobiphenyl-2-yl)-3-chlorofluoromethyl-1-methyl-1H-pyrazole-4-carboxamide | epoxiconazole | thiophanate-methyl |
| I-II-II.126 | N-(2'-fluoro-4'-chloro-5'-methyl-biphenyl-2-yl)-1-methyl-3-trifluoromethyl-1H-pyrazole-4-carboxamide | epoxiconazole | benomyl |
| I-II-II.127 | N-(3',4',5'-trifluorobiphenyl-2-yl)-1-methyl-3-trifluoromethyl-1H-pyrazole-4-carboxamide | epoxiconazole | benomyl |
| I-II-II.128 | N-(3',4',5'-trifluorobiphenyl-2-yl)-1-methyl-3-difluoromethyl-1H-pyrazole-4-carboxamide | epoxiconazole | benomyl |
| I-II-II.129 | N-(2',4',5'-trifluorobiphenyl-2-yl)-1-methyl-3-difluoromethyl-1H-pyrazole-4-carboxamide | epoxiconazole | benomyl |
| I-II-II.130 | N-(3',4',5'-trifluorobiphenyl-2-yl)-3-chlorofluoromethyl-1-methyl-1H-pyrazole-4-carboxamide | epoxiconazole | benomyl |
| I-II-II.131 | N-(2'-fluoro-4'-chloro-5'-methyl-biphenyl-2-yl)-1-methyl-3-trifluoromethyl-1H-pyrazole-4-carboxamide | epoxiconazole | fenpropimorph |
| I-II-II.132 | N-(3',4',5'-trifluorobiphenyl-2-yl)-1-methyl-3-trifluoromethyl-1H-pyrazole-4-carboxamide | epoxiconazole | fenpropimorph |
| I-II-II.133 | N-(3',4',5'-trifluorobiphenyl-2-yl)-1-methyl-3-difluoromethyl-1H-pyrazole-4-carboxamide | epoxiconazole | fenpropimorph |
| I-II-II.134 | N-(2',4',5'-trifluorobiphenyl-2-yl)-1-methyl-3-difluoromethyl-1H-pyrazole-4-carboxamide | epoxiconazole | fenpropimorph |
| I-II-II.135 | N-(3',4',5'-trifluorobiphenyl-2-yl)-3-chlorofluoromethyl-1-methyl-1H-pyrazole-4-carboxamide | epoxiconazole | fenpropimorph |
| I-II-II.136 | N-(2'-fluoro-4'-chloro-5'-methyl-biphenyl-2-yl)-1-methyl-3-trifluoromethyl-1H-pyrazole-4-carboxamide | epoxiconazole | metrafenone |
| I-II-II.137 | N-(3',4',5'-trifluorobiphenyl-2-yl)-1-methyl-3-trifluoromethyl-1H-pyrazole-4-carboxamide | epoxiconazole | metrafenone |
| I-II-II.138 | N-(3',4',5'-trifluorobiphenyl-2-yl)-1-methyl-3-difluoromethyl-1H-pyrazole-4-carboxamide | epoxiconazole | metrafenone |
| I-II-II.139 | N-(2',4',5'-trifluorobiphenyl-2-yl)-1-methyl-3-difluoromethyl-1H-pyrazole-4-carboxamide | epoxiconazole | metrafenone |
| I-II-II.140 | N-(3',4',5'-trifluorobiphenyl-2-yl)-3-chlorofluoromethyl-1-methyl-1H-pyrazole-4-carboxamide | epoxiconazole | metrafenone |
| I-II-II.141 | N-(2'-fluoro-4'-chloro-5'-methyl-biphenyl-2-yl)-1-methyl-3-trifluoromethyl-1H-pyrazole-4-carboxamide | epoxiconazole | metalaxyl |
| I-II-II.142 | N-(3',4',5'-trifluorobiphenyl-2-yl)-1-methyl-3-trifluoromethyl-1H-pyrazole-4-carboxamide | epoxiconazole | metalaxyl |
| I-II-II.143 | N-(3',4',5'-trifluorobiphenyl-2-yl)-1-methyl-3-difluoromethyl-1H-pyrazole-4-carboxamide | epoxiconazole | metalaxyl |

TABLE 9-continued

Active compound combinations of compounds I with two active compounds II:

| Mixture | Compound of the formula I | Active compound II | Active compound II |
|---|---|---|---|
| I-II-II.144 | N-(2',4',5'-trifluorobiphenyl-2-yl)-1-methyl-3-difluoromethyl-1H-pyrazole-4-carboxamide d | epoxiconazole | metalaxyl |
| I-II-II.145 | N-(3',4',5'-trifluorobiphenyl-2-yl)-3-chlorofluoromethyl-1-methyl-1H-pyrazole-4-carboxamide | epoxiconazole | metalaxyl |
| I-II-II.146 | N-(2'-fluoro-4'-chloro-5'-methyl-biphenyl-2-yl)-1-methyl-3-trifluoromethyl-1H-pyrazole-4-carboxamide | epoxiconazole | iprodione |
| I-II-II.147 | N-(3',4',5'-trifluorobiphenyl-2-yl)-1-methyl-3-trifluoromethyl-1H-pyrazole-4-carboxamide | epoxiconazole | iprodione |
| I-II-II.148 | N-(3',4',5'-trifluorobiphenyl-2-yl)-1-methyl-3-difluoromethyl-1H-pyrazole-4-carboxamide | epoxiconazole | iprodione |
| I-II-II.149 | N-(2',4',5'-trifluorobiphenyl-2-yl)-1-methyl-3-difluoromethyl-1H-pyrazole-4-carboxamide | epoxiconazole | iprodione |
| I-II-II.150 | N-(3',4',5'-trifluorobiphenyl-2-yl)-3-chlorofluoromethyl-1-methyl-1H-pyrazole-4-carboxamide | epoxiconazole | iprodione |
| I-II-II.151 | N-(2'-fluoro-4'-chloro-5'-methyl-biphenyl-2-yl)-1-methyl-3-trifluoromethyl-1H-pyrazole-4-carboxamide | epoxiconazole | pyrimethanil |
| I-II-II.152 | N-(3',4',5'-trifluorobiphenyl-2-yl)-1-methyl-3-trifluoromethyl-1H-pyrazole-4-carboxamide | epoxiconazole | pyrimethanil |
| I-II-II.153 | N-(3',4',5'-trifluorobiphenyl-2-yl)-1-methyl-3-difluoromethyl-1H-pyrazole-4-carboxamide | epoxiconazole | pyrimethanil |
| I-II-II.154 | N-(2',4',5'-trifluorobiphenyl-2-yl)-1-methyl-3-difluoromethyl-1H-pyrazole-4-carboxamide | epoxiconazole | pyrimethanil |
| I-II-II.155 | N-(3',4',5'-trifluorobiphenyl-2-yl)-3-chlorofluoromethyl-1-methyl-1H-pyrazole-4-carboxamide | epoxiconazole | pyrimethanil |
| I-II-II.156 | N-(2'-fluoro-4'-chloro-5'-methyl-biphenyl-2-yl)-1-methyl-3-trifluoromethyl-1H-pyrazole-4-carboxamide | metconazole | 5-chloro-7-(4-methylpiperidin-1-yl)-6-(2,4,6-trifluorophenyl)-[1,2,4]triazolo[1,5-a]pyrimidine |
| I-II-II.157 | N-(3',4',5'-trifluorobiphenyl-2-yl)-1-methyl-3-trifluoromethyl-1H-pyrazole-4-carboxamide | metconazole | 5-chloro-7-(4-methylpiperidin-1-yl)-6-(2,4,6-trifluorophenyl)-[1,2,4]triazolo[1,5-a]pyrimidine |
| I-II-II.158 | N-(3',4',5'-trifluorobiphenyl-2-yl)-1-methyl-3-difluoromethyl-1H-pyrazole-4-carboxamide | metconazole | 5-chloro-7-(4-methylpiperidin-1-yl)-6-(2,4,6-trifluorophenyl)-[1,2,4]triazolo[1,5-a]pyrimidine |
| I-II-II.159 | N-(2',4',5'-trifluorobiphenyl-2-yl)-1-methyl-3-difluoromethyl-1H-pyrazole-4-carboxamide | metconazole | 5-chloro-7-(4-methylpiperidin-1-yl)-6-(2,4,6-trifluorophenyl)-[1,2,4]triazolo[1,5-a]pyrimidine |
| I-II-II.160 | N-(3',4',5'-trifluorobiphenyl-2-yl)-3-chlorofluoromethyl-1-methyl-1H-pyrazole-4-carboxamide | metconazole | 5-chloro-7-(4-methylpiperidin-1-yl)-6-(2,4,6-trifluorophenyl)-[1,2,4]triazolo[1,5-a]pyrimidine |
| I-II-II.161 | N-(2'-fluoro-4'-chloro-5'-methyl-biphenyl-2-yl)-1-methyl-3-trifluoromethyl-1H-pyrazole-4-carboxamide | metconazole | carbendazim |
| I-II-II.162 | N-(3',4',5'-trifluorobiphenyl-2-yl)-1-methyl-3-trifluoromethyl-1H-pyrazole-4-carboxamide | metconazole | carbendazim |

TABLE 9-continued

Active compound combinations of compounds I with two active compounds II:

| Mixture | Compound of the formula I | Active compound II | Active compound II |
|---|---|---|---|
| I-II-II.163 | N-(3',4',5'-trifluorobiphenyl-2-yl)-1-methyl-3-difluoromethyl-1H-pyrazole-4-carboxamide | metconazole | carbendazim |
| I-II-II.164 | N-(2',4',5'-trifluorobiphenyl-2-yl)-1-methyl-3-difluoromethyl-1H-pyrazole-4-carboxamide | metconazole | carbendazim |
| I-II-II.165 | N-(3',4',5'-trifluorobiphenyl-2-yl)-3-chlorofluoromethyl-1-methyl-1H-pyrazole-4-carboxamide | metconazole | carbendazim |
| I-II-II.166 | N-(2'-fluoro-4'-chloro-5'-methyl-biphenyl-2-yl)-1-methyl-3-trifluoromethyl-1H-pyrazole-4-carboxamide | metconazole | thiophanate-methyl |
| I-II-II.167 | N-(3',4',5'-trifluorobiphenyl-2-yl)-1-methyl-3-trifluoromethyl-1H-pyrazole-4-carboxamide | metconazole | thiophanate-methyl |
| I-II-II.168 | N-(3',4',5'-trifluorobiphenyl-2-yl)-1-methyl-3-difluoromethyl-1H-pyrazole-4-carboxamide | metconazole | thiophanate-methyl |
| I-II-II.169 | N-(2',4',5'-trifluorobiphenyl-2-yl)-1-methyl-3-difluoromethyl-1H-pyrazole-4-carboxamide | metconazole | thiophanate-methyl |
| I-II-II.170 | N-(3',4',5'-trifluorobiphenyl-2-yl)-3-chlorofluoromethyl-1-methyl-1H-pyrazole-4-carboxamide | metconazole | thiophanate-methyl |
| I-II-II.171 | N-(2'-fluoro-4'-chloro-5'-methyl-biphenyl-2-yl)-1-methyl-3-trifluoromethyl-1H-pyrazole-4-carboxamide | metconazole | benomyl |
| I-II-II.172 | N-(3',4',5'-trifluorobiphenyl-2-yl)-1-methyl-3-trifluoromethyl-1H-pyrazole-4-carboxamide | metconazole | benomyl |
| I-II-II.173 | N-(3',4',5'-trifluorobiphenyl-2-yl)-1-methyl-3-difluoromethyl-1H-pyrazole-4-carboxamide | metconazole | benomyl |
| I-II-II.174 | N-(2',4',5'-trifluorobiphenyl-2-yl)-1-methyl-3-difluoromethyl-1H-pyrazole-4-carboxamide | metconazole | benomyl |
| I-II-II.175 | N-(3',4',5'-trifluorobiphenyl-2-yl)-3-chlorofluoromethyl-1-methyl-1H-pyrazole-4-carboxamide | metconazole | benomyl |
| I-II-II.176 | N-(2'-fluoro-4'-chloro-5'-methyl-biphenyl-2-yl)-1-methyl-3-trifluoromethyl-1H-pyrazole-4-carboxamide | metconazole | fenpropimorph |
| I-II-II.177 | N-(3',4',5'-trifluorobiphenyl-2-yl)-1-methyl-3-trifluoromethyl-1H-pyrazole-4-carboxamide | metconazole | fenpropimorph |
| I-II-II.178 | N-(3',4',5'-trifluorobiphenyl-2-yl)-1-methyl-3-difluoromethyl-1H-pyrazole-4-carboxamide | metconazole | fenpropimorph |
| I-II-II.179 | N-(2',4',5'-trifluorobiphenyl-2-yl)-1-methyl-3-difluoromethyl-1H-pyrazole-4-carboxamide | metconazole | fenpropimorph |
| I-II-II.180 | N-(3',4',5'-trifluorobiphenyl-2-yl)-3-chlorofluoromethyl-1-methyl-1H-pyrazole-4-carboxamide | metconazole | fenpropimorph |
| I-II-II.181 | N-(2'-fluoro-4'-chloro-5'-methyl-biphenyl-2-yl)-1-methyl-3-trifluoromethyl-1H-pyrazole-4-carboxamide | metconazole | metrafenone |
| I-II-II.182 | N-(3',4',5'-trifluorobiphenyl-2-yl)-1-methyl-3-trifluoromethyl-1H-pyrazole-4-carboxamide | metconazole | metrafenone |
| I-II-II.183 | N-(3',4',5'-trifluorobiphenyl-2-yl)-1-methyl-3-difluoromethyl-1H-pyrazole-4-carboxamide | metconazole | metrafenone |
| I-II-II.184 | N-(2',4',5'-trifluorobiphenyl-2-yl)-1-methyl-3-difluoromethyl-1H-pyrazole-4-carboxamide | metconazole | metrafenone |
| I-II-II.185 | N-(3',4',5'-trifluorobiphenyl-2-yl)-3-chlorofluoromethyl-1-methyl-1H-pyrazole-4-carboxamide | metconazole | metrafenone |

TABLE 9-continued

Active compound combinations of compounds I with two active compounds II:

| Mixture | Compound of the formula I | Active compound II | Active compound II |
|---|---|---|---|
| I-II-II.186 | N-(2'-fluoro-4'-chloro-5'-methyl-biphenyl-2-yl)-1-methyl-3-trifluoromethyl-1H-pyrazole-4-carboxamide | metconazole | metalaxyl |
| I-II-II.187 | N-(3',4',5'-trifluorobiphenyl-2-yl)-1-methyl-3-trifluoromethyl-1H-pyrazole-4-carboxamide | metconazole | metalaxyl |
| I-II-II.188 | N-(3',4',5'-trifluorobiphenyl-2-yl)-1-methyl-3-difluoromethyl-1H-pyrazole-4-carboxamide | metconazole | metalaxyl |
| I-II-II.189 | N-(2',4',5'-trifluorobiphenyl-2-yl)-1-methyl-3-difluoromethyl-1H-pyrazole-4-carboxamide | metconazole | metalaxyl |
| I-II-II.190 | N-(3',4',5'-trifluorobiphenyl-2-yl)-3-chlorofluoromethyl-1-methyl-1H-pyrazole-4-carboxamide | metconazole | metalaxyl |
| I-II-II.191 | N-(2'-fluoro-4'-chloro-5'-methyl-biphenyl-2-yl)-1-methyl-3-trifluoromethyl-1H-pyrazole-4-carboxamide | metconazole | iprodione |
| I-II-II.192 | N-(3',4',5'-trifluorobiphenyl-2-yl)-1-methyl-3-trifluoromethyl-1H-pyrazole-4-carboxamide | metconazole | iprodione |
| I-II-II.193 | N-(3',4',5'-trifluorobiphenyl-2-yl)-1-methyl-3-difluoromethyl-1H-pyrazole-4-carboxamide | metconazole | iprodione |
| I-II-II.194 | N-(2',4',5'-trifluorobiphenyl-2-yl)-1-methyl-3-difluoromethyl-1H-pyrazole-4-carboxamide | metconazole | iprodione |
| I-II-II.195 | N-(3',4',5'-trifluorobiphenyl-2-yl)-3-chlorofluoromethyl-1-methyl-1H-pyrazole-4-carboxamide | metconazole | iprodione |
| I-II-II.196 | N-(2'-fluoro-4'-chloro-5'-methyl-biphenyl-2-yl)-1-methyl-3-trifluoromethyl-1H-pyrazole-4-carboxamide | metconazole | pyrimethanil |
| I-II-II.197 | N-(3',4',5'-trifluorobiphenyl-2-yl)-1-methyl-3-trifluoromethyl-1H-pyrazole-4-carboxamide | metconazole | pyrimethanil |
| I-II-II.198 | N-(3',4',5'-trifluorobiphenyl-2-yl)-1-methyl-3-difluoromethyl-1H-pyrazole-4-carboxamide | metconazole | pyrimethanil |
| I-II-II.199 | N-(2',4',5'-trifluorobiphenyl-2-yl)-1-methyl-3-difluoromethyl-1H-pyrazole-4-carboxamide | metconazole | pyrimethanil |
| I-II-II.200 | N-(3',4',5'-trifluorobiphenyl-2-yl)-3-chlorofluoromethyl-1-methyl-1H-pyrazole-4-carboxamide | metconazole | pyrimethanil |
| I-II-II.201 | N-(2'-fluoro-4'-chloro-5'-methyl-biphenyl-2-yl)-1-methyl-3-trifluoromethyl-1H-pyrazole-4-carboxamide | triticonazole | 5-chloro-7-(4-methylpiperidin-1-yl)-6-(2,4,6-trifluorophenyl)-[1,2,4]triazolo[1,5-a]pyrimidine |
| I-II-II.202 | N-(3',4',5'-trifluorobiphenyl-2-yl)-1-methyl-3-trifluoromethyl-1H-pyrazole-4-carboxamide | triticonazole | 5-chloro-7-(4-methylpiperidin-1-yl)-6-(2,4,6-trifluorophenyl)-[1,2,4]triazolo[1,5-a]pyrimidine |
| I-II-II.203 | N-(3',4',5'-trifluorobiphenyl-2-yl)-1-methyl-3-difluoromethyl-1H-pyrazole-4-carboxamide | triticonazole | 5-chloro-7-(4-methylpiperidin-1-yl)-6-(2,4,6-trifluorophenyl)-[1,2,4]triazolo[1,5-a]pyrimidine |
| I-II-II.204 | N-(2',4',5'-trifluorobiphenyl-2-yl)-1-methyl-3-difluoromethyl-1H-pyrazole-4-carboxamide | triticonazole | 5-chloro-7-(4-methylpiperidin-1-yl)-6-(2,4,6-trifluorophenyl)-[1,2,4]triazolo[1,5-a]pyrimidine |

TABLE 9-continued

Active compound combinations of compounds I with two active compounds II:

| Mixture | Compound of the formula I | Active compound II | Active compound II |
|---|---|---|---|
| I-II-II.205 | N-(3',4',5'-trifluorobiphenyl-2-yl)-3-chlorofluoromethyl-1-methyl-1H-pyrazole-4-carboxamide | triticonazole | 5-chloro-7-(4-methylpiperidin-1-yl)-6-(2,4,6-trifluorophenyl)-[1,2,4]triazolo[1,5-a]pyrimidine |
| I-II-II.206 | N-(2'-fluoro-4'-chloro-5'-methyl-biphenyl-2-yl)-1-methyl-3-trifluoromethyl-1H-pyrazole-4-carboxamide | triticonazole | carbendazim |
| I-II-II.207 | N-(3',4',5'-trifluorobiphenyl-2-yl)-1-methyl-3-trifluoromethyl-1H-pyrazole-4-carboxamide | triticonazole | carbendazim |
| I-II-II.208 | N-(3',4',5'-trifluorobiphenyl-2-yl)-1-methyl-3-difluoromethyl-1H-pyrazole-4-carboxamide | triticonazole | carbendazim |
| I-II-II.209 | N-(2',4',5'-trifluorobiphenyl-2-yl)-1-methyl-3-difluoromethyl-1H-pyrazole-4-carboxamide | triticonazole | carbendazim |
| I-II-II.210 | N-(3',4',5'-trifluorobiphenyl-2-yl)-3-chlorofluoromethyl-1-methyl-1H-pyrazole-4-carboxamide | triticonazole | carbendazim |
| I-II-II.211 | N-(2'-fluoro-4'-chloro-5'-methyl-biphenyl-2-yl)-1-methyl-3-trifluoromethyl-1H-pyrazole-4-carboxamide | triticonazole | thiophanate-methyl |
| I-II-II.212 | N-(3',4',5'-trifluorobiphenyl-2-yl)-1-methyl-3-trifluoromethyl-1H-pyrazole-4-carboxamide | triticonazole | thiophanate-methyl |
| I-II-II.213 | N-(3',4',5'-trifluorobiphenyl-2-yl)-1-methyl-3-difluoromethyl-1H-pyrazole-4-carboxamide | triticonazole | thiophanate-methyl |
| I-II-II.214 | N-(2',4',5'-trifluorobiphenyl-2-yl)-1-methyl-3-difluoromethyl-1H-pyrazole-4-carboxamide | triticonazole | thiophanate-methyl |
| I-II-II.215 | N-(3',4',5'-trifluorobiphenyl-2-yl)-3-chlorofluoromethyl-1-methyl-1H-pyrazole-4-carboxamide | triticonazole | thiophanate-methyl |
| I-II-II.216 | N-(2'-fluoro-4'-chloro-5'-methyl-biphenyl-2-yl)-1-methyl-3-trifluoromethyl-1H-pyrazole-4-carboxamide | triticonazole | benomyl |
| I-II-II.217 | N-(3',4',5'-trifluorobiphenyl-2-yl)-1-methyl-3-trifluoromethyl-1H-pyrazole-4-carboxamide | triticonazole | benomyl |
| I-II-II.218 | N-(3',4',5'-trifluorobiphenyl-2-yl)-1-methyl-3-difluoromethyl-1H-pyrazole-4-carboxamide | triticonazole | benomyl |
| I-II-II.219 | N-(2',4',5'-trifluorobiphenyl-2-yl)-1-methyl-3-difluoromethyl-1H-pyrazole-4-carboxamide id | triticonazole | benomyl |
| I-II-II.220 | N-(3',4',5'-trifluorobiphenyl-2-yl)-3-chlorofluoromethyl-1-methyl-1H-pyrazole-4-carboxamide | triticonazole | benomyl |
| I-II-II.221 | N-(2'-fluoro-4'-chloro-5'-methyl-biphenyl-2-yl)-1-methyl-3-trifluoromethyl-1H-pyrazole-4-carboxamide | triticonazole | fenpropimorph |
| I-II-II.222 | N-(3',4',5'-trifluorobiphenyl-2-yl)-1-methyl-3-trifluoromethyl-1H-pyrazole-4-carboxamide | triticonazole | fenpropimorph |
| I-II-II.223 | N-(3',4',5'-trifluorobiphenyl-2-yl)-1-methyl-3-difluoromethyl-1H-pyrazole-4-carboxamide | triticonazole | fenpropimorph |
| I-II-II.224 | N-(2',4',5'-trifluorobiphenyl-2-yl)-1-methyl-3-difluoromethyl-1H-pyrazole-4-carboxamide | triticonazole | fenpropimorph |
| I-II-II.225 | N-(3',4',5'-trifluorobiphenyl-2-yl)-3-chlorofluoromethyl-1-methyl-1H-pyrazole-4-carboxamide | triticonazole | fenpropimorph |
| I-II-II.226 | N-(2'-fluoro-4'-chloro-5'-methyl-biphenyl-2-yl)-1-methyl-3-trifluoromethyl-1H-pyrazole-4-carboxamide | triticonazole | metrafenone |

TABLE 9-continued

Active compound combinations of compounds I with two active compounds II:

| Mixture | Compound of the formula I | Active compound II | Active compound II |
|---|---|---|---|
| I-II-II.227 | N-(3',4',5'-trifluorobiphenyl-2-yl)-1-methyl-3-trifluoromethyl-1H-pyrazole-4-carboxamide | triticonazole | metrafenone |
| I-II-II.228 | N-(3',4',5'-trifluorobiphenyl-2-yl)-1-methyl-3-difluoromethyl-1H-pyrazole-4-carboxamide | triticonazole | metrafenone |
| I-II-II.229 | N-(2',4',5'-trifluorobiphenyl-2-yl)-1-methyl-3-difluoromethyl-1H-pyrazole-4-carboxamide | triticonazole | metrafenone |
| I-II-II.230 | N-(3',4',5'-trifluorobiphenyl-2-yl)-3-chlorofluoromethyl-1-methyl-1H-pyrazole-4-carboxamide | triticonazole | metrafenone |
| I-II-II.231 | N-(2'-fluoro-4'-chloro-5'-methyl-biphenyl-2-yl)-1-methyl-3-trifluoromethyl-1H-pyrazole-4-carboxamide | triticonazole | metalaxyl |
| I-II-II.232 | N-(3',4',5'-trifluorobiphenyl-2-yl)-1-methyl-3-trifluoromethyl-1H-pyrazole-4-carboxamide | triticonazole | metalaxyl |
| I-II-II.233 | N-(3',4',5'-trifluorobiphenyl-2-yl)-1-methyl-3-difluoromethyl-1H-pyrazole-4-carboxamide | triticonazole | metalaxyl |
| I-II-II.234 | N-(2',4',5'-trifluorobiphenyl-2-yl)-1-methyl-3-difluoromethyl-1H-pyrazole-4-carboxamide | triticonazole | metalaxyl |
| I-II-II.235 | N-(3',4',5'-trifluorobiphenyl-2-yl)-3-chlorofluoromethyl-1-methyl-1H-pyrazole-4-carboxamide | triticonazole | metalaxyl |
| I-II-II.236 | N-(2'-fluoro-4'-chloro-5'-methyl-biphenyl-2-yl)-1-methyl-3-trifluoromethyl-1H-pyrazole-4-carboxamide | triticonazole | iprodione |
| I-II-II.237 | N-(3',4',5'-trifluorobiphenyl-2-yl)-1-methyl-3-trifluoromethyl-1H-pyrazole-4-carboxamide | triticonazole | iprodione |
| I-II-II.238 | N-(3',4',5'-trifluorobiphenyl-2-yl)-1-methyl-3-difluoromethyl-1H-pyrazole-4-carboxamide | triticonazole | iprodione |
| I-II-II.239 | N-(2',4',5'-trifluorobiphenyl-2-yl)-1-methyl-3-difluoromethyl-1H-pyrazole-4-carboxamide | triticonazole | iprodione |
| I-II-II.240 | N-(3',4',5'-trifluorobiphenyl-2-yl)-3-chlorofluoromethyl-1-methyl-1H-pyrazole-4-carboxamide | triticonazole | iprodione |
| I-II-II.241 | N-(2'-fluoro-4'-chloro-5'-methyl-biphenyl-2-yl)-1-methyl-3-trifluoromethyl-1H-pyrazole-4-carboxamide | triticonazole | pyrimethanil |
| I-II-II.242 | N-(3',4',5'-trifluorobiphenyl-2-yl)-1-methyl-3-trifluoromethyl-1H-pyrazole-4-carboxamide | triticonazole | pyrimethanil |
| I-II-II.243 | N-(3',4',5'-trifluorobiphenyl-2-yl)-1-methyl-3-difluoromethyl-1H-pyrazole-4-carboxamide | triticonazole | pyrimethanil |
| I-II-II.244 | N-(2',4',5'-trifluorobiphenyl-2-yl)-1-methyl-3-difluoromethyl-1H-pyrazole-4-carboxamide | triticonazole | pyrimethanil |
| I-II-II.245 | N-(3',4',5'-trifluorobiphenyl-2-yl)-3-chlorofluoromethyl-1-methyl-1H-pyrazole-4-carboxamide | fluquinconazole | pyrimethanil |
| I-II-II.246 | N-(2'-fluoro-4'-chloro-5'-methyl-biphenyl-2-yl)-1-methyl-3-trifluoromethyl-1H-pyrazole-4-carboxamide | fluquinconazole | 5-chloro-7-(4-methylpiperidin-1-yl)-6-(2,4,6-trifluorophenyl)-[1,2,4]triazolo[1,5-a]pyrimidine |
| I-II-II.247 | N-(3',4',5'-trifluorobiphenyl-2-yl)-1-methyl-3-trifluoromethyl-1H-pyrazole-4-carboxamide | fluquinconazole | 5-chloro-7-(4-methylpiperidin-1-yl)-6-(2,4,6-trifluorophenyl)-[1,2,4]triazolo[1,5-a]pyrimidine |

TABLE 9-continued

Active compound combinations of compounds I with two active compounds II:

| Mixture | Compound of the formula I | Active compound II | Active compound II |
|---|---|---|---|
| I-II-II.248 | N-(3',4',5'-trifluorobiphenyl-2-yl)-1-methyl-3-difluoromethyl-1H-pyrazole-4-carboxamide | fluquinconazole | 5-chloro-7-(4-methylpiperidin-1-yl)-6-(2,4,6-trifluorophenyl)-[1,2,4]triazolo[1,5-a]pyrimidine |
| I-II-II.249 | N-(2',4',5'-trifluorobiphenyl-2-yl)-1-methyl-3-difluoromethyl-1H-pyrazole-4-carboxamide | fluquinconazole | 5-chloro-7-(4-methylpiperidin-1-yl)-6-(2,4,6-trifluorophenyl)-[1,2,4]triazolo[1,5-a]pyrimidine |
| I-II-II.250 | N-(3',4',5'-trifluorobiphenyl-2-yl)-3-chlorofluoromethyl-1-methyl-1H-pyrazole-4-carboxamide | fluquinconazole | 5-chloro-7-(4-methylpiperidin-1-yl)-6-(2,4,6-trifluorophenyl)-[1,2,4]triazolo[1,5-a]pyrimidine |
| I-II-II.251 | N-(2'-fluoro-4'-chloro-5'-methyl-biphenyl-2-yl)-1-methyl-3-trifluoromethyl-1H-pyrazole-4-carboxamide | fluquinconazole | carbendazim |
| I-II-II.252 | N-(3',4',5'-trifluorobiphenyl-2-yl)-1-methyl-3-trifluoromethyl-1H-pyrazole-4-carboxamide | fluquinconazole | carbendazim |
| I-II-II.253 | N-(3',4',5'-trifluorobiphenyl-2-yl)-1-methyl-3-difluoromethyl-1H-pyrazole-4-carboxamide | fluquinconazole | carbendazim |
| I-II-II.254 | N-(2',4',5'-trifluorobiphenyl-2-yl)-1-methyl-3-difluoromethyl-1H-pyrazole-4-carboxamide | fluquinconazole | carbendazim |
| I-II-II.266 | N-(2'-fluoro-4'-chloro-5'-methyl-biphenyl-2-yl)-1-methyl-3-trifluoromethyl-1H-pyrazole-4-carboxamide | fluquinconazole | fenpropimorph |
| I-II-II.267 | N-(3',4',5'-trifluorobiphenyl-2-yl)-1-methyl-3-trifluoromethyl-1H-pyrazole-4-carboxamide | fluquinconazole | fenpropimorph |
| I-II-II.268 | N-(3',4',5'-trifluorobiphenyl-2-yl)-1-methyl-3-difluoromethyl-1H-pyrazole-4-carboxamide | fluquinconazole | fenpropimorph |
| I-II-II.269 | N-(2',4',5'-trifluorobiphenyl-2-yl)-1-methyl-3-difluoromethyl-1H-pyrazole-4-carboxamide | fluquinconazole | fenpropimorph |
| I-II-II.270 | N-(3',4',5'-trifluorobiphenyl-2-yl)-3-chlorofluoromethyl-1-methyl-1H-pyrazole-4-carboxamide | fluquinconazole | fenpropimorph |
| I-II-II.271 | N-(2'-fluoro-4'-chloro-5'-methyl-biphenyl-2-yl)-1-methyl-3-trifluoromethyl-1H-pyrazole-4-carboxamide | fluquinconazole | metrafenone |
| I-II-II.272 | N-(3',4',5'-trifluorobiphenyl-2-yl)-1-methyl-3-trifluoromethyl-1H-pyrazole-4-carboxamide | fluquinconazole | metrafenone |
| I-II-II.273 | N-(3',4',5'-trifluorobiphenyl-2-yl)-1-methyl-3-difluoromethyl-1H-pyrazole-4-carboxamide | fluquinconazole | metrafenone |
| I-II-II.274 | N-(2',4',5'-trifluorobiphenyl-2-yl)-1-methyl-3-difluoromethyl-1H-pyrazole-4-carboxamide | fluquinconazole | metrafenone |
| I-II-II.275 | N-(3',4',5'-trifluorobiphenyl-2-yl)-3-chlorofluoromethyl-1-methyl-1H-pyrazole-4-carboxamide | fluquinconazole | metrafenone |
| I-II-II.276 | N-(2'-fluoro-4'-chloro-5'-methyl-biphenyl-2-yl)-1-methyl-3-trifluoromethyl-1H-pyrazole-4-carboxamide | fluquinconazole | metalaxyl |
| I-II-II.277 | N-(3',4',5'-trifluorobiphenyl-2-yl)-1-methyl-3-trifluoromethyl-1H-pyrazole-4-carboxamide | fluquinconazole | metalaxyl |
| I-II-II.278 | N-(3',4',5'-trifluorobiphenyl-2-yl)-1-methyl-3-difluoromethyl-1H-pyrazole-4-carboxamide | fluquinconazole | metalaxyl |

TABLE 9-continued

Active compound combinations of compounds I with two active compounds II:

| Mixture | Compound of the formula I | Active compound II | Active compound II |
|---|---|---|---|
| I-II-II.279 | N-(2',4',5'-trifluorobiphenyl-2-yl)-1-methyl-3-difluoromethyl-1H-pyrazole-4-carboxamide | fluquinconazole | metalaxyl |
| I-II-II.280 | N-(3',4',5'-trifluorobiphenyl-2-yl)-3-chlorofluoromethyl-1-methyl-1H-pyrazole-4-carboxamide | fluquinconazole | metalaxyl |
| I-II-II.281 | N-(2'-fluoro-4'-chloro-5'-methyl-biphenyl-2-yl)-1-methyl-3-trifluoromethyl-1H-pyrazole-4-carboxamide | fluquinconazole | iprodione |
| I-II-II.282 | N-(3',4',5'-trifluorobiphenyl-2-yl)-1-methyl-3-trifluoromethyl-1H-pyrazole-4-carboxamide | fluquinconazole | iprodione |
| I-II-II.283 | N-(3',4',5'-trifluorobiphenyl-2-yl)-1-methyl-3-difluoromethyl-1H-pyrazole-4-carboxamide | fluquinconazole | iprodione |
| I-II-II.284 | N-(2',4',5'-trifluorobiphenyl-2-yl)-1-methyl-3-difluoromethyl-1H-pyrazole-4-carboxamide | fluquinconazole | iprodione |
| I-II-II.285 | N-(3',4',5'-trifluorobiphenyl-2-yl)-3-chlorofluoromethyl-1-methyl-1H-pyrazole-4-carboxamide | fluquinconazole | iprodione |
| I-II-II.286 | N-(2'-fluoro-4'-chloro-5'-methyl-biphenyl-2-yl)-1-methyl-3-trifluoromethyl-1H-pyrazole-4-carboxamide | fluquinconazole | pyrimethanil |
| I-II-II.287 | N-(3',4',5'-trifluorobiphenyl-2-yl)-1-methyl-3-trifluoromethyl-1H-pyrazole-4-carboxamide | fluquinconazole | pyrimethanil |
| I-II-II.288 | N-(3',4',5'-trifluorobiphenyl-2-yl)-1-methyl-3-difluoromethyl-1H-pyrazole-4-carboxamide | fluquinconazole | pyrimethanil |
| I-II-II.289 | N-(2',4',5'-trifluorobiphenyl-2-yl)-1-methyl-3-difluoromethyl-1H-pyrazole-4-carboxamide | fluquinconazole | pyrimethanil |
| I-II-II.290 | N-(3',4',5'-trifluorobiphenyl-2-yl)-3-chlorofluoromethyl-1-methyl-1H-pyrazole-4-carboxamide | fluquinconazole | pyrimethanil |
| I-II-II.291 | N-(2'-fluoro-4'-chloro-5'-methyl-biphenyl-2-yl)-1-methyl-3-trifluoromethyl-1H-pyrazole-4-carboxamide | prothioconazole | 5-chloro-7-(4-methylpiperidin-1-yl)-6-(2,4,6-tri-fluorophenyl)-[1,2,4]triazolo[1,5-a]pyrimidine |
| I-II-II.292 | N-(3',4',5'-trifluorobiphenyl-2-yl)-1-methyl-3-trifluoromethyl-1H-pyrazole-4-carboxamide | prothioconazole | 5-chloro-7-(4-methylpiperidin-1-yl)-6-(2,4,6-tri-fluorophenyl)-[1,2,4]triazolo[1,5-a]pyrimidine |
| I-II-II.293 | N-(3',4',5'-trifluorobiphenyl-2-yl)-1-methyl-3-difluoromethyl-1H-pyrazole-4-carboxamide | prothioconazole | 5-chloro-7-(4-methylpiperidin-1-yl)-6-(2,4,6-tri-fluorophenyl)-[1,2,4]triazolo[1,5-a]pyrimidine |
| I-II-II.294 | N-(2',4',5'-trifluorobiphenyl-2-yl)-1-methyl-3-difluoromethyl-1H-pyrazole-4-carboxamide | prothioconazole | 5-chloro-7-(4-methylpiperidin-1-yl)-6-(2,4,6-tri-fluorophenyl)-[1,2,4]triazolo[1,5-a]pyrimidine |
| I-II-II.295 | N-(3',4',5'-trifluorobiphenyl-2-yl)-3-chlorofluoromethyl-1-methyl-1H-pyrazole-4-carboxamide | prothioconazole | 5-chloro-7-(4-methylpiperidin-1-yl)-6-(2,4,6-tri-fluorophenyl)-[1,2,4]triazolo[1,5-a]pyrimidine |
| I-II-II.296 | N-(2'-fluoro-4'-chloro-5'-methyl-biphenyl-2-yl)-1-methyl-3-trifluoromethyl-1H-pyrazole-4-carboxamide | prothioconazole | carbendazim |
| I-II-II.297 | N-(3',4',5'-trifluorobiphenyl-2-yl)-1-methyl-3-trifluoromethyl-1H-pyrazole-4-carboxamide | prothioconazole | carbendazim |

TABLE 9-continued

Active compound combinations of compounds I with two active compounds II:

| Mixture | Compound of the formula I | Active compound II | Active compound II |
|---|---|---|---|
| I-II-II.298 | N-(3',4',5'-trifluorobiphenyl-2-yl)-1-methyl-3-difluoromethyl-1H-pyrazole-4-carboxamide | prothioconazole | carbendazim |
| I-II-II.299 | N-(2',4',5'-trifluorobiphenyl-2-yl)-1-methyl-3-difluoromethyl-1H-pyrazole-4-carboxamide | prothioconazole | carbendazim |
| I-II-II.300 | N-(3,4',5'-trifluorobiphenyl-2-yl)-3-chlorofluoromethyl-1-methyl-1H-pyrazole-4-carboxamide | prothioconazole | carbendazim |
| I-II-II.301 | N-(2'-fluoro-4'-chloro-5'-methyl-biphenyl-2-yl)-1-methyl-3-trifluoromethyl-1H-pyrazole-4-carboxamide | prothioconazole | thiophanate-methyl |
| I-II-II.302 | N-(3',4',5'-trifluorobiphenyl-2-yl)-1-methyl-3-trifluoromethyl-1H-pyrazole-4-carboxamide | prothioconazole | thiophanate-methyl |
| I-II-II.303 | N-(3',4',5'-trifluorobiphenyl-2-yl)-1-methyl-3-difluoromethyl-1H-pyrazole-4-carboxamide | prothioconazole | thiophanate-methyl |
| I-II-II.304 | N-(2',4',5'-trifluorobiphenyl-2-yl)-1-methyl-3-difluoromethyl-1H-pyrazole-4-carboxamide | prothioconazole | thiophanate-methyl |
| I-II-II.305 | N-(3',4',5'-trifluorobiphenyl-2-yl)-3-chlorofluoromethyl-1-methyl-1H-pyrazole-4-carboxamide | prothioconazole | thiophanate-methyl |
| I-II-II.306 | N-(2'-fluoro-4'-chloro-5'-methyl-biphenyl-2-yl)-1-methyl-3-trifluoromethyl-1H-pyrazole-4-carboxamide | prothioconazole | benomyl |
| I-II-II.307 | N-(3',4',5'-trifluorobiphenyl-2-yl)-1-methyl-3-trifluoromethyl-1H-pyrazole-4-carboxamide | prothioconazole | benomyl |
| I-II-II.308 | N-(3',4',5'-trifluorobiphenyl-2-yl)-1-methyl-3-difluoromethyl-1H-pyrazole-4-carboxamide | prothioconazole | benomyl |
| I-II-II.309 | N-(2',4',5'-trifluorobiphenyl-2-yl)-1-methyl-3-difluoromethyl-1H-pyrazole-4-carboxamide | prothioconazole | benomyl |
| I-II-II.310 | N-(3',4',5'-trifluorobiphenyl-2-yl)-3-chlorofluoromethyl-1-methyl-1H-pyrazole-4-carboxamide | prothioconazole | benomyl |
| I-II-II.311 | N-(2'-fluoro-4'-chloro-5'-methyl-biphenyl-2-yl)-1-methyl-3-trifluoromethyl-1H-pyrazole-4-carboxamide | prothioconazole | fenpropimorph |
| I-II-II.312 | N-(3',4',5'-trifluorobiphenyl-2-yl)-1-methyl-3-trifluoromethyl-1H-pyrazole-4-carboxamide | prothioconazole | fenpropimorph |
| I-II-II.313 | N-(3',4',5'-trifluorobiphenyl-2-yl)-1-methyl-3-difluoromethyl-1H-pyrazole-4-carboxamide | prothioconazole | fenpropimorph |
| I-II-II.314 | N-(2',4',5'-trifluorobiphenyl-2-yl)-1-methyl-3-difluoromethyl-1H-pyrazole-4-carboxamide | prothioconazole | fenpropimorph |
| I-II-II.315 | N-(3',4',5'-trifluorobiphenyl-2-yl)-3-chlorofluoromethyl-1-methyl-1H-pyrazole-4-carboxamide | prothioconazole | fenpropimorph |
| I-II-II.316 | N-(2'-fluoro-4'-chloro-5'-methyl-biphenyl-2-yl)-1-methyl-3-trifluoromethyl-1H-pyrazole-4-carboxamide | prothioconazole | metrafenone |
| I-II-II.317 | N-(3',4',5'-trifluorobiphenyl-2-yl)-1-methyl-3-trifluoromethyl-1H-pyrazole-4-carboxamide | prothioconazole | metrafenone |
| I-II-II.318 | N-(3',4',5'-trifluorobiphenyl-2-yl)-1-methyl-3-difluoromethyl-1H-pyrazole-4-carboxamide | prothioconazole | metrafenone |
| I-II-II.319 | N-(2',4',5'-trifluorobiphenyl-2-yl)-1-methyl-3-difluoromethyl-1H-pyrazole-4-carboxamide | prothioconazole | metrafenone |
| I-II-II.320 | N-(3',4',5'-trifluorobiphenyl-2-yl)-3-chlorofluoromethyl-1-methyl-1H-pyrazole-4-carboxamide | prothioconazole | metrafenone |

TABLE 9-continued

Active compound combinations of compounds I with two active compounds II:

| Mixture | Compound of the formula I | Active compound II | Active compound II |
|---|---|---|---|
| I-II-II.321 | N-(2'-fluoro-4'-chloro-5'-methyl-biphenyl-2-yl)-1-methyl-3-trifluoromethyl-1H-pyrazole-4-carboxamide | prothioconazole | metalaxyl |
| I-II-II.322 | N-(3',4',5'-trifluorobiphenyl-2-yl)-1-methyl-3-trifluoromethyl-1H-pyrazole-4-carboxamide | prothioconazole | metalaxyl |
| I-II-II.323 | N-(3',4',5'-trifluorobiphenyl-2-yl)-1-methyl-3-difluoromethyl-1H-pyrazole-4-carboxamide | prothioconazole | metalaxyl |
| I-II-II.324 | N-(2',4',5'-trifluorobiphenyl-2-yl)-1-methyl-3-difluoromethyl-1H-pyrazole-4-carboxamide | prothioconazole | metalaxyl |
| I-II-II.325 | N-(3',4',5'-trifluorobiphenyl-2-yl)-3-chlorofluoromethyl-1-methyl-1H-pyrazole-4-carboxamide | prothioconazole | metalaxyl |
| I-II-II.326 | N-(2'-fluoro-4'-chloro-5'-methyl-biphenyl-2-yl)-1-methyl-3-trifluoromethyl-1H-pyrazole-4-carboxamide | prothioconazole | iprodione |
| I-II-II.327 | N-(3',4',5'-trifluorobiphenyl-2-yl)-1-methyl-3-trifluoromethyl-1H-pyrazole-4-carboxamide | prothioconazole | iprodione |
| I-II-II.328 | N-(3',4',5'-trifluorobiphenyl-2-yl)-1-methyl-3-difluoromethyl-1H-pyrazole-4-carboxamide | prothioconazole | iprodione |
| I-II-II.329 | N-(2',4',5'-trifluorobiphenyl-2-yl)-1-methyl-3-difluoromethyl-1H-pyrazole-4-carboxamide | prothioconazole | iprodione |
| I-II-II.330 | N-(3',4',5'-trifluorobiphenyl-2-yl)-3-chlorofluoromethyl-1-methyl-1H-pyrazole-4-carboxamide | prothioconazole | iprodione |
| I-II-II.331 | N-(2'-fluoro-4'-chloro-5'-methyl-biphenyl-2-yl)-1-methyl-3-trifluoromethyl-1H-pyrazole-4-carboxamide | prothioconazole | pyrimethanil |
| I-II-II.332 | N-(3',4',5'-trifluorobiphenyl-2-yl)-1-methyl-3-trifluoromethyl-1H-pyrazole-4-carboxamide | prothioconazole | pyrimethanil |
| I-II-II.333 | N-(3',4',5'-trifluorobiphenyl-2-yl)-1-methyl-3-difluoromethyl-1H-pyrazole-4-carboxamide | prothioconazole | pyrimethanil |
| I-II-II.334 | N-(2',4',5'-trifluorobiphenyl-2-yl)-1-methyl-3-difluoromethyl-1H-pyrazole-4-carboxamide | prothioconazole | pyrimethanil |
| I-II-II.335 | N-(3',4',5'-trifluorobiphenyl-2-yl)-3-chlorofluoromethyl-1-methyl-1H-pyrazole-4-carboxamide | prothioconazole | pyrimethanil |
| I-II-II.336 | N-(2'-fluoro-4'-chloro-5'-methyl-biphenyl-2-yl)-1-methyl-3-trifluoromethyl-1H-pyrazole-4-carboxamide | tebuconazole | 5-chloro-7-(4-methylpiperidin-1-yl)-6-(2,4,6-trifluorophenyl)-[1,2,4]triazolo[1,5-a]pyrimidine |
| I-II-II.337 | N-(3',4',5'-trifluorobiphenyl-2-yl)-1-methyl-3-trifluoromethyl-1H-pyrazole-4-carboxamide | tebuconazole | 5-chloro-7-(4-methylpiperidin-1-yl)-6-(2,4,6-trifluorophenyl)-[1,2,4]triazolo[1,5-a]pyrimidine |
| I-II-II.338 | N-(3',4',5'-trifluorobiphenyl-2-yl)-1-methyl-3-difluoromethyl-1H-pyrazole-4-carboxamide | tebuconazole | 5-chloro-7-(4-methylpiperidin-1-yl)-6-(2,4,6-trifluorophenyl)-[1,2,4]triazolo[1,5-a]pyrimidine |
| I-II-II.339 | N-(2',4',5'-trifluorobiphenyl-2-yl)-1-methyl-3-difluoromethyl-1H-pyrazole-4-carboxamide | tebuconazole | 5-chloro-7-(4-methylpiperidin-1-yl)-6-(2,4,6-trifluorophenyl)-[1,2,4]triazolo[1,5-a]pyrimidine |

TABLE 9-continued

Active compound combinations of compounds I with two active compounds II:

| Mixture | Compound of the formula I | Active compound II | Active compound II |
|---|---|---|---|
| I-II-II.340 | N-(3',4',5'-trifluorobiphenyl-2-yl)-3-chlorofluoromethyl-1-methyl-1H-pyrazole-4-carboxamide | tebuconazole | 5-chloro-7-(4-methylpiperidin-1-yl)-6-(2,4,6-trifluorophenyl)-[1,2,4]triazolo[1,5-a]pyrimidine |
| I-II-II.341 | N-(2'-fluoro-4'-chloro-5'-methyl-biphenyl-2-yl)-1-methyl-3-trifluoromethyl-1H-pyrazole-4-carboxamide | tebuconazole | carbendazim |
| I-II-II.342 | N-(3',4',5'-trifluorobiphenyl-2-yl)-1-methyl-3-trifluoromethyl-1H-pyrazole-4-carboxamide | tebuconazole | carbendazim |
| I-II-II.343 | N-(3',4',5'-trifluorobiphenyl-2-yl)-1-methyl-3-difluoromethyl-1H-pyrazole-4-carboxamide | tebuconazole | carbendazim |
| I-II-II.344 | N-(2',4',5'-trifluorobiphenyl-2-yl)-1-methyl-3-difluoromethyl-1H-pyrazole-4-carboxamide | tebuconazole | carbendazim |
| I-II-II.345 | N-(3',4',5'-trifluorobiphenyl-2-yl)-3-chlorofluoromethyl-1-methyl-1H-pyrazole-4-carboxamide | tebuconazole | carbendazim |
| I-II-II.346 | N-(2'-fluoro-4'-chloro-5'-methyl-biphenyl-2-yl)-1-methyl-3-trifluoromethyl-1H-pyrazole-4-carboxamide | tebuconazole | thiophanate-methyl |
| I-II-II.347 | N-(3',4',5'-trifluorobiphenyl-2-yl)-1-methyl-3-trifluoromethyl-1H-pyrazole-4-carboxamide | tebuconazole | thiophanate-methyl |
| I-II-II.348 | N-(3',4',5'-trifluorobiphenyl-2-yl)-1-methyl-3-difluoromethyl-1H-pyrazole-4-carboxamide | tebuconazole | thiophanate-methyl |
| I-II-II.349 | N-(2',4',5'-trifluorobiphenyl-2-yl)-1-methyl-3-difluoromethyl-1H-pyrazole-4-carboxamide | tebuconazole | thiophanate-methyl |
| I-II-II.350 | N-(3',4',5'-trifluorobiphenyl-2-yl)-3-chlorofluoromethyl-1-methyl-1H-pyrazole-4-carboxamide | tebuconazole | thiophanate-methyl |
| I-II-II.351 | N-(2'-fluoro-4'-chloro-5'-methyl-biphenyl-2-yl)-1-methyl-3-trifluoromethyl-1H-pyrazole-4-carboxamide | tebuconazole | benomyl |
| I-II-II.352 | N-(3',4',5'-trifluorobiphenyl-2-yl)-1-methyl-3-trifluoromethyl-1H-pyrazole-4-carboxamide | tebuconazole | benomyl |
| I-II-II.353 | N-(3',4',5'-trifluorobiphenyl-2-yl)-1-methyl-3-difluoromethyl-1H-pyrazole-4-carboxamide | tebuconazole | benomyl |
| I-II-II.354 | N-(2',4',5'-trifluorobiphenyl-2-yl)-1-methyl-3-difluoromethyl-1H-pyrazole-4-carboxamide | tebuconazole | benomyl |
| I-II-II.355 | N-(3',4',5'-trifluorobiphenyl-2-yl)-3-chlorofluoromethyl-1-methyl-1H-pyrazole-4-carboxamide | tebuconazole | benomyl |
| I-II-II.356 | N-(2'-fluoro-4'-chloro-5'-methyl-biphenyl-2-yl)-1-methyl-3-trifluoromethyl-1H-pyrazole-4-carboxamide | tebuconazole | fenpropimorph |
| I-II-II.357 | N-(3',4',5'-trifluorobiphenyl-2-yl)-1-methyl-3-trifluoromethyl-1H-pyrazole-4-carboxamide | tebuconazole | fenpropimorph |
| I-II-II.358 | N-(3',4',5'-trifluorobiphenyl-2-yl)-1-methyl-3-difluoromethyl-1H-pyrazole-4-carboxamide | tebuconazole | fenpropimorph |
| I-II-II.359 | N-(2',4',5'-trifluorobiphenyl-2-yl)-1-methyl-3-difluoromethyl-1H-pyrazole-4-carboxamide | tebuconazole | fenpropimorph |
| I-II-II.360 | N-(3',4',5'-trifluorobiphenyl-2-yl)-3-chlorofluoromethyl-1-methyl-1H-pyrazole-4-carboxamide | tebuconazole | fenpropimorph |
| I-II-II.361 | N-(2'-fluoro-4'-chloro-5'-methyl-biphenyl-2-yl)-1-methyl-3-trifluoromethyl-1H-pyrazole-4-carboxamide | tebuconazole | metrafenone |

TABLE 9-continued

Active compound combinations of compounds I with two active compounds II:

| Mixture | Compound of the formula I | Active compound II | Active compound II |
|---|---|---|---|
| I-II-II.362 | N-(3',4',5'-trifluorobiphenyl-2-yl)-1-methyl-3-trifluoromethyl-1H-pyrazole-4-carboxamide | tebuconazole | metrafenone |
| I-II-II.363 | N-(3',4',5'-trifluorobiphenyl-2-yl)-1-methyl-3-difluoromethyl-1H-pyrazole-4-carboxamide | tebuconazole | metrafenone |
| I-II-II.364 | N-(2',4',5'-trifluorobiphenyl-2-yl)-1-methyl-3-difluoromethyl-1H-pyrazole-4-carboxamide | tebuconazole | metrafenone |
| I-II-II.365 | N-(3',4',5'-trifluorobiphenyl-2-yl)-3-chlorofluoromethyl-1-methyl-1H-pyrazole-4-carboxamide | tebuconazole | metrafenone |
| I-II-II.366 | N-(2'-fluoro-4'-chloro-5'-methyl-biphenyl-2-yl)-1-methyl-3-trifluoromethyl-1H-pyrazole-4-carboxamide | tebuconazole | metalaxyl |
| I-II-II.367 | N-(3',4',5'-trifluorobiphenyl-2-yl)-1-methyl-3-trifluoromethyl-1H-pyrazole-4-carboxamide | tebuconazole | metalaxyl |
| I-II-II.368 | N-(3',4',5'-trifluorobiphenyl-2-yl)-1-methyl-3-difluoromethyl-1H-pyrazole-4-carboxamide | tebuconazole | metalaxyl |
| I-II-II.369 | N-(2',4',5'-trifluorobiphenyl-2-yl)-1-methyl-3-difluoromethyl-1H-pyrazole-4-carboxamide | tebuconazole | metalaxyl |
| I-II-II.370 | N-(3',4',5'-trifluorobiphenyl-2-yl)-3-chlorofluoromethyl-1-methyl-1H-pyrazole-4-carboxamide | tebuconazole | metalaxyl |
| I-II-II.371 | N-(2'-fluoro-4'-chloro-5'-methyl-biphenyl-2-yl)-1-methyl-3-trifluoromethyl-1H-pyrazole-4-carboxamide | tebuconazole | iprodione |
| I-II-II.372 | N-(3',4',5'-trifluorobiphenyl-2-yl)-1-methyl-3-trifluoromethyl-1H-pyrazole-4-carboxamide | tebuconazole | iprodione |
| I-II-II.373 | N-(3',4',5'-trifluorobiphenyl-2-yl)-1-methyl-3-difluoromethyl-1H-pyrazole-4-carboxamide | tebuconazole | iprodione |
| I-II-II.374 | N-(2',4',5'-trifluorobiphenyl-2-yl)-1-methyl-3-difluoromethyl-1H-pyrazole-4-carboxamide | tebuconazole | iprodione |
| I-II-II.375 | N-(3',4',5'-trifluorobiphenyl-2-yl)-3-chlorofluoromethyl-1-methyl-1H-pyrazole-4-carboxamide | tebuconazole | iprodione |
| I-II-II.376 | N-(2'-fluoro-4'-chloro-5'-methyl-biphenyl-2-yl)-1-methyl-3-trifluoromethyl-1H-pyrazole-4-carboxamide | tebuconazole | pyrimethanil |
| I-II-II.377 | N-(3',4',5'-trifluorobiphenyl-2-yl)-1-methyl-3-trifluoromethyl-1H-pyrazole-4-carboxamide | tebuconazole | pyrimethanil |
| I-II-II.378 | N-(3',4',5'-trifluorobiphenyl-2-yl)-1-methyl-3-difluoromethyl-1H-pyrazole-4-carboxamide | tebuconazole | pyrimethanil |
| I-II-II.379 | N-(2',4',5'-trifluorobiphenyl-2-yl)-1-methyl-3-difluoromethyl-1H-pyrazole-4-carboxamide | tebuconazole | pyrimethanil |
| I-II-II.380 | N-(3',4',5'-trifluorobiphenyl-2-yl)-3-chlorofluoromethyl-1-methyl-1H-pyrazole-4-carboxamide | tebuconazole | pyrimethanil |
| I-II-II.381 | N-(2'-fluoro-4'-chloro-5'-methyl-biphenyl-2-yl)-1-methyl-3-trifluoromethyl-1H-pyrazole-4-carboxamide | 5-chloro-7-(4-methylpiperidin-1-yl)-6-(2,4,6-tri-fluorophenyl)-[1,2,4]triazolo-[1,5-a]pyrimidine | carbendazim |
| I-II-II.382 | N-(3',4',5'-trifluorobiphenyl-2-yl)-1-methyl-3-trifluoromethyl-1H-pyrazole-4-carboxamide | 5-chloro-7-(4-methylpiperidin-1-yl)-6-(2,4,6-tri-fluorophenyl)-[1,2,4]triazolo-[1,5-a]pyrimidine | carbendazim |

TABLE 9-continued

Active compound combinations of compounds I with two active compounds II:

| Mixture | Compound of the formula I | Active compound II | Active compound II |
|---|---|---|---|
| I-II-II.383 | N-(3',4',5'-trifluorobiphenyl-2-yl)-1-methyl-3-difluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | carbendazim |
| I-II-II.384 | N-(2',4',5'-trifluorobiphenyl-2-yl)-1-methyl-3-difluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | carbendazim |
| I-II-II.385 | N-(3',4',5'-trifluorobiphenyl-2-yl)-3-chlorofluoromethyl-1-methyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | carbendazim |
| I-II-II.386 | N-(2'-fluoro-4'-chloro-5'-methylbiphenyl-2-yl)-1-methyl-3-trifluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | thiophanate-methyl |
| I-II-II.387 | N-(3',4',5'-trifluorobiphenyl-2-yl)-1-methyl-3-trifluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | thiophanate-methyl |
| I-II-II.388 | N-(3',4',5'-trifluorobiphenyl-2-yl)-1-methyl-3-difluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | thiophanate-methyl |
| I-II-II.389 | N-(2',4',5'-trifluorobiphenyl-2-yl)-1-methyl-3-difluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | thiophanate-methyl |
| I-II-II.390 | N-(3',4',5'-trifluorobiphenyl-2-yl)-3-chlorofluoromethyl-1-methyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | thiophanate-methyl |
| I-II-II.391 | N-(2'-fluoro-4'-chloro-5'-methylbiphenyl-2-yl)-1-methyl-3-trifluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | benomyl |
| I-II-II.392 | N-(3',4',5'-trifluorobiphenyl-2-yl)-1-methyl-3-trifluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | benomyl |
| I-II-II.393 | N-(3',4',5'-trifluorobiphenyl-2-yl)-1-methyl-3-difluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | benomyl |
| I-II-II.394 | N-(2',4',5'-trifluorobiphenyl-2-yl)-1-methyl-3-difluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | benomyl |

TABLE 9-continued

Active compound combinations of compounds I with two active compounds II:

| Mixture | Compound of the formula I | Active compound II | Active compound II |
|---|---|---|---|
| I-II-II.395 | N-(3',4',5'-trifluorobiphenyl-2-yl)-3-chlorofluoromethyl-1-methyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | benomyl |
| I-II-II.396 | N-(2'-fluoro-4'-chloro-5'-methyl-biphenyl-2-yl)-1-methyl-3-trifluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | fenpropimorph |
| I-II-II.397 | N-(3',4',5'-trifluorobiphenyl-2-yl)-1-methyl-3-trifluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | fenpropimorph |
| I-II-II.398 | N-(3',4',5'-trifluorobiphenyl-2-yl)-1-methyl-3-difluoromethyl-1H-pyrazole-4-carboxamide | 5-chloro-7-(4-methylpiperidin-1-yl)-6-(2,4,6-trifluorophenyl)-[1,2,4]triazolo[1,5-a]pyrimidine | fenpropimorph |
| I-II-II.399 | N-(2',4',5'-trifluorobiphenyl-2-yl)-1-methyl-3-difluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | fenpropimorph |
| I-II-II.400 | N-(3',4',5'-trifluorobiphenyl-2-yl)-3-chlorofluoromethyl-1-methyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | fenpropimorph |
| I-II-II.401 | N-(2'-fluoro-4'-chloro-5'-methyl-biphenyl-2-yl)-1-methyl-3-trifluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | metrafenone |
| I-II-II.402 | N-(3',4',5'-trifluorobiphenyl-2-yl)-1-methyl-3-trifluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | metrafenone |
| I-II-II.403 | N-(3',4',5'-trifluorobiphenyl-2-yl)-1-methyl-3-difluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | metrafenone |
| I-II-II.404 | N-(2',4',5'-trifluorobiphenyl-2-yl)-1-methyl-3-difluoromethyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | metrafenone |
| I-II-II.405 | N-(3',4',5'-trifluorobiphenyl-2-yl)-3-chlorofluoromethyl-1-methyl-1H-pyrazole-4-carboxamide | 5-chloro-7-(4-methylpiperidin-1-yl)-6-(2,4,6-trifluorophenyl)-[1,2,4]triazolo-[1,5-a]pyrimidine | metrafenone |

The mixtures of compound(s) I and at least one of the active compounds II, or at least one compound I and at least one of the active compounds II applied simultaneously, that is jointly or separately, have excellent activity against a broad spectrum of phytopathogenic fungi, in particular from the class of the Ascomycetes, Basidiomycetes, Deuteromycetes and Peronosporomycetes (syn. Oomycetes). Some of them are systemically effective and can be employed in crop protection as foliar fungicides, as fungicides for seed dressing and as soil fungicides. They can also be used for treating seed.

They are particularly important in the control of a multitude of fungi on various cultivated plants, such as wheat, rye, barley, oats, rice, corn, lawns, bananas, cotton, soybean, coffee, sugar cane, grapevines, fruits and ornamental plants, and vegetables such as cucumbers, beans, tomatoes, potatoes and cucurbits, and on the seeds of these plants.

They are especially suitable for controlling the following plant diseases:

*Alternaria* species on vegetables, oilseed rape, sugar beet and fruit and rice, for example, *A. solani* or *A. alternata* on potatoes and tomatoes;

*Aphanomyces* species on sugar beet and vegetables;

*Ascochyta* species on cereals and vegetables;

*Bipolaris* and *Drechslera* species on corn, cereals, rice and lawns, for example, *D. maydis* on corn;

*Blumeria graminis* (powdery mildew) on cereals;

*Botlytis cinerea* (gray mold) on strawberries, vegetables, flowers and grapevines;

*Bremia lactucae* on lettuce;

*Cercospora* species on corn, soybeans, rice and sugar beet;

*Cochliobolus* species on corn, cereals, rice, for example *Cochliobolus sativus* on cereals, *Cochliobolus miyabeanus* on rice;

*Colletotricum* species on soybeans and cotton;

*Drechslera* species, *Pyrenophora* species on corn, cereals, rice and lawns, for example, *D. teres* on barley or *D. tritici-repentis* on wheat;

Esca on grapevines, caused by *Phaeoacremonium chlamydosporium*, *Ph. Aleophilum* and *Formitipora punctata* (syn. *Phellinus punctatus*),

*Exserohilum* species on corn;

*Erysiphe cichoracearum* and *Sphaerotheca fuliginea* on cucumbers;

*Fusarium* and *Verticillium* species on various plants, for example, *F graminearum* or *F. culmorum* on cereals or *F. oxysporum* on a multitude of plants, such as, for example, tomatoes;

*Gaeumanomyces graminis* on cereals;

*Gibberella* species on cereals and rice (for example *Gibberella fujikuroi* on rice);

Grainstaining complex on rice;

*Helminthosporium* species on corn and rice;

*Michrodochium nivale* on cereals;

*Mycosphaerella* species on cereals, bananas and peanuts, for example, *M. graminicola* on wheat or *M. fijiensis* on bananas;

*Peronospora* species on cabbage and bulbous plants, for example, *P. brassicae* on cabbage or *P. destructor* on onions;

*Phakopsara pachyrhizi* and *Phakopsara meibomiae* on soybeans;

*Phomopsis* species on soybeans and sunflowers;

*Phytophthora infestans* on potatoes and tomatoes;

*Phytophthora* species on various plants, for example, *P. capsici* on bell pepper;

*Plasmopara viticola* on grapevines;

*Podosphaera leucotricha* on apples;

*Pseudocercosporella herpotrichoides* on cereals;

*Pseudoperonospora* on various plants, for example, *P. cubensis* on cucumber or *P. humili* on hops;

*Puccinia* species on various plants, for example, *P. triticina*, *P. striformins*, *P.*, *hordei* or *P. graminis* on cereals or *P. asparagi* on asparagus;

*Pyrlcularia oryzae*, *Corticium sasakii*, *Sarocladium oryzae*, *S. attenuatum*, *Entyloma oryzae* on rice;

*Pyricularia grisea* on lawns and cereals;

*Pythium* spp. on lawns, rice, corn, cotton, oilseed rape, sunflowers, sugar beet, vegetables and other plants, for example, *P. ultiumum* on various plants, *P. aphanidermatum* on lawns;

*Rhizoctonia* species on cotton, rice, potatoes, lawns, corn, oilseed rape, sugar beet, vegetables and on various plants, for example, *R. solani* on beet and various plants;

*Rhynchosporium secalis* on barley, rye and triticale;

*Sclerotinia* species on oilseed rape and sunflowers;

*Septoria tritici* and *Stagonospora nodorum* on wheat;

*Erysiphe* (syn. *Uncinula*) *necator* on grapevines;

*Setospaeria* species on corn and lawns;

*Sphacelotheca reilinia* on corn;

*Thievaliopsis* species on soybeans and cotton;

*Tilletia* species on cereals;

*Ustilago* species on cereals, corn and sugar cane, for example, *U. maydis* on corn;

*Venturia* species (scab) on apples and pears, for example, *V. inaequalis* on apples.

The mixtures according to the invention are also suitable for controlling harmful fungi in the protection of materials (for example wood, paper, paint dispersions, fibers or fabrics) and in the protection of stored products. In the protection of wood, particular attention is paid to the following harmful fungi: Ascomycetes, such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes, such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes, such as *Aspergillus* spp., *Cladosporium* spp., *Penicillium* spp., *Trichoderma* spp., *Alternaria* spp., *Paecilomyces* spp. and Zygomycetes, such as *Mucor* spp., additionally in the protection of materials the following yeasts: *Candida* spp. and *Saccharomyces cerevisae*.

The compound(s) I and at least one of the active compounds II can be applied simultaneously, that is jointly or separately, or in succession, the sequence, in the case of separate application, generally not having any effect on the result of the control measures.

When preparing the mixtures, it is preferred to employ the pure active compounds I and II, to which further compounds active against harmful fungi or other pests, such as insects, arachnids or nematodes, or else herbicidal or growth-regulating active compounds or fertilizers can be added.

Such mixtures of three active compounds comprise, for example, a compound of the formula I, in particular N-(2'-fluoro-4'-chloro-5'-methylbiphenyl-2-yl)-1-methyl-3-trifluoro-methyl-1H-pyrazole-4-carboxamide, N-(3',4',5'-trifluorobiphenyl-2-yl)-1-methyl-3-tri-fluoromethyl-1H-pyrazole-4-carboxamide, N-(3',4',5'-trifluorobiphenyl-2-yl)-1-methyl-3-difluoromethyl-1H-pyrazole-4-carboxamide, N-(2',4',5'-trifluorobiphenyl-2-yl)-1-methyl-3-difluoromethyl-1H-pyrazole-4-carboxamide or N-(3',4',5'-trifluorobiphenyl-2-yl)-3-chlorofluoromethyl-1-methyl-1H-pyrazole-4-carboxamide, an azole from group A), in particular epoxiconazole, metconazole, triticonazole or fluquinconazole, and an insecticide, suitable insecticides being in particular fipronil and neonicotinoids, such as acetamiprid, clothianidin, dinotefuran, imidacloprid, nitenpyram, thiaclorprid and thiamethoxam.

Usually, mixtures of at least one compound I and at least one active compound II are employed. However, mixtures of at least one compound I with two or, if desired, more active components may also offer particular advantages.

Suitable further active components in the above sense are particularly the active compounds II mentioned at the outset and in particular the preferred active compounds II mentioned above.

Compound(s) I and active compound(s) II are usually employed in a weight ratio of from 100:1 to 1:100, preferably from 20:1 to 1:20, in particular from 10:1 to 1:10.

The further active components are, if desired, mixed in a ratio of from 20:1 to 1:20 to the compound I.

Depending on the type of the compounds I and II and the desired effect, the application rates of the mixtures according to the invention, especially on agricultural crop areas, are from 5 g/ha to 2000 g/ha, preferably from 20 to 1500 g/ha, in particular from 50 to 1000 g/ha.

Correspondingly, the application rates for the compound(s) I are generally from 1 to 1000 g/ha, preferably from 10 to 900 g/ha, in particular from 20 to 750 g/ha.

Correspondingly, the application rates for the active compound II are generally from 1 to 2000 g/ha, preferably from 10 to 1500 g/ha, in particular from 40 to 1000 g/ha.

In the treatment of seed, application rates of mixture are generally from 1 to 1000 g per 100 kg of seed, preferably from 1 to 750 g per 100 kg, in particular from 5 to 500 g per 100 kg of seed.

The method for controlling harmful fungi is carried out by the separate or joint application of compound(s) I and at least one of the active compounds II, or a mixture of compound(s) I and at least one of the active compounds II, by spraying or dusting the seeds, the plants or the soils before or after sowing of the plants or before or after emergence of the plants.

The fungicidal mixtures according to the invention, or the compound(s) I and at least one of the active compounds II, can be converted into the customary formulations, for example solutions, emulsions, suspensions, dusts, powders, pastes and granules. The use form depends on the particular intended purpose; in each case, it should ensure as fine and even a distribution of the mixture according to the invention as possible.

The formulations are prepared in a manner known per se, for example by extending the active compounds with solvents and/or carriers, if desired using emulsifiers and dispersants. Solvents/auxiliaries suitable for this purpose are essentially:

water, aromatic solvents (for example Solvesso® products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone, N-octylpyrrolidone), acetates (glycol diacetate), glycols, fatty acid dimethylamides, fatty acids and fatty acid esters. In principle, solvent mixtures may also be used.

carriers such as ground natural minerals (for example kaolins, clays, talc, chalk) and ground synthetic minerals (for example highly disperse silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone and water.

Powders, materials for spreading and dustable products can be prepared by mixing or concomitantly grinding the active substances with at least one solid carrier.

Granules, for example coated granules, impregnated granules and homogeneous granules, can be prepared by binding the active compounds to at least one solid carrier. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the compound(s) I and at least one of the active compounds II or the mixture of compound(s) I with at least one of the active compounds II. The active compounds are employed in a purity of from 90% to 100%, preferably 95% to 100% (according to NMR or HPLC spectrum).

The following are examples of formulations: 1. Products for dilution with water

A) Water-Soluble Concentrates (SL)

10 parts by weight of a mixture according to the invention are dissolved in 90 parts by weight of water or in a water-soluble solvent. As an alternative, wetting agents or other auxiliaries are added. The active compounds dissolve upon dilution with water. In this way, a formulation having a total content of 10% by weight of active compound is obtained.

B) Dispersible Concentrates (DC)

20 parts by weight of a mixture according to the invention are dissolved in 70 parts by weight of cyclohexanone with addition of 10 parts by weight of a dispersant, for example polyvinylpyrrolidone. Dilution with water gives a dispersion. The active compound content is 20% by weight C) Emulsifiable Concentrates (EC)

15 parts by weight of a mixture according to the invention are dissolved in 75 parts by weight of xylene with addition of calcium dodecylbenzenesulfonate and castor oil ethoxylate (in each case 5 parts by weight). Dilution with water gives an emulsion. The formulation has an active compound content of 15% by weight.

D) Emulsions (EW, EO)

25 parts by weight of a mixture according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (e.g. Ultraturrax) and made into a homogeneous emulsion. Dilution with water gives an emulsion. The formulation has an active compound content of 25% by weight.

E) Suspensions (SC, OD)

In an agitated ball mill, 20 parts by weight of a mixture according to the invention are comminuted with addition of 10 parts by weight of dispersants and wetting agents and 70 parts by weight of water or an organic solvent to give a fine active compound suspension. Dilution with water gives a stable suspension of the active compounds. The active compound content in the formulation is 20% by weight.

F) Water-Dispersible Granules and Water-Soluble Granules (WG, SG)

50 parts by weight of a mixture according to the invention are ground finely with addition of 50 parts by weight of dispersants and wetting agents and prepared as water-dispersible or water-soluble granules by means of technical appliances (for example extrusion, spray tower, fluidized bed). Dilution with water gives a stable dispersion or solution of the active compounds. The formulation has an active compound content of 50% by weight.

G) Water-Dispersible Powders and Water-Soluble Powders (WP, SP)

75 parts by weight of a mixture according to the invention are ground in a rotor-stator mill with addition of 25 parts by weight of dispersants, wetting agents and silica gel. Dilution with water gives a stable dispersion or solution of the active compounds. The active compound content of the formulation is 75% by weight.

2. Products to be Applied Undiluted

H) Dustable Powders (DP)

5 parts by weight of a mixture according to the invention are ground finely and mixed intimately with 95 parts by weight of finely divided kaolin. This gives a dustable product having an active compound content of 5% by weight.

J) Granules (GR, FG, GG, MG)

0.5 part by weight of a mixture according to the invention is ground finely and associated with 99.5 parts by weight of carriers. Current methods are extrusion, spray-drying or the fluidized bed. This gives granules to be applied undiluted having an active compound content of 0.5% by weight.

K) ULV Solutions (UL)

10 parts by weight of a mixture according to the invention are dissolved in 90 parts by weight of an organic solvent, for example xylene. This gives a product to be applied undiluted having an active compound content of 10% by weight.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetting agent, tackifier, dispersant or emulsifier. However, it is also possible to prepare concentrates composed of active substance, wetting agent, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), it being possible to apply formulations comprising over 95% by weight of active compound, or even to apply the active compound without additives.

Oils of various types, wetting agents, adjuvants, herbicides, other pest control agents or bactericides may be added to the active compounds, even, if desired, not until immediately prior to use (tank mix). These agents are typically mixed with the mixtures according to the invention in a weight ratio of from 1:100 to 100:1, preferably from 1:10 to 10:1.

Suitable adjuvants in this context are, in particular: organically modified polysiloxanes, e.g. Break Thru S 240®; alcohol alkoxylates, e.g. Atplus 245®, Atplus MBA 1303®, Plurafac LF 300® and Lutensol ON 30®; EO/PO block polymers, e.g. Pluronic RPE 2035® and Genapol B®; alcohol ethoxylates, e.g. Lutensol XP 80®; and sodium dioctylsulfosuccinate, e.g. Leophen RA®.

The compounds I and II or the mixtures or the corresponding formulations are applied by treating the harmful fungi, their habitat or the plants, seeds, soils, areas, materials or spaces to be kept free from them with a fungicidally effective amount of the mixture or, in the case of separate application, of the compounds I and II. Application can be before or after the infection by harmful fungi.

USE EXAMPLES

The fungicidal action of the individual compounds and of the mixtures according to the invention was demonstrated by the tests below.

The active compounds, separately or jointly, were prepared as a stock solution comprising 25 mg of active compound which was made up to 10 ml using a mixture of acetone and/or dimethyl sulfoxide and the emulsifier Uniperol® EL (wetting agent having an emulsifying and dispersing action based on ethoxylated alkylphenols) in a ratio by volume of solvent/emulsifier of 99:1. The mixture was then made up to 100 ml with water. This stock solution was diluted with the solvent/emulsifier/water mixture described to give the concentration of active compound stated below.

As an alternative, the active compounds epoxiconazole, triticonazole and pyraclostrobin were used as commercially available ready-to-use formulation and diluted to the specified active compound concentration with water.

The visually determined percentages of infected leaf areas were converted into efficacies in % of the untreated control:

The efficacy (E) is calculated as follows using Abbot's formula:

$$E = (1 - \alpha/\beta) \cdot 100$$

α corresponds to the fungicidal infection of the treated plants in % and

β corresponds to the fungicidal infection of the untreated (control) plants in %

An efficacy of 0 means that the infection level of the treated plants corresponds to that of the untreated control plants; an efficacy of 100 means that the treated plants are not infected.

The expected efficacies of active compound combinations were determined using Colby's formula (Colby, S. R. "Calculating synergistic and antagonistic responses of herbicide combinations", Weeds, 15, 20-22, 1967) and compared with the observed efficacies.

Colby's formula:

$$E = x + y - x \cdot y / 100$$

E expected efficacy, expressed in % of the untreated control, when using the mixture of the active compounds A and B at the concentrations a and b;

x efficacy, expressed in % of the untreated control, when using the active compound A at the concentration a;

y efficacy, expressed in % of the untreated control, when using the active compound B at the concentration b.

Use Example 1

Activity Against Early Blight of Tomato Caused by *Alternaria solani*

Leaves of potted tomato plants were sprayed to runoff point with an aqueous suspension having the active compound concentration stated below. The next day, the leaves were infected with an aqueous spore suspension of *Alternaria solani* in a 2% biomalt solution having a density of 0.17×10⁶ spores/ml. The plants were then placed in a water vapor-saturated chamber at temperatures between 20 and 22° C. After 5 days, the disease on the untreated but infected control plants had developed to such an extent that the infection could be determined visually in %.

| Active compounds/active compound mixture | Concentration [mg/l] | Ratio | Observed activity (% infection) | Activity calculated according to Colby (%) |
|---|---|---|---|---|
| (Control) | — | — | 0 (90% infection) | — |
| No. Ia.719 | 4 | — | 0 | — |
| prochloraz | 16 | — | 30 | — |
| pyraclostrobin | 4 | — | 50 | — |
| metiram | 63 | — | 0 | — |
| chlorthalonil | 63 | — | 0 | — |
| No. Ia.719 + prochloraz | 4 + 16 | 1:4 | 60 | 30 |
| No. Ia.719 + pyraclostrobin | 4 + 4 | 1:1 | 93 | 50 |
| No. Ia.719 + metiram | 4 + 63 | 1:4 | 70 | 0 |
| No. Ia.179 + chlorthalonil | 4 + 63 | 1:4 | 70 | 0 |

Use Example 2

Activity Against Gray Mold on Bell Pepper Leaves Caused by *Botrytis cinerea*, 1 Day of Protective Application Bell pepper seedlings of the cultivar "Neusiedler Ideal Elite" were, after 2-3 leaves were well developed, sprayed to runoff point with an aqueous suspension in the active compound concentration specified below. The next day, the treated plants were inoculated with a spore suspension of *Botrytis cinerea* which contained 1.7×10⁶ spores/ml in a 2% strength aqueous biomalt solution. The test plants were then placed in a climatized chamber at 22 to 24° C., darkness and high atmospheric humidity. After 5 days, the extent of the fungal infection on the leaves could be determined visually in %.

| Active compounds/active compound mixture | Concentration [mg/l] | Ratio | Observed activity (% infection) | Activity calculated according to Colby (%) |
|---|---|---|---|---|
| (Control) | — | — | 0 (100% infection) | — |
| No. Id.344 | 1 | — | 40 | — |
| No. Ia.344 | 16 | — | 60 | — |
| No. Ij.344 | 4 | — | 22 | — |
|  | 1 | — | 0 | — |
| triticonazole | 4 | — | 0 | — |
| prochloraz | 4 | — | 11 | — |
| dimethomorph | 63 | — | 0 | — |
|  | 16 | — | 0 | — |
|  | 4 | — | 0 | — |
| metiram | 16 | — | 0 | — |
| metrafenone | 63 | — | 0 | — |
|  | 16 | — | 0 | — |
|  | 4 | — | 0 | — |
| No. Id.344 + dimethomorph | 1 + 4 | 1:4 | 80 | 40 |
| No. Id.344 + metiram | 1 + 16 | 1:16 | 70 | 40 |
| No. Id.344 + metrafenone | 1 + 4 | 1:4 | 60 | 40 |
| No. Ia.344 + dimethomorph | 16 + 63 | 1:4 | 85 | 60 |
| No. Ia.344 + metrafenone | 16 + 63 | 1:4 | 90 | 60 |
| No. Ij.344 + triticonazole | 4 + 4 | 1:1 | 78 | 22 |
| No. Ij.344 + prochloraz | 1 + 4 | 1:4 | 92 | 11 |
| No. Ij.344 + dimethomorph | 4 + 16 | 1:4 | 78 | 22 |
| No. Ij.344 + metrafenone | 4 + 16 | 1:4 | 100 | 22 |

Use Example 3

Curative Activity Against Brown Rust of Wheat Caused by *Puccinia recondita*

Leaves of potted wheat seedlings of the cultivar "Kanzler" were inoculated with a spore suspension of brown rust (*Puccinia recondita*). The pots were then placed in a chamber with high atmospheric humidity (90 to 95%) and 20 to 22° C. for 24 hours. During this time, the spores germinated and the germ tubes penetrated into the leaf tissue. The next day, the infected plants were sprayed to runoff point with the above-described active compound solution having the active compound concentration stated below. After the spray coating had dried on, the test plants were cultivated in a greenhouse at temperatures between 20 and 22° C. and 65 to 70% relative atmospheric humidity for 7 days. The extent of the rust fungal development on the leaves was then determined.

| Active compounds/active compound mixture | Concentration [mg/l] | Ratio | Observed activity (% infection) | Activity calculated according to Colby (%) |
|---|---|---|---|---|
| (Control) | — | — | 0 (90% infection) | — |
| No. Id.344 | 1 | — | 0 | — |
| No. Ij.344 | 1 | — | 0 | — |
| No. Ia.719 | 0.25 | — | 0 | — |
| epoxiconazole | 0.063 | — | 0 | — |
| triticonazole | 1 | — | 0 | — |
| pyraclostrobin | 1 | — | 0 | — |
| chlorthalonil | 16 | — | 0 | — |

99

-continued

| Active compounds/active compound mixture | Concentration [mg/l] | Ratio | Observed activity (% infection) | Activity calculated according to Colby (%) |
|---|---|---|---|---|
| 5-chloro-7-(4-methyl-piperidin-1-yl)-6-(2,4,6-trifluorophenyl)-[1,2,4]tri-azolo[1,5-a]pyrimidine | 4 | — | 40 | — |
| No. Id.344 + triticonazole | 1 + 1 | 1:1 | 56 | 0 |
| No. Id.344 + pyraclostrobin | 1 + 1 | 1:1 | 83 | 0 |
| No. Id.344 + chlorthalonil | 1 + 16 | 1:16 | 78 | 0 |
| No. Ij.344 + 5-chloro-7-(4-methylpiperidin-1-yl)-6-(2,4,6-trifluorophenyl)-[1,2,4]tri-azolo[1,5-a]pyrimidine | 1 + 4 | 1:4 | 100 | 40 |
| No. Ia.719 + epoxiconazole | 0.25 + 0.063 | 4:1 | 30 | 0 |

Use Example 4

Activity Against Net Blotch of Barley Caused by *Pyrenophora teres*, 1 Day Protective Application Leaves of potted barley seedlings were sprayed to runoff point with an aqueous suspension having the active compound concentration stated below. 24 hours after the spray coating had dried on, the test plants were inoculated with an aqueous spore suspension of *Pyrenophora* [syn. *Drechslera*] *teres*, the net blotch pathogen. The test plants were then placed in a greenhouse at temperatures between 20 and 24° C. and 95 to 100% relative atmospheric humidity. After 6 days, the extent of the development of the disease was determined visually in % infection of the entire leaf area.

| Active compounds/active compound mixture | Concentration [mg/l] | Ratio | Observed activity (% infection) | Activity calculated according to Colby (%) |
|---|---|---|---|---|
| (Control) | — | — | 0 (90% infection) | — |
| No. Id.344 | 0.25 | — | 67 | — |
| epoxiconazole | 0.063 | — | 0 | — |
| No. Id.344 + epoxiconazole | 0.25 + 0.063 | 4:1 | 83 | 67 |

The test results show that, by virtue of the synergism, the mixtures according to the invention are considerably more active than had been predicted using Colby's formula.

100

The invention claimed is:

1. A fungicidal mixture comprising,
   1) at least one compound of formula I

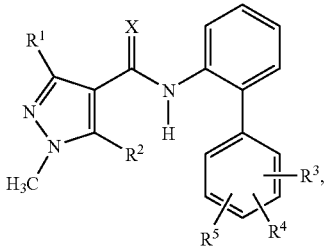

wherein:

X is oxygen;

$R^1$ is $C_1$-$C_4$-alkyl or $C_1$-$C_4$-haloalkyl;

$R^2$ is hydrogen;

$R^3$, $R^4$ and $R^5$ independently of one another are halogen; and 2) at least one active compound II selected from the group consisting of:

A) bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thiabendazole, fuberidazole, ethaboxam, etridiazole and hymexazole;

B) azoxystrobin, dimoxystrobin, enestroburin, fluoxastrobin, kresoxim-methyl, methominostrobin, orysastrobin, picoxystrobin, pyraclostrobin, trifloxystrobin, enestroburin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate and methyl 2-(ortho-(2,5-dimethylphenyloxymethylene)phenyl)-3-methoxyacrylate;

C) carboxin, benalaxyl, boscalid, fenhexamid, flutolanil, furametpyr, mepronil, metalaxyl, mefenoxam, ofurace, oxadixyl, oxycarboxin, penthiopyrad, thifluzamide, tiadinil, 3,4-dichloro-N-(2-cyanophenyl)isothiazole-5-carboxamide, dimethomorph, flumorph, flumetover, fluopicolide (picobenzamid), zoxamide, carpropamid, diclocymet, mandipropamid, N-(2-(4-[3-(4-chlorophenyl)prop-2-ynyloxy]-3-methoxyphenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide, methyl 3-(4-chlorophenyl)-3-(2-isopropoxycarbonylamino-3-methylbutyrylamino)propionate, compounds of formula III

III

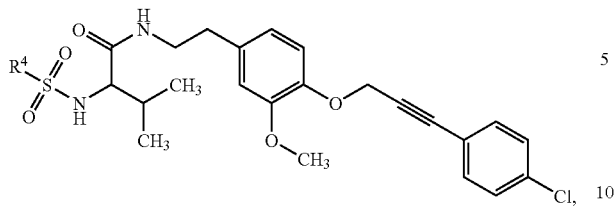

wherein: R⁴ of formula III is methyl or ethyl, N-(4'-bromobiphenyl-2-yl)-4-difluoromethyl-2-methylthiazole-5-carboxamide, N-(4'-trifluoromethyl-biphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(3',4'-dichloro-5-fluorobiphenyl-2-yl)-3-difluoromethyl-1-methylpyrazole-4-carboxamide and N-(2-cyanophenyl)-3,4-dichloroisothiazole-5-carboxamide;

D) fluazinam, pyrifenox, bupirimate, cyprodinil, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, probenazole, 5-chloro-7-(4-methylpiperidin-1-yl)-6-(2,4,6-trifluorophenyl)-[1,2,4]triazolo[1,5-a]pyrimidine, anilazine, diclomezine, pyroquilon, proquinazid, tricyclazole, a compound of formula IV (2-butoxy-6-iodo-3-propylchromen-4-one)

IV

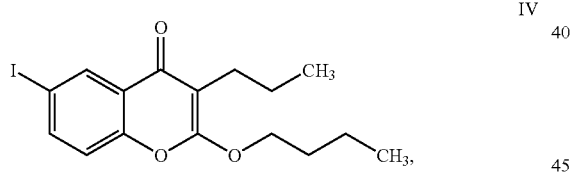

acibenzolar-S-methyl, captafol, captan, dazomet, folpet, fenoxanil, quinoxyfen and N,N-dimethyl-3-(3-bromo-6-fluoro-2-methylindole-1-sulfonyl)-[1,2,4]triazole-1-sulfonamide of formula V

V

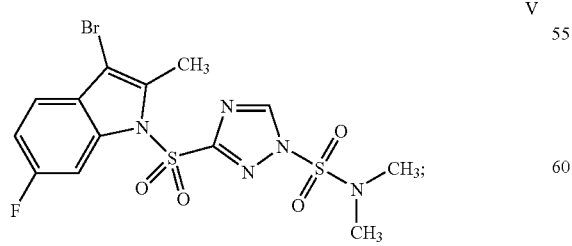

E) mancozeb, maneb, metam, metiram, ferbam, propineb, thiram, zineb, ziram, diethofencarb, iprovalicarb, flubenthiavalicarb, propamocarb, 4-fluorophenyl N-(1-(1-(4-cyanophenyl)ethanesulfonyl)but-2-yl)carbamate, methyl 3-(4-chlorophenyl)-3-(2-isopropoxycarbonylamino-3-methyl-butyrylamino) propanoate of formula VI

VI

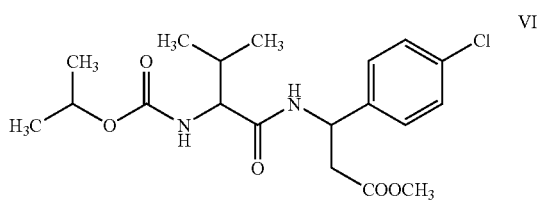

and carbamate oxime ethers of formula VII

VII

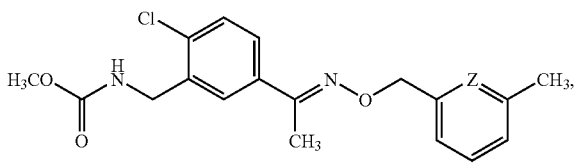

wherein: Z is N or CH;

F) guanidine, dodine, iminoctadine, guazatine, kasugamycin, streptomycin, polyoxin, validamycin A,
binapacryl, dinocap, dinobuton,
dithianon, isoprothiolane,
fentin salts,
edifenphos, iprobenfos, fosetyl, fosetyl-aluminum, phosphorous acid and its salts, pyrazophos, tolclofos-methyl,
chlorothalonil, dichlofluanid, flusulfamide, hexachlorobenzene, phthalide, pencycuron, quintozene, thiophanate-methyl, tolylfluanid,
Bordeaux mixture, copper acetate, copper hydroxide, copper oxychloride,
basic copper sulfate, sulfur,
cyflufenamid, cymoxanil, dimethirimol, ethirimol, furalaxyl, metrafenone and spiroxamine;
wherein the at least one compound of formula I and the at least one active compound II are present in a synergistically effective amount.

2. The fungicidal mixture of claim 1, wherein the at least one compound I is selected from the group consisting of:
N-(3',4',5'-trifluorobiphenyl-2-yl)-3 trifluoromethyl-1-methyl-1H-pyrazole-4-carboxamide,
N-(2',4',5'-trifluorobiphenyl-2-yl)-3-trifluoromethyl-1-methyl-1H-pyrazole-4-carboxamide,
N-(2',3',4'-trifluorobiphenyl-2-yl)-3-trifluoromethyl-1-methyl-1H-pyrazole-4-carboxamide,
N-(3',4',5'-trifluorobiphenyl-2-yl)-3 difluoromethyl-1-methyl-1H-pyrazole-4-carboxamide,
N-(2',4',5'-trifluorobiphenyl-2-yl)-3-difluoromethyl-1-methyl-1H-pyrazole-4-carboxamide,
N-(3',4',5'-trifluorobiphenyl-2-yl)-3-fluoromethyl-1-methyl-1H-pyrazole-4-carboxamide,
N (3',4',5'-trifluorobiphenyl-2-yl)-3-chlorodifluoromethyl-1-methyl-1H-pyrazole-4-carboxamide,
N-(3',4',5'-trifluorobiphenyl-2-yl)-3-chlorofluoromethyl-1-methyl-1H-pyrazole-4-carboxamide, N-(2',3',4'-trifluorobiphenyl-2-yl)-3-fluoromethyl-1 methyl-1H-pyrazole-4-carboxamide
and
N-(2',4',5'-trifluorobiphenyl-2-yl)-3 fluoromethyl-1-methyl-1H-pyrazole-4-carboxamide.

3. The fungicidal mixture of claim 1, wherein the at least one compound of formula I and the at least one active compound II are present in a weight ratio of from 100:1 to 1:100.

4. The fungicidal mixture of claim 1, wherein the at least one compound of formula I and the at least one active compound II are present in a weight ratio of from 100:1 to 1:100.

5. The fungicidal mixture of claim 2, wherein the at least one compound of formula I and the at least one active compound II are present in a weight ratio of from 100:1 to 1:100.

6. The fungicidal mixture of claim 1, further comprising at least one liquid or solid carrier.

7. The fungicidal mixture of claim 1, further comprising at least one liquid or solid carrier.

8. The fungicidal mixture of claim 2, further comprising at least one liquid or solid carrier.

9. A method for controlling phytopathogenic harmful fungi comprising,
contacting fungi, their habitat or the plants, soil, seeds, areas, materials or spaces to be protected against fungal attack with a fungicidal mixture of claim 1,
wherein the at least one compound of formula I and the at least one active compound II are present in a synergistically effective amount;
wherein phytopathogenic harmful fungi are controlled.

10. The method of claim 9, wherein the at least one compound of formula I and the at least one active compound II are applied simultaneously, separately, or in succession.

11. The method of claim 9, wherein the at least one compound of formula I and the at least one active compound II are applied in an amount of from 5 g/ha to 2000 g/ha.

12. The method of claim 9, wherein the at least one compound of formula I and the at least one active compound II are applied in an amount of from 1 g to 1000 g per 100 kg of seed.

13. The method of claim 9, wherein the at least one compound I is selected from the group consisting of:
N-(3',4',5'-trifluorobiphenyl-2-yl)-3 trifluoromethyl-1-methyl-1H-pyrazole-4-carboxamide,
N-(2',4',5'-trifluorobiphenyl-2-yl)-3-trifluoromethyl-1-methyl-1H-pyrazole-4-carboxamide,
N-(2',3',4'-trifluorobiphenyl-2-yl)-3-trifluoromethyl-1-methyl-1H-pyrazole-4-carboxamide,
N-(3',4',5'-trifluorobiphenyl-2-yl)-3 difluoromethyl-1-methyl-1H-pyrazole-4-carboxamide,
N-(2',4',5'-trifluorobiphenyl-2-yl)-3-difluoromethyl-1-methyl-1H-pyrazole-4-carboxamide,
N-(3',4',5'-trifluorobiphenyl-2-yl)-3-fluoromethyl-1-methyl-1H-pyrazole-4-carboxamide,
N (3',4',5'-trifluorobiphenyl-2-yl)-3-chlorodifluoromethyl-1-methyl-1H-pyrazole-4-carboxamide,
N-(3',4',5'-trifluorobiphenyl-2-yl)-3-chlorofluoromethyl-1-methyl-1H-pyrazole-4-carboxamide,
N-(2',3',4'-trifluorobiphenyl-2-yl)-3-fluoromethyl-1 methyl-1H-pyrazole-4-carboxamide
and
N-(2',4',5'-trifluorobiphenyl-2-yl)-3 fluoromethyl-1-methyl-1H-pyrazole-4-carboxamide.

14. A seed, treated with a fungicidal mixture of claim 1, wherein the at least one compound of formula I and the at least one active compound II are present in a synergistically effective amount.

15. The seed of claim 14, wherein the at least one compound of formula I and the at least one active compound II are present in an amount of from 1 g to 1000 g per 100 kg of seed.

16. The seed of claim 14, wherein the at least one formula I is selected from the group consisting of:
N-(3',4',5'-trifluorobiphenyl-2-yl)-3 trifluoromethyl-1-methyl-1H-pyrazole-4-carboxamide,
N-(2',4',5'-trifluorobiphenyl-2-yl)-3-trifluoromethyl-1-methyl-1H-pyrazole-4-carboxamide,
N-(2',3',4'-trifluorobiphenyl-2-yl)-3-trifluoromethyl-1-methyl-1H-pyrazole-4-carboxamide,
N-(3',4',5'-trifluorobiphenyl-2-yl)-3 difluoromethyl-1-methyl-1H-pyrazole-4-carboxamide,
N-(2',4',5'-trifluorobiphenyl-2-yl)-3-difluoromethyl-1-methyl-1H-pyrazole-4-carboxamide,
N-(3',4',5'-trifluorobiphenyl-2-yl)-3-fluoromethyl-1-methyl-1H-pyrazole-4-carboxamide,
N (3',4',5'-trifluorobiphenyl-2-yl)-3-chlorodifluoromethyl-1-methyl-1H-pyrazole-4-carboxamide,
N-(3',4',5'-trifluorobiphenyl-2-yl)-3-chlorofluoromethyl-1-methyl-1H-pyrazole-4-carboxamide,
N-(2',3',4'-trifluorobiphenyl-2-yl)-3-fluoromethyl-1 methyl-1H-pyrazole-4-carboxamide
and
N-(2',4',5'-trifluorobiphenyl-2-yl)-3 fluoromethyl-1-methyl-1H-pyrazole-4-carboxamide.

* * * * *

UNITED STATES PATENT AND TRADEMARK OFFICE
CERTIFICATE OF CORRECTION

PATENT NO. : 8,153,819 B2  
APPLICATION NO. : 11/997860  
DATED : April 10, 2012  
INVENTOR(S) : Jochen Dietz et al.

Page 1 of 1

It is certified that error appears in the above-identified patent and that said Letters Patent is hereby corrected as shown below:

On the Title Page: Item (87), should be PCT Publ. No.: WO2007/017416

Signed and Sealed this
Fourth Day of September, 2012

David J. Kappos
*Director of the United States Patent and Trademark Office*